(12) United States Patent
Carroll et al.

(10) Patent No.: US 11,292,783 B2
(45) Date of Patent: Apr. 5, 2022

(54) SUBSTITUTED 1,2,3,4-TETRAHYDROISOQUINOLINES AS KAPPA OPIOID ANTAGONISTS

(71) Applicant: Research Triangle Institute, Research Triangle Park, NC (US)

(72) Inventors: Frank Ivy Carroll, Research Triangle Park, NC (US); Chad M. Kormos, Research Triangle Park, NC (US); Pauline W. Ondachi, Research Triangle Park, NC (US); Scott P. Runyon, Research Triangle Park, NC (US); Hernan A. Navarro, Research Triangle Park, NC (US); James B. Thomas, Research Triangle Park, NC (US); S. Wayne Mascarella, Research Triangle Park, NC (US)

(73) Assignee: Research Triangle Institute, Research Triangle Park (NC)

( * ) Notice: Subject to any disclaimer, the term of this patent is extended or adjusted under 35 U.S.C. 154(b) by 55 days.

(21) Appl. No.: 16/333,849

(22) PCT Filed: Sep. 15, 2017

(86) PCT No.: PCT/US2017/051707
§ 371 (c)(1),
(2) Date: Mar. 15, 2019

(87) PCT Pub. No.: WO2018/053222
PCT Pub. Date: Mar. 22, 2018

(65) Prior Publication Data
US 2019/0263781 A1 Aug. 29, 2019

Related U.S. Application Data
(60) Provisional application No. 62/395,750, filed on Sep. 16, 2016.

(51) Int. Cl.
| | | |
|---|---|---|
| A61K 31/472 | (2006.01) | |
| C07D 217/26 | (2006.01) | |
| C07D 401/12 | (2006.01) | |
| A61P 25/34 | (2006.01) | |
| A61P 25/36 | (2006.01) | |
| A61P 25/32 | (2006.01) | |
| A61P 25/18 | (2006.01) | |
| A61P 25/24 | (2006.01) | |
| C07D 211/18 | (2006.01) | |
| C07D 413/12 | (2006.01) | |
| C07D 487/08 | (2006.01) | |
| A61P 25/00 | (2006.01) | |

(52) U.S. Cl.
CPC .......... *C07D 401/12* (2013.01); *A61P 25/00* (2018.01); *A61P 25/18* (2018.01); *A61P 25/24* (2018.01); *A61P 25/32* (2018.01); *A61P 25/34* (2018.01); *A61P 25/36* (2018.01); *C07D 211/18* (2013.01); *C07D 217/26* (2013.01); *C07D 413/12* (2013.01); *C07D 487/08* (2013.01)

(58) Field of Classification Search
CPC ............................. A61K 31/472; C07D 217/26
USPC ........................................... 514/307; 546/146
See application file for complete search history.

(56) References Cited

U.S. PATENT DOCUMENTS

| | | |
|---|---|---|
| 5,571,792 A | 11/1996 | Bolton et al. |
| 5,932,590 A | 8/1999 | Ciccarone et al. |
| 6,166,060 A | 12/2000 | Phillips et al. |
| 9,273,027 B2 | 3/2016 | Carroll et al. |
| 2007/0037823 A1 | 2/2007 | Soeberdt et al. |
| 2007/0293469 A1 | 12/2007 | Guichard et al. |

(Continued)

FOREIGN PATENT DOCUMENTS

| | | |
|---|---|---|
| JP | 5612628 | 3/1981 |
| JP | H11506106 A | 6/1999 |
| JP | 2006520361 A | 9/2006 |

(Continued)

OTHER PUBLICATIONS

International Preliminary Report on Patentability issued in counterpart PCT Application No. PCT/US2017/051707 dated Mar. 19, 2019.

(Continued)

*Primary Examiner* — Douglas M Willis
(74) *Attorney, Agent, or Firm* — Olive Law Group, PLLC; Nathan P. Letts

(57) ABSTRACT

Potent opioid receptor antagonists of formula (I) and their use as pharmacotherapies for treating depression, anxiety, schizophrenia, eating disorders, and addiction to cocaine, methamphetamine, nicotine, alcohol, and opiates are disclosed. More specifically, the disclosure provides potent and selective kappa opioid receptor antagonist compounds, pharmaceutical compositions of those compounds and uses of those compounds to ameliorate or treat addictions, eating disorders, etc.

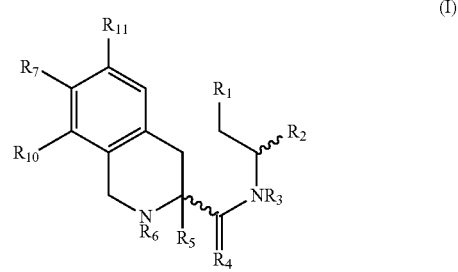

(I)

25 Claims, 6 Drawing Sheets

(56) References Cited

U.S. PATENT DOCUMENTS

Figure 1:
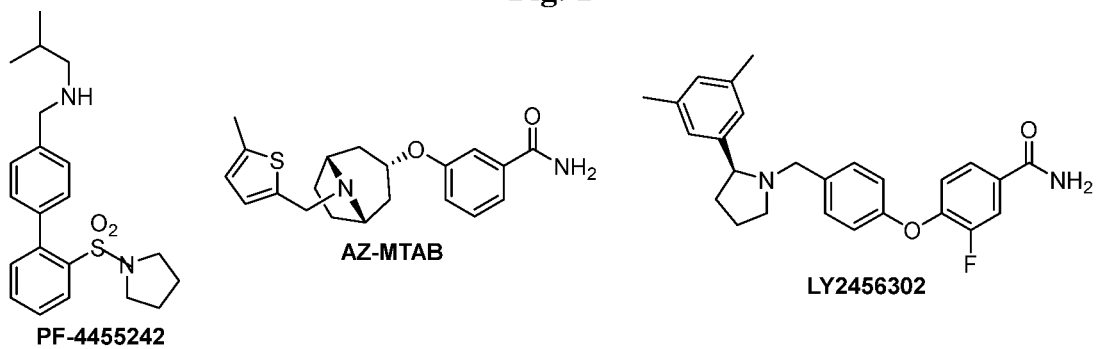
Figure 1:
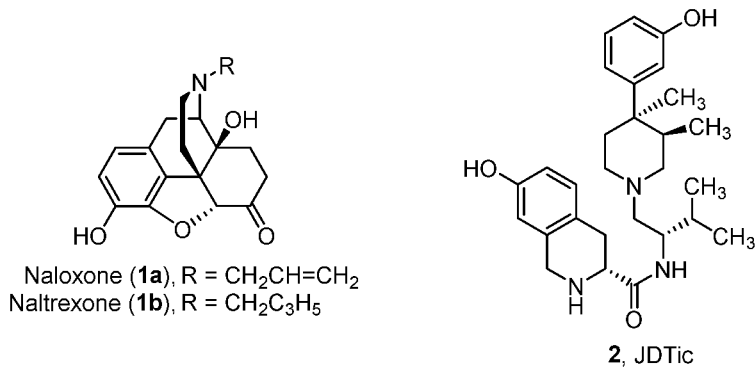

2016/0095854 A1    4/2016    Carroll et al.

FOREIGN PATENT DOCUMENTS

| JP | 2009522234 A | 6/2009 |
|---|---|---|
| WO | 199638142 A1 | 12/1996 |
| WO | 2007074169 A3 | 7/2007 |
| WO | 2009128974 A1 | 10/2009 |
| WO | 2015109080 A1 | 7/2015 |

OTHER PUBLICATIONS

Cai, Tingwei Bill et al. 2008. "Synthesis and In Vitro Opioid Receptor Functional Antagonism of Analogues of the Selective Kappa Opioid Receptor Antagonist (3R)-7-Hydroxy-N-((1S)-1-{[(3R,4R)-4-(3-hydroxyphenyl)-3,4-dimethyl-1-peridinyl]methyl}-2-methylpropyl)-1,2,3,4-tetrahydro-3-isoquinolinecarboxamide (JDTic)." J. Med. Chem. vol. 51. 1849-1860.

Carroll, F. Ivy and Carlezon, William A. Jr. 2013. "Development of [kappa] Opioid Receptor Antagonists." J. Med. Chem. vol. 56. 2178-2195.

Carroll, F. Ivy. 2015. "Design, synthesis, and pharmacological evaluation of JDTic analogs to examine the significance of the 3- and 4-methyl substituents." Bioorganic & Medicinal Chemistry. vol. 23. 6379-6388 (available online Jul. 25, 2015).

Huang, Xuefei, et al. 2002. "Absolute Configurational Assignments of Secondary Amines by CD-Sensitive Dimeric Zinc Porphyrin Host." J. Am. Chem. Soc. vol. 124. 10320-10335 (XP-002396669).

International Search Report and Written Opinion issued in related PCT Application No. PCT/US2015/011581 dated May 4, 2015 (four (4) pages).

International Search Report and Written Opinion issued in parent PCT Application No. PCT/US2017/051707 dated Nov. 17, 2017 (seventeen (17) pages).

Kormos, Chad M. et al. 2013. "Discovery of N-{4-[(3-Hydroxyphenyl)-3-methylpiperazin-1-yl]methyl-2-methylpropyl}-4-phenoxybenzamide Analogues as Selective Kappa Opioid Receptor Antagonists." vol. 56. 4551-4567.

Kormos, Chad M. et al. 2016. "Design, synthesis, and pharmacological evaluation of JDTic analogs to examine the significance of replacement of the 3-hydroxyphenyl group with pyridine or thiophene bioisosteres." Bioorganic & Medicinal Chemistry. vol. 24. pp. 3842-3848 (available online Jun. 15, 2016).

Online Database Registry. XP-002775080. Entered May 16, 2016. Aurora Fine Chemicals.

Online Database Registry. XP-002775081. Entered Apr. 20, 2014.

Online Database Registry. XP-002775082. Entered Jun. 28, 2016. FCH Group.

Online Database Registry. XP-002775083. Entered Jun. 13, 2011. Ryan Scientific.

Foreign Office Action in related Mexican Application No. MX/A/2019/000735 filed Jan. 17, 2019, dated Mar. 9, 2021. (6 pages) with English translation (6 pages).

Ho, Bin, et al. Synthesis and structure-activity relationships of potential anticonvulsants based on 2-piperidinecarboxylic acid and related pharmacophores. Eur. J. Med. Chem., 36, 265-286 (2001).

Li, Xiaoguang, et al. 3D QSAR and docking studies of a series of histone deacetylase inhibitors. Med Chem. Res., 23, 2229-2241 (2014).

Zhang, Yingjie, et al. Design, synthesis and preliminary activity assay of 1,2,3,4-tetrahydroisoquinoline-3-carboxylic acid derivatives as novel Histone deacetylases (HDACs) inhibitors. Bioorganic & Medicinal Chemistry, 18, 1761-1772 (2010).

Kukkola, Paivi J., et al. Optimization of Retro-Thiorphan for Inhibition of Endothelin Converting Enzyme. Bioorganic & Medicinal Chemistry Letters, 6(6), 619-624 (1996).

Chemical Abstracts Services No. 1309008-99-8, Registry (STN) [online], 2011, [searched on Feb. 9, 2021].

Chemical Abstracts Services No. 1940807-38-4, Registry (STN) [online], Jun. 28, 2016, [searched on Feb. 9, 2021].

Chemical Abstracts Services No. 1582927-57-8, Registry (STN) [online], 2014, [searched on Feb. 9, 2021].

Chemical Abstracts Services No. 1582584-99-3, Registry (STN) [online], 2014, [searched on Feb. 9, 2021].

Chemical Abstracts Services No. 1348722-92-8, Registry (STN) [online], 2011, [searched on Feb. 9, 2021].

Chemical Abstracts Services No. 1348246-19-4, Registry (STN) [online], 2011, [searched on Feb. 9, 2021].

Chemical Abstracts Services No. 794485-86-2, Registry (STN) [online], 2004, [searched on Feb. 9, 2021].

Chemical Abstracts Services No. 1587301-92-5, Registry (STN) [online], 2014, [searched on Feb. 9, 2021].

Chemical Abstracts Services No. 1910416-53-3, Registry (STN) [online], May 15, 2016, [searched on Feb. 9, 2021].

Foreign Office Action in related Japanese Application No. 2019-502757 filed Jan. 18, 2019, dated Aug. 3, 2021 with translation (total pp. 11).

Office Action dated Nov. 8, 2021 in counterpart Chinese Application No. 201780057796.6 (12 pages).

Translation/summarization of Office Action dated Nov. 8, 2021 in counterpart Chinese Application No. 201780057796.6 (6 pages).

Figure 2:
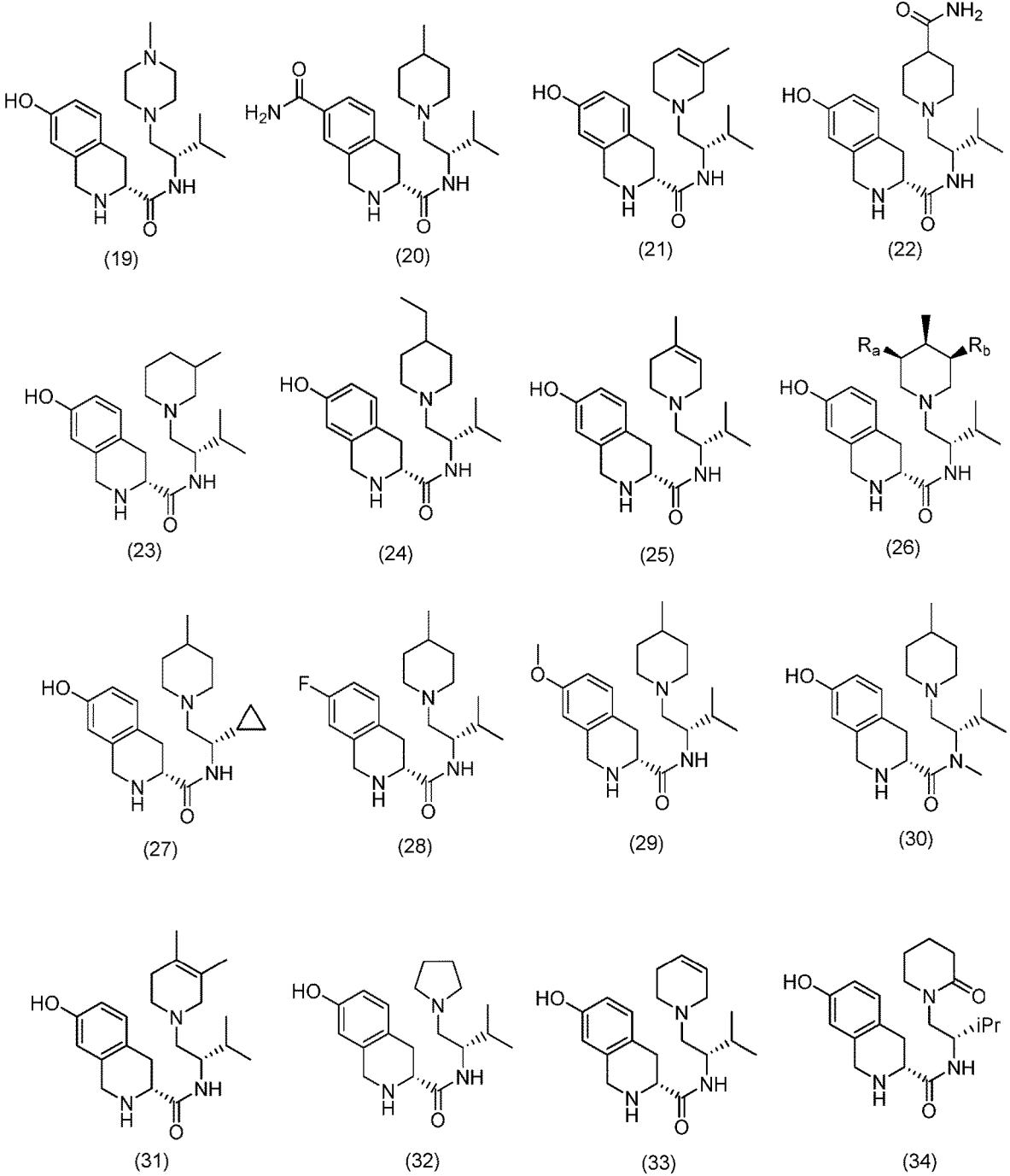

Fig. 2-1
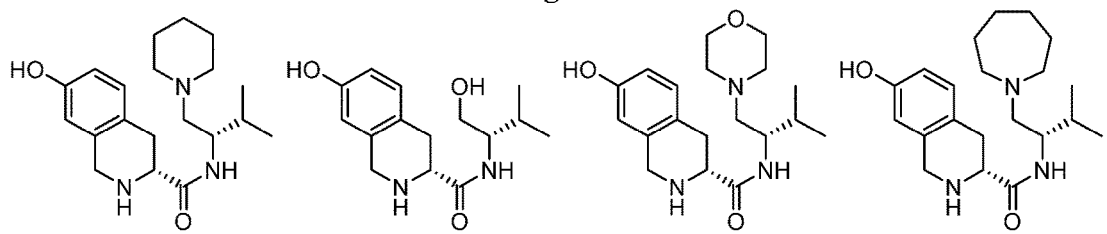
(3) (4) (5) (6)
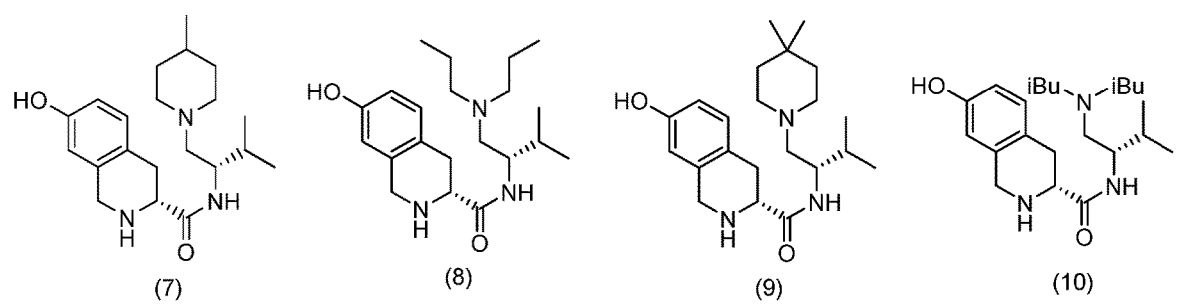
(7) (8) (9) (10)
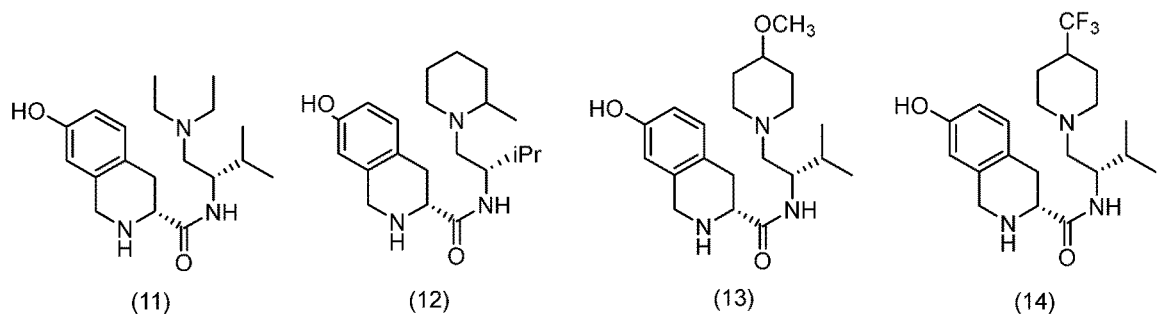
(11) (12) (13) (14)
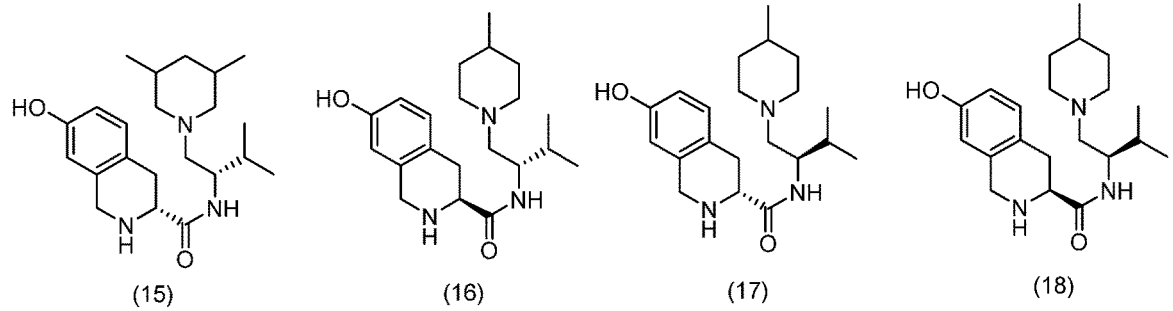
(15) (16) (17) (18)

Figures 2, 3, 4:
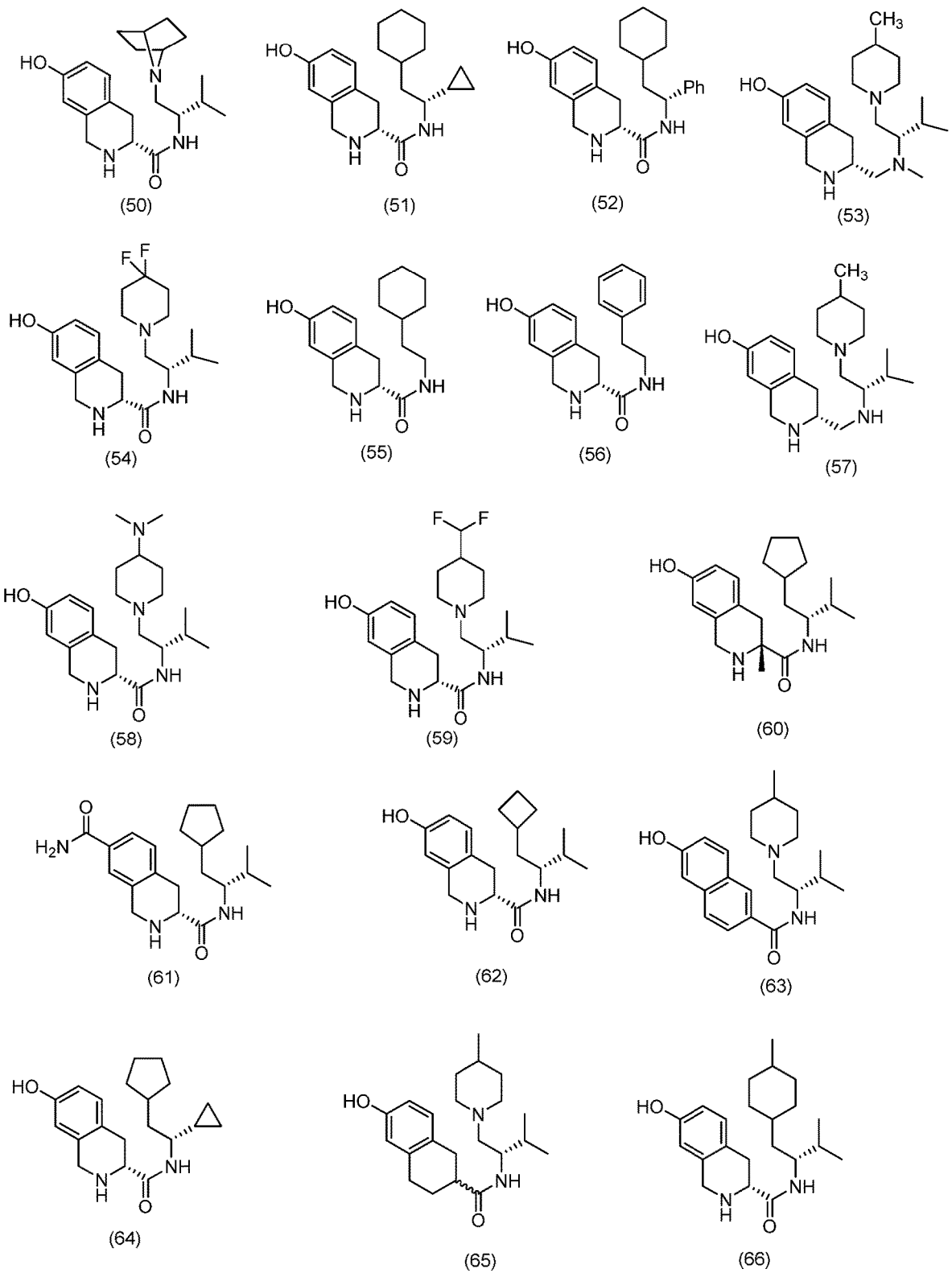
Figures 1, 3:
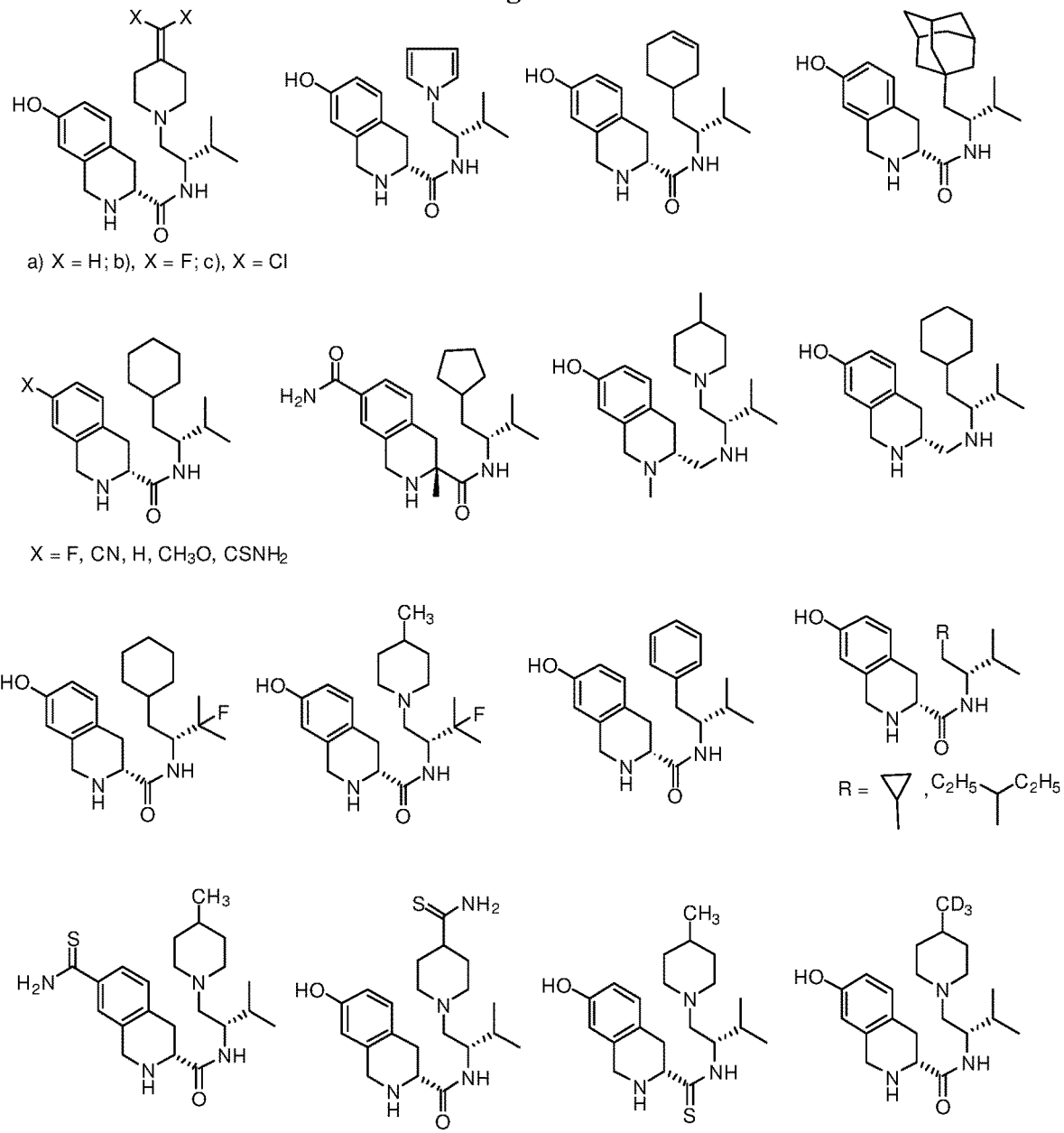

Fig. 2-3
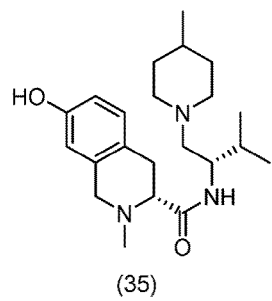
(35)  (36)  (37)
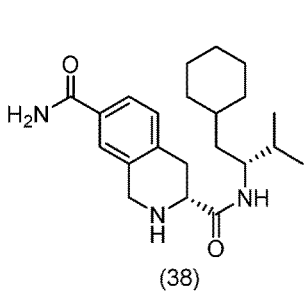 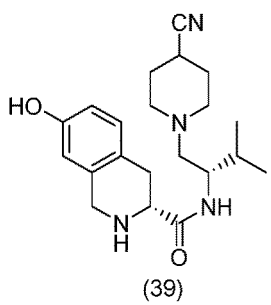 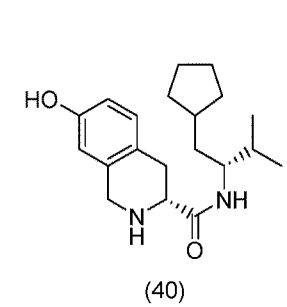 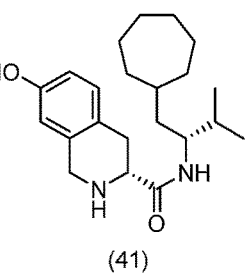
(38)  (39)  (40)  (41)
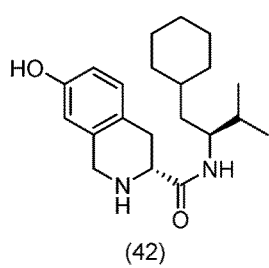 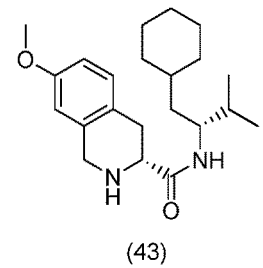 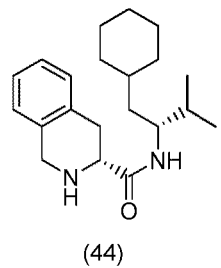 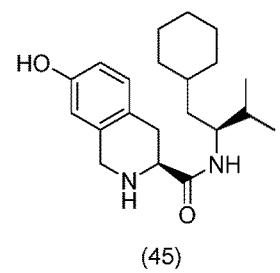
(42)  (43)  (44)  (45)
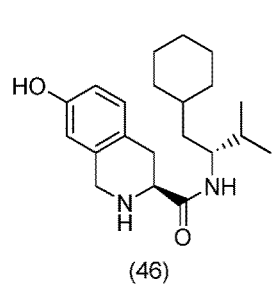 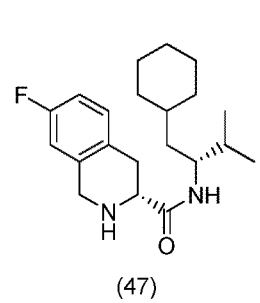 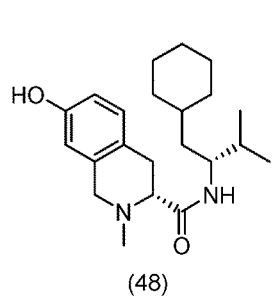 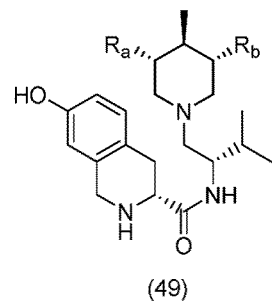
(46)  (47)  (48)  (49)

a) X = H; b), X = F; c), X = Cl

X = F, CN, H, CH3O, CSNH2

SUBSTITUTED 1,2,3,4-TETRAHYDROISOQUINOLINES AS KAPPA OPIOID ANTAGONISTS

CROSS REFERENCE TO RELATED APPLICATIONS

This application is a § 371 U.S. National Stage of International Application PCT/US2017/051707, filed Sep. 15, 2017, which claims the benefit of U.S. Provisional Appn. 62/395,750 filed Sep. 16, 2016, Carroll et al., which are hereby incorporated by reference in their entireties.

STATEMENT REGARDING FEDERALLY SPONSORED RESEARCH OR DEVELOPMENT

This invention was made with government support under Grant No. DA009045 awarded by the National Institutes of Health. The United States Government has certain rights in the invention.

1. FIELD

The present disclosure relates generally to the discovery of potent opioid receptor antagonists and there use as pharmacotherapies for treating depression, anxiety, schizophrenia, eating disorders, and addiction to cocaine, methamphetamine, nicotine, alcohol, and opiates.

2. BACKGROUND

2.1. Introduction

The opioid receptors, μ, δ, κ, and the opioid-like receptor ORL-1 belong to the super family of G-protein coupled receptors (GPCRs) that possess seven helical trans-membrane spanning domains in their architecture.[1] The majority of research efforts focused upon this group of proteins has been directed toward the μ receptor since it mediates the actions of both the opiate and opioid analgesics such as morphine and fentanyl, respectively.[2] However, over the years it has become increasingly clear that the entire family of proteins is actively involved in a host of biological processes.[2] Furthermore, the advent of selective antagonists has demonstrated that pharmacotherapeutic opportunities exist via both negative and positive modulation of this receptor family.[3-8]

The opioid receptor system has been extensively studied, and thousands of compounds have been synthesized and evaluated by in vitro binding and functional assays as well as by animal models.[2] An integral part of the effort to characterize the opioid receptor system has been the discovery of potent, pure antagonists. Naloxone (1a) and naltrexone (1b), both competitive antagonists at μ, δ, and κ opioid receptors,[9] have been extensively used as pharmacological tools to identify and characterize opioid systems. See FIG. 1. Additionally, naloxone is approved to treat heroin overdose and to reverse respiratory depression caused by morphine.[9] Naltrexone is used to treat heroin and alcohol abuse.

In earlier studies we reported the discovery of the potent and selective κ opioid receptor antagonist JDTic (2),[6-8,10] which shows activity in rat models of depression,[11] anxiety,[12] and stress-induced cocaine relapse[11] and has proceeded through phase 1 clinical studies.[11,13] AZ-MTAB,[14,15] PF-4455242,[16] and LY2456302[17] have been reported as selective κ opioid receptor antagonists. Examination of these compounds shows that their structures are different from any of our compounds. The reported studies are reviewed in our recent published *Journal of Medicinal Chemistry* perspective review.[18]

No drugs for the treatment of cocaine and methamphetamine abuse, however, are currently available. Further, nicotine replacement therapy (NRT), bupropion, and varenicline are used to treat nicotine addiction, but no more than 25% of patients respond to these treatments. Naltrexone is used to treat alcoholism, but is not very satisfactory. A number of antidepressants are on the market, but many patients do not respond to any of them. In addition, all of these therapeutic agents have undesirable side effects. Accordingly, kappa opioid antagonists remain of interest to the pharmaceutical industry, as well as health institutes.

3. SUMMARY OF THE DISCLOSURE

The present disclosure provides a compound of formula (I):

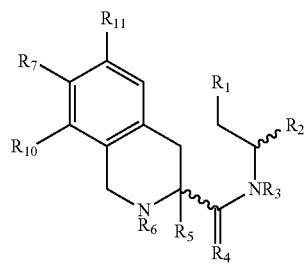

I wherein: $R_1$ is aryl, $C_{1-6}$ alkyl, $C_{3-8}$ cycloalkyl, $C_{5-8}$ cycloalkenyl, H, heteroaryl, heterocycloalkyl, $NR_8R_9$, OH, or $OR_8$; $R_2$ is aryl, $C_{1-4}$ alkyl, $C_{3-6}$ cycloalkyl, $CH_2(CH_2)_n$ OH, or H; each $R_3$, $R_5$ and $R_6$ is independently $C_{1-4}$ alkyl or H; $R_4$ is O, or S, or H and H; $R_7$ is $C_{1-8}$ alkoxy, $CF_3$, $CH_2(CH_2)_nY$, CN, $CONR_8R_9$, $CO_2R_8$, $CSNR_8R_9$, H, halogen, OH, $OR_8$, $N_3$, $NHCOR_8$, $NHCO_2R_8$, $NH_2$, $NO_2$ or $SO_2CF_3$; each $R_{10}$ and $R_{11}$ are independently $C_{1-8}$ alkoxy, $C_{1-8}$ alkyl, $C_{3-8}$ cycloalkyl, $C_{3-8}$ alkynyl, or H; wherein each $R_8$ or $R_9$ is independently $C_{1-8}$ alkenyl, $C_{1-8}$ alkyl, $C_{3-8}$ cycloalkyl or H; or $R_8$ or $R_9$ together form a $C_3$-$C_8$ heterocycloalkyl group; wherein Y is $CF_3$, $CO_2R_8$, H, or $NR_8R_9$; wherein n is 0-8; and pharmaceutically acceptable salts thereof. Examples of $OR_8$ include $OCF_3$ and $OCH_2CF_3$.

The compound of par. [0008] may have the formula (II), (III) or (IV)

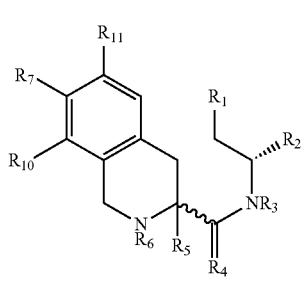

II

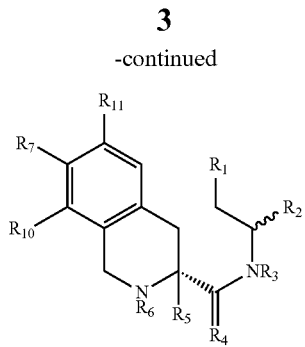

III

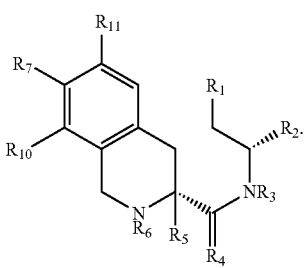

IV

In compound of any of par. [0008]-[0009], $R_1$ may be $C_{2-6}$ alkyl, $C_{3-8}$ cycloalkyl, $C_{5-8}$ cycloalkenyl or phenyl.

In compound of par. [0010], $R_1$ may be $C_{3-8}$ cycloalkyl.

In compound of any of par. [0008]-[0009], $R_1$ may be heteroaryl, heterocycloalkyl, $NR_8R_9$, or OH.

In compound of par. [0012], $R_1$ may be heteroaryl, heterocycloalkenyl or heterocycloalkyl containing at least one nitrogen heteroatom.

In compound of par. [0013], $R_1$ may be heterocycloalkyl.

In compound of par. [0014], $R_1$ may be a six or seven member heterocycloalkyl.

In compound of any of par. [0008]-[0015], either $R_2$ $C_{3-4}$ alkyl, $C_{3-4}$ cycloalkyl, $CH_2OH$, H or phenyl.

In compound of any of par. [0008]-[0016], $R_3$ may be $CH_3$ or H.

In compound of any of par. [0008]-[0017], $R_4$ may be O.

In compound of any of par. [0008]-[0018], either $R_5$ or $R_6$ may be $CH_3$ or H.

In compound of any of par. [0008]-[0019], $R_3$, $R_5$ and $R_6$ may be H.

In compound of any of par. [0008]-[0020], $R_7$ may be $CONH_2$, H, halogen, or OH. In some embodiments, $R_7$ may be $OCF_3$ or $OCH_2CF_3$.

In compound of any of par. [0008]-[0021], $R_{10}$ or $R_{11}$ may be H. Alternatively, both $R_{10}$ or $R_{11}$ are H.

The compound of par. [0008] may be (3R)-7-Hydroxy-N-[(1S)-2-methyl-1-(piperidin-1-ylmethyl)propyl]-1,2,3,4-tetrahydroisoquinoline-3-carboxamide, (3R)-7-Hydroxy-N-[(1S)-1-(hydroxymethyl)-2-methylpropyl]-1,2,3,4-tetrahydroisoquinoline-3-carboxamide, (3R)-7-Hydroxy-N-[(1S)-2-methyl-1-(morpholin-4-ylmethyl)propyl]-1,2,3,4-tetrahydroisoquinoline-3-carboxamide, (3R)—N-[(1S)-1-(Azepan-1-ylmethyl)-2-methylpropyl]-7-hydroxy-1,2,3,4-tetrahydroisoquinoline-3-carboxamide, (3R)-7-Hydroxy-N-{(1S)-2-methyl-1-[(4-methylpiperidin-1-yl)methyl]propyl}-1,2,3,4-tetrahydroisoquinoline-3-carboxamide, (3R)—N-{(1S)-1-[(Dipropylamino)methyl]-2-methylpropyl}-7-hydroxy-1,2,3,4-tetrahydroisoquinoline-3-carboxamide, (3R)—N-{(1S)-1-[(4,4-Dimethylpiperidin-1-yl)methyl]-2-methylpropyl}-7-hydroxy-1,2,3,4-tetrahydroisoquinoline-3-carboxamide, (3R)-N-{(1S)-1-{[Bis(2-methylpropyl)amino]methyl}-2-methylpropyl]-7-hydroxy-1,2,3,4-tetrahydroisoquinoline-3-carboxamide, (3R)-N-{(1S)-1-[(4,4-Diethylamino)methyl]-2-methylpropyl}-7-hydroxy-1,2,3,4-tetrahydroisoquinoline-3-carboxamide, (3R)-7-Hydroxy-N-{(1S)-2-methyl-1-[(2-methylpiperidin-1-yl)methyl]propyl}-1,2,3,4-tetrahydroisoquinoline-3-carboxamide, (3R)-7-Hydroxy-N-{(1S)-2-methyl-1-[(4-methoxypiperidin-1-yl)methyl]propyl}-1,2,3,4-tetrahydroisoquinoline-3-carboxamide, (3R)-7-Hydroxy-N-[(1S)-2-methyl-1-{[4-(trifluoromethyl)piperidin-1-yl]methyl}propyl]-1,2,3,4-tetrahydroisoquinoline-3-carboxamide, (3R)—N-{(1S)-1-[(3,5-Dimethylpiperidin-1-yl)methyl]-2-methylpropyl}-7-hydroxy-1,2,3,4 tetrahydroisoquinoline-3-carboxamide, (3S)-7-Hydroxy-N-{(1S)-2-methyl-1-[(4-methylpiperidin-1-yl)methyl]propyl}-1,2,3,4-tetrahydroisoquinoline-3-carboxamide, (3R)-7-Hydroxy-N-{(1R)-2-methyl-1-[(4-methylpiperidin-1-yl)methyl]propyl}-1,2,3,4-tetrahydroisoquinoline-3-carboxamide, (3S)-7-Hydroxy-N-{(1R)-2-methyl-1-[(4-methylpiperidin-1-yl)methyl]propyl}-1,2,3,4-tetrahydroisoquinoline-3-carboxamide, (3R)-7-Hydroxy-N-{(1S)-2-methyl-1-[(4-methylpiperizin-1-yl)methyl]propyl}-1,2,3,4-tetrahydroisoquinoline-3-carboxamide, (3R)-$N^3$-{(1S)-2-methyl-1-[(4-methylpiperidin-1-yl)methyl]propyl}-1,2,3,4-tetrahydroisoquinoline-3,7-dicarboxamide, (3R)-7-Hydroxy-N-{(1S)-2-methyl-1-[(5-methyl-3,6-dihydropyridin-1(2H)-yl)methyl]propyl}-1,2,3,4-tetrahydroisoquinoline-3-carboxamide, (3R)—N-{(1S)-1-[(4-Carbamoylpiperidin-1-yl)methyl]-2-methylprolyl}-7-hydroxy-1,2,3,4-tetrahydroisoquinoline-3-carboxamide, (3R)-7-Hydroxy-N-{(1S)-2-methyl-1-[(3-methylpiperidin-1-yl)methyl]propyl}-1,2,3,4-tetrahydroisoquinoline-3-carboxamide, (3R)—N-{(1S)-1-[(4-Ethylpiperidin-1-yl)methyl]-2-methylpropyl}-7-hydroxy-1,2,3,4-tetrahydroisoquinoline-3-carboxamide, (3R)-7-hydroxy-N-{(1S)-2-methyl-1-[(4-methyl-3,6-dihydropyridin-1(2H)-yl)methyl]propyl}-1,2,3,4-tetrahydroisoquinoline-3-carboxamide, (3R)—N-[(1 S)-1-Cyclopropyl-2-(4-methylpiperidine-1-yl)ethyl]-7-hydroxy-1,2,3,4-tetrahydroisoquinoline-3-carboxamide, (3R)-7-Fluoro-N-{(1S)-2-methyl-1-[(4-methylpiperidin-1-yl)methyl]propyl}-1,2,3,4-tetrahydroisoquinoline-3-carboxamide, (3R)-7-Methoxy-N-{(1S)-2-methyl-1-[(4-methylpiperidin-1-yl)methyl]propyl}-1,2,3,4-tetrahydroisoquinoline-3-carboxamide, (3R)-7-Hydroxy-N-methyl-N-{(1S)-2-methyl-1-[(4-methylpiperidin-1-yl)methyl]propyl}-1,2,3,4-tetrahydroisoquinoline-3-carboxamide, (3R)—N-{(1S)-1-[(4,5-dimethyl-3,6-dihydropyridin-1(2H)-yl)methyl]-2-methylpropyl}-7-hydroxy-1,2,3,4-tetrahydroisoquinoline-3-carboxamide, (3R)-7-Hydroxy-N-[(1S)-2-methyl-1-(pyrrolidin-1-ylmethyl)propyl]-1,2,3,4-tetrahydroisoquinoline-3-carboxamide, (3R)—N-[(1S)-1-(3,6-dihydropyridin-1(2H)-ylmethyl)-2-methylpropyl]-7-hydroxy-1,2,3,4-tetrahydroisoquinoline-3-carboxamide, (3R)-7-Hydroxy-N-{(1 S)-2-methyl-1-[(2-oxopiperidin-1-yl)methyl]propyl}-1,2,3,4-tetrahydroisoquinoline-3-carboxamide, (3R)-7-Hydroxy-N-(2-piperidin-1-ylethyl)-1,2,3,4-tetrahydroisoquinoline-3-carboxamide, (3R)—N-[(1R)-1-(Cyclohexylmethyl)-2-methylpropyl]-7-hydroxy-1,2,3,4-tetrahydroisoquinoline-3-carboxamide, (3R)—$N^3$-[(1R)-1-(Cyclohexylmethyl)-2-methylpropyl]-1,2,3,4-tetrahydroisoquinoline-3,7-dicarboxamide, (3R)—N-{(1S)-1-[(4-Cyanopiperidin-1-yl)methyl]-2-methylprolyl}-7-hydroxy-1,2,3,4-tetrahydroisoquinoline-3-carboxamide, (3R)—N-[(1R)-1-(Cyclopentylmethyl)-2-methylpropyl]-7-hydroxy-1,2,3,4-tetrahydroisoquinoline-3-carboxamide, (3R)—N-[(1R)-1-(Cycloheptylmethyl)-2-methylpropyl]-7-hydroxy-1,2,3,4-tetrahydroisoquinoline-3-carboxamide, (3R)—N-[(1S)-1-(Cyclohexylmethyl)-2-methylpropyl]-7- hydroxy-1,2,3,4-tetrahydroisoquinoline-3-carboxamide, (3R)—N-[(1R)-1-(cyclohexylmethyl)-2-methylpropyl]-7-methoxy-1,2,3,4-tetrahydroisoquinoline-3-carboxamide, (3R)—N-[(1R)-1-(Cyclohexylmethyl)-2-methylpropyl]-1,2,3,4-tetrahydroisoquinoline-3-carboxamide, (3S)—N-[(1S)-1-(Cyclohexylmethyl)-2-methylpropyl]-7-hydroxy-1,2,3,4-tetrahydroisoquinoline-3-carboxamide, (3S)—N-[(1R)-1-(Cyclohexylmethyl)-2-methylpropyl]-7-hydroxy-1,2,3,4-tetrahydroisoquinoline-3-carboxamide, (3R)—N-[(1R)-1-(Cyclohexylmethyl)-2-methylpropyl]-7-fluoro-1,2,3,4-tetrahydroisoquinoline-3-carboxamide, (3R)—N-[(1R)-1-(C yclohexylmethyl)-2-methylpropyl]-7-hydroxy-2-methyl-1,2,3,4-tetrahydroisoquinoline-3-carboxamide, (3R)—N-[(1S)-1-{[(3S,4R)-3,4-Dimethylpiperidin-1-yl]methyl}-2-methylpropyl]-7-hydroxy-1,2,3,4-tetrahydroisoquinoline-3-carboxamide, (3R)—N-[(1S)-1-{[(3S, 4R)-3,4-Dimethylpiperidin-1-yl]methyl}-2-methylpropyl]-7-hydroxy-1,2,3,4-tetrahydroisoquinoline-3-carboxamide, (3R)—N-[(1 S)-1-(7-Azabicyclo[2.2.1]hept-7-ylmethyl)-2-methylpropyl]-7-hydroxy-1,2,3,4-tetrahydroisoquinoline-3-carboxamide, (3R)—N-[(1R)-2-Cyclohexyl-1-cyclopropylethyl]-7-hydroxy-1,2,3,4-tetrahydroisoquinoline-3-carboxamide, (3R)-N-[(1R)-2-Cyclohexyl-1-phenylethyl]-7-hydroxy-1,2,3,4-tetrahydroisoquinoline-3-carboxamide, (3R)-3-[(Methyl{(1S)-2-methyl-1-[(4-methylpiperidin-1-yl)methyl]propyl}amino)methyl]-1,2,3,4-tetrahydroisoquinolin-7-ol, (3R)—N-{[(1S)-1-[4,4-Difluoropiperidin-1-yl]methyl]-2-methylpropyl}-7-hydroxy-1,2,3,4-tetrahydroisoquinoline-3-carboxamide, (3R)—N-(2-Cyclohexylethyl)-7-hydroxy-1,2,3,4-tetrahydroisoquinoline-3-carboxamide, (3R)-7-Hydroxy-N-(2-phenylethyl)-1,2,3,4-tetrahydroisoquinoline-3-carboxamide, (3R)-3-[({(1S)-2-Methyl-1-[(4-methylpiperidin-1-yl)methyl]propyl}amino)methyl]-1,2,3,4-tetrahydroisoquinolin-7-ol, (3R)—N-[(1S)-1-{[4-(Dimethylamino)piperidin-1-yl]methyl}-2-methylpropyl]-7-hydroxy-1,2,3,4-tetrahydroisoquinoline-3-carboxamide, (3R)—N-[(1S)-1-{[4-(Difluoromethyl)piperidin-1-yl]methyl}-2-methylpropyl]-7-hydroxy-1,2,3,4-tetrahydroisoquinoline-3-carboxamide, (3R)—N-[(1R)-1-(Cyclopentylmethyl)-2-methylpropyl]-7-hydroxy-3-methyl-1,2,3,4-tetrahydroisoquinoline-3-carboxamide, (3R)—N$^3$-[(1R)-1-(Cyclopentylmethyl)-2-methylpropyl]-1,2,3,4-tetrahydroisoquinoline-3,7-dicarboxamide, (3R)—N-[(1R)-1-(Cyclobutylmethyl)-2-methylpropyl]-7-hydroxy-1,2,3,4-tetrahydroisoquinoline-3-carboxamide, 6-Hydroxy-N-{(1S)-2-methyl-1-[(4-methylpiperidine-1-yl)methyl]propyl}naphthalene-2-carboxamide, (3R)—N-[(1R)-2-Cyclopentyl-1-cyclopropylethyl]-7-hydroxy-1,2,3,4-tetrahydroisoquinoline-3-carboxamide, 6-Hydroxy-N-{(1S)-2-methyl-1-[(4-methylpiperidine-1-yl)methyl]propyl}-1,2,3,4-tetrahydronaphthalene-2-carboxamide, or (3R)-7-Hydroxy-N-{(1R)-2-methyl-1-[(4-methylcyclohexyl)methyl]propyl}-1,2,3,4-tetrahydroisoquinoline-3-carboxamide or a salt thereof.

A pharmaceutical composition comprising at least one pharmaceutically acceptable excipient and a therapeutically effective amount of the compound of any of par. [0008]-[0023].

The pharmaceutical composition of par. [0024], wherein the therapeutically effective amount is an amount effective for treating alcohol addiction, nicotine addiction, cocaine addiction or methamphetamine addiction.

The pharmaceutical composition of par. [0024], wherein the therapeutically effective amount is an amount effective for treating anxiety, depression, eating disorders, or schizophrenia.

A method of treating alcohol addiction, nicotine addiction, cocaine addiction or methamphetamine addiction, comprising administering to a subject in need thereof of an effective amount of a compound represented by the formula (I), (II), (III) or (IV) or any of those compounds described in par. [0008]-[0023].

A method of treating anxiety, depression, eating disorders, or schizophrenia, comprising administering to a subject in need thereof of an effective amount of a compound represented by the formula (I), (II), (III) or (IV) or any of those compounds described in par. [0008]-[0023].

4. BRIEF DESCRIPTION OF THE FIGURES

FIG. 1 shows the chemical structures of representative opioid receptor antagonists known in the art;

FIG. 2-1 FIG. 2-4 show the chemical structures of representative compounds synthesized and characterized in the present disclosure;

FIG. 3-1 shows additional tetrahydroisoquinoline compounds.

5. DETAILED DESCRIPTION OF THE DISCLOSURE 5.1. Definitions

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or there below. Furthermore, the phrases "less than about [a value]" or "greater than about [a value]" should be understood in view of the definition of the term "about" provided herein. The terms "about" and "approximately" may be used interchangeably.

"Alkenyl" refers to an unsaturated branched, straight-chain or cyclic alkyl group having at least one carbon-carbon double bond derived by the removal of one hydrogen atom from a single carbon atom of a parent alkene. The group may be in either the Z- and E-forms (or cis or trans conformation) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. The alkenyl group may be substituted or unsubstituted. In certain embodiments, an alkenyl group has from 2 to 20 carbon atoms and in other embodiments from 2 to 8 carbon atoms.

"Alkoxy" refers to a radical —OR where R represents an alkyl, cycloalkyl, aryl, or heteroaryl group as defined herein. Representative examples include, but are not limited to, methoxy, ethoxy, propoxy, butoxy, cyclohexyloxy, and the like. The alkoxy group may be substituted or unsubstituted.

"Alkyl" refers to a saturated, branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. The alkyl group may be substituted or unsubstituted; for example with a halogen(s) such as difluoro or trifluoro. In certain embodiments, an alkyl group comprises from 1 to 20 carbon atoms. Alternatively, an alkyl group may comprise from 1 to 8 carbon atoms.

"Alkynyl" refers to an unsaturated branched or straight-chain having at least one carbon-carbon triple bond derived by the removal of one hydrogen atom from a single carbon atom of a parent alkyne. Typical alkynyl groups include, but are not limited to, ethynyl, propynyl, butynyl, 2-pentynyl, 3-pentynyl, 2-hexynyl, 3-hexynyl and the like. The alkynyl group may be substituted or unsubstituted. In certain embodiments, an alkynyl group has from 3 to 20 carbon atoms and in other embodiments from 3 to 8 carbon atoms.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene or cyclopentadiene; bicyclic ring systems wherein at least one ring is carbocyclic and aromatic, for example, naphthalene, indane; or two aromatic ring systems, for example benzyl phenyl, biphenyl, diphenylethane, diphenylmethane. The aryl group may be substituted or unsubstituted, for example with a halogen, such as fluorine.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. The cycloalkyl group may be substituted or unsubstituted. In certain embodiments, the cycloalkyl group can be $C_3$-10 cycloalkyl, such as, for example, $C_6$ cycloalkyl or $cC_6H_{12}$. The cycloalkyl group may also be a bridged bicyclic cycloalkyl group, a fused cycloalkyl group or a spiro cycloalkyl group. Non-limiting examples of bridged bicyclic cycloalkyl groups are bicyclo[2.2.1]heptane, bicyclo[2.1.1]hexane, bicyclo[2.2.2]octane. An example of a fused cycloalkyl group is bicyclo[4.4.0]decane or decalin. Non-limiting examples of spiro cycloalkyl groups are spiro [3.3] heptane, spiro [4.3] octane, or spiro [5.4] decane.

"Disease" refers to any disease, disorder, condition, symptom, or indication.

"Halogen" refers to a fluoro, chloro, bromo, or iodo group.

"Heteroaryl" refers to a monovalent heteroaromatic group derived by the removal of one hydrogen atom from a single atom of a parent heteroaromatic ring system. Heteroaryl encompasses: 5- to 7-membered aromatic, monocyclic rings containing one or more, for example, from 1 to 4, or in certain embodiments, from 1 to 3, heteroatoms chosen from N, O, and S, with the remaining ring atoms being carbon; and polycyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. The heteroaryl group may be substituted or unsubstituted.

For example, heteroaryl includes a 5- to 7-membered heteroaromatic ring fused to a 5- to 7-membered cycloalkyl ring and a 5- to 7-membered heteroaromatic ring fused to a 5- to 7-membered heterocycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, piperidine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from benzofuran, benzothiophene, imidazole, indole, oxazole, and pyrazine, pyridine, pyrrolidine, pyrrole, quinoline, and thiophene.

"Heterocycloalkenyl" refers to a non-aromatic monocyclic ring or fused non-aromatic polycyclic rings with one or more heteroatom(s) independently selected from N, S and O, with the remaining ring atoms being carbon, wherein at least one heteroatom is present in each non-aromatic ring and the ring contains a single double bond. The heterocycloalkenyl group may be a five-member ring, a six-member ring or a seven-member ring. The heterocycloalkenyl group may be substituted or unsubstituted.

"Heterocycloalkyl" refers to a non-aromatic monocyclic ring or fused non-aromatic polycyclic rings with one or more heteroatom(s) independently selected from N, S and O, with the remaining ring atoms being carbon and wherein at least one heteroatom is present in each non-aromatic ring. The heterocycloalkyl group may be a three-member ring, a four-member ring, a five-member ring, a six-member ring or a seven-member ring. In certain embodiments, the heterocycloalkyl group is pyrrolidine, 1,3-dioxolane, imidazolidine, piperidine, 1,4-dioxane, morpholine; 1,4-dithiane, piperazine or 1,3,5-trithiane. The heterocycloalkyl group may be bicyclic such as an heterospiro compound, e.g., heterospiro [3.3] heptanyl, heterospiro [3.4] octanyl, or heterospiro [5.5] undecanyls. The heterocycloalkyl group may be substituted or unsubstituted. Thus, heterocycloalkyl group encompasses heterocycloalkyl groups substituted with one or more halogens, such as 3,3-difluoropiperidine, or 4,4-difluoropiperidine. The heterocycloalkyl group may also be a bridged bicyclic heterocycloalkyl group, a fused heterocycloalkyl group or a spiro heterocycloalkyl group. In otherwords a heteroatom containing bridged bicyclic group, fused cycloalkyl group or spiro cycloalkyl groups. Non-limiting examples of bridged bicyclic heterocycloalkyl groups are 7-azabicyclo[2.2.1]heptane, 3-azabicyclo[3.1.0]hexane, 2-azabicycle[2.2.2]octane. An example of a fused cycloalkyl group is 3-azabicyclo[4.4.0]decane or 3-azadecalin. Non-limiting examples of spiro cycloalkyl groups are 2-azaspiro [3.3] heptane, 3-azaspiro [4.3] octane, or 3-azaspiro [5.4] decane.

"Prodrug" refers to a precursor or derivative form of a pharmaceutically active substance that is less bioactive compared to the parent drug and is capable of being enzymatically activated or converted into the more active parent form. Prodrug forms of the compounds described herein may be designed to improve bioavailability or stability or reduce toxicity. For example, compounds of the invention having free amino, amido, carboxylic, hydroxyl, or thiol groups can be converted into prodrugs. See Rautio et al., 2008 Nat Rev Drug Dis 7 255-270. For instance, free carboxyl groups can be derivatized as amides, carbamates, esters, or N-Mannich bases. Free hydroxy groups may be derivatized using groups including but not limited to carbonates, dimethylaminoacetates, ethers, hemisuccinates, phosphate esters, and phosphoryloxymethyloxycarbonyls, as outlined in Fleisher et al., 1996 Advanced Drug Delivery Reviews 19, 115-130. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in Robinson et al., 1996 J Med Chem 39 10-18. Free amines can also be derivatized as amides, carbamates, imines, N-Mannich bases, oximes, phosphonamides, or sulfonamides. Carbonyls may be derivatized to imine or oxime prodrugs. Thiols may be derivatized as esters or ethers. Prodrugs may also include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes beta-alanine, citrulline, desmosine, gamma-aminobutyric acid, homocysteine, homoserine, 4-hydroxyproline, hydroxylysine, isodemosine, 3-methylhistidine, norvalin, methionine sulfone, and ornithine.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereoisomers."

"Subject" includes mammals and humans. The terms "human" and "subject" are used interchangeably herein.

"Substituted" refers to a group in which one or more hydrogen atoms are each independently replaced with the same or different substituent(s). Typical substituents include, but are not limited to, $CO_2H$, cyano, difluoro, halogen, hydroxyl, —$N_3$, —N(alkyl)$_2$, —$NH_2$, —$SO_2C_1$-$C_8$ alkyl, —$SO_2H$, —SH, —$CONH_2$, —$CSNH_2$, or trifluoro.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

5.2. Chemical Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Pairs of the functional groups defined herein may be combined in a chemically rational way. For example, $C_1$-$C_8$ alkyl amino means the functional group $C_1$-$C_8$ alkyl, e.g., -$nC_5H_{11}$, is combined with the functional group, amino, e.g., —$NH_2$ to form in this example -$nC_5H_{10}NH_2$. Similarly, $C_1$-$C_8$ alkoxy aryl means the functional group $C_1$-$C_8$ alkoxy, e.g., —$CH_2CH_2OCH_2CH_3$ or —$OCH_2CH_3$ combined with an aryl group, e.g., —$C_6H_5F$ to form —$CH_2CH_2OCH_2CH_2$—$C_6H_5F$ or —$OCH_2CH_3$—$C_6H_5F$, respectively.

5.3. Deuterated and Other Isotopic Variants

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^2H$ (deuterium), $^3H$ (tritium) $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^3H$ or $^{14}C$ are incorporated, are useful in drug and/or substrate tissue distribution studies. Tritiated and carbon-14, i.e., $^{14}C$, isotopes are particularly preferred for their ease of preparation and detectability. Substitution with positron emitting isotopes, such as $^{11}C$, $^{18}F$, $^{15}O$ and can be useful in Positron Emission Topography (PET) studies.

Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents. In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art.

Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. Alternatively, deuterium may be also incorporated into a compound using methods such as through reduction such as using $LiAlD_4$ or $NaBD_4$, catalytic hydrogenation or acidic or basic isotopic exchange using appropriate deuterated reagents such as deuterides, $D_2$ and $D_2O$. In addition to the above, PCT publications, WO2014/169280; WO2015/058067; U.S. Pat. Nos. 8,354,557; 8,704,001 and US Patent Application Publication Nos.; 2010/0331540; 2014/0081019; 2014/0341994; 2015/0299166, the methods are hereby incorporated by reference.

5.4. Pharmaceutical Compositions

In the pharmaceutical compositions of the disclosure, the compound of the present disclosure is present in an effective amount. As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy. Preferably, the compound is present in the composition in an amount of from 0.1 to 50 wt. %, more preferably from 1 to 30 wt. %, most preferably from 5 to 20 wt. %.

The interrelationship of dosages for animals and humans (based on milligrams per meter squared of body surface) is described in Freireich et al., (1966) Cancer Chemother. Rep 50: 219. Body surface area may be approximately determined from height and weight of the subject. See, e.g., Scientific Tables, Geigy Pharmaceuticals, Ardsley, N.Y., 1970,537.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

The compounds for use in the method of the disclosure can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily treatment dose or one of multiple daily treatment doses (e.g., about 1 to 4 or more times per day). When multiple daily treatment doses are used, the unit dosage form can be the same or different for each dose.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

Studies with selective κ opioid antagonists have shown that this system is intimately involved in brain processes that relate to stress, fear, and anxiety as well as reward-seeking behavior.[18] Studies have shown that JDTic (2) and nor-BNI, another κ opioid selective antagonist, dose-dependently reduce fear and stress-induced responses in multiple behavioral paradigms with rodents (immobility in the forced-swim assay,[11,19] reduction of exploratory behavior in the elevated plus maze, and fear-potentiated startle).[12] Furthermore, selective κ antagonists have been shown to reduce stress-induced reinstatement of cocaine self-administration in rats,[11] to block the stress-induced potentiation of cocaine place preference conditioning,[20-22] to decrease dependence-induced ethanol self-administration,[23] to diminish deprivation-induced eating in rats,[24] and to prevent pre-pulse inhibition mediated by the selective κ opioid receptor agonist U50,488.[25] These observations regarding the behavioral consequences of receptor blockade in several animal tests suggest that κ antagonists will be useful for treating anxiety, depression, schizophrenia, substance abuse addiction, and eating disorders.

Previously reported non-selective opioid receptor antagonists such as LY255582 have been found to increase metabolic energy consumption and reduce the weight in obese rats while maintaining muscle mass. These reports suggest that opioid receptor antagonists may be useful in preventing, treating, and/or ameliorating the effect of obesity. Eli Lilly and Company has developed new classes of opioid receptor antagonists that interact with the μ, δ, and κ receptors (termed non-selective) as potential pharmacotherapies to treat obesity and related diseases.[26,27] The Lilly patents suggest that their compounds will be useful for the treatment and/or prophylaxis of obesity and related diseases including eating disorders (bulimia, anorexia nervosa, etc.), diabetes, diabetic complications, diabetic retinopathy, sexual/reproductive disorders, depression, anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, hyperlipoproteinemia, substance abuse, drug overdose, compulsive behavior disorders (such as paw licking in dog), and addictive behaviors such as for example gambling and alcoholism.

5.5. Formulations

The presently disclosed pharmaceutical compositions and formulations include pharmaceutical compositions of compounds of formula (I), alone or in combination with one or more additional therapeutic agents, in admixture with a physiologically compatible carrier, which can be administered to a subject, for example, a human subject, for therapeutic or prophylactic treatment. As used herein, "physiologically compatible carrier" refers to a physiologically acceptable diluent including, but not limited to water, phosphate buffered saline, or saline, and, in some embodiments, can include an adjuvant. Acceptable carriers, excipients, or stabilizers are nontoxic to recipients at the dosages and concentrations employed, and can include buffers such as phosphate, citrate, and other organic acids; antioxidants including ascorbic acid, BHA, and BHT; low molecular weight (less than about 10 residues) polypeptides; proteins, such as serum albumin, gelatin or immunoglobulins; hydrophilic polymers, such as polyvinylpyrrolidone, amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as Tween, Pluronics, or PEG. Adjuvants suitable for use with the presently disclosed compositions include adjuvants known in the art including, but not limited to, incomplete Freund's adjuvant, aluminum phosphate, aluminum hydroxide, and alum.

Compositions to be used for in vivo administration must be sterile, which can be achieved by filtration through sterile filtration membranes, prior to or following lyophilization and reconstitution. Therapeutic compositions may be placed into a container having a sterile access port, for example, an intravenous solution bag or vial having a stopper pierceable by a hypodermic injection needle.

One of skill in the art will recognize that the pharmaceutical compositions include the pharmaceutically acceptable salts of the compounds described above. The term "pharmaceutically acceptable salts" is meant to include salts of active compounds, which are prepared with relatively nontoxic acids or bases, depending on the particular substituent moieties found on the compounds described herein.

When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include alkali or alkaline earth metal salts including, but not limited to, sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids including, but not limited to, hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids, such as acetic (acetates), propionic (propionates), isobutyric (isobutyrates), maleic (maleates), malonic, benzoic (benzoates), succinic (succinates), suberic, fumaric (fumarates), lactic (lactates), mandelic (mandelates), phthalic (phthalates), benzenesulfonic (benzosulfonates), p-tolylsulfonic, citric (citrates), tartaric (tartrates, e.g., (+)-tartrates, (−)-tartrates or mixtures thereof including racemic mixtures), methanesulfonic, and the like. Other pharmaceutically acceptable salts, include, but are not limited to, besylate, bicarbonate, bitartrate, bromide, calcium edetate, carnsylate, carbonate, edetate, edisylate, estolate, esylate, gluceptate, gluconate, glutamate, glycollylarsanilate, hexylresorcinate, hydrabamine, hydroxynaphthoate, iodide, isethionate, lactobionate, malate, mesylate, mucate, napsylate, nitrate, pamoate (embonate), pantothenate, phosphate/diphosphate, polygalacturonate, salicylate, stearate, subacetate, sulfate, tannate, and teoclate, also are included.

Also included are salts of amino acids, such as arginate and the like, and salts of organic acids, such as, glucuronic or galactunoric acids, and the like. See, for example, Berge et al., "Pharmaceutical Salts", Journal of Pharmaceutical Science, 1977, 66, 1-19. Some compounds of the present disclosure can contain both basic and acidic functionalities, which allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties. For example, salts tend to be more soluble in aqueous or other protonic solvents than are the corresponding free base forms.

In particular embodiments, the pharmaceutically acceptable salt of a compound of formula (I) is selected from the group consisting of HCl, a sulfonate, a sulfate, phosphate, a malonate, a succinate, a fumarate, a maleate, a tartrate, a 3-sulfopropanoic acid salt, and a citrate.

Certain compounds of the present disclosure can exist in unsolvated forms, as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds that can be in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

5.6. Combination Therapies

In certain embodiments, presently disclosed subject matter also includes combination therapies. Depending on the particular disease, disorder, or condition to be treated or prevented, additional therapeutic agents, which are normally administered to treat or prevent that condition, may be administered in combination with the compounds of this disclosure. These additional agents may be administered separately, as part of a multiple dosage regimen, from the composition comprising a compound of formula (I). Alternatively, these agents may be part of a single dosage form, mixed together with the compound of formula (I) in a single composition.

By "in combination with" is meant the administration of a compound of formula (I) with one or more therapeutic agents either simultaneously, sequentially, or a combination thereof. Therefore, a cell or a subject administered a combination of a compound of formula (I) can receive a compound of formula (I) and one or more therapeutic agents at the same time (i.e., simultaneously) or at different times (i.e., sequentially, in either order, on the same day or on different days), so long as the effect of the combination of both agents is achieved in the cell or the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of formula (I) and one or more therapeutic agents are administered simultaneously, they can be administered to the cell or administered to the subject as separate pharmaceutical compositions, each comprising either a compound of formula (I) or one or more therapeutic agents, or they can contact the cell as a single composition or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered compound is not diminished by the sequential, simultaneous or separate administration of the subsequent compound(s).

5.7. Dosage and Mode of Administration

The presently disclosed pharmaceutical compositions can be administered using a variety of methods known in the art depending on the subject and the particular disease, disorder, or condition being treated. The administering can be carried out by, for example, intravenous infusion; injection by intravenous, intraperitoneal, intracerebral, intramuscular, intraocular, intraarterial or intralesional routes; or topical or ocular application.

More particularly, as described herein, the presently disclosed compounds can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art. For example, for ocular administration, an eyedrop formulation can include an effective concentration of a compound of formula (I) together with other components, such as buffers, wetting agents and the like. Intravitreal injection also may be employed to administer a presently disclosed compound to the eye.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

For intracerebral use, the compounds can be administered continuously by infusion into the fluid reservoirs of the CNS, although bolus injection may be acceptable. The presently disclosed compounds can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the presently disclosed compounds can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention.

The presently disclosed pharmaceutical compositions can be manufactured in a manner known in the art, e.g. by means of conventional mixing, dissolving, granulating, dragee-making, levitating, emulsifying, encapsulating, entrapping or lyophilizing processes.

More particularly, pharmaceutical compositions for oral use can be obtained through combination of active compounds with a solid excipient, optionally grinding a resulting mixture, and processing the mixture of granules, after adding suitable auxiliaries, if desired, to obtain tablets or dragee cores. Suitable excipients include, but are not limited to, carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl cellulose; and gums including arabic and tragacanth; and proteins, such as gelatin and collagen; and polyvinylpyrrolidone (PVP:povidone). If desired, disintegrating or solubilizing agents, such as cross-linked polyvinyl pyrrolidone, agar, alginic acid, or a salt thereof, such as sodium alginate, also can be added to the compositions.

Dragee cores are provided with suitable coatings, such as concentrated sugar solutions, which also can contain gum arabic, talc, polyvinylpyrrolidone, carbopol gel, polyethylene glycol (PEG), and/or titanium dioxide, lacquer solutions, and suitable organic solvents or solvent mixtures. Dyestuffs or pigments can be added to the tablets or dragee coatings for product identification or to characterize the quantity of active compound, e.g., dosage, or different combinations of active compound doses.

Pharmaceutical compositions suitable for oral administration include push-fit capsules made of gelatin, as well as soft, sealed capsules made of gelatin and a coating, e.g., a plasticizer, such as glycerol or sorbitol. The push-fit capsules can contain active ingredients admixed with a filler or binder, such as lactose or starches, lubricants, such as talc or magnesium stearate, and, optionally, stabilizers. In soft capsules, the active compounds can be dissolved or suspended in suitable liquids, such as fatty oils, liquid paraffin, or liquid polyethylene glycols (PEGs), with or without stabilizers. Stabilizers can be added as warranted.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al., J. Biomed. Mater. Res. 15:167, 1981; Langer, Chem. Tech. 12:98, 1982), ethylene vinyl acetate (Langer et al., Id), or poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy. Such materials can comprise an implant, for example, for sustained release of the presently disclosed compounds, which, in some embodiments, can be implanted at a particular, predetermined target site.

Pharmaceutical compositions for parenteral administration include aqueous solutions of active compounds. For injection, the presently disclosed pharmaceutical compositions can be formulated in aqueous solutions, for example, in some embodiments, in physiologically compatible buffers, such as Hank's solution, Ringer' solution, or physiologically buffered saline. Aqueous injection suspensions can contain substances that increase the viscosity of the suspension, such as sodium carboxymethyl cellulose, sorbitol, or dextran. Additionally, suspensions of the active compounds or vehicles include fatty oils, such as sesame oil, or synthetic fatty acid esters, such as ethyl oleate or triglycerides, or liposomes. Optionally, the suspension also can contain suitable stabilizers or agents that increase the solubility of the compounds to allow for the preparation of highly concentrated solutions.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

In other embodiments, the pharmaceutical composition can be a lyophilized powder, optionally including additives, such as 1 mM-50 mM histidine, 0.1%-2% sucrose, 2%-7% mannitol at a pH range of 4.5 to 5.5 that is combined with buffer prior to use.

The presently disclosed subject matter also includes the use of a compound of formula (I) in the manufacture of a medicament for treating a disease, disorder, or condition associated with a κ opioid receptor.

Regardless of the route of administration selected, the presently disclosed compounds, which may be used in a suitable hydrated form, and/or the pharmaceutical compositions are formulated into pharmaceutically acceptable dosage forms such as described below or by other conventional methods known to those of skill in the art.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Actual dosage levels of the active ingredients in the presently disclosed pharmaceutical compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular compound employed, or salt thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of formula (I) employed in the pharmaceutical composition at levels lower than that required to achieve the desired therapeutic effect and gradually increase the dosage until the desired effect is achieved. Accordingly, the dosage range for administration will be adjusted by the physician as necessary. It will be appreciated that an amount of a compound required for achieving the desired biological response may be different from the amount of compound effective for another purpose.

In general, a suitable daily dose of a compound of formula (I) will be that amount of the compound that is the lowest dose effective to produce a therapeutic effect. Such an effective dose will generally depend upon the factors described above. Generally, doses of the compounds of formula (I) will range from about 0.0001 to about 1000 mg per kilogram of body weight of the subject per day. In certain embodiments, the dosage is between about 1 μg/kg and about 500 mg/kg, more preferably between about 0.01 mg/kg and about 50 mg/kg. For example, in certain embodiments, a dose can be about 1, 5, 10, 15, 20, or 40 mg/kg/day.

If desired, the effective daily dose of the active compound can be administered as two, three, four, five, six or more sub-doses administered separately at appropriate intervals throughout the day, optionally, in unit dosage forms.

5.8. Kits and/or Pharmaceutical Systems

The presently disclosed compounds and compositions can be assembled into kits or pharmaceutical systems for use in treating or preventing diseases, disorders, or conditions associated with a κ opioid receptor. In some embodiments, the presently disclosed kits or pharmaceutical systems include a compound of formula (I), or pharmaceutically acceptable salts thereof. In particular embodiments, the compounds of formula (I), or a pharmaceutically acceptable salt thereof, are in unit dosage form. In further embodiments, the compound of formula (I), or a pharmaceutically acceptable salt, can be present together with a pharmaceutically acceptable solvent, carrier, excipient, or the like, as described herein.

In some embodiments, the presently disclosed kits comprise one or more containers, including, but not limited to a vial, tube, ampule, bottle and the like, for containing the compound. The one or more containers also can be carried within a suitable carrier, such as a box, carton, tube or the like. Such containers can be made of plastic, glass, laminated paper, metal foil, or other materials suitable for holding medicaments.

In some embodiments, the container can hold a composition that is by itself or when combined with another composition effective for treating or preventing the condition and may have a sterile access port (for example the container may be an intravenous solution bag or a vial having a stopper pierceable by a hypodermic injection needle). Alternatively, or additionally, the article of manufacture may further include a second (or third) container including a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The presently disclosed kits or pharmaceutical systems also can include associated instructions for using the compounds for treating or preventing a disease, disorder, or condition associated with a κ opioid receptor. In some embodiments, the instructions include one or more of the following: a description of the active compound; a dosage schedule and administration for treating or preventing a disease, disorder, or condition associated with a κ opioid receptor; precautions; warnings; indications; counter-indications; overdosage information; adverse reactions; animal pharmacology; clinical studies; and references. The instructions can be printed directly on a container (when present), as a label applied to the container, as a separate sheet, pamphlet, card, or folder supplied in or with the container.

As used herein, the verb "comprise" as is used in this description and in the claims and its conjugations are used in its non-limiting sense to mean that items following the word are included, but items not specifically mentioned are not excluded.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Unless defined otherwise, all technical and scientific terms used herein have the same meanings as commonly understood by one of ordinary skill in the art to which this disclosure belongs. Preferred methods, devices, and materials are described, although any methods and materials similar or equivalent to those described herein can be used in the practice or testing of the present disclosure. All references cited herein are incorporated by reference in their entirety.

The following Examples further illustrate the disclosure and are not intended to limit the scope. In particular, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

6. EXAMPLES

6.1. Synthetic Summaries

Schemes A-BK show the synthesis of compounds (3)-(66) that are the subject of this disclosure. The compounds were synthesized and characterized as shown below. The structures of compounds (3)-(66) are shown in FIGS. 2-1 to 2-4. The compounds in FIG. 3-1 may be synthesized using methods known to one of ordinary skill in the art.

Compound (3) was synthesized as shown in Scheme A. Compound A2 was synthesized by coupling piperidine with N-Boc-L-valine. Treatment of A2 with hydrochloric acid in methanol to remove the tert-butyloxycarbonyl group followed by reduction of the intermediate with borane yielded A4. Coupling of A4 with Boc-7-hydroxy-D-Tic-OH using EDC·HCl and triethylamine in dichloromethane gave A5 which yielded (3) on treatment with hydrochloric acid in methanol.

Scheme B shows the synthesis of (4) and (5). L-Valinol was prepared according to literature method.[28] The amino alcohol was coupled with Boc-7-hydroxy-D-Tic using DCC to afford B2. Intermediate B2 was treated with trifluoroacetic acid to afford (4). The phenol in B2 was protected as the methyl ether using trimethylsilyldiazomethane then the alcohol was oxidized with Des s-Martin periodinane to afford the aldehyde B3. Reductive amination with morpholine using sodium triacetoxyborohydride followed by methyl ether deprotection with boron tribromide afforded (5).

Scheme C shows the preparation of (6). Reductive amination of B3 with homopiperidine using triacetoxyborohydride followed by methyl ether deprotection with boron tribromide afforded (6).

Scheme D gives the methods used for the synthesis of (7). The coupling of 4-methylpyridine (D1) with N-Boc-L-valine using HBTU in acetonitrile yielded D2. Treatment of D2 with hydrogen chloride in a solvent mixture of dioxane and acetonitrile provided D3 which on reduction with boron dimethyl sulfide complex in tetrahydrofuran gave D4. Coupling of D4 with Boc-7-hydroxy-D-Tic-OH using EDC·HCl in the presence of HOBt and triethylamine in dichloromethane afforded D5 which yielded (7) upon removing the tert-butyloxycarbonyl protecting group with hydrogen chloride in a solvent mixture of dioxane and acetonitrile.

(8) (Scheme E), (9) (Scheme F), (10) (Scheme G), (11) (Scheme H), (12) (Scheme I), (13) (Scheme J), (14) (Scheme K), (15) (Scheme L), (19) (Scheme P), (21) (Scheme R), (23) (Scheme T), (24) (Scheme U), (25) (Scheme V), (26) (Scheme W), (31) (Scheme AB), (32) (Scheme AC), (33) (Scheme AD), (54) (Scheme AY), and (58) (Scheme BC) were all prepared by procedure analogous to that described for (7) using dipropylamine, 4,4-dimethylpiperidine, diisobutylamine, diethylamine, 2-methylpiperidine, 4-methoxpiperidine, 4-(trifluoromethyl)piperidine, 3,5-dimethylpiperidine, 4-methylpiperazine, 3-methylpiperidine, 4-ethylpiperidine, 4-methyl-1,2,3,6-tetrahydropyridine, cis-3,4-dimethylpiperidine, 3,4-dimethyl-1,2,5,6-tetrahydropyridine, pyrrolidine, 1,2,3,6-tetrahydropyridine, 3-methyl-1,2,5,6-tetrahydropyridine, 4,4-difluoropiperidine, and 4-(dimethylamino)piperidine in place of 4-methylpiperidine.

Compound (16) was synthesized as outlined in Scheme M. Coupling of D4 with Boc-7-hydroxy-L-Tic-OH using EDC·HCl with added HOBt and triethylamine in dichloromethane gave M1 which yielded (16) after treatment with hydrogen chloride in a solvent mixture of dioxane and acetonitrile.

The synthesis of (17) is outlined in Scheme N. Coupling of 4-methylpiperidine (D1) with N-Boc-D-valine using HBTU in acetonitrile provided N1 which yielded N2 after removal of the protected tert-butyl-oxycarbonyl group when treated with hydrogen choride in a dioxane and acetonitrile solvent mixture. Reduction of N2 with boron dimethyl sulfide complex gave N3. Coupling of N3 with Boc-7-hydroxy-D-Tic-OH using EDC·HCl with added HOBt and triethylamine in dichloromethane yielded N4. Treatment of N4 with hydrogen chloride in a solvent mixture of dioxane and acetonitrile gave (17).

Compound (18) was synthesized by the route shown in Scheme O. Coupling of N3 with Boc-7-hydroxy-L-Tic-OH using EDC·HCl with added HOBt and triethylamine in dichloromethane yielded O1 which gave (18) after removal of the protecting tert-butyloxycarbonyl group using hydrogen chloride in a solvent mixture of dioxane and acetonitrile.

The synthesis of (20) is given in Scheme Q. Compound Q1 was prepared as previously reported.[29] Compound Q1 was coupled with (D4) using HBTU in acetonitrile to give Q2. Removal of the tert-butyloxycarbonyl protecting group using HCl in dioxane and acetonitrile afforded (20).

Scheme S shows the synthesis of (22). The starting 4-cyanopiperidine (S1) was converted to S4 using a procedural analogous to that used to convert 4-methylpiperidine to compound D4 shown in Scheme D. Subjection of S4 to hydrolysis using aqueous sulfuric acid followed by sodium hydroxide treatment afforded S5. Coupling of S5 with Boc-7-hydroxy-D-Tic-OH using EDC·HCl with added HOBt and triethylamine in dichloromethane gave S6. Removal of the protecting tert-butyloxycarbonyl group using HCl in dioxane and acetonitrile yielded (22).

(27) was prepared according to procedure analogous to (7), substituting Boc-L-cyclopropylglycine for Boc-L-valine, as shown in Scheme X.

Scheme Y illustrates the synthesis of (28) via the coupling of amine D4 with Boc-7-fluoro-D-Tic(OH).

The phenol of D5 was converted to the methyl ether to afford (29), as shown in Scheme Z.

Synthesis of (30) began with amine D4 as shown in Scheme AA. The amine was converted to the ethyl carbamate AA1 which was reduced to the N-methyl compound AA2. The challenging coupling reaction with Boc-7-hydroxy-D-Tic(OH) was effected with PyBrop. Boc deprotection then afforded (30).

Scheme AE illustrates the synthesis of (34). Starting with L-valinol, the amine was protected as a benzylcarbamate (AE2) and the alcohol converted to mesylate (AE3). AE3 was reacted with 2-hydroxypyridine in the presence of tetrabutylammonium bromide, potassium carbonate, toluene and catalytic amount of water, heated at reflux to provide AE4. Catalytic hydrogenation of AE4 provided AE5, which was subsequently coupled with Boc-7-hydroxy-D-Tic(OH) to afford AE6. Removal of the tert-butyloxycarbonyl protecting group using HCl in dioxane and acetonitrile afforded (34).

Compound (35) was synthesized from (7) as shown in Scheme AF. Methylation of (7) was accomplished by treating it with aqueous formaldehyde and sodium triacetoxyborohydride in dichloroethane to afford (35).

As shown in Scheme AG, 2-(1-piperidinyl)ethanamine (AG1) was coupled with 7-hydroxy-Boc-D-Tic(OH) using dicyclohexylcarbodiimide (DCC) in THF to afford AG2. Removal of the tert-butyloxycarbonyl protecting group using HCl in methanol afforded (36).

Compounds (37), (40), and (41) were prepared according to the sequences shown in Schemes AH, AK, and AL, respectively. The appropriate cycloacetaldehyde was condensed with (R)-tert-butylsulfinamide. The resulting sulfinimine reacted with isopropylgrignard reagent in dichloromethane to afford a high diastereomeric excess of the tert-butylsulfinamide shown. Upon treatment with hydrogen chloride in dioxane and methanol, the sulfonamide yielded the amine hydrochloride which was found to be the pure salt upon concentration. The salt could be used directly in the presence of triethylamine, coupling with the HOBt ester prepared from DCC and Boc-7-hydroxy-D-Tic(OH) or, in the case of (38) as shown in Scheme AI, from Boc-7-carbamoyl-D-Tic(OH). Boc cleavage afforded the cycloalkyl products (37), (38), (40) and (41).

(39) was prepared from the amine S4 as shown in Scheme AJ. Coupling with Boc-7-hydroxy-D-Tic(OH) was followed by Boc deprotection to afford (39).

The diastereomers of (37), ((42), (45), and (46)), were prepared analogously to (37) using the appropriate chiral starting materials, as shown in Schemes AM, AP, and AQ, respectively. (43) was prepared by methylation of the Boc-protected (37) (AN1) with iodomethane in dimethylformamide and potassium carbonate as base. Acid deprotection afforded the desired O-methyl product as shown in Scheme AN. (44) and (47) were prepared from amine AH4 and the commercially available Boc-D-Tic(OH) and Boc-7-fluoro-D-Tic(OH) as shown in Schemes AO and AR, respectively. As shown in Scheme AS, (48) was prepared by reductive amination of (37) with formaldehyde and sodium triacetoxyborohydride in dichloroethane.

The synthesis of the trans-3,4-dimethyl analog (49) was accomplished as outlined in Scheme AT. The pentadioic acid AT1 prepared in three steps following a literature precedence,[30] was subjected to ring closure by heating in neat urea to provide AT2 as a mixture of the trans and cis isomers in the ratio of 2:1 respectively. Recrystallization of the mixture from ethyl acetate with hexanes was employed to provide the clean trans product that was carried on in the following reactions. Reduction of the dione in AT2 in tetrahydrofuran was accomplished using sodium borohydride followed by addition of boron triflouride diethyl etherate stirred at room temperature for a couple of hours then heated at reflux for an additional couple of hours. The reaction mixture was cooled to 0° C. and treated with an aqueous solution of piperizine and further heated at reflux overnight. Upon work-up, the amine AT3 was obtained in about 96% yield. Compound AT3 was subsequently reacted in the usual manner with N-Boc-L-valine, deprotected with acid, and reduced with borane dimethyl sulfide to afford the diamine AT5. Coupling Boc-7-hydroxy-D-Tic and AT5 using 1-ethyl-3-(3-dimethylaminopropyl)carbodiimide (EDC) provided AT6 which upon removal of the Boc group afforded (49).

Compound (50) was prepared according to Scheme AU. Amine AU1 was coupled to Boc-L-Valine. Deprotection of the Boc protecting group using trifluoroacetic acid was followed by reduction of the amide. The resulting amine (AU2) was then coupled to 7-hydroxy-Boc-D-Tic(OH). Deprotection using trifluoroacetic acid afforded the desired (50).

Compounds (51), (52), (62), and (64) were prepared according to Scheme AV, Scheme AW, Scheme BG, and Scheme BI, respectively. The appropriate chiral sulfinimine (AH2, BG3, or AK2) was treated with the appropriate Grignard reagent. Hydrolysis of the resulting sulfinamide (AV1, AW1, BG4, or BI1) with 4N HCl afforded the amines (AV2, AW2, BG5, or BI2) as freebase or hydrochloride depending on work-up. The amines were then coupled to 7-hydroxy-Boc-D-Tic(OH) using the appropriate coupling agent. Deprotection using HCl or trifluoroacetic acid afforded the desired products (51, 52, 62, or 64).

Compounds (53) and (57) were prepared according to Scheme AX and Scheme BB, respectively, via borane reduction of (30) and (7). Compounds (55) and (56) were prepared according to Scheme AZ and Scheme BA, respectively. The appropriate commercially-available amine (AZ1 or BA1) was coupled to 7-hydroxy-Boc-D-Tic(OH) using DCC. Deprotection with 4N HCl afforded the desired products (55 and 56).

Compound (59) was synthesized as illustrated in Scheme BD. Boc-protected BD1 was converted to BD2 in three steps via an aldehyde which was then converted to 1-N-Boc-difluoromethylpiperidine using diethylaminosulfur trifluoride (DAST). Removal of the Boc protection using trifluoroacetic acid provided compound BD2 which was subjected to reactions analogous to other piperidines described above to provide the final compound 59.

Compound (60) was prepared according to Scheme BE. Amine AK4 was coupled to the acid BE1 using DCC and deprotected with boron tribromide to afford (60).

Compound (61) was prepared according to Scheme BF. Phenol BF1 was converted to the aryl triflate BF2, which was aminocarbonylated to carboxamide BF3. Final product (61) was afforded by 4N HCl catalyzed Boc-deprotection.

Synthesis of compound (63) as shown in Scheme BH was accomplished by cross-coupling 6-hydroxynapthalene-2-carboxylic acid (BH1) with (2S)-3-methyl-1-(4-methylpiperidine-1-yl)butan-2-amine (D4) to furnish (63). Similarly, as illustrated in Scheme BJ, compound (65) was obtained from 6-methoxy-1,2,3,4-tetrahydronaphthalene-2-carboxylic acid (BJ1) which converted via hydrogen bromide demethylation to provide (BJ2). Coupling of BJ2 with D4 furnished (65) as a mixture of diastereomers.

Compound (66) was prepared according to Scheme BK. Birch reduction of 2-(4-methylphenyl)ethanol (BK1) was followed by catalytic hydrogenation and subsequent Swern oxidation to afford aldehyde BK2. The chiral sulfinimine BK3 was prepared using (R)-tert-butylsulfinamide and converted to the final product 66 in a manner analogous to the preparation of compounds (51), (52), (62), and (64).

6.2. Biology

Measures of opioid receptor antagonism and specificity were obtained by monitoring the ability of selected test compounds to inhibit stimulation of [$^{35}$S]GTPγS binding produced by the selective agonists (D-Ala$^2$,MePhe$^4$,Gly-ol$^5$) enkephalin (DAMGO, μ receptor) cyclo[D-Pen$^2$,D-Pen$^5$] enkephalin (DPDPE, δ) and 5,7,8-(−)-N-methyl-N-[7-(1-pyrrolidinyl)-1-oxaspiro[4,5]dec-8-yl]benzeneacetamide (U69,593, κ) in cloned human receptors (Table 1). The methodology is published in Carroll et al.[31]

6.3. Results and Discussion

We have made the unexpected and novel finding that compounds having the general structures I, II, III and IV are potent and selective kappa opioid receptor antagonists. This finding is in complete contrast to all previously reported data for opioid antagonists including all analogs of JDTic. Even though (3) has only a simple piperidine ring where JDTic has a structurally complex trans-3,4-dimethyl-4-(3-hydroxyphenyl) piperidine group the compound has a $K_e$=6.80 nM at the kappa receptor and is 21- and >441-fold selective for the kappa receptor relative to the μ and δ receptor (Table 1). Even more unexpected and novel is the finding that (37) which does not have the piperidine amino group that is present in (3) has a $K_e$=0.14 nM at the KOR and is 1729 and 4571 selective for the KOR relative to the MOR and DOR, respectively. Highly interesting is the finding that (7), which has a methyl group added to the 4-position (3) has a $K_e$=0.37 nM at the kappa receptor and is now 645- and 8100-fold selective for the kappa receptor. (9) which is the 4,4-dimethyl analog of (3) has $K_e$ values of 2.09, 142 and 847 at the κ, μ, and δ receptors, respectively, and is thus, 68- and 405-fold selective for the kappa receptor relative to the μ and δ receptors (Table 1). Replacement of the phenolic hydroxyl group in (37) with a carboxamide give (38) which has a $K_e$=0.24 nM at κ and is 742- and 5083-fold selective for κ relative to the μ and δ receptors, respectively. It is particularly interesting to note that (40) has a $K_e$=0.058 nM at the κ opioid receptor and is 5900- and 27,000-fold selective for the κ relative to the μ and δ opioid receptor and (41) has a $K_e$=0.20 at the κ opioid receptor and is 292- and 3750-fold selective for the κ relative to the μ and δ receptors. Compounds (50), (51), and (56), with $K_e$ values of 2.58, 0.64, 2.04, and 1.27 nM at the κ opioid receptor, respectively, with 103- to 417-fold selectivity relative to the μ opioid receptor and over a 1000-fold selective for selectivity relative to the δ opioid receptor, are also of high interest. The table also shows other compounds that have interesting kappa opioid receptor in vitro properties.

TABLE 1

Inhibition of Agonist-Stimulated [$^{35}$S]GTPγS Binding in Cloned Human μ, δ, and κ Opioid Receptors

| # | □, DAMGO $K_e$ (nM) | □, DPDPE $K_e$ (nM) | □, U69, 593 $K_e$ (nM) | □/□ | □/□ |
|---|---|---|---|---|---|
| JDTic | 25 ± 4 | 74 ± 2 | 0.02 ± 0.01 | 1250 | 3800 |
| 3 | 144 ± 37 | >3000 | 6.80 ± 2.1 | 21 | >441 |
| 4 | >3000 | >3000 | 39.1 ± 3.8 | >76 | >76 |
| 5 | >3000 | >3000 | 396 ± 140 | 8 | >8 |
| 6 | 701 ± 37 | >3000 | 17.0 ± 4.7 | 41 | >177 |
| 7 | 239 ± 22 | >3000 | 0.37 ± 0.09 | 645 | >8100 |
| 8 | 300 ± 27 | >3000 | 14.5 ± 0.5 | 20.7 | 207 |
| 9 | 142 ± 25 | 847 ± 180 | 2.09 ± 0.42 | 68 | 405 |
| 10 | >3000 | >3000 | 137 ± 24 | >22 | >22 |
| 11 | 690 ± 110 | >3000 | 41.8 ± 12 | 16.5 | >72 |
| 12 | 44.9 ± 11 | >3000 | 15.1 ± 4.2 | 3 | 199 |
| 13 | 198 ± 48 | >3000 | 6.53 ± 1.8 | 30 | >459 |
| 14 | 67.9 ± 12 | >3000 | 4.69 ± 0.29 | 14 | >640 |
| 15 | 30.3 ± 1.0 | >3000 | 3.46 ± 0.54 | 9 | >867 |
| 16 | 955 ± 280 | >3000 | 9.29 ± 3.2 | 103 | >323 |
| 17 | 479 ± 150 | >3000 | 11.5 ± 1.9 | 42 | >261 |
| 18 | >3000 | >3000 | 42.8 ± 4.0 | >70 | >70 |
| 19 | 915 ± 303 | >3000 | 98.8 ± 28 | 9 | >333 |
| 20 | 41.3 ± 11 | >3000 | 1.37 ± 0.32 | 30 | >2190 |
| 21 | 28.9 ± 3.7 | >3000 | 9.43 ± 2.9 | 3 | 318 |
| 22 | 129 ± 26 | >3000 | 3.22 ± 0.78 | 43 | 932 |
| 23 | 139 ± 1 | >3000 | 15.6 ± 2.3 | 43 | 192 |
| 24 | 74.8 ± 23 | 2490 ± 620 | 2.48 ± 0.70 | 30 | 1004 |
| 25 | 11.8 ± 1.2 | >3000 | 0.88 ± 0.18 | 13.4 | >3410 |
| 26 | 108 ± 26 | >3000 | 1.26 ± 0.08 | 86 | 2381 |
| 27 | 586 ± 130 | >3000 | 5.58 ± 1.6 | 105 | >538 |
| 28 | >3000 | >3000 | 182 ± 19 | >17 | >177 |
| 29 | 1200 ± 140 | >3000 | 25.6 ± 6.3 | 47 | >117 |
| 30 | 406 ± 86 | >3000 | 88.4 ± 17 | 4.6 | 34 |
| 31 | 1.09 ± 0.11 | 1930 ± 330 | 1.81 ± 0.27 | 0.62 | 1066 |
| 32 | 702 ± 120 | >3000 | 48.5 ± 12 | 14 | 62 |
| 33 | 37.7 ± 7.9 | >3000 | 1.07 ± 0.11 | 35 | >2804 |
| 34 | 916 ± 130 | >3000 | 61.5 ± 9.3 | 15 | >49 |
| 35 | 752 ± 140 | >3000 | 36.7 ± 5.6 | 21 | >82 |
| 36 | >3000 | >3000 | 113 ± 21 | 27 | >27 |
| 37 | 242 ± 36 | 640 ± 170 | 0.14 ± 0.03 | 1729 | 4571 |
| 38 | 178 ± 47 | 1220 ± 160 | 0.24 ± 0.05 | 742 | 5083 |
| 39 | 647 ± 150 | >3000 | 12.7 ± 3.1 | 51 | >236 |
| 40 | 344 ± 100 | 1570 ± 380 | 0.058 ± 0.006 | 5900 | 27,000 |
| 41 | 58.3 ± 4.2 | 751 ± 80 | 0.2 ± 0.05 | 292 | 3750 |
| 42 | 521 ± 160 | >3000 | 12.6 ± 4.3 | 41 | >238 |
| 43 | 995 ± 230 | >3000 | 77.4 ± 23 | 13 | >39 |
| 44 | 1100 ± 260 | >3000 | 5.49 ± 0.79 | 200 | >547 |
| 45 | >3000 | >3000 | 4.40 ± 1.2 | >682 | 682 |
| 46 | 1140 ± 330 | >3000 | 14.2 ± 4.5 | 80 | >211 |
| 47 | >3000 | >3000 | 10.7 ± 3.1 | >80 | 280 |
| 48 | 245 ± 62 | >3000 | 4.23 ± 1.1 | 58 | >709 |
| 49 | 50.9 ± 7.7 | 2350 ± 390 | 2.3 ± 0.64 | 22 | 1022 |
| 50 | 749 ± 59 | >3000 | 2.58 ± 0.6 | 186 | >1163 |
| 51 | 267 ± 33 | >3000 | 0.64 ± 0.2 | 417 | >4700 |
| 52 | 880 ± 120 | >3000 | 15.2 ± 1.7 | 58 | >197 |
| 53 | 647 ± 150 | >3000 | 18.4 ± 2.0 | 35 | >163 |
| 54 | 604 ± 83 | >3000 | 11.8 ± 3.0 | 51 | >254 |
| 55 | 750 ± 150 | >3000 | 23.5 ± 3.8 | 32 | >127 |
| 56 | 277 ± 77 | >3000 | 23.3 ± 7.1 | 12 | >129 |
| 57 | 569 ± 110 | >3000 | 17.2 ± 5.8 | 33 | >174 |
| 58 | 318 ± 8.4 | >3000 | 8.08 ± 1.2 | 39 | >371 |
| 59 | 70.9 ± 9.4 | >3000 | 3.45 ± 1.2 | 21 | >870 |
| 60 | 1650 ± 3 | >3000 | 6.20 ± 1.4 | 266 | >484 |
| 61 | 209 ± 27 | 2540 ± 160 | 2.04 ± 0.60 | 103 | 1245 |
| 62 | 180 ± 17 | >3000 | 2.61 ± 0.73 | 69 | >1150 |
| 63 | 431 ± 110 | >3000 | 20.5 ± 4.6 | 21 | >146 |
| 64 | 325 ± 33 | >3000 | 3.74 ± 0.8 | 87 | >802 |
| 65 | 153 ± 37 | >3000 | 11.1 ± 2.9 | 14 | >270 |
| 66 | 221 ± 41 | >3000 | 1.27 ± 0.23 | 174 | >2400 |

Conclusions

Compounds of the present invention disclosure novel potent κ opioid receptor antagonists as determined in an in vitro functional test. Some compounds showed high potency and high selectivity for the κ relative to the μ and δ opioid receptors. Compounds (7), (16), (27), (37), (38), (40), (41), (50), (51), (61), and (66) have high potential for the development as clinical candidates for the treatment of various CNS disorders discussed in the introduction to the Invention Disclosure.

6.4. Experimentals

Melting points were determined using a MEL-TEMP II capillary melting point apparatus. Nuclear magnetic resonance ($^1$H NMR and $^{13}$C NMR) spectra were obtained on a Bruker Avance DPX-300 MHz NMR spectrometer or a Varian Unity Inova 500 MHz NMR spectrometer. Chemical shifts are reported in parts per million (ppm) with reference to internal solvent. Mass spectra (MS) were run on a Perkin-Elmer Sciex API 150 EX mass spectrometer equipped with APCI (atmospheric pressure chemical ionization) or ESI (turbospray) sources or on a Hewlett Packard 5989A instrument by electron impact. Elemental analyses were performed by Atlantic Microlab Inc., Atlanta, Ga. Optical rotations were measured on an AutoPol III polarimeter, purchased from Rudolf Research. Analytical thin-layer chromatography (TLC) was carried out using EMD silica gel 60 $F_{254}$ TLC plates. TLC visualization was achieved with a UV lamp or in an iodine chamber. Flash column chromatography was done on a CombiFlash Companion system using Isco prepacked silica gel columns or using EM Science silica gel 60 Å (230-400 mesh). Solvent system: CMA80 (or DMA80)=80:18:2 $CHCl_3$(or $CH_2Cl_2$):MeOH: conc. $NH_4OH$. Unless otherwise stated, reagent-grade chemicals were obtained from commercial sources and were used without further purification. All moisture- and air-sensitive reactions and reagent transfers were carried out under dry nitrogen.

6.5. General Synthetic Procedures

General Method 1. Coupling of the Amine with N-Boc-L-valine. A solution of the amine in acetonitrile (40 mL) was treated with N-Boc-L-valine (1.3 equiv), HBTU (1.3 equiv) and TEA (4.0 equiv) and the mixture was stirred at room temperature overnight. The solvent was removed under reduced pressure and to the residue was added aqueous $NaHCO_3$ (30 mL). The organic product was extracted with EtOAc (3×50 mL). Combined organic layers were dried ($Na_2SO_4$), concentrated in vacuo and the residue was purified on silica gel eluted with EtOAc/hexanes. In some cases, the organic product was carried on to the Boc-removal step without purification.

General Method 2. Removal of Boc-protection. The Boc-protected compound in acetonitrile was treated with HCl (4M in 1,4-dioxane, 4 equiv.) and stirred at room temperature overnight. The solvent was then removed in vacuo and the residue was neutralized with 1N NaOH until the pH of 8-9 was obtained. Purification of the residue on silica gel and eluted with CMA80/$CH_2Cl_2$ provided the product. Alternatively, the Boc-protected compound was dissolved in $CH_3OH$ (5 mL) then treated with 6 N HCl aq. (5 mL) and stirred at room temperature overnight. The solvent was evaporated and the residue purified as above.

General Method 3. Reduction of the amide. To a cooled (0° C.) solution of the amide compound in THF (40 mL) was added borane dimethyl sulfide (2.0 equiv). The mixture was warmed up and stirred at room temperature overnight, after which it was heated at reflux for 3 h, cooled to 0° C., quenched with MeOH (10 mL) and stirred at room temperature for 1 h. The mixture was treated with an aqueous 2M HCl solution (5 mL) and heated at reflux for an additional 2 hours. After cooling, the solvent was removed in vacuo and resultant crude material was purified on silica gel, eluted with CMA 80/$CH_2Cl_2$ to provide the diamine. Alternatively, the amide was dissolved in THF at 0° C., treated with $LiAlH_4$ then allowed to warm to room temperature. The reaction was diluted with ether, cooled to 0° C., then treated sequentially with (per 1 g LAH used) 1 mL water, 1 mL 15 wt % NaOH aq., then 3 mL water. The resulting suspension was filtered, concentrated, and the residue subject to chromatography on silica gel to afford the desired amine.

General Method 4. Coupling of the diamine with Boc-7-hydroxy-D-Tic-OH. To a solution of the diamine (1.0 equiv) in dichloromethane (30-50 mL) was added Boc-7-hydroxy-D-Tic-OH (1.1 equiv), EDC (1.2 equiv), HOBt (0.11 equiv) and TEA (5.0-8.0 equiv). The mixture was stirred at room temperature overnight. Aqueous $NaHCO_3$ (30 mL) was added to the mixture and the organic product extracted with DCM (3×30 mL). The combined organic layers were dried (anhydrous $Na_2SO_4$), filtered through Celite and concentrated in vacuo. Purification of the residue on silica gel eluted with CMA 80/$CH_2Cl_2$ provide the desired product Boc-protected product that was then subjected to General Method 2 for the cleavage of the Boc group. Alternatively, acid in THF (0.1 M) was treated with DCC (1.2 eq.) and HOBt (1.1 eq). After 1 h at room temperature, the amine (1.2 eq) was added. If the amine was a hydrochloride salt, $NEt_3$ (3 eq) was also added. After 12 h, the reaction was filtered, concentrated, and the residue subjected to silica gel chromatography to afford the desired amide.

General Method 5. Sulfinimine formation. Magnesium sulfate (5.0 g, 42 mmol) was added to a solution of aldehyde (17 mmol), R-(tert-butyl)sulfinamide (1.06 g, 8.7 mmol), and pyridinium p-toluenesulfonate (100 mg, 0.4 mmol) in $CH_2Cl_2$ (14 mL). After 12 h, the suspension was filtered and concentrated and the residue subjected to chromatography on silica gel eluting with a gradient up to 25% EtOAc in hexanes to afford the desired sulfinimine.

General Method 6. Grignard addition. A solution of sulfinimine (6.4 mmol) in $CH_2Cl_2$ (35 mL) at −78° C. was treated with a Grignard reagent (6 ml, 2.0 M in THF). The solution was allowed to warm to room temperature overnight, then was quenched by the addition of $NH_4Cl$ (sat.). The organic layer was washed with $NaHCO_3$ (sat.) and dried ($Na_2SO_4$). The concentrated residue was subjected to chromatography on silica gel eluting with a gradient of EtOAc in hexanes to afford the desired sulfinamide.

General Method 7. Sulfinamide hydrolysis. The sulfinamide (3.4 mmol) was dissolved in methanol (1.7 mL) and treated with HCl in dioxane (1.7 mL, 4 N). After 30 minutes at room temperature, the solution was concentrated to afford desired amine hydrochloride.

Scheme A.[a]

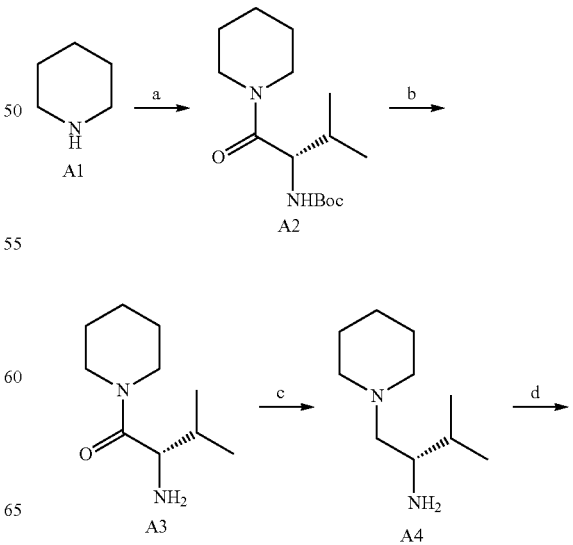

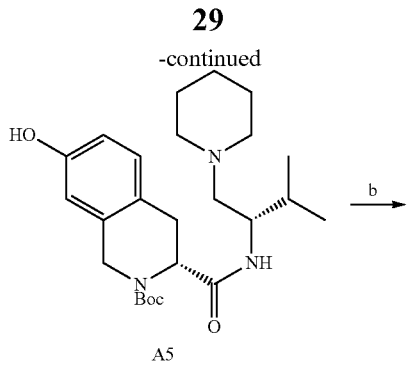

A5

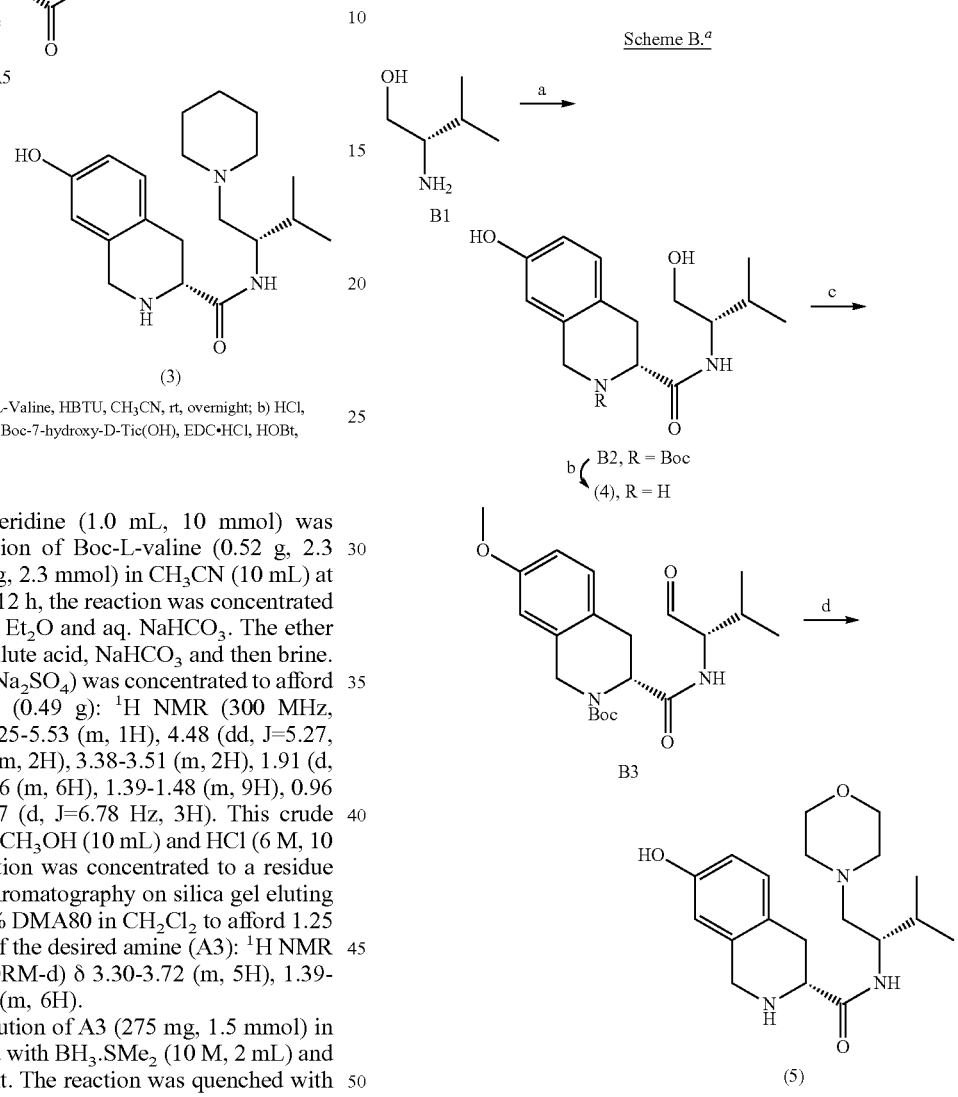

*Reagents and conditions: a) N-Boc-L-Valine, HBTU, CH₃CN, rt, overnight; b) HCl, CH₃OH; c) BH₃, THF, reflux, 3 h; d) Boc-7-hydroxy-D-Tic(OH), EDC·HCl, HOBt, NEt₃, CH₂Cl₂, rt, overnight.

Synthesis of A3. Piperidine (1.0 mL, 10 mmol) was slowly added to a solution of Boc-L-valine (0.52 g, 2.3 mmol) and HBTU (0.88 g, 2.3 mmol) in CH₃CN (10 mL) at room temperature. After 12 h, the reaction was concentrated then partitioned between Et₂O and aq. NaHCO₃. The ether layer was washed with dilute acid, NaHCO₃ and then brine. The dried organic layer (Na₂SO₄) was concentrated to afford the crude A2 as an oil (0.49 g): $^1$H NMR (300 MHz, CHLOROFORM-d) δ 5.25-5.53 (m, 1H), 4.48 (dd, J=5.27, 9.04 Hz, 1H), 3.51-3.66 (m, 2H), 3.38-3.51 (m, 2H), 1.91 (d, J=5.46 Hz, 1H), 1.49-1.76 (m, 6H), 1.39-1.48 (m, 9H), 0.96 (d, J=6.78 Hz, 3H), 0.87 (d, J=6.78 Hz, 3H). This crude mixture was dissolved in CH₃OH (10 mL) and HCl (6 M, 10 mL). After 1 h, the reaction was concentrated to a residue which was purified by chromatography on silica gel eluting with a gradient up to 33% DMA80 in CH₂Cl₂ to afford 1.25 g (67% over two steps) of the desired amine (A3): $^1$H NMR (300 MHz, CHLOROFORM-d) δ 3.30-3.72 (m, 5H), 1.39-1.96 (m, 9H), 0.72-1.13 (m, 6H).

Synthesis of A4. A solution of A3 (275 mg, 1.5 mmol) in THF (10 mL) was treated with BH₃·SMe₂ (10 M, 2 mL) and heated to reflux overnight. The reaction was quenched with the addition of methanol, then acidified with HCl (6 M, 10 mL). The reaction mixture was concentrated and the residue subjected to silica gel chromatography eluting with a gradient of DMA80 in CH₂Cl₂ to afford 216 mg (85%) of the desired amine A4: $^1$H NMR (300 MHz, CHLOROFORM-d) δ 3.59-3.80 (m, 1H), 2.22-3.28 (m, 6H), 1.79-2.07 (m, 3H), 1.37-1.75 (m, 6H), 0.80-1.11 (m, 6H); MS (ESI) m/z 171.3 (M+H)⁺.

(3R)-7-Hydroxy-N-[(1S)-2-methyl-1-(piperidin-1-ylmethyl)propyl]-1,2,3,4-tetrahydroisoquinoline-3-carboxamide (3) Dihydrochloride. Amine A4 was reacted according to General Method 4 using EDC to afford the (3) free base: $^1$H NMR (CDCl₃) δ 7.07 (d, J=9.80 Hz, 1H), 6.86 (d, J=8.10 Hz, 1H), 6.55 (dd, J=2.35, 8.19 Hz, 1H), 6.39 (d, J=2.07 Hz, 1H), 4.24 (t, J=10.64 Hz, 1H), 3.52-3.76 (m, 2H), 3.20 (dd, J=5.18, 11.59 Hz, 1H), 2.89 (dd, J=5.09, 16.58 Hz, 1H), 2.55-2.76 (m, 3H), 2.38 (br. s., 2H), 2.16-2.31 (m, 2H), 1.83 (dd, J=6.78, 11.68 Hz, 1H), 1.65 (d, J=4.71 Hz, 4H), 1.47 (d, J=5.46 Hz, 2H), 0.83-0.99 (m, 6H); $^{13}$C NMR (CDCl₃) δ 173.4, 155.0, 137.5, 130.7, 125.1, 113.7, 112.1, 60.2, 56.6, 54.6, 49.4, 48.4, 31.9, 29.2, 25.0, 24.0, 18.9, 18.1; MS (ESI) m/z 346.2 M+H)⁺. The free base was converted to the dihydrochloride salt (48.4 mg) white powder: mp 138-142° C. (fusion); [α]$^{25}_D$=+66.5 (c 0.36, CH₃OH). Anal. (C₂₀H₃₃Cl₂N₃O₂·2.25 H₂O) C, H, N.

Scheme B.$^a$

*Reagents and conditions: a) Boc-7-hydroxy-D-Tic(OH), DCC, HOBt, NEt₃, THF, rt, 72 h; b) TFA, CH₂Cl₂; c) i, TMSCHN₂, DIPEA, CH₃CN, CH₃OH, rt, overnight; ii. Dess-Martin, CH₂Cl₂, rt, 1 h; d) i. Morpholine, NaBH(OAc)₃; ii. BBr₃, -78° C. to rt overnight; iii. NH₄OH aq. reflux, 1 h.

Synthesis of B2. A solution of L-valinol (prepared according to literature method: *J. Org. Chem.* 65, 5037-5042) (2.0 g, 19 mmol), Boc-7-hydroxy-D-Tic (5.0 g, 17 mmol), and HOBt (2.3 g, 17 mmol) in THF (60 mL) in an ice bath was treated with a solution of DCC (4.0 g, 19 mmol) in THF (10 mL). After stirring 72 h, the solution was filtered and the solids washed with ether. The concentrated residue was taken up in ether, washed (2 M HCl, aq NaHCO₃, brine), dried (Na₂SO₄), and concentrated. The resulting residue was subjected to chromatography on silica gel using a gradient up to 5% isopropanol in CH₂Cl₂ to afford 4.5 g (71%) of the desired Boc-protected intermediate (B2).

(3R)-7-Hydroxy-N-[(1S)-1-(hydroxymethyl)-2-methylpropyl]-1,2,3,4-tetrahydroisoquinoline-3-carboxamide (4) Hydrochloride. A 50 mg sample of B2 was treated with TFA (5 mL) and concentrated under a stream of $N_2$. The concentrated residue was dissolved in CMA80 and stirred for 30 min. The solution was concentrated, then subjected to a plug of silica gel eluting with CMA8. The resulting isolated free base was converted to 36.7 mg (83% from the Boc compound) of the hydrochloride salt 4 HCl as a white powder: $^1$H NMR (300 MHz, $CD_3OD$) δ 8.21 (br. s., 1H), 7.06 (d, J=6.22 Hz, 1H), 6.54-6.78 (m, 2H), 4.31 (br. s., 2H), 4.04-4.21 (m, 1H), 3.47-3.82 (m, 3H), 2.93-3.14 (m, 1H), 1.74-1.96 (m, 1H), 0.91 (d, J=5.84 Hz, 6H); $^{13}$C NMR (75 MHz, $CD_3OD$) δ0 170.1, 158.1, 131.3, 129.9, 122.3, 117.0, 113.8, 63.2, 58.6, 58.5, 57.3, 45.7, 30.7, 30.3, 20.2, 18.9; MS (ESI) m/z 279.3 (M+H)$^+$; mp 95-99° C. (fusion); $[α]^{25}_D$+86.4 (c 0.295, $CH_3OH$). Anal. ($C_{15}H_{23}ClN_2O_3·H_2O$) C, H, N.

Synthesis of B3. A solution of B2 (380 mg, 1 mmol) and diisopropylethylamine (0.25 mL, 1.4 mmol) in acetonitrile (4 mL) and methanol (1 mL) was treated with trimethylsilyldiazomethane (1.4 mL, 1.0 M solution in ether, 1.4 mmol). After stirring overnight, the excess reagent was quenched with a small volume of acetic acid. The resulting solution was concentrated to afford a quantitative yield of the desired methyl ether intermediate. $^1$H NMR ($CDCl_3$) δ 7.13 (d, J=8.10 Hz, 1H), 6.79 (d, J=6.97 Hz, 2H), 6.02 (br. s., 1H), 5.63 (br. s., 1H), 4.66 (d, J=5.27 Hz, 2H), 4.40 (br. s., 1H), 3.79 (s, 3H), 3.46 (br. s., 2H), 3.24 (d, J=15.26 Hz, 2H), 3.04 (br. s., 1H), 1.70 (br. s., 1H), 1.49 (br. s., 9H), 0.70-0.94 (m, 6H). A solution of the methyl ether intermediate (312 mg, 0.8 mmol) in $CH_2Cl_2$ (50 mL) was treated with Dess-Martin periodinane (500 mg, 1.2 mmol). After stirring 30 min, the reaction was quenched with sodium thiosulfate and aq $NaHCO_3$ and extracted with ether. The ether layer was washed (aq. $NaHCO_3$, then brine), dried ($Na_2SO_4$) and concentrated to afford 0.30 g (96%) of the desired aldehyde (B3) which was carried forward without further purification. $^1$H NMR ($CDCl_3$) δ 9.20-9.52 (m, 1H), 7.00-7.22 (m, 1H), 6.56-6.89 (m, 2H), 4.81-5.17 (m, 1H), 4.23-4.79 (m, 3H), 3.63-3.91 (m, 4H), 2.88-3.35 (m, 2H), 1.67-1.98 (m, 1H), 1.50 (br. s., 9H), 0.71-1.02 (m, 6H).

(3R)-7-Hydroxy-N-[(1S)-2-methyl-1-(morpholin-4-ylmethyl)propyl]-1,2,3,4-tetrahydroisoquinoline-3-carboxamide (5) Dihydrochloride. A solution of tent-butyl B3 (0.15 g, 0.4 mmol) in dichloroethane (3 mL) was treated with morpholine (0.09 mL, 1 mmol) then sodium triacetoxyborohydride (200 mg, 0.9 mmol). After 12 h, the solution was washed with aq $NaHCO_3$, dried ($Na_2SO_4$), and subjected to chromatography on silica gel eluting with EtOAc to afford 100 mg (54%) of the protected intermediate. The intermediate was dissolved in $CH_2Cl_2$ (10 mL), cooled to −78° C., treated with $BBr_3$ (5 mL, 1.0 M in $CH_2Cl_2$, 5 mmol) and allowed to warm overnight. The solution was cooled to −78° C., quenched with methanol, concentrated and then dissolved in dilute aq $NH_4OH$. The aqueous solution was briefly refluxed, then concentrated. The residue was subjected to chromatography on silica gel eluting with a gradient up to 50% CMA80 in $CH_2Cl_2$ to afford the desired free base: $^1$H NMR ($CDCl_3$) δ 7.10 (d, J=9.80 Hz, 1H), 6.91 (d, J=8.29 Hz, 1H), 6.60 (dd, J=2.45, 8.29 Hz, 1H), 6.45 (d, J=2.07 Hz, 1H), 4.11-4.18 (m, 1H), 3.63-3.78 (m, 6H), 3.37 (dd, J=5.18, 10.83 Hz, 1H), 2.98 (dd, J=5.09, 16.39 Hz, 1H), 2.47-2.68 (m, 4H), 2.29-2.43 (m, 3H), 1.85 (dd, J=6.78, 11.87 Hz, 1H), 0.89-0.96 (m, 6H); $^{13}$C NMR ($CDCl_3$) δ 173.5, 154.7, 137.1, 130.4, 125.3, 114.0, 112.2, 66.6, 60.5, 56.7, 53.8, 49.7, 47.8, 31.1, 29.8, 19.2, 17.8; MS (ESI) m/z 348.3 M+H)$^+$. The free base was converted 42.2 mg (44%) of the dihydrochloride salt as a white powder: mp 186-190° C. (fusion), $[α]^{25}_D$+62 (c 0.16, $CH_3OH$). Anal. ($C_{19}H_{31}C_{12}N_3O_3·1.5H_2O$) C, H, N.

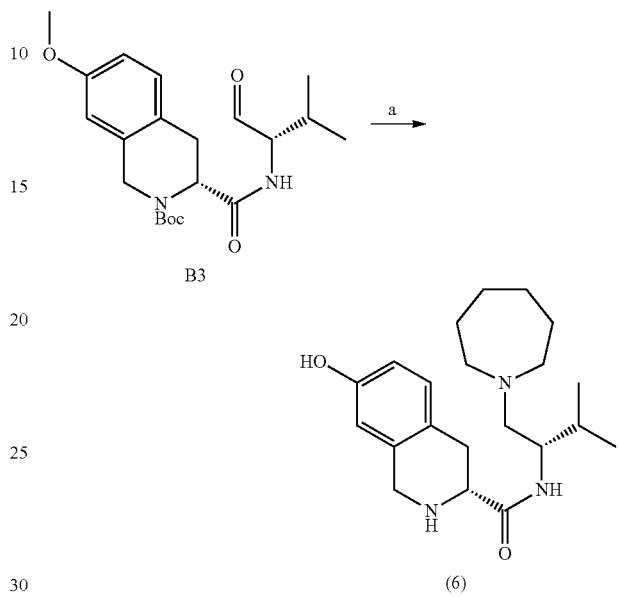

Scheme C.$^a$

B3

(6)

$^a$Reagents and conditions: a) i. Azepane, $NaBH(OAc)_3$; ii. $BBr_3$, -78° C. to rt overnight; iii. $NH_4OH$ aq. reflux, 1 h.

(3R)—N-[(1S)-1-(Azepan-1-ylmethyl)-2-methylpropyl]-7-hydroxy-1,2,3,4-tetrahydroisoquinoline-3-carboxamide (6) Dihydrochloride. A solution of B3 (0.15 g, 0.4 mmol) and homopiperidine (110 mg, 1 mmol) in 1,2-dichloroethane (3 mL) was treated with sodium triacetoxyborohydride (200 mg, 0.9 mmol). After 12 h, the solution was washed with aq $NaHCO_3$, dried ($Na_2SO_4$), and subjected to chromatography on silica gel eluting with a gradient up to 10% $CH_3OH$ in EtOAc to afford 99 mg (52%) of the protected intermediate. The intermediate was dissolved in $CH_2Cl_2$ (10 mL) and treated with $BBr_3$ (5 mL, 1.0 M in $CH_2Cl_2$, 5 mmol) at 78° C., then allowed to warm overnight. The solution was cooled to −78° C., quenched with methanol, concentrated and then dissolved in dilute aq $NH_4OH$. The aqueous solution was briefly refluxed, then concentrated. The residue was subjected to chromatography on silica gel eluting with a gradient up to 50% CMA80 in $CH_2Cl_2$ to afford the desired free base: $^1$H NMR ($CDCl_3$) δ 7.23 (d, J=9.42 Hz, 1H), 6.85 (d, J=8.29 Hz, 1H), 6.49 (d, J=8.29 Hz, 1H), 6.43 (s, 1H), 4.14 (td, J=7.30, 14.41 Hz, 1H), 3.57-3.76 (m, 2H), 3.30 (dd, J=5.09, 11.49 Hz, 1H), 2.75-3.03 (m, 5H), 2.69 (d, J=6.78 Hz, 2H), 2.35 (dd, J=11.96, 15.92 Hz, 1H), 1.77-1.94 (m, 1H), 1.46-1.78 (m, 8H), 0.94 (dd, J=1.79, 6.69 Hz, 6H); $^{13}$C NMR ($CDCl_3$) δ 173.5, 154.9, 137.2, 130.4, 125.1, 113.8, 112.2, 57.4, 56.8, 55.0, 50.6, 48.1, 31.4, 29.7, 27.4, 25.5, 19.1, 18.0; MS (ESI) m/z 360.4 M+H)$^+$. The free base was converted 25.5 mg (27%) of the dihydrochloride salt as a pale yellow powder: mp 160-164° C. (fusion), $[α]^{25}_D$+65.5 (c 0.165, $CH_3OH$). Anal. ($C_{21}H_{35}Cl_2N_3O_2·1.5H_2O$) C, H, N.

Scheme D.[a]

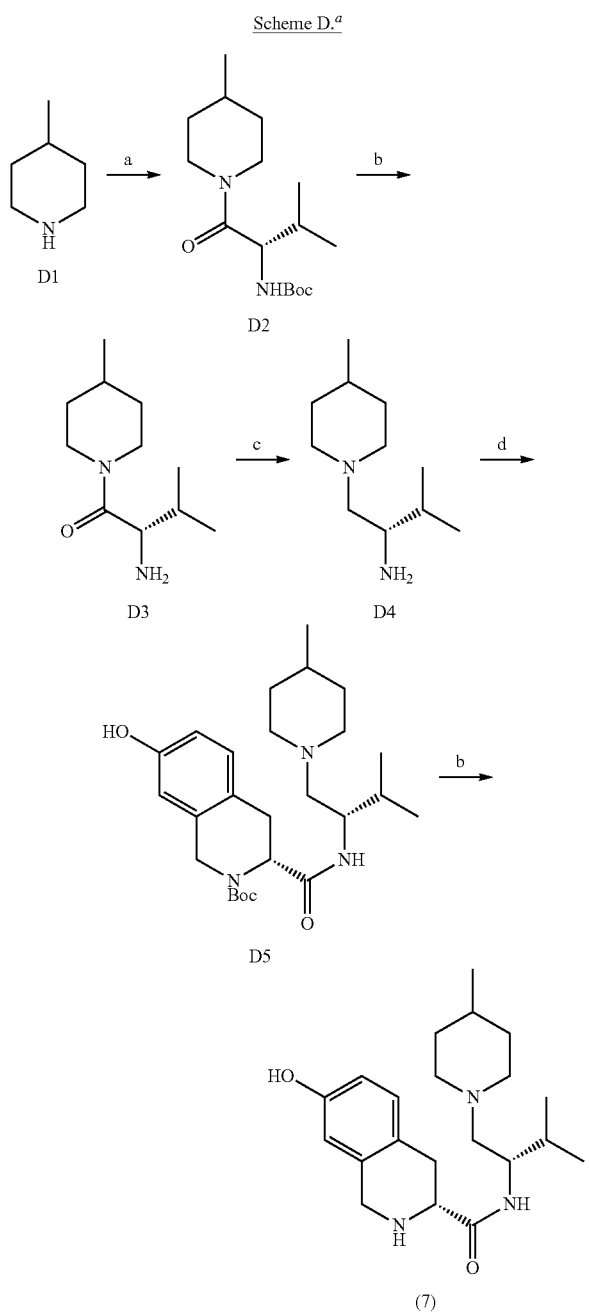

[a]Reagents and conditions: a) N-Boc-L-Valine, HBTU, CH₃CN, rt, overnight; b) HCl in 1,4-dioxane, CH₃CN, rt, 3 h; c) BH₃•SMe₂, THF, reflux, 3 h; d) Boc-7-hydroxy-D-Tic(OH), EDC•HCl, HOBt, NEt₃, CH₂Cl₂, rt, overnight.

Synthesis of D2. A solution of the 4-methylpiperidine (D1) (916 mg, 9.92 mmol) in acetonitrile (40 mL) was treated with N-Boc-L-valine (2.61 g, 12.01 mmol), HBTU (5.91 g, 4.55 mmol) and TEA (5.5 mL, 4.0 equiv). The mixture was stirred at room temperature overnight. The solvent was removed under reduced pressure and to the residue was added aqueous NaHCO₃ (50 mL). The organic product was extracted with EtOAc (3×50 mL). Combined organic layers were dried (Na₂SO₄), concentrated in vacuo and the residue was purified on silica gel eluted with EtOAc/hexanes to provide 3.0 g (100%) of compound D2. $^1$H NMR (CDCl₃) δ 0.87-0.91 (m, 3H), 0.94-0.98 (m, 6H), 1.10-1.95 (m, 2H), 1.43 (d, J=3.3 Hz, 1H), 1.45 (s, 9H), 1.65-1.77 (m, 2H), 1.86-1.95 (m, 1H), 2.04 (s, 1H), 2.53-2.64 (tt, J=13.1, 4.7, 2.0 Hz, 1H), 2.98-3.07 (m, 1H), 3.90-3.94 (d, J=11.7 Hz, 1H), 4.45-4.51 (m, 1H), 4.54-4.59 (d, J=15.4 Hz, 1H), 5.39-5.42 (d, J=5.2 Hz, 1H); $^{13}$C NMR (CDCl₃) δ 16.9, 19.6, 21.6, 28.3 (3 C+s), 31.1, 31.5, 33.7, 34.6, 42.3, 45.8, 54.7, 79.2, 155.9, 170.2; MS (ESI) m/z 299.5 M+H)⁺.

Synthesis of D3. Compound D2 (3.0 g, 10.4 mmol) in acetonitrile was treated with HCl (4M in 1,4-dioxane, (10.4 mL, 4 equiv) and stirred at room temperature overnight. The solvent was then removed in vacuo and the residue was purified on silica gel and eluted with CMA80/CH₂Cl₂ to provide the amide 2.0 g of D3 (100% yield) as a pale yellow oil. $^1$H NMR (300 MHz, CD₃OD) δ 0.98-1.28 (m, 9H), 1.64-1.88 (m, 2H), 2.17 (br s, 1H), 2.69-2.78 (t, J=9.4 Hz, 1H), 3.12-3.21 (m, 1H), 3.37 (s, 3H), 3.95-4.00 (d, J=4.4 Hz, 1H), 4.33 (d, J=7.7 Hz, 1H), 4.52 (t, J=7.4 Hz, 1H); $^{13}$C NMR (CD₃OD) δ 17.3, 19.4 22.2, 31.5, 32.2, 34.0, 35.6, 43.9, 47.2, 56.4, 168.9; MS (ESI) m/z 199.6 M+H)⁺.

Synthesis of D4. To a cooled (0° C.) solution of compound D3 (2.2 g, 11.1 mmol) in THF (40 mL) was added borane dimethyl sulfide (2.2 mL, 2.0 equiv). The mixture was warmed up and stirred at room temperature overnight, after which it was heated at reflux for 3 h, cooled to 0° C. and quenched with MeOH (10 mL) and stirred at room temperature for 1 h. The mixture was treated with an aqueous 2M HCl solution (5 mL) and heated at reflux for an additional 2 hours. After cooling, the solvent was removed in vacuo and resultant crude material was purified on silica gel, eluted with CMA 80/CH₂Cl₂ to provide the diamine D4 (618 mg, 30% yield) as a white solid. $^1$H NMR (300 MHz, CD₃OD) δ 0.96-1.06 (m, 9H), 1.20-1.45 (m, 3H), 1.68-1.71 (m, 2H), 1.82-1.92 (m, 1H), 1.99-2.07 (td, J=10.3, 2.2 Hz, 1H), 2.31-2.39 (td, J=12.9, 2.9 Hz, 1H), 2.41-2.49 (dd, J=11.0, 10.0 Hz, 1H), 2.54-2.59 (dd J=4.8, 4.1 Hz, 1H), 2.82-2.87 (d, J=14.5 Hz, 1H), 3.00-3.12 (m, 2H); $^{13}$C NMR (CD₃OD) δ 18.6, 18.9, 22.1, 31.1, 31.7, 34.9, 35.3, 53.8, 55.2, 56.5, 59.5; MS (ESI) m/z 185.3 M+H)⁺.

Synthesis of D5. To a solution of the diamine D4 (908 mg, 3.53 mmol) in dichloromethane (50 mL) was added Boc-7-hydroxy-D-Tic-OH (1.14 g, 3.88 mmol), EDC (812 mg, 4.23 mmol), HOBt (59 mg, 0.39 mmol) and TEA (1.2 mL, 8.48 mmol). The mixture was stirred at room temperature overnight. Aqueous NaHCO₃ (30 mL) was added to the mixture and the organic product extracted with DCM (3×30 mL). The combined organic layers were dried (anhydrous Na₂SO₄), filtered through Celite and concentrated in vacuo. Purification of the residue on silica gel eluted with CMA 80/CH₂Cl₂ provide the desired product D5 (1.1 g, 68% yield). $^1$H NMR (CDCl₃) δ 0.78-0.88 (m, 9H), 1.02-1.30 (m, 3H), 1.4-1.6 (m, 3H), 1.50 (s, 9H), 1.70-1.87 (m, 3H), 2.03-2.25 (m, 2H) 2.4-2.63 (m, 2H), 2.95-3.02 (d, J=11.4 Hz, 1H), 3.17-3.29 (m, 1H), 3.45 (s, 1H), 3.80 (br s, 1H), 4.41-4.58 (m, 2H), 5.90-6.00 (m, 1H), 6.60 (s, 1H), 6.65 (d, J=9.7 Hz, 1H), 6.96 (d, J=9.2 Hz, 1H); δ; $^{13}$C NMR (CDCl₃) δ 17.4, 18.9, 21.8, 28.4 (3Cs), 30.2, 30.5, 34.0, 34.2, 44.8, 45.1, 51.3, 53.5, 54.3, 56.5, 56.9, 59.3, 81.4, 113.1, 114.7, 123.9, 129.1, 134.1, 155.6, 171.6; MS (ESI) m/z 460.2 M+H)⁺.

(3R)-7-Hydroxy-N-{(1S)-2-methyl-1-[(4-methylpiperidin-1-yl)methyl]propyl}-1,2,3,4-tetrahydroisoquinoline-3-carboxamide (7) Dihydrochloride. Compound D5 (1.1 g, 2.3 mmol) in acetonitrile (20 mL) was subjected to Boc cleavage using HCl (4M in 1,4-dioxane) and stirred at room temperature overnight. The solvent was removed under reduced pressure and the residue purified on silica gel eluted with CMA 80/CH$_2$Cl$_2$ to provide the hydrochloride salt (594 mg) of final of compound (7). Analysis for the free base. $^1$H NMR (300 MHz, CD$_3$OD) δ 0.97-1.00 (m, 9H), 1.39-1.63 (m, 3H), 1.78-1.91 (m, 3H), 1.96 (s, 1H), 2.71-2.79 (t, J=13.6, 2.8 Hz, 1H), 2.86-2.96 (m, 2H), 3.00-3.07 (m, 1H), 3.10-3.17 (m, 2H), 3.31-3.39 (m, 2H), 3.37 (s, 1H) 3.58-3.64 (m, 1H), 3.83-3.89 (dd, J=5.6, 5.2 Hz, 1H), 3.96-4.06 (m, 1H), 4.09 (d, J=3.3 Hz, 1H), 4.16-4.21 (m, 1H), 6.58 (d, J=2.5 Hz, 1H), 6.68 (dd, J=8.4, 2.9 Hz, 1H), 6.96 (d, J=8.7 Hz, 1H); $^{13}$C NMR (CD$_3$OD) δ 18.5, 20.0, 21.6, 30.1, 31.5, 32.5, 32.6, 47.5, 50.0, 51.1, 53.5, 55.5, 58.1, 60.7, 113.5, 115.7, 124.5, 131.2, 135.0, 157.2, 174.5; MS (ESI) m/z 360.3 M+H)$^+$. A white solid was obtained as hydrochloride salt of (7): mp 180° C.; [α]$^{25}_D$=+65 (c 1.1, CH$_3$OH). Anal. (C$_2$H$_{35}$Cl$_2$N$_3$O$_2$·1.25 H$_2$O) C, H, N.

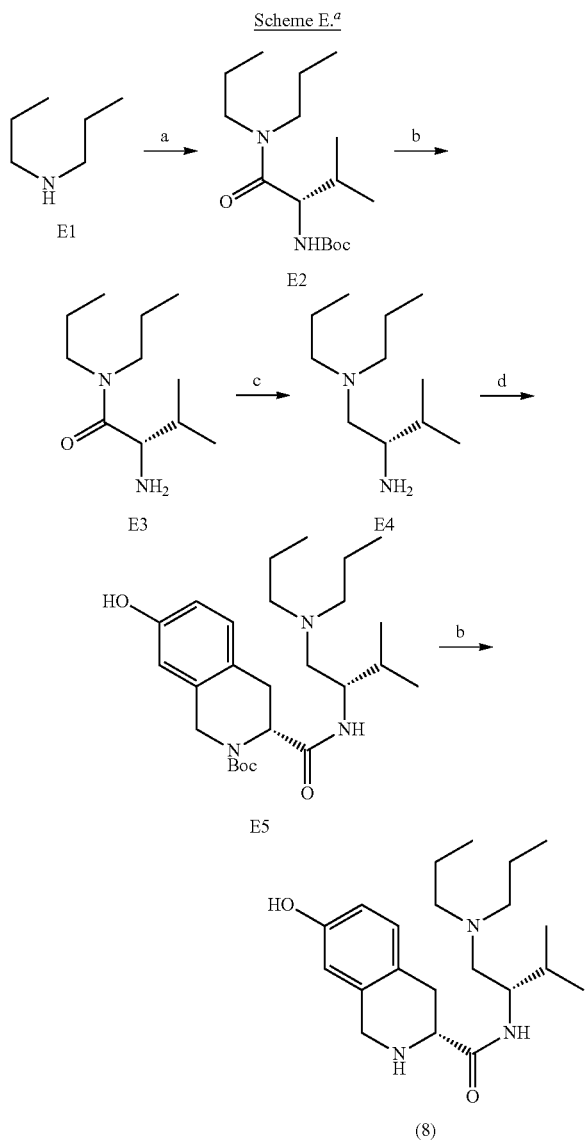

Scheme E.$^a$ $^a$Reagents and conditions: a) N-Boc-L-Valine, HBTU, CH$_3$CN, rt, overnight; b) HCl in 1,4-dioxane, CH$_3$CN, rt, 3 h; c) BH$_3$•SMe$_2$, THF, reflux, 3 h; d) Boc-7-hydroxy-D-Tic(OH), EDC•HCl, HOBt, NEt$_3$, CH$_2$Cl$_2$, rt, overnight.

Synthesis of E2. A solution of the dipropylamine (E1) (1.2 g, 12.0 mmol) in acetonitrile (40 mL) was treated with N-Boc-L-valine (3.38 g, 15.59 mmol), HBTU (5.91 g, 15.59 mmol) and TEA (7 mL, 4.0 equiv). The mixture was stirred at room temperature overnight. The solvent was removed and to the residue was added aqueous NaHCO$_3$ (50 mL). The organic product was extracted with EtOAc (3×50 mL). The combined organic layers were dried Na$_2$SO$_4$), concentrated in vacuo and purified on silica gel eluted with EtOAc/hexanes to provide 3.44 g (95%) of compound E2. $^1$H NMR (CDCl$_3$) δ 0.86-0.96 (m, 12H), 1.43 (s, 9H), 1.51-1.63 (m, 3H), 1.89-1.95 (m, 1H), 3.00-3.04 (m, 1H), 3.14-3.24 (m, 1H), 3.31-3.41 (m, 1H), 3.54-3.64 (m, 1H), 4.10-4.30 (m, 2H), 4.37-4.42 (dd, J=6.4, 9.7 Hz, 1H); $^{13}$C NMR (CDCl$_3$) δ 11.1, 11.3, 17.4, 19.6, 20.8 (3 C's), 32.1, 47.5, 49.5, 55.0, 79.2, 96.8, 155.7, 171.9; MS (ESI) m/z 301.5 M+H)$^+$.

Synthesis of E3. Compound E2 (3.78 g, 12.6 mmol) in acetonitrile was treated with HCl (4M in 1,4-dioxane, (12.6 mL, 4 equiv) and stirred at room temperature overnight. The solvent was then removed in vacuo and the residue was purified on silica gel and eluted with CMA80/CH$_2$Cl$_2$ to provide the amide E3 (99% yield) as a brownish oil. $^1$H NMR (300 MHz, CD$_3$OD) δ 0.89-1.10 (m, 12H), 1.17-1.22 (m, 3H), 1.52-1.72 (m, 3H), 2.08-2.15 (m, 1H), 3.02-3.12 (m, 1H), 3.17-3.26 (m, 1H), 3.36-3.47 (m, 2H), 3.59-3.66 (m, 2H), 4.00-4.02 (d, J=6.4 Hz, 1H); $^{13}$C NMR (CD$_3$OD) δ 11.4, 11.7, 17.3, 19.6, 21.8, 23.3, 32.1, 50.7, 56.8, 58.4, 171.4; MS (ESI) m/z 201.3 M+H)$^+$.

Synthesis of E4. To a cooled (0° C.) solution of compound E3 (3.59 g, 17.9 mmol) in THF (40 mL) was added borane dimethyl sulfide (3.4 mL, 2.0 equiv). The mixture was warmed up and stirred at room temperature overnight, after which it was heated at reflux for 3 h, cooled to 0° C. and quenched with MeOH (10 mL) and stirred at room temperature for 1 h. The mixture was treated with an aqueous 2M HCl solution (5 mL) and heated at reflux for an additional 2 hours. After cooling, the solvent was removed in vacuo and resultant crude material was purified on silica gel, eluted with CMA 80/CH$_2$Cl$_2$ to provide the diamine E4 (2.92 g, 86% yield) as a white solid. $^1$H NMR (300 MHz, CD$_3$OD) δ 0.92-0.97 (m, 6H), 1.03-1.09 (m, 6H), 1.49-1.65 (m, 3H), 1.86-1.97 (m, 1H), 2.53-2.70 (m, 5H), 2.82 (dd, J=10.1, 3.0 Hz, 1H), 3.01-3.09 (m, 1H); $^{13}$C NMR (CD$_3$OD) δ 12.0, 12.1, 18.7, 19.1, 20.0, 20.1, 20.4, 31.1, 31.3, 55.9, 56.6; MS (ESI) m/z 187.2 (M+H)$^+$.

Synthesis of E5. To a solution of the diamine E4 (544 mg, 2.1 mmol) in dichloromethane (45 mL) was added Boc-7-hydroxy-D-Tic-OH (677 mg, 2.31 mmol), EDC (483 mg, 2.52 mmol), HOBt (35.3 mg, 0.23 mmol) and TEA (0.7 mL, 5.04 mmol). The mixture was stirred at room temperature overnight. Aqueous NaHCO$_3$ (30 mL) was added to the mixture and the organic product extracted with DCM (3×30 mL). The combined organic layers were dried (anhydrous Na$_2$SO$_4$), filtered through Celite and concentrated in vacuo. Purification of the residue on silica gel eluted with CMA 80/CH$_2$Cl$_2$ provide the desired product E5 (864.8 mg, 89% yield). $^1$H NMR (CDCl$_3$) δ 0.76-0.85 (m, 12H), 1.26-1.34 (m, 4H), 1.50 (s, 9H), 1.95-2.40 (m, 7H), 2.95-3.02 (dd, J=6.7, 4.7 Hz, 1H), 3.16 (d, J=11.4 Hz, 1H), 3.47 (s, 1H), 3.69 (br. s., 1H), 4.38-4.67 (m, 3H), 5.90-6.00 (m, 1H), 6.59 (s, 1H), 6.67 (d, J=9.5 Hz, 1H), 6.95 (d, J=8.7 Hz, 1H); δ; $^{13}$C NMR (CDCl$_3$) δ 11.8, 16.9, 18.8, 19.6, 28.3, 28.4, 28.9, 30.0, 31.1, 44.9, 50.3, 51.9, 54.2, 55.9, 56.7, 81.5, 113.1, 114.7, 123.9, 124.1, 129.0, 134.2, 155.6, 172.0; MS (ESI) m/z 462.8 (M+H)$^+$.

(3R)—N-{(1S)-1-[(Dipropylamino)methyl]-2-methylpropyl}-7-hydroxy-1,2,3,4-tetrahydroisoquinoline-3-carboxamide (8) Dihydrochloride. Compound E5 was subjected to Boc cleavage using HCl (4M in 1,4-dioxane) and stirred at room temperature overnight. The solvent was removed under reduced pressure and the residue purified on silica gel eluted with CMA 80/CH$_2$Cl$_2$ to provide the hydrochloride salt of final compound (8). Analysis for the free base. $^1$H NMR (300 MHz, CD$_3$OD) δ 0.88-1.04 (m, 12H), 1.43-1.56 (m, 4H), 1.91-1.97 (m, 1H), 2.33-2.64 (m, 6H), 2.74-2.82 (m, 1H), 2.92-2.99 (dd, J=5.2, 3.4 Hz, 1H), 3.37 (s, 1H) 3.53-3.58 (dd, J=10.7, 4.5 Hz, 1H), 3.92 (d, J=2.2 Hz, 1H), 3.90-4.30 (m, 1H), 6.50 (d, J=2.9 Hz, 1H), 6.61 (dd, J=8.3, 2.9 Hz, 1H), 6.91 (d, J=8.1 Hz, 1H); $^{13}$C NMR (CD$_3$OD) δ 12.3, 17.7, 19.3, 20.3, 20.8, 21.0, 31.6, 32.3, 48.1, 53.0, 56.0, 57.2, 57.4, 58.3, 113.3, 115.1, 125.6, 130.9, 137.3, 156.9, 175.4; MS (ESI) m/z 362.4 M+H)$^+$. A white solid was obtained as hydrochloride salt of (8): mp 160° C.; [α]$^{25}_D$=+55.1 (c 1.1, CH$_3$OH). Anal. (C$_{21}$H$_{37}$Cl$_2$N$_3$O$_2$.2.0H$_2$O) C, H, N.

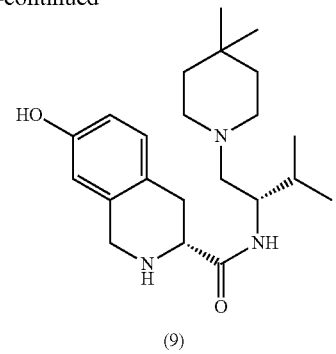

(9)

$^a$Reagents and conditions: a) N-Boc-L-Valine, HBTU, CH$_3$CN, rt, overnight; b) HCl in 1,4-dioxane, CH$_3$CN, rt, 3 h; c) BH$_3$·SMe$_2$, THF, reflux, 3 h; d) Boc-7-hydroxy-D-Tic(OH), EDC·HCl, HOBt, NEt$_3$, CH$_2$Cl$_2$, rt, overnight.

Synthesis of F3. 4,4-Dimethylpiperidine (F1) (598 mg, 3.99 mmol) and N-Boc-L-valine (944mg, 5.2 mmol) were coupled according to procedure General Method 1 to provide compound F2 (1.24 g, 100%). Compound F2 was the subjected to the General Method 2 for the removal of Boc group to provide compound F3 (800 mg, 99%). $^1$H NMR (300 MHz, CD$_3$OD) δ 0.80-1.49 (m, 12 H), 1.49-1.82 (m, 2H), 2.00 (br. s., 1H), 2.55-3.08 (m, 4H), 3.25-3.72 (m, 5H); $^{13}$C NMR (CD$_3$OD) δ 19.6, 21.8, 29.9, 30.6, 31.9, 40.4, 43.7, 46.7, 50.7, 52.3, 57.7, 168.1; MS (ESI) m/z 213.2 M+H)$^+$.

Synthesis of F4. A solution of compound F3 (1.142 g, 5.38 mmol) in THF (40 mL) was subjected to the reduction of the amide group using borane dimethyl sulfide (1 mL, 10.7mmol) following the protocol described in General Method 3 to provide 764 mg (74%) of the diamine F4. $^1$H NMR (300 MHz, CD$_3$OD) δ 1.01-1.36 (m, 12 H), 1.57-1.82 (m, 2H), 2.00 (br. s., 1H), 2.75-2.94 (m, 4H), 3.08-3.31 (m, 3H), 3.31-3.59 (m, 3H); $^{13}$C NMR (CD$_3$OD) δ 18.7, 19.2, 28.4, 29.1, 31.3, 38.7, 48.0, 50.1, 51.4, 54.7, 59.1, 62.9; MS (ESI) m/z 198.6 M+H)$^+$.

Synthesis of F5. The diamine F4 (764 mg, 2.82 mmol) in dichloromethane (50 mL) was coupled with Boc-7-hydroxy-D-Tic-OH (826 mg, 2.82 mmol) following the protocol described in General Method 4 to provide 673 mg (50%) of the product F5. $^1$H NMR (CDCl$_3$) δ 0.78-0.88 (m, 12H), 1.18-1.35 (m, 3H), 1.50 (s, 9H), 1.00-1.93 (m, 1H), 2.05-2.27 (m, 4H) 2.78-2.88 (m, 1H), 2.83 (s, 1H), 2.96-3.02 (dd, J=6.0, 14.6 Hz, 1H), 3.19-3.24 (d, J=14.2 Hz, 1H), 3.79 (br. s., 1H), 4.39-4.57 (m, 2H), 4.71-4.88 (m, 1H), 5.92-6.22 (m, 1H), 6.54 (s, 1H), 6.66 (dd, J=2.6, 8.4 Hz, 1H), 6.97 (d, J=8.2 Hz, 1H); $^{13}$C NMR (CDCl$_3$) δ 17.4, 19.0, 28.1, 28.2, 28.4 (3Cs), 29.6, 30.2, 30.7, 38.5, 38.6, 44.8, 50.0, 51.3, 54.5, 56.5, 59.3, 81.5, 113.0, 114.8, 124.2, 129.2, 134.0, 155.6, 171.4; MS (ESI) m/z 474.7 M+H)$^+$.

(3R)—N-{(1S)-1-[(4,4-Dimethylpiperidin-1-yl)methyl]-2-methylpropyl}-7-hydroxy-1,2,3,4-tetrahydroisoquinoline-3-carboxamide (9) Dihydrochloride. Compound F5 (673 mg, 1.42 mmol) in acetonitrile (20 mL) was subjected to Boc cleavage following the General Method 2 to provide the hydrochloride salt (390 mg) of final compound (9). $^1$H NMR (300 MHz, CD$_3$OD) δ 0.91-1.05 (m, 12H), 1.14-1.24 (m, 1H), 1.46-1.63 (m, 4H), 1.82-1.91 (m, 1H), 2.74-2.99 (m, 6H), 3.36 (s, 1H) 3.61-3.76 (m, 2H), 3.93-4.16 (m, 3H), 4.09 (d, J=3.3 Hz, 1H), 4.16-4.21 (m, 1H), 6.52 (d, J=2.6 Hz, 1H), 6.65 (dd, J=8.4, 2.6 Hz, 1H), 6.96 (d, J=8.6 Hz, 1H); $^{13}$C NMR (CD$_3$OD) δ 18.3, 18.5, 20.0, 28.3, 29.0, 31.9, 32.6, 38.0, 47.9, 50.0, 51.1, 51.6, 57.1, 58.1, 61.0, 113.4, 115.3,

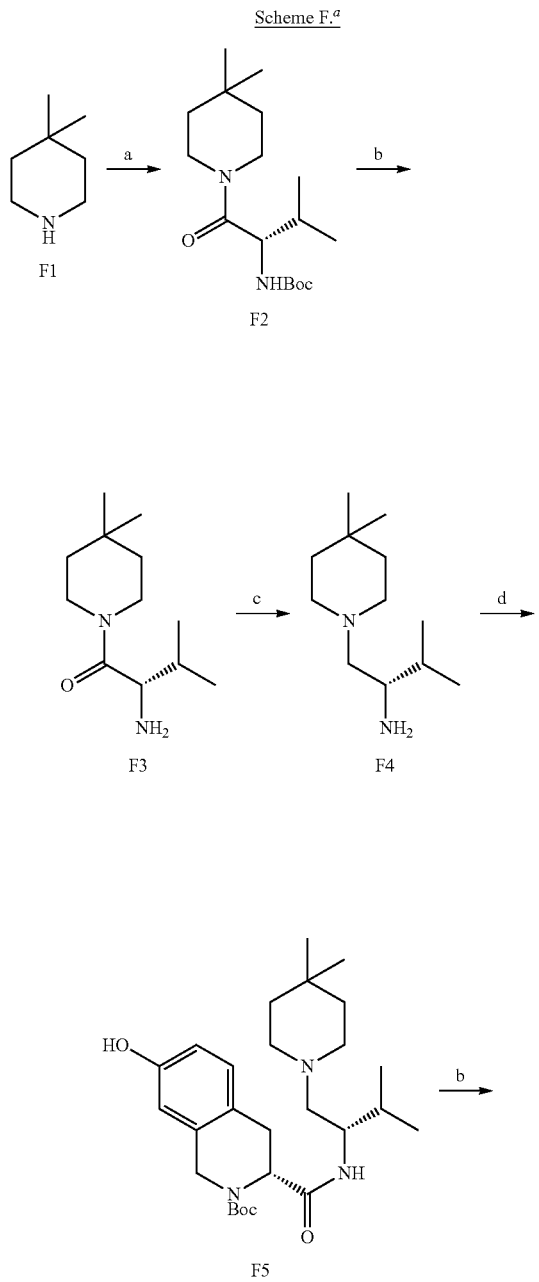

Scheme F.$^a$

F1

F2

F3

F4

F5

125.1, 131.0, 136.4, 157.0, 175.2; MS (ESI) m/z 374.5 M+H)+. A white solid was obtained as hydrochloride salt of (9): mp 192-195° C.; [α]$^{25}_D$=+73.7 (c 1.1, CH$_3$OH). Anal. (C$_{22}$H$_{37}$C$_2$N$_3$O$_2$.1.25 H$_2$O) C, H, N.

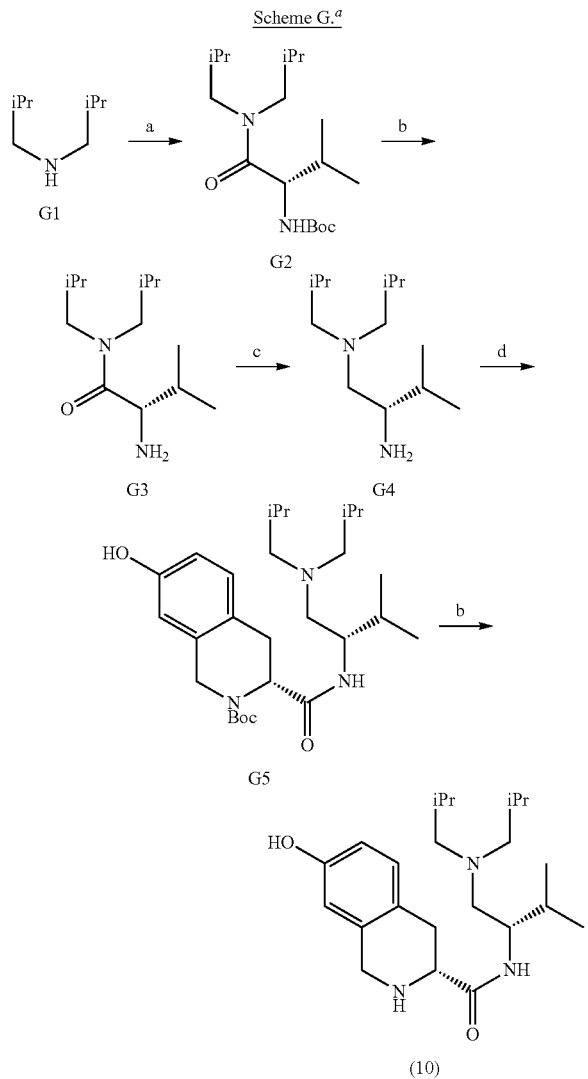

(10)

$^a$Reagents and conditions: a) N-Boc-L-Valine, HBTU, CH$_3$CN, rt, overnight; b) HCl in 1,4-dioxane, CH$_3$CN, rt, 3 h; c) BH$_3$•SMe$_2$, THF, reflux, 3 h; d) Boc-7-hydroxy-D-Tic(OH), EDC•HCl, HOBt, NEt$_3$, CH$_2$Cl$_2$, rt, overnight.

Synthesis of G2. Diisobutylamine (800 mg, 6.19 mmol) (G1) and N-Boc-L-valine (1.75 g, 8.05 mmol) were coupled according to procedure General Method 1 to provide compound G2 (1.91 g, 98%). $^1$H NMR (300 MHz, CDCl$_3$) δ 0.85-0.98 (m, 18H), 1.42 (s, 9H), 1.91-208 (m, 3H), 2.68-2.75 (dd, J=7.6, 13.3 Hz 1 H), 3.06-3.13 (dd, J=6.4, 14.6 Hz 1 H), 3.22-3.29 (dd, J=8.8, 15.6 Hz 1 H), 3.64-3.71 (dd, J=7.3, 13.3 Hz 1 H), 4.46-4.51 (dd, J=5.8, 9.2 Hz 1 H), 5.30 (d, J=9.2 Hz 1H); $^{13}$C NMR (CDCl$_3$) δ 17.0, 19.2, 19.6, 19.9, 20.1, 20.2, 26.3, 27.7, 28.1 (3 C's), 31.9, 53.1, 54.9, 55.3, 78.9, 155.5, 172.4; MS (ESI) m/z 329.4 M+H)+.

Synthesis of G3. Deprotection of the Boc group was accomplished as compound G2 was the subjected to the General Method 2 to provide the amide G3 (1.66 g, 94%). $^1$H NMR (300 MHz, CDCl$_3$) δ0 0.77-1.36 (m, 18H), 1.98-2.08 (m, 3H), 2.60-2.80 (m, 2H), 2.80-3.50 (m, 2H) 3.45-3.85 (m, 2H), 4.22 (m, 1H); $^{13}$C NMR (CDCl$_3$) δ 16.6, 19.9, 20.1, 20.2, 20.6, 20.7, 26.4, 27.7, 30.1, 50.3, 53.6, 55.9, 168.5; MS (ESI) m/z 229.5 M+H)+.

Synthesis of G4. A solution of compound G3 (1.66 g, 7.26 mmol) in THF (40 mL) was subjected to the reduction of the amide group using borane dimethyl sulfide (1.4 mL, 14.5 mmol) following the protocol described in General Method 3 to provide a hygroscopic diamine G4. $^1$H NMR (300 MHz, CD$_3$OD) δ 0.77-1.36 (m, 18H), 1.62-1.87 (m, 2H), 1.95-2.08 (m, 1H), 2.18-2.37 (m, 4H) 2.42-2.58 (m, 1H), 2.62-2.73 (m, 1H) 6,68-7.72 (br s, 2H (NH); $^{13}$C NMR (CD$_3$OD) δ 18.9, 19.0, 21.5, 26.4, 27.2, 30.5, 56.4, 57.3, 65.0; MS (ESI) m/z 215.4 M+H)+.

Synthesis of G5. The diamine G4 (865 mg, 2.82 mmol) in dichloromethane (30 mL) was coupled with Boc-7-hydroxy-D-Tic-OH (803 mg, 2.74 mmol) following the protocol described in General Method 4 to provide 537 mg (40%) of the product G5. $^1$H NMR (CDCl$_3$) δ 0.70-0.96 (m, 18H), 1.46-1.70 (m, 3H), 1.50 (s, 9H), 1.90-2.18 (m, 6H), 2.05 (s, 1H) 2.25-2.50 (m, 3H), 2.51-2.78 (m, 2H), 2.95-3.02 (dd, J=6.2, 16.2 Hz, 1H), 3.17-3.24 (dd, J=3.8, 15.6 Hz, 1H), 3.77 (br. s., 1H), 4.43-4.55 (m, 2H), 4.70-4.85 (m, 1H), 6.25-6.40 (m, 1H), 6.61 (s, 1H), 6.66 (dd, J=2.6, 8.3 Hz, 1H), 6.94 (d, J=8.2 Hz, 1H), 7.78 (br. s., (NH), 1H); $^{13}$C NMR (CDCl$_3$) δ 15.7, 19.6, 20.8, 20.9, 26.3, 26.4, 28.0, 28.4 (3Cs), 29.4, 31.4, 44.9, 52.0, 56.6, 56.9, 64.1, 81.5, 113.1, 114.8, 124.3, 129.0, 134.3, 155.6, 171.8; MS (ESI) m/z 490.7 M+H)+.

(3R)—N-{(1S)-1-{[Bis(2-methylpropyl)amino]methyl}-2-methylpropyl]-7-hydroxy-1,2,3,4-tetrahydroisoquinoline-3-carboxamide (10) Dihydrochloride. Compound G5 (655 mg, 1.34 mmol) in acetonitrile (20 mL) was subjected to Boc cleavage following the General Method 2 to provide the hydrochloride salt (332 mg, 72% yield) of final compound (10). $^1$H NMR (300 MHz, CD$_3$OD) δ 0.89-1.05 (m, 18H), 1.67-1.80 (m, 2H), 2.05-2.20 (m, 5H), 2.23-2.30 (dd, J=7 .2, 13.3 Hz, 1H), 2.48-2.55 (dd, J=7 .6, 13.4 Hz, 1H), 2.72-2.81 (dd, J=10.5, 15.8 Hz, 1H), 2.94-3.01 (dd, J=4.3, 15.8 Hz, 1H), 3.53-3.59 (dd, J=4.7, 11.5 Hz, 1H), 3.95 (s, 1H), 3.96-4.01 (m, 2H), 6.51 (d, J=2.1 Hz, 1H), 6.61 (dd, J=2.8, 8.4 Hz, 1H), 6.93 (d, J=8.6 Hz, 1H); $^{13}$C NMR (CD$_3$OD) δ 16.8, 20.5, 21.5, 27.7, 30.7, 32.4, 47.9, 53.3, 58.2, 58.9, 113.2, 115.1, 125.5, 130.8, 137.1, 156.9, 175.1; MS (ESI) m/z 374.5 M+H)+. A white solid was obtained as hydrochloride salt of (10): mp 178-180° C.; [α]$^{25}_D$=+75.5 (c 1.1, CH$_3$OH). Anal. (C$_{22}$H$_{37}$Cl$_2$N$_3$O$_2$.1.5H$_2$O) C, H, N.

Scheme H.$^a$

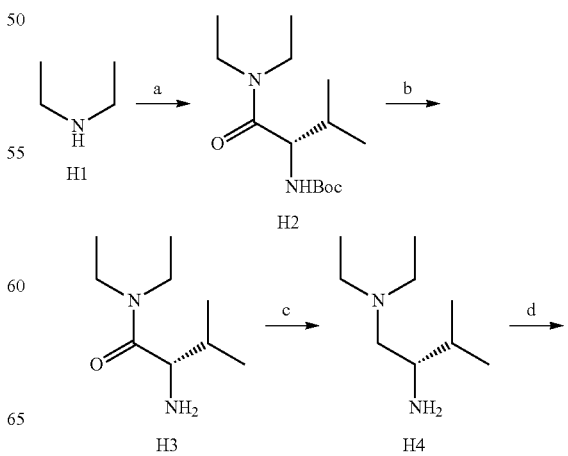

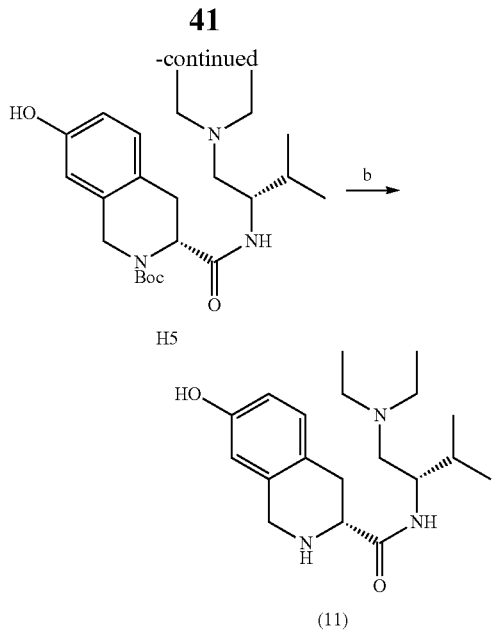

(11)

[a]Reagents and conditions: a) N-Boc-L-Valine, HBTU, CH₃CN, rt, overnight; b) HCl in 1,4-dioxane, CH₃CN, rt, 3 h; c) BH₃·SMe₂, THF, reflux, 3 h; d) Boc-7-hydroxy-D-Tic(OH), EDC·HCl, HOBt, NEt₃, CH₂Cl₂, rt, overnight.

Synthesis of H3. Diethylamine (1.07 g, 14.6 mol) (H1) and N-Boc-L-valine (3.86 g, 17.8 mol) were coupled according to procedure General Method 1 to provide compound H2 (4.0 g, 99%). $^1$H NMR (300 MHz, CDCl₃) δ 0.88-0.97 (m, 1H), 1.10-1.15 (t, J=7.1 Hz, 3H), 1.20-1.25 (t, J=7.2 Hz, 3H), 1.43 (s, 9H), 1.88-1.99 (m, 1 H), 3.11-3.22 (m, 1H), 3.24-3.52 (m, 2H), 3.56-3.67 (m, 1H), 4.35-4.40 (m, 1H), 5.26-5.29 (d, J=10.7 Hz 1H); $^{13}$C NMR (CDCl₃) δ 12.9, 14.5, 17.5, 19.5, 28.3 (3 C's), 32.0, 40.2, 42.0, 54.9, 79.2, 155.7, 171.4; MS (ESI) m/z 273.4 (M+H)⁺. Removal of the Boc-protection group was accomplished as compound H2 was the subjected to the General Method 2 to provide the hydrochloride salt of H3 (3.8 mg, 99%). $^1$H NMR (300 MHz, CDCl₃) δ 1.00-1.16 (m, 6H), 1.20-1.51 (m, 3H), 2.15-2.45 (m, 1H), 3.30-3.60 (m, 5H), 3.65-3.80 (m, 1H), 3.85-3.96 (m, 1H), 4.15-4.24 (m, 1H), 8.20-8.48 (m, 2H); $^{13}$C NMR (CDCl₃) δ 12.6, 14.1, 16.9, 19.0, 30.2, 40.4, 42.5, 55.5, 167.5; MS (ESI) m/z 173.7 M+H)⁺.

Synthesis of H4. A solution of compound H3 (4.29 g, 17.5 mmol) in THF (40 mL) was subjected to the reduction of the amide group using borane dimethyl sulfide (4.7 mL, 48.8 mmol) following the protocol described in General Method 3 to provide a very hygroscopic diamine H4. $^1$H NMR (300 MHz, CD₃OD) δ 1.01-1.18 (m, 7H), 1.37-1.52 (m, 6H), 1.90-2.16 (m, 1H), 2.08 (s, 1H), 2.29 (br s, 1H), 3.36-3.41 (m, 1H), 3.41-3.65 (m, 4H), 3.66-3.87 (m, 1H); $^{13}$C NMR (CD₃OD) δ 7.9, 8.4, 16.8, 17.0, 17.8, 18.1, 30.3, 52.3, 53.2; MS (ESI) m/z 159.3 (M+H)⁺.

Synthesis of H5. The diamine H4 (336 mg, 1.45 mmol) in dichloromethane (30 mL) was coupled with Boc-7-hydroxy-D-Tic-OH (426 mg, 1.45 mmol) following the protocol described in General Method 4 to provide 200 mg (32%) of the product H5. $^1$H NMR (CDCl₃) δ 0.78-1.07 (m, 11H), 1.18-1.35 (m, 3H), 1.24-1.31 (m, 1H), 1.49 (s, 9H), 1.83-2.12 (m, 2H), 2.05 (s, 1H) 2.25-2.50 (m, 3H), 2.51-2.78 (m, 2H), 2.95-3.02 (dd, J=6.2, 16.2 Hz, 1H), 3.17-3.24 (dd, J=3.8, 15.6 Hz, 1H), 3.77 (br s, 1H), 4.43-4.55 (m, 2H), 4.70-4.85 (m, 1H), 6.25-6.40 (m, 1H), 6.61 (s, 1H), 6.66 (dd, J=2.6, 8.3 Hz, 1H), 6.94 (d, J=8.2 Hz, 1H), 7.78 (br. s., (NH), 1H); $^{13}$C NMR (CDCl₃) δ 14.1, 17.4, 18.8, 21.0, 28.4 (3Cs), 29.4, 30.9, 44.9, 46.5, 51.7, 52.9, 56.7, 81.5, 113.2, 114.6, 124.2, 129.1, 134.1, 155.6, 171.8; MS (ESI) m/z 434.5 M+H)⁺.

(3R)—N-{(1S)-1-[(4,4-Diethylamino)methyl]-2-methyl-propyl]-7-hydroxy-1,2,3,4-tetrahydroisoquinoline-3-carboxamide (11) Dihydrochloride. Compound H5 (517 mg, 1.19 mmol) in acetonitrile (20 mL) was subjected to Boc cleavage following the General Method 2 to provide the hydrochloride salt (332 mg) of final compound (11). $^1$H NMR (300 MHz, CD₃OD) δ 0.91-1.05 (m, 6H), 1.28-1.34 (m, 5H), 1.84-1.95 (m, 1H), 2.84 3.07 (m, 2H), 3.36 (s, 1H) 3.10-3.33 (m, 5H), 3.83-3.89 (dd, J=5.1, 11.3 Hz, 1H), 4.11 (s, 1H), 4.06-4.21 (m, 2H), 6.57 (d, J=2.6 Hz, 1H), 6.68 (dd, J=8.4, 2.6 Hz, 1H), 6.98 (d, J=8.6 Hz, 1H); $^{13}$C NMR (CD₃OD) δ 9.2, 18.5, 20.0, 31.3, 32.6, 47.3, 51.2, 55.4, 58.1, 113.5, 115.7, 124.7, 131.2, 134.7, 157.2, 174.5; MS (ESI) m/z 334.5 M+H)⁺. A white solid was obtained as hydrochloride salt of (11): mp 152-155° C.; [α]$^{25}_D$=70.5 (c 1.1, CH₃OH). Anal. (C₂₂H₃₇Cl₂N₃O₂·1.25H₂O) C, H, N.

Scheme I.[a]

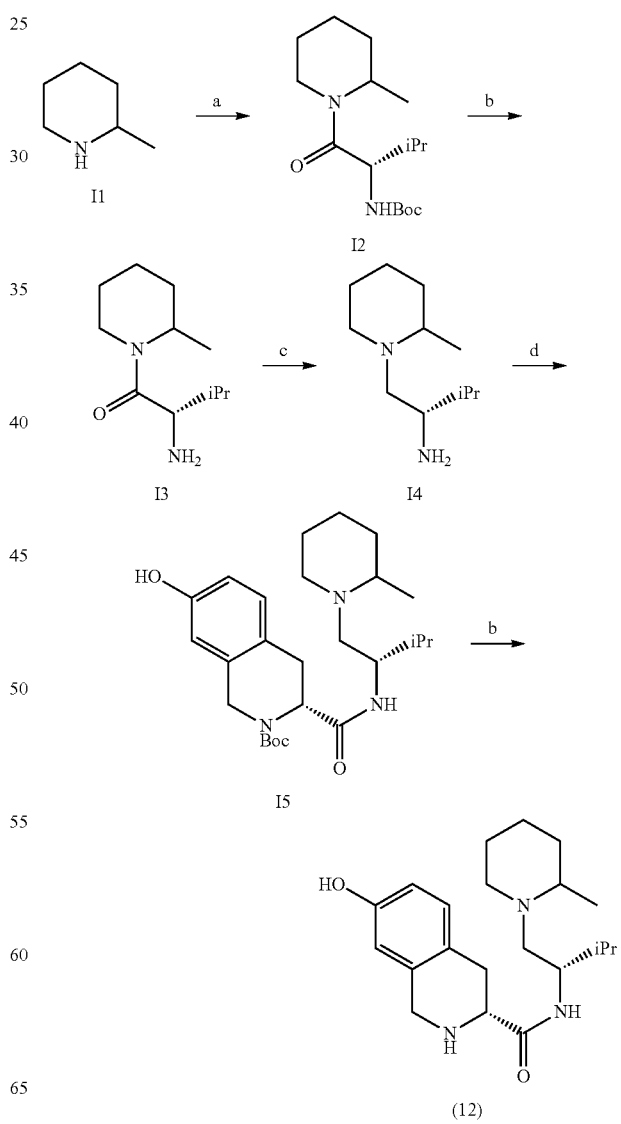

(12)

<sup>a</sup>Reagents and conditions: a) N-Boc-L-Valine, HBTU, CH<sub>3</sub>CN, rt, overnight; b) HCl in 1,4-dioxane, CH<sub>3</sub>CN, rt, 3 h; c) BH<sub>3</sub>•SMe<sub>2</sub>, THF, reflux, 3 h; d) Boc-7-hydroxy-D-Tic(OH), EDC•HCl, HOBt, NEt<sub>3</sub>, CH<sub>2</sub>Cl<sub>2</sub>, rt, overnight.

Synthesis of 12. A solution of the 2-methylpiperidine (I1) (1.56 g, 15.8 mmol) in acetonitrile (40 mL) was treated with N-Boc-L-valine (2.61 g, 12.01 mmol), HBTU (5.91 g, 4.55 mmol) and TEA (5.5 mL, 4.0 equiv) according to the General Method 1 to provide 4.5 g (95%) of compound 12. $^1$H NMR (CD$_3$OD) δ 0.88-1.01 (m, 6H), 1.16-1.20 (d, J=6.6 Hz, 2H), 1.32-1.35 (t, J=6.6 Hz, 1H), 1.45 (s, 9H), 1.58-1.77 (m, 4H), 1.92-2.02 (m, 1H), 2.04 (s, 1H), 2.53-2.64 (tt, J=13.1, 4.7, 2.0 Hz, 1H), 2.98-3.07 (m, 1H), 3.90-3.94 (d, J=11.7 Hz, 1H), 4.45-4.51 (m, 1H), 4.54-4.59 (d, J=15.4 Hz, 1H), 5.39-5.42 (d, J=5.2 Hz, 1H); $^{13}$C NMR (CD$_3$OD) δ 16.4, 18.4, 19.8, 26.9, 28.8, 31.1, 32.0, 37.9, 39.0, 42.0, 45.9, 56.7, 80.4, 157.9, 172.4; MS (ESI) m/z 299.6 M+H)$^+$.

Synthesis of 13. Removal of the Boc-protection from compound 12 was accomplished according to General Method 2 to provide 2.33 g of the amide 13 (79% yield) as a pale yellow oil. $^1$H NMR (300 MHz, CD$_3$OD) δ 0.96-1.02 (m, 3H), 1.07-1.24 (m, 4H), 1.33-1.39 (m, 2H), 1.64-1.88 (m, 4H), 2.18 (br. s., 1H), 2.83 (s, 3H), 3.24-3.36 (m, 2H), 3.76 (s, 1H), 4.26-4.40 (m, 2H); $^{13}$C NMR (CD$_3$OD) δ 16.3, 17.3, 19.6, 26.9, 30.8, 31.5, 38.4, 39.1, 42.8, 46.4, 57.0, 168.3; MS (ESI) m/z 199.6 M+H)$^+$.

Synthesis of 14. Compound 13 (2.33 g, 11.7 mmol) was treated with borane dimethyl sulfide (2.2 mL, 2.0 equiv) according to the General Method 3 to provide the diamine 14 (2.34 g, 77% yield) as a white solid. $^1$H NMR (300 MHz, CD$_3$OD) δ 1.03-1.18 (m, 6H), 1.29-1.46 (m, 3H), 1.50-1.74 (m, 4H), 1.75-2.34 (m, 6H), 2.92-3.09 (m, 1H), 3.42-3.49 (m, 1H), 3.70-3.95 (m, 2H); $^{13}$C NMR (CD$_3$OD) δ 17.6, 18.9, 22.1, 31.1, 31.7, 34.2, 35.3, 53.7, 54.2, 56.8, 59.4; MS (ESI) m/z 185.2 M+H)$^+$.

Synthesis of I5. The diamine 14 (1.37 g, 5.34 mmol) and Boc-7-hydroxy-D-Tic-OH (1.57 g, 5.34 mmol) were reacted according to the General Method 4 to provide desired product 15 (1.1 g, 44% yield). $^1$H NMR (CDCl$_3$) δ 0.74-0.96 (m, 6H), 1.02-1.29 (m, 2H), 1.30-1.45 (m, 1H), 1.50 (s, 9H), 1.65-1.69 (m, 1H), 1.78-1.98 (m, 1H) 2.10-2.60 (m, 2H), 2.82-3.05 (m, 2H), 3.13-3.23 (m, 1H), 3.63-3.85 (m, 3H) 3.98 (br. s., 1H), 4.43-4.58 (m, 2H), 4.70-4.84 (m, 1H), 5.70-6.40 (br. m., 3H) 6.48 (d, J=3.2 Hz, 1H), 6.67 (d, J=7.6 Hz, 1H) 6.95 (d, J=9.3 Hz, 1H); $^{13}$C NMR (CDCl$_3$) δ 16.4, 18.7, 23.2, 25.7, 28.4 (3Cs), 29.9, 30.7, 33.8, 34.2, 47.1, 52.2, 56.0, 62.4, 81.6, 113.1, 114.5, 124.0, 129.1, 130.0, 134.0, 135.1, 155.6, 173.4; MS (ESI) m/z 460.5 M+H)$^+$.

(3R)-7-Hydroxy-N-{(1S)-2-methyl-1-[(2-methylpiperidin-1-yl)methyl]propyl}-1,2,3,4-tetrahydroisoquinoline-3-carboxamide (12) Dihydrochloride. Compound 15 (1.1 g, 2.4 mmol) was treated according to the General Method 2 to remove the Boc-protection to provide 873 mg of the amine as the final compound (12). Analysis for the free base. $^1$H NMR (300 MHz, CD$_3$OD) δ 0.85-0.96 (m, 9H), 1.39-1.47 (m, 1H), 1.55-1.72 (m, 2H), 1.80-1.87 (m, 1H), 2.38-2.56 (m, 1H), 2.80-2.99 (m, 4H), 3.00-3.07 (m, 1H), 3.10-3.17 (m, 2H), 3.31-3.39 (m, 2H), 3.35 (s, 1H) 3.53-3.64 (m, 2H), 3.93-3.95 (dd, J=5.6, 5.2 Hz, 1H), 4.01-4.10 (m, 1H), 6.50 (d, J=2.4 Hz, 1H), 6.63 (dd, J=8.2, 2.6 Hz, 1H), 6.95 (d, J=8.3 Hz, 1H); $^{13}$C NMR (CD$_3$OD) δ 18.1, 18.5, 20.0, 31.8, 32.2, 32.6, 43.1, 50.0, 52.2, 58.3, 61.2, 61.9, 63.5, 67.0, 113.3, 115.1, 125.6, 131.0, 137.2, 175.4; MS (ESI) m/z 360.3 M+H)$^+$. A white solid was obtained as hydrochloride salt of (12): mp 164-166° C.; [α]$^{22.7}_D$=+76.2 (c 1.1, CH$_3$OH). Anal. (C$_{21}$H$_{35}$Cl$_2$N$_3$O$_2$.1.25H$_2$O) C, H, N.

Scheme J.<sup>a</sup>

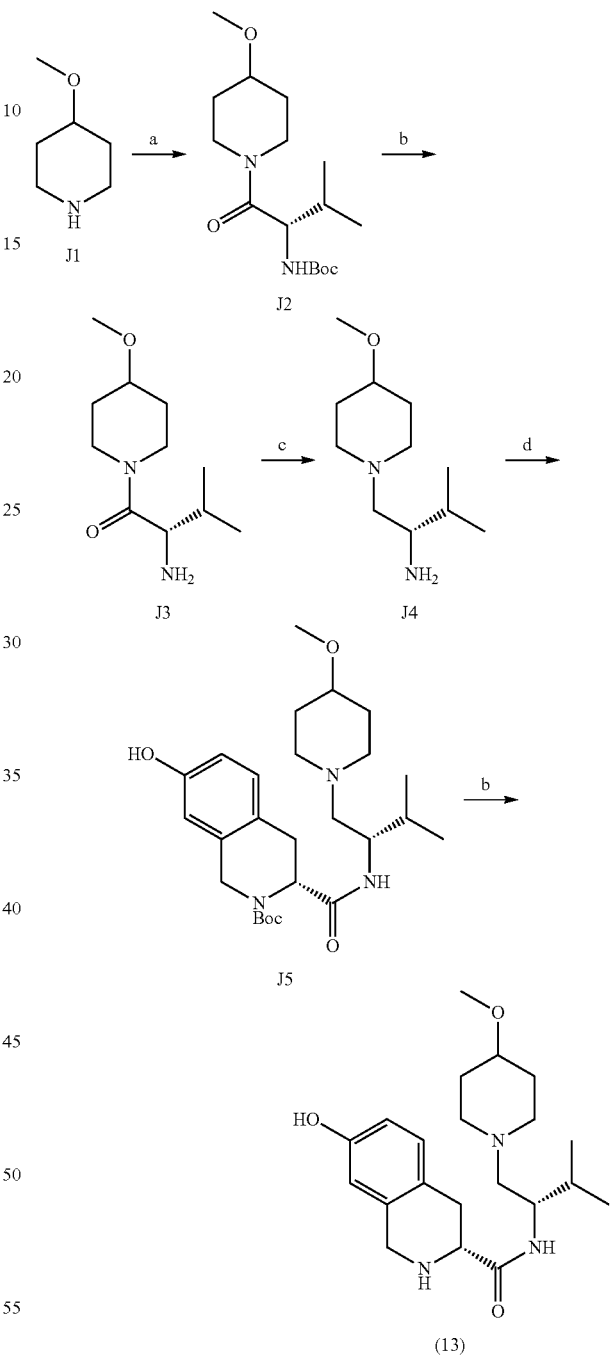

<sup>a</sup>Reagents and conditions: a) N-Boc-L-Valine, HBTU, CH<sub>3</sub>CN, rt, overnight; b) HCl in 1,4-dioxane, CH<sub>3</sub>CN, rt, 3 h; c) BH<sub>3</sub>•SMe<sub>2</sub>, THF, reflux, 3 h; d) Boc-7-hydroxy-D-Tic(OH), EDC•HCl, HOBt, NEt<sub>3</sub>, CH<sub>2</sub>Cl<sub>2</sub>, rt, overnight.

Synthesis of J2. A solution of the 4-methoxypiperidine (J1) (1.0 g, 8.68 mmol) in acetonitrile (40 mL) was treated with N-Boc-L-valine (2.1 g, 9.55 mmol), HBTU (4.28 g, 11.3 mmol) and TEA (4.8 mL, 4.0 equiv) according to the General Method 1 to provide 2.2 g (82%) of compound J2. $^1$H NMR (CD$_3$OD) δ 0.86-0.97 (m, 6H), 1.18-1.28 (m, 1H), 1.43 (s, 9H), 1.55-1.65 (m, 2H), 1.79-1.94 (m, 2H), 2.04 (s, 1H), 3.28-3.49 (m, 2H), 3.36 (s, 3H), 3.65-3.95 (m, 2H), 4.45-4.51 (m, 1H), 5.35-5.39 (d, J=5.2 Hz, 1H); $^{13}$C NMR (CD$_3$OD) δ 17.1, 19.6, 28.3 (3 C's), 30.2, 31.1, 31.6, 39.0, 42.7, 54.7, 55.8, 75.0, 79.3, 156.1, 170.4; MS (ESI) m/z 315.4 (M+H)$^+$.

Synthesis of J3. Removal of the Boc-protection from compound J2 was accomplished according to General Method 2 to provide 1.1 g of the amide J3 (70% yield). $^1$H NMR (300 MHz, CD$_3$OD) δ 0.91-1.01 (m, 6H), 1.12-1.27 (m, 1H), 1.49-1.63 (m, 2H), 1.84-1.96 (m, 3H), 2.82 (s, 1H), 3.25-3.49 (m, 2H), 3.39 (s, 3H), 3.47-3.54 (m, 1H), 3.67-3.70 (m, 1H), 3.78-4.02 (m, 2H); $^{13}$C NMR (CD$_3$OD) δ 17.2, 20.1, 31.5, 32.3, 33.3, 39.0, 40.4, 44.9, 56.1, 56.6, 76.8, 174.6; MS (ESI) m/z 215.4 M+H)$^+$.

Synthesis of J4. Compound J3 1.1 g, 4.95 mmol) was treated with borane -THF complex (49.5 mL, 1.0 M in THF) according to the General Method 3 to provide the diamine J4 (812 mg, 82% yield). $^1$H NMR (300 MHz, CD$_3$OD) δ 0.93-1.02 (m, 6H), 1.09-1.18 (m, 1H), 1.29-1.37 (m, 3H), 1.52-1.80 (m, 1H),2.70-3.00 (m, 4H) 2.83 (s, 1H), 2.89 (s, 3H), 3.18-3.44 (m, 3H), 3.43-3.62 (m, 1H); $^{13}$C NMR (CD$_3$OD) δ 17.0, 19.5, 27.6, 28.3, 31.7, 38.9, 40.7, 43.9, 56.1, 55.7, 64.2; MS (ESI) m/z 201.4 M+H)$^+$.

Synthesis of J5. The diamine J4 (766 mg, 3.57 mmol) and Boc-7-hydroxy-D-Tic-OH (1.26 g, 4.29 mmol) were reacted according to the General Method 4 to provide desired product J5 (1.6 g, 93% yield). $^1$H NMR (CDCl$_3$) δ 0.78-0.90 (m, 6H), 1.21-1.30 (m, 2H), 1.50 (s, 9H), 1.75-2.28 (m, 6H), 2.42-2.60 (m, 2H) 2.95-3.02 (m, 1H), 3.10-3.22 (m, 2H), 3.30 (s, 3H), 3.79 (br. s., 1H), 4.41-4.58 (m, 2H), 4.70-4.84 (m, 1H), 5.94 (br s, 1H) 6.63 (d, J=3.2 Hz, 1H), 6.67 (d, J=7.6 Hz, 1H) 6.97 (d, J=9.3 Hz, 1H); $^{13}$C NMR (CDCl$_3$) δ 17.4, 18.9, 28.4 (3Cs), 30.2, 30.4, 30.6, 44.8, 50.8, 51.3, 55.3, 58.8, 60.4, 81.3, 113.3, 114.9, 124.2, 129.1, 134.0, 134.0, 155.7, 171.6; MS (ESI) m/z 476.6 M+H)$^+$.

(3R)-7-Hydroxy-N-{(1S)-2-methyl-1-[(4-methoxypiperidin-1-yl)methyl]propyl}-1,2,3,4-tetrahydroisoquinoline-3-carboxamide (13) Dihydrochloride. Compound J5 (1.2 g, 2.4 mmol) was treated according to the General Method 2 to remove the Boc-protection to provide 731 mg (80% yield) of the amine as the final compound (13). Analysis for the free base. $^1$H NMR (300 MHz, CD$_3$OD) δ 0.91-0.96 (m, 6H), 1.45-1.62 (m, 2H), 1.81-1.90 (m, 3H), 2.08-2.27 (m, 2H), 2.41-2.44 (m, 2H), 2.70-2.98 (m, 4H),3.21-3.26 (m, 1H), 3.33 (s, 3H), 3.56-3.58 (m, 1H), 3.92-4.0 (m, 3H), 6.50 (d, J=2.5 Hz, 1H), 6.63 (dd, J=8.4, 2.5 Hz, 1H), 6.95 (d, J=8.4 Hz, 1H); $^{13}$C NMR (CD$_3$OD) δ 18.0, 20.0, 31.8, 32.4, 32.6, 48.0, 50.0, 52.1, 52.5, 55.8, 58.2, 61.1, 77.7, 113.3, 115.0, 125.6, 130.9, 137.4, 156.8, 175.4; MS (ESI) m/z 376.5 M+H)$^+$. A white solid was obtained as hydrochloride salt of (13): mp 184-186° C.; [α]$^{20.8}_D$=+75.1 (c 1.1, CH$_3$OH). Anal. (C$_2$H$_{35}$Cl$_2$N$_3$O$_3$.1.0 H$_2$O) C, H, N.

Scheme K.$^a$

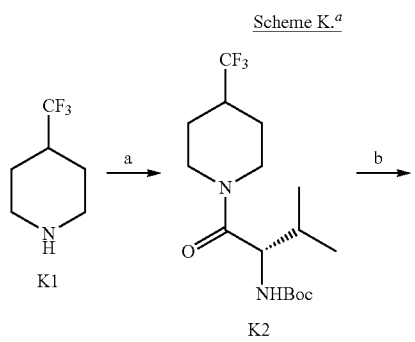

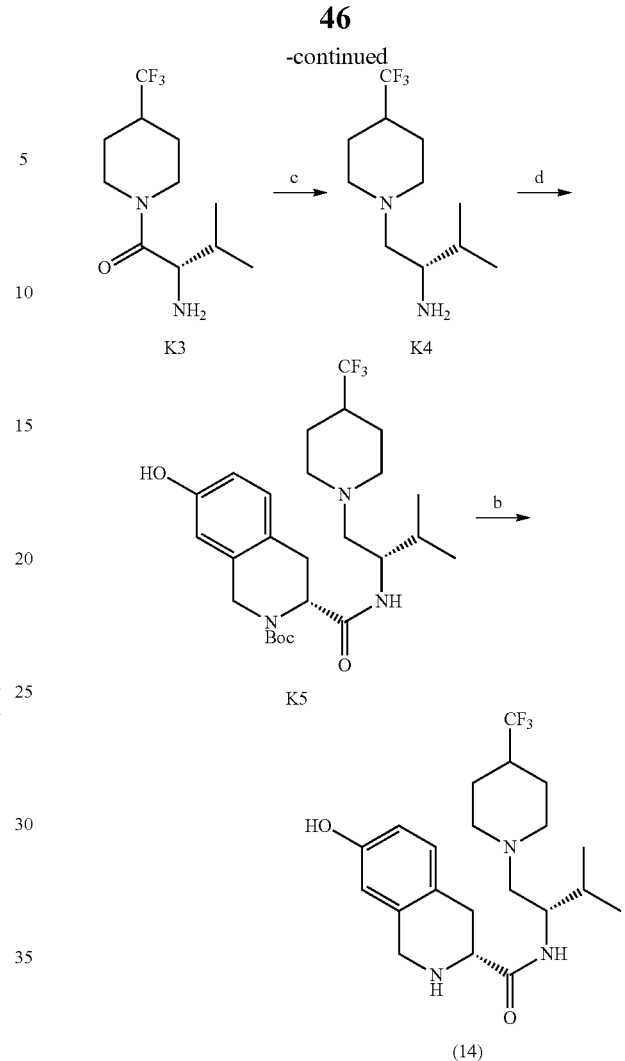

$^a$Reagents and conditions: a) N-Boc-L-Valine, HBTU, CH$_3$CN, rt, overnight; b) HCl in 1,4-dioxane, CH$_3$CN, rt, 3 h; c) BH$_3$•SMe$_2$, THF, reflux, 3 h; d) Boc-7-hydroxy-D-Tic(OH), EDC•HCl, HOBt, NEt$_3$, CH$_2$Cl$_2$, rt, overnight.

Synthesis of K2. A solution of the 4-trifluoromethylpiperidine (K1) (1.4 g, 7.40 mmol) in acetonitrile (40 mL) was treated with N-Boc-L-valine (2.1 g, 9.6 mmol), HBTU (4.28 g, 11.3 mmol) and TEA (4.8 mL, 4.0 equiv) according to the General Method 1 to provide 2.5 g (96%) of compound K2. $^1$H NMR (CD$_3$OD) δ 0.88-0.99 (m, 6H), 1.23-1.28 (m, 2H), 1.43 (s, 9H), 1.47-1.64 (m, 2H), 1.88-1.99 (m, 3H), 2.04 (s, 1H), 2.22-2.34 (m, 1H), 2.54-2.65 (m, 1H), 3.01-3.14 (m, 1H), 4.06-4.16 (m, 2H), 4.43-449 (m, 1H), 4.69-4.78 (m, 1H), 5.32-5.38 (m, 1H); $^{13}$C NMR (CD$_3$OD) δ 17.3 ($J_{CF}$=14.7 Hz), 19.6 ($J_{CF}$=12.6 Hz), 24.2 ($J_{CF}$=17.1 Hz), 25.3 ($J_{CF}$=17.1 Hz), 28.3 (3 C's), 31.4 ($J_{CF}$=9.4 Hz), 40.9 (d, $J_{CF}$=16.6 Hz), 44.8 (JcF =30.9 Hz), 54.8, 60.3, 79.5, 128.9 ($J_{CF}$=271.8 Hz), 155.9, 170.7; MS (ESI) m/z 353.5 M+H)$^+$.

Synthesis of K3. Removal of the Boc-protection from compound K2 was accomplished according to General Method 2 to provide 1.6 g of the amide K3 (100% yield). $^1$H NMR (300 MHz, CD$_3$OD) δ 0.90-1.02 (m, 6H), 1.33-1.67 (m, 2H), 1.80-2.05 (m, 3H), 2.47-2.60 (m, 1H), 2.64-2.75 (m, 1H), 3.11-3.20 (td, J=13.9, 1.2 Hz, 1H), 3.59-3.70 (m, 1H), 4.12-4.16 (d, J=13.6 Hz, 1H), 4.68-4.72 (d, J=13.4 Hz, 1H); $^{13}$C NMR (CD$_3$OD) δ 17.2, 20.1 ($J_{CF}$=22.0 Hz), 25.5 ($J_{CF}$=11.0 Hz), 26.4, 33.4, 42.1 ($J_{CF}$=27.3 Hz), 45.3, 45.8, 56.8 ($J_{CF}$=16.3 Hz), 128.6 ($J_{CF}$=272 Hz), 174.1; MS (ESI) m/z 253.2 M+H)$^+$.

Synthesis of K4. Compound K3 (2.68 g, 10.6 mmol) was treated with borane -THF complex (32 mL, 1.0 M in THF) according to the General Method 3 to provide the diamine K4 (1.27 g, 50% yield). $^1$H NMR (300 MHz, CD$_3$OD) δ 0.90-1.02 (m, 6H), 1.33-1.67 (m, 2H), 1.80-2.05 (m, 3H), 2.47-2.60 (m, 1H), 2.64-2.75 (m, 1H), 3.11-3.20 (td, J=13.9, 1.2 Hz, 1H), 3.59-3.70 (m, 1H), 4.12-4.16 (d, J=13.6 Hz, 1H), 4.68-4.72 (d, J=13.4 Hz, 1H); $^{13}$C NMR (CD$_3$OD) δ 18.9, 19.7, 25.9, (J$_{CF}$=14.2 Hz), 30.5, 33.1, 41.3 (J$_{CF}$=40 Hz), 52.4, 54.3 (J$_{CF}$=19.8 Hz), 56.2, 63.4 (J$_{CF}$=10.8 Hz), 129.1 (J$_{CF}$=272 Hz); MS (ESI) m/z 239.2 M+H)$^+$.

Synthesis of K5. The diamine K4 (766 mg, 3.57 mmol) and Boc-7-hydroxy-D-Tic-OH (1.26 g, 4.29 mmol) were reacted according to the General Method 4 to provide desired product K5 (1.6 g, 93% yield). $^1$H NMR (CDCl$_3$) δ 0.79-0.87 (m, 6H), 1.21-1.30 (m, 2H), 1.51 (s, 9H), 1.63-2.02 (m, 6H), 2.10-2.20 (m, 2H), 2.62-2.78 (m, 2H) 2.95-3.02 (dd, J=13.8, 6.6 Hz, 1H), 3.18-3.24 (d, J=16.8 Hz, 1H), 3.81 (br. s., 1H), 4.38-4.55 (m, 2H), 4.70-4.84 (m, 1H), 5.82-6.17 (m, 1H), 6.60 (d, J=3.2 Hz, 1H), 6.68 (d, J=7.6 Hz, 1H) 6.98 (d, J=9.3 Hz, 1H); $^{13}$C NMR (CDCl$_3$) δ 17.1, 19.1, 24.5, 28.3 (3Cs), 29.9, 39.5 (J$_{CF}$=27.6 Hz), 40.2 (J$_{CF}$=23.2 Hz), 44.9, 51.3, 52.1, 52.6, 59.4, 60.4, 81.1, 113.0, 114.8, 124.1, 127.5 (J$_{CF}$=272 Hz), 129.1, 134.0, 155.6, 171.3; MS (ESI) m/z 514.6 M+H)$^+$.

(3R)-7-Hydroxy-N-[(1S)-2-methyl-1-{[4-(trifluoromethyl)piperidin-1-yl]methyl}propyl]-1,2,3,4-tetrahydroisoquinoline-3-carboxamide (14) Dihydrochloride. Compound K5 (1.6 g, 3.03 mmol) was treated according to the General Method 2 to remove the Boc protection to provide 1.1 g (88% yield) of the amine as the final compound (14). Analysis for the free base. $^1$H NMR (300 MHz, CD$_3$OD) δ 0.89-1.04 (m, 6H), 1.50-1.65 (m, 2H), 1.81-1.98 (m, 4H), 2.04-2.12 (m, 2H), 2.40-2.47 (m, 2H), 2.78-3.09 (m, 4H), 3.56-3.61 (dd, J=7.7, 2.9 Hz, 1H), 3.89-4.03 (m, 3H), 6.51 (d, J=2.4 Hz, 1H), 6.63 (dd, J=8.4, 2.4 Hz, 1H), 6.95 (d, J=8.4 Hz, 1H); $^{13}$C NMR (CD$_3$OD) δ 18.0, 20.0, 25.7, 32.3, 32.4, 41.1, 47.8, 52.5, 53.0, 54.2, 58.2, 61.2, 113.3, 115.1, 125.5, 120.9 (JcF =272 Hz), 130.9, 137.4, 156.8, 175.4; MS (ESI) m/z 376.5 M+H)$^+$. A beige solid was obtained as hydrochloride salt of (14): mp 200-203° C.; [α]$^{22.4}_D$=+67.1 (c 2.01, CH$_3$OH). Anal. (C$_{21}$H$_{32}$C$_{12}$F$_3$N$_3$O$_3$·1.0 H$_2$O) C, H, N.

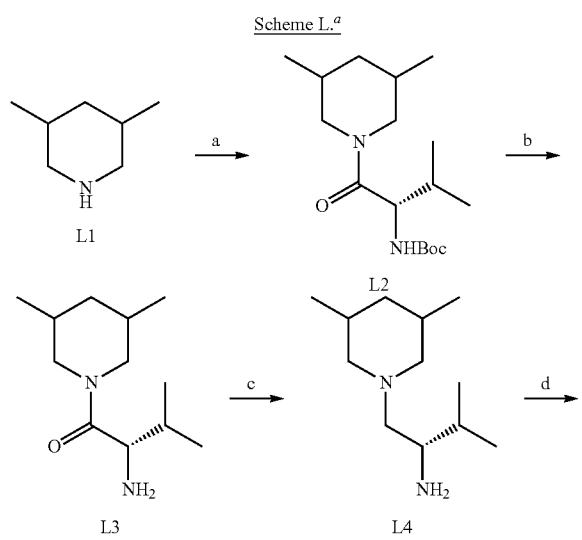

Scheme L.$^a$

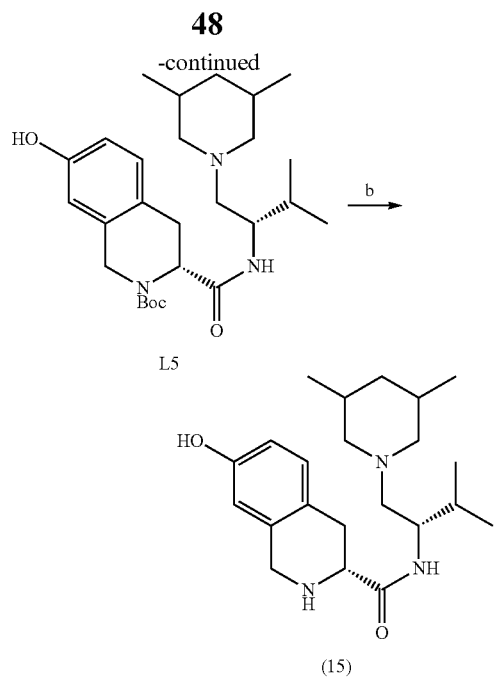

$^a$Reagents and conditions: a) N-Boc-L-Valine, HBTU, CH$_3$CN, rt, overnight; b) HCl in 1,4-dioxane, CH$_3$CN, rt, 3 h; c) BH$_3$·SMe$_2$, THF, reflux, 3 h; d) Boc-7-hydroxy-D-Tic(OH), EDC·HCl, HOBt, NEt$_3$, CH$_2$Cl$_2$, rt, overnight.

Synthesis of L2. A solution of the 3,5-dimethylpiperidine (L1) (1.4 g, 12.3 mmol) in acetonitrile (60 mL) was treated with N-Boc-L-valine (2.9 g, 13.6 mmol), HBTU (6.1 g, 16 mmol) and TEA (7 mL, 4.0 equiv) according to the General Method 1 to provide compound L2. A small amount of L2 was purified for analysis while the rest was subjected to Boc deprotection. Analysis for compound L2; $^1$H NMR (CD$_3$OD) δ 0.78-0.99 (m, 12H), 1.46 (s, 9H), 1.52-1.66 (m, 1H), 1.82-1.89 (m, 1H), 1.94-2.03 (m, 1H), 2.08-2.17 (td, J=13.1, 2.0 Hz, 1H), 2.56-2.66 (td, J=13.1, 5.1 Hz, 1H), 2.82 (m, 3H), 3.98-4.07 (d, J=7.9 Hz, 1H), 4.33-4.53 (m, 2H); $^{13}$C NMR (CD$_3$OD) δ 18.3, 19.5, 20.2, 28.8 (3 C's), 32.1, 32.4, 33.5, 39.0, 43.5, 50.5, 54.9, 56.8, 80.5, 157.8, 172.0; MS (ESI) m/z 313.6 M+H)$^+$.

Synthesis of L3. Removal of the Boc-protection from compound L2 was accomplished according to General Method 2 to provide 2.05 g of the amide L3 (78% yield over two steps). $^1$H NMR (300 MHz, CD$_3$OD) δ 0.80-1.21 (m, 12H), 1.55-1.88 (m, 2H), 2.01-2.21 (m, 2H), 2.70-2.91 (m, 3H), 3.37-3.98 (m, 4H), 4.42-4.49 (m, 1H); $^{13}$C NMR (CD$_3$OD) δ 17.8, 19.5, 19.7, 31.3, 32.7, 33.5, 39.7, 43.4, 50.8, 54.9, 56.7, 167.9; MS (ESI) m/z 213.1 M+H)$^+$.

Synthesis of L4. Compound L3 (4.3 g, 20.2 mmol) was treated with borane dimethyl sulfide complex (4.8 mL, 50.4 mmol) according to the General Method 3 to provide the diamine L4 (2.42 g, 44% yield). $^1$H NMR (300 MHz, CD$_3$OD) δ 0.80-1.12 (m, 12H), 1.55-1.88 (m, 2H), 2.01-2.21 (m, 2H), 2.70-2.91 (m, 3H), 3.37-3.98 (m, 4H), 4.42-4.49 (m, 1H); $^{13}$C NMR (CD$_3$OD) δ 17.8, 19.5, 19.7, 31.3, 32.7, 33.5, 39.7, 43.4, 50.8, 54.9, 56.7, 167.9; MS (ESI) m/z 199.0 (M+H)$^+$.

Synthesis of L5. The diamine L4 (766 mg, 3.57 mmol) and Boc-7-hydroxy-D-Tic-OH (1.26 g, 4.29 mmol) were reacted according to the General Method 4 to provide desired product L5 (1.6 g, 93% yield). $^1$H NMR (CDCl$_3$) δ 0.78-0.90 (m, 6H), 1.21-1.30 (m, 2H), 1.50 (s, 9H), 1.75-2.28 (m, 6H), 2.42-2.60 (m, 2H) 2.95-3.02 (m, 1H), 3.10-3.22 (m, 2H), 3.30 (s, 3H), 3.79 (br. s., 1H), 4.41-4.58 (m, 2H), 4.70-4.84 (m, 1H), 5.94 (br. s., 1H) 6.63 (d, J=3.2 Hz, 1H), 6.67 (d, J=7.6 Hz, 1H) 6.97 (d, J=9.3 Hz, 1H); $^{13}$C NMR (CDCl$_3$) δ 17.4, 18.9, 28.4 (3Cs), 30.2, 30.4, 30.6, 44.8, 50.8, 51.3, 55.3, 58.8, 60.4, 81.3, 113.3, 114.9, 124.2, 129.1, 134.0, 134.0, 155.7, 171.6; MS (ESI) m/z 476.6 M+H)$^+$.

(3R)—N-{(1S)-1-[(3,5-Dimethylpiperidin-1-yl)methyl]-2-methylpropyl}-7-hydroxy-1,2,3,4 tetrahydroisoquinoline-3-carboxamide (15) Dihydrochloride. Compound L5 (1.5 g, 2.43 mmol) was treated according to the General Method 2 to remove the Boc-protection to provide 845 mg (93% yield) of the amine as the final compound (15). Analysis for the free base. $^1$H NMR (300 MHz, CD$_3$OD) δ 0.91-0.96 (m, 6H), 1.45-1.62 (m, 2H), 1.07-1.09 (m, 3H), 1.13-1.18 (t, J=7.0 Hz, 1H), 1.25-1.35(m, 2H), 1.44-1.65 (m, 4H), 1.80-1.95 (m, 1H), 2.12-2.20 (td, J=2.4, 11.4 Hz, 1H), 2.24-2.38 (m, 2H), 2.41-2.46 (dd, J=3.7, 12.6 Hz, 1H), 2.74-2.98 (m, 4H), 3.37 (s, 1H), 3.52-3.57 (dd, J=4.8, 10.2 Hz, 1H), 3.91-3.95 (m, 2H), 4.00-4.05 (m, 1H), 6.50 (d, J=2.0 Hz, 1H), 6.62 (dd, J=2.0, 8.4 Hz, 1H), 6.94 (d, J=8.4 Hz, 1H); $^{13}$C NMR (CD$_3$OD) δ 17.3, 18.1, 20.1, 26.8, 32.0, 32.8, 35.2, 48.0, 50.0, 51.9, 52.8, 53.2, 56.8, 57.8, 58.2, 113.3, 115.0, 125.6, 130.9, 137.5, 156.8, 175.3; MS (ESI) m/z 374.2 M+H)$^+$. A white solid was obtained as hydrochloride salt of (15): mp 158° C.; $[α]^{22.5}_D$=+74.5 (c 1.1, CH$_3$OH). Anal. (C$_{22}$H$_{37}$C$_2$N$_3$O$_3$·1.5 H$_2$O) C, H, N.

Synthesis of M1. The diamine D4 (401 mg, 2.18 mmol) and Boc-7-hydroxy-L-Tic-OH (491 mg, 1.67 mmol) were reacted according to the General Method 4 to provide desired product M1 (727 mg, 95% yield). $^1$H NMR (CDCl$_3$) δ 0.45-0.59 (m, 5H), 0.82-0.95 (m, 4H), 1.10-1.36 (m, 6H), 1.4-1.6 (m, 3H), 1.51 (s, 9H), 1.85-1.92 (m, 2H), 2.20-2.25 (m, 2H) 2.74-2.82 (m, 2H), 2.95-3.02 (m, 1H), 3.18-3.24 (dd, J=2.5, 15.3 Hz, 1H), 3.83 (br. s., 1H), 4.40-4.58 (m, 2H), 4.69-4.79 (br. s., 1H), 5.90-6.30 (m, 1H), 6.64 (s, 1H), 6.67 (d, J=8.3 Hz, 1H), 6.96 (d, J=8.1 Hz, 1H); $^{13}$C NMR (CDCl$_3$) δ 16.6, 18.5, 21.8, 28.4 (3Cs), 29.6, 30.5, 30.8, 31.4, 34.1, 45.1, 51.2, 53.8, 54.3, 57.9, 59.5, 65.8, 81.1, 113.2, 114.7, 123.9, 129.1, 134.0, 155.2, 171.8; MS (ESI) m/z 460.4 M+H)$^+$.

(3S)-7-Hydroxy-N-{(1S)-2-methyl-1-[(4-methylpiperidin-1-yl)methyl]propyl}-1,2,3,4-tetrahydroisoquinoline-3-carboxamide (16) Dihydrochloride. Compound M1 (696 mg, 1.5 mmol) was treated according to the General Method 2 for removal of the Boc-protection to provide 479 mg (88% yield) of the amine as the final compound (16). Analysis for the free base. $^1$H NMR (300 MHz, CD$_3$OD) δ 0.88-0.95 (m, 9H), 1.11-1.40 (m, 4H), 1.49-1.65 (m, 3H), 1.77-2.13 (m, 3H), 2.04-2.13 (td, J=13.6, 2.8 Hz, 1H), 2.37-2.51 (m, 2H), 2.72-2.82 (m, 2H), 2.91-2.98 (m, 2H), 3.31-3.39 (m, 1H), 3.37 (s, 1H), 3.51-3.56 (dd, J=5.3, 4.4 Hz, 1H), 3.90-4.03 (m, 3H), 6.50 (d, J=2.5 Hz, 1H), 6.60 (dd, J=8.4, 2.4 Hz, 1H), 6.90 (d, J=8.3 Hz, 1H); $^{13}$C NMR (CD$_3$OD) δ 18.1, 19.9, 22.4, 28.9, 31.9, 32.5, 35.3, 48.3, 52.4, 51.1, 54.5, 55.9, 58.3, 61.6, 113.4, 115.1, 125.7, 137.2, 135.3, 156.9, 175.6; MS (ESI) m/z 360.3 M+H)$^+$. A white solid was obtained as hydrochloride salt of (16): mp>230° C.; $[α]^{22.2}_D$=−37.0 (c 1.1, CH$_3$OH). Anal. (C$_{21}$H$_{35}$Cl$_2$N$_3$O$_2$·1.25H$_2$O) C, H, N.

Scheme M.$^a$

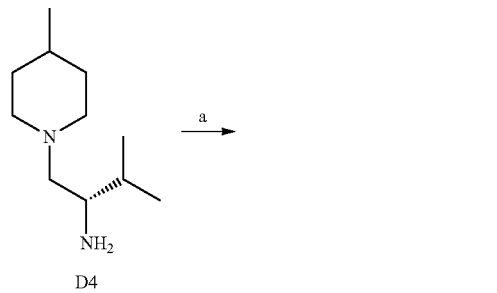

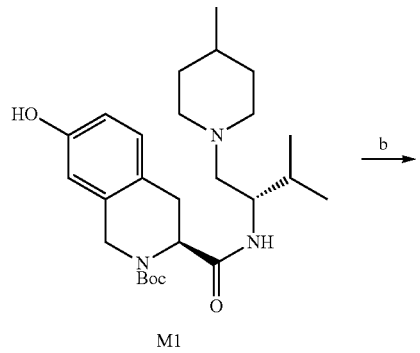

$^a$Reagents and conditions: a) Boc-7-hydroxy-L-Tic(OH), EDC•HCl, HOBt, NEt$_3$, CH$_2$Cl$_2$, rt, overnight; b) HCl in 1,4-dioxane, CH$_3$CN, rt, 3 h.

Scheme N.$^a$

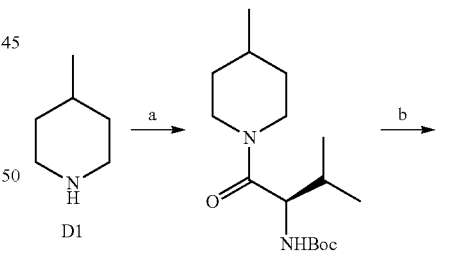

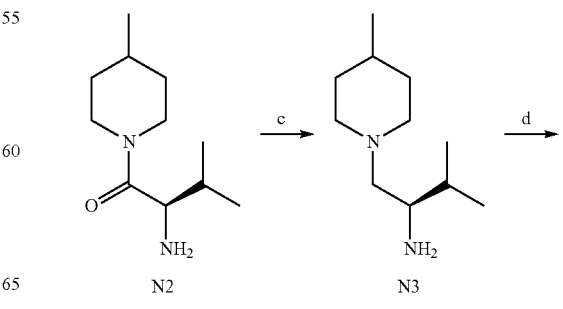

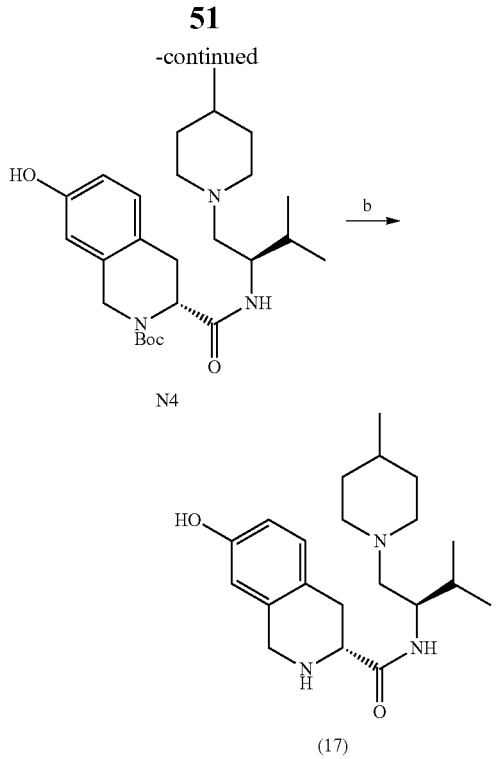

(17)

*Reagents and conditions: a) N-Boc-D-Valine, HBTU, CH₃CN, rt, overnight; b) HCl in 1,4-dioxane, CH₃CN, rt, 3 h; c) BH₃·SMe₂, THF, reflux, 3 h; d) Boc-7-hydroxy-D-Tic(OH), EDC·HCl, HOBt, NEt₃, CH₂Cl₂, rt, overnight.

Synthesis of N1. A solution of the 4-methylpiperidine D1 (2.26 g, 22.8 mmol) in acetonitrile (30 mL) was treated with N-Boc-D-valine (5.44 g, 25.1 mmol), HBTU (10.4 g, 27.4 mmol) and TEA (13 mL, 4.0 equiv) according to the General Method 1 to provide 6.6 g (97%) of compound N1. $^1$H NMR (CDCl$_3$) δ 0.84-0.89 (m, 3H), 0.93-0.98 (m, 6H), 1.02-1.15 (m, 2H), 1.44 (s, 9H), 1.56-1.78 (m, 3H), 1.87-1.95 (m, 1H), 2.55-2.63 (tt, J=13.1, 4.7, 2.0 Hz, 1H), 2.98-3.10 (m, 1H), 3.89-3.94 (d, J=11.7 Hz, 1H), 4.46-4.58 (m, 2H), 5.38-5.41 (d, J=5.2 Hz, 1H); $^{13}$C NMR (CDCl$_3$) δ 17.0, 19.8, 21.6, 28.4 (3 C's), 31.1, 31.6, 33.8, 34.7, 42.4, 45.9, 54.7, 79.3, 155.9, 170.3; MS (ESI) m/z 299.5 M+H)$^+$.

Synthesis of N2. Compound N1 (6.6 g, 22.1 mmol) in acetonitrile was treated with HCl (4M in 1,4-dioxane, (22 mL, 4 equiv) according to the General Method 2 to provide 4.0 g (100%) of N2. $^1$H NMR (300 MHz, CD$_3$OD) δ 0.73-0.99 (m, 9H), 1.00-1.12 (m, 2H), 1.42-1.62 (m, 3H), 1.75 (s, 1H), 1.89-2.02 (m, 1H), 2.18 (br. s., 1H), 2.46-2.56 (t, J=9.4 Hz, 1H), 2.90-2.99 (td, J=13.4, 4.8 Hz, 1H), 3.74-3.78 (d, J=11.2 Hz, 1H), 4.04-4.13 (m, 1H), 4.24-4.32 (t, J=7.4 Hz, 1H); $^{13}$C NMR (CD$_3$OD) δ 17.7, 19.9 22.4, 31.5, 32.2, 35.0, 35.9, 43.9, 47.3, 56.4, 169.3; MS (ESI) m/z 199.1 M+H)$^+$.

Synthesis of N3. A solution of N2 (4.0 g, 20.1 mmol) in THF (40 mL) was treated with borane dimethyl sulfide (3.8 mL, 40.2 equiv) according to the General Method 3 to provide 1.14 g of the diamine N3 (low yield obtained due to an accidental spillage). $^1$H NMR (300 MHz, CD$_3$OD) δ 0.94-1.03 (m, 9H), 1.20-1.45 (m, 3H), 1.65-1.78 (m, 3H), 1.89-1.96 (td, J=11.0, 3.0 Hz, 1H), 2.20-2.26 (td, J=14.0, 3.0 Hz, 1H), 2.33-2.46 (m, 2H), 2.81-2.90 (m, 2H), (d, J=14.5 Hz, 1H), 3.34-3.37 (m, 2H); $^{13}$C NMR (CD$_3$OD) δ 19.0, 19.2, 22.3, 31.9, 32.3, 35.3, 35.4, 54.0, 54.7, 56.8, 58.4; MS (ESI) m/z 185.3 M+H)$^+$.

Synthesis of N4. The diamine N3 (377 mg, 2.04 mmol) and Boc-7-hydroxy-D-Tic-OH (599 mg, 2.04 mmol) were reacted according to the General Method 4 to provide desired product N4 (689 mg, 73% yield). $^1$H NMR (CDCl$_3$) δ 0.45-0.59 (m, 3H), 0.85-0.95 (m, 3H), 1.12-1.33 (m, 6H), 1.4-1.6 (m, 3H), 1.51 (s, 9H), 1.85-1.92 (m, 2H), 2.20-2.25 (m, 2H) 2.74-2.82 (m, 2H), 2.95-3.02 (m, 1H), 3.18-3.24 (dd, J=2.5, 15.3 Hz, 1H), 3.83 (br. s., 1H), 4.40-4.58 (m, 2H), 4.71-4.80 (br. s., 1H), 5.97-6.41 (m, 1H), 6.65 (s, 1H), 6.67 (d, J=8.3 Hz, 1H), 6.95 (d, J=8.1 Hz, 1H); $^{13}$C NMR (CDCl$_3$) δ 16.6, 18.5, 21.8, 28.4 (3Cs), 29.6, 30.5, 30.8, 31.4, 34.1, 45.1, 51.2, 53.8, 54.3, 57.9, 59.5, 65.8, 81.1, 113.2, 114.7, 123.9, 129.1, 134.0, 155.2, 171.8; MS (ESI) m/z 460.4 M+H)$^+$.

(3R)-7-Hydroxy-N-{(1R)-2-methyl-1-[(4-methylpiperidin-1-yl)methyl]propyl}-1,2,3,4-tetrahydroisoquinoline-3-carboxamide (17) Dihydrochloride. Compound N4 (689 mg, 1.5 mmol) was treated according to the General Method 2 for removal of the Boc-protection to provide 348 mg (64% yield) of the amine as the final compound (17). Analysis for the free base. $^1$H NMR (300 MHz, CD$_3$OD) δ 0.88-0.95 (m, 9H), 1.11-1.40 (m, 4H), 1.49-1.65 (m, 3H), 1.77-2.13 (m, 3H), 2.04-2.13 (td, J=13.6, 2.8 Hz, 1H), 2.37-2.51 (m, 2H), 2.72-2.82 (m, 2H), 2.91-2.98 (m, 2H), 3.31-3.39 (m, 1H), 3.37 (s, 1H), 3.51-3.56 (dd, J=5.3, 4.4 Hz, 1H), 3.90-4.03 (m, 3H), 6.50 (d, J=2.5 Hz, 1H), 6.60 (dd, J=8.4, 2.4 Hz, 1H), 6.90 (d, J=8.3 Hz, 1H); $^{13}$C NMR (CD$_3$OD) δ 18.1, 19.9, 22.4, 28.9, 31.9, 32.5, 35.3, 48.3, 52.4, 51.1, 54.5, 55.9, 58.3, 61.6, 113.4, 115.1, 125.7, 137.2, 135.3, 156.9, 175.6; MS (ESI) m/z 360.3 M+H)$^+$. A white solid was obtained as hydrochloride salt of (17): mp>228° C.; [α]$^{22}_D$=+36.6 (c 1.1, CH$_3$OH). Anal. (C$_{21}$H$_{35}$Cl$_2$N$_3$O$_2$·1.0H$_2$O) C, H, N.

Scheme O.$^a$

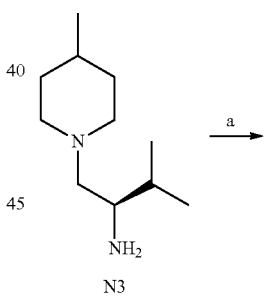

N3

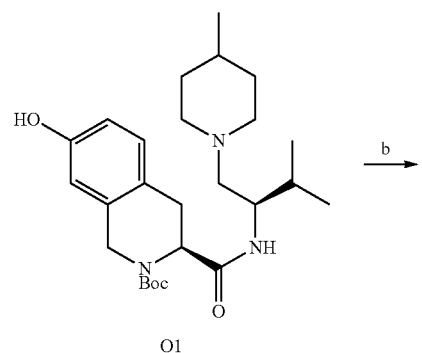

O1

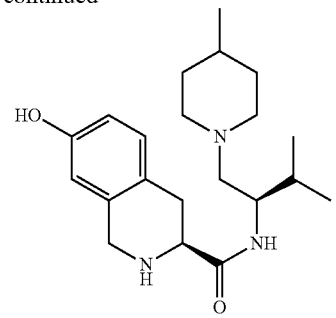

(18)

<sup>a</sup>Reagents and conditions: a) Boc-7-hydroxy-L-Tic(OH), EDC•HCl, HOBt, NEt₃, CH₂Cl₂, rt, overnight; b) HCl in 1,4-dioxane, CH₃CN, rt, 3 h.

Synthesis of O1. The diamine N3 (353 mg, 1.92 mmol) and Boc-7-hydroxy-L-Tic-OH (511 mg, 1.74 mmol) were reacted according to the General Method 4 to provide desired product O1 (428 mg, 53.5% yield). $^1$H NMR (CDCl$_3$) δ 0.78-0.87 (m, 6H), 1.01-1.25 (m, 2H), 1.4-1.6 (m, 3H), 1.50 (s, 9H), 1.70-1.85 (m, 2H), 2.20-2.23 (m, 2H) 2.50-2.61 (m, 1H), 2.94-3.02 (m, 1H), 3.16-3.23 (dd, J=2.5, 15.3 Hz, 1H), 3.86 (br. s., 1H), 4.40-4.61 (m, 2H), 4.70-4.85 (br. s., 1H), 6.00-6.29 (m, 1H), 6.60 (s, 1H), 6.68 (d, J=8.3 Hz, 1H), 6.96 (d, J=8.1 Hz, 1H); $^{13}$C NMR (CDCl$_3$) δ 17.4, 19.0, 21.8, 28.4 (3Cs), 30.3, 30.5, 34.0, 31.4, 34.1, 45.1, 51.2, 53.4, 54.3, 58.1, 59.3, 81.1, 113.1, 114.7, 124.0, 129.1, 134.0, 156.0, 171.6; MS (ESI) m/z 460.4 M+H)$^+$.

(3S)-7-Hydroxy-N-{(1R)-2-methyl-1-[(4-methylpiperidin-1-yl)methyl]propyl}-1,2,3,4-tetrahydroisoquinoline-3-carboxamide (18) Dihydrochloride. Compound O1 (428 mg, 0.935 mmol) was treated according to the General Method 2 for removal of the Boc-protection to provide 266 mg (79% yield) of the amine as the final compound (18). Analysis for the free base. $^1$H NMR (300 MHz, CDCl$_3$) δ 0.86-0.95 (m, 9H), 1.31-1.53 (m, 3H), 1.60-1.72 (m, 2H), 1.77-1.88 (m, 1H), 2.16-2.24 (t, J=10.9 Hz, 1H), 2.35-2.42 (t, J=10.9 Hz, 1H), 2.53-2.68 (m, 2H), 2.80-2.87 (dd, J=3.8, 15.8 Hz, 1H), 3.12-3.16 (d, J=11.6 Hz, 1H), 3.35-3.42 (m, 2H), 3.65-3.73 (m, 2H), 4.11-4.23 (br. s., 1H), 5.2-5.4 (m, 3H), 6.49 (s, 1H), 6.64 (d, J=11.2, Hz, 1H), 6.82 (d, J=8.4 Hz, 1H), 7.55-7.58 (d, J=8.4 Hz, 1H); $^{13}$C NMR (CDCl$_3$) δ 18.1, 19.2, 21.3, 29.8, 30.0, 31.4, 32.1, 47.4, 49.4, 52.3, 55.2, 57.0, 58.0, 59.5, 112.3, 114.1, 124.4, 130.2, 136.0, 155.1, 173.6; MS (ESI) m/z 360.3 M+H)$^+$. A pale-yellow solid was obtained as hydrochloride salt of (18): mp >230° C.; [α]$^{22.6}_D$=−77.0 (c 1.1, Anal. (C$_{21}$H$_{35}$Cl$_2$N$_3$O$_2$·0.5H$_2$O) C, H, N.

Scheme P.$^a$

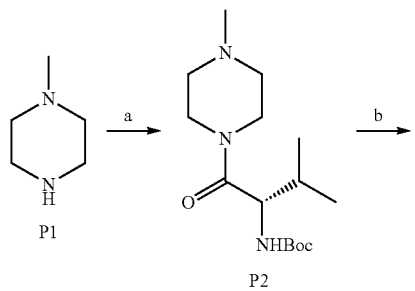

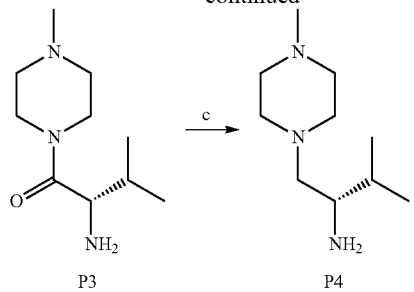

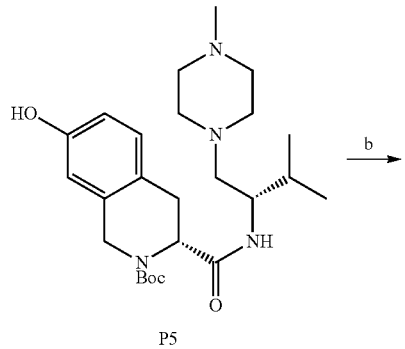

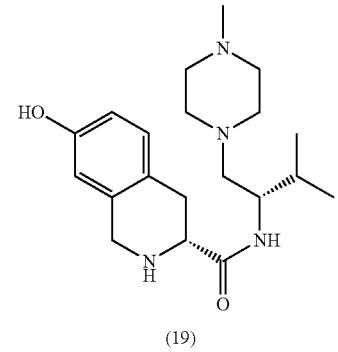

(19)

$^a$Reagents and conditions: a) N-Boc-L-Valine, HBTU, CH₃CN, rt, overnight; b) HCl in 1,4-dioxane, CH₃CN, rt, 3 h; c) BH₃•SMe₂, THF, reflux, 3 h; d) Boc-7-hydroxy-D-Tic(OH), EDC•HCl, HOBt, NEt₃, CH₂Cl₂, rt, overnight.

Synthesis of P2. A solution of the 4-methylpiperazine (P1) (2.13 g, 21.3 mmol) in acetonitrile (40 mL) was treated with N-Boc-D-valine (5.10 g, 23.4 mmol), HBTU (10.4 g, 25.6 mmol) and TEA (12 mL, 4.0 equiv) according to the General Method 1 to provide 6.4 g (100%) of compound P2. $^1$H NMR (CDCl$_3$) δ 0.84-0.96 (m, 6H), 1.17-1.23 (m, 1H), 1.45 (s, 9H), 1.88-1.94 (m, 1H), 2.35 (s, 3H), 2.42-2.55 (m, 3H), 3.54-3.76 (m 4H), 4.44 (br. s., 1H), 5.44 (d, J=8.2 Hz, 1H); $^{13}$C NMR (CDCl$_3$) δ 17.0, 19.6, 28.2 (3 C's), 31.4, 38.5, 41.6, 45.3, 45.6, 54.5, 54.9, 79.3, 155.7, 170.4; MS (ESI) m/z 300.4 M+H)$^+$.

Synthesis of P3. Compound P2 (6.4 g, 22.1 mmol) in acetonitrile was treated with HCl (4M in 1,4-dioxane, (27 mL, 4 equiv) according to the General Method 2 to provide 4.2 g (100%) of P3. $^1$H NMR (300 MHz, CD3OD) δ 0.91-1.00 (m, 6H), 1.80-1.91 (m, 1H), 2.33 (s, 3H), 2.42-2.51 (m, 4H), 3.59-3.72 (m, 5H); $^{13}$C NMR (CD$_3$OD) δ 17.2, 20.2, 22.4, 33.4, 42.8, 46.1, 46.4, 55.7, 56.2, 56.6, 175.1; MS (ESI) m/z 200.6 M+H)$^+$.

Synthesis of P4. A solution of P3 (4.0 g, 20.3 mmol) in THF (40 mL) was treated with borane dimethyl sulfide (4 mL, 40.6 equiv) according to the General Method 3 to provide 2.68 g (71%) of the diamine P4. $^1$H NMR (300 MHz, CD3OD) δ 0.94-0.97 (m, 6H), 1.54-1.66 (m, 1H), 2.21-2.30 (m, 2H), 2.30 (s, 3H), 2.32-2.40 (m, 2H), 2.42-2.68 (m, 5H), 2.69-2.77 (m, 2H); $^{13}$C NMR (CD$_3$OD) δ 18.8, 19.4, 32.9, 46.1, 54.1, 56.1, 58.3, 63.1; MS (ESI) m/z 186.2 M+H)$^+$.

Synthesis of P5. The diamine P4 (937 mg, 5.06 mmol) and Boc-7-hydroxy-D-Tic-OH (1.6 g, 5.31 mmol) were coupled using HBTU as described in the General Method 1 to provide desired product P5 (1.82 g mg, 78% yield). $^1$H NMR (CDCl$_3$) δ 0.45-0.59 (m, 3H), 0.85-0.95 (m, 3H), 1.12-1.33 (m, 6H), 1.4-1.6 (m, 3H), 1.51 (s, 9H), 1.85-1.92 (m, 2H), 2.20-2.25 (m, 2H) 2.74-2.82 (m, 2H), 2.95-3.02 (m, 1H), 3.18-3.24 (dd, J=2.5, 15.3 Hz, 1H), 3.83 (br. s., 1H), 4.40-4.58 (m, 2H), 4.71-4.80 (br. s., 1H), 5.97-6.41 (m, 1H), 6.65 (s, 1H), 6.67 (d, J=8.3 Hz, 1H), 6.95 (d, J=8.1 Hz, 1H); $^{13}$C NMR (CDCl$_3$) δ 16.6, 18.5, 21.8, 28.4 (3Cs), 29.6, 30.5, 30.8, 31.4, 34.1, 45.1, 51.2, 53.8, 54.3, 57.9, 59.5, 65.8, 81.1, 113.2, 114.7, 123.9, 129.1, 134.0, 155.2, 171.8; MS (ESI) m/z 460.4 M+H)$^+$.

(3R)-7-Hydroxy-N-{(1S)-2-methyl-1-[(4-methylpiperizin-1-yl)methyl]propyl}-1,2,3,4-tetrahydroisoquinoline-3-carboxamide (19) Trihydrochloride. Compound P5 (689 mg, 1.5 mmol) was treated according to the General Method 2 for removal of the Boc-protection to provide 348 mg (64% yield) of the amine as the final compound (19). Analysis for the free base. $^1$H NMR (300 MHz, CD3OD) δ 0.93-0.96 (m, 6H), 1.78-1.87 (m, 1H), 2.45-2.57 (m, 3H), 2.48 (s, 3H), 2.60-2.80 (m, 6H), 2.87-3.08 (m, 2H), 3.78-3.82 (dd, J=5.0, 4.4 Hz, 1H), 3.95-4.01 (m, 1H), 4.07-4.16 (m, 2H), 6.56 (d, J=2.5 Hz, 1H), 6.66 (dd, J=8.4, 2.4 Hz, 1H), 6.97 (d, J=8.3 Hz, 1H); $^{13}$C NMR (CD$_3$OD) δ 18.3, 18.5, 20.2, 31.8, 32.2, 45.1, 47.1, 52.6, 52.8, 55.4, 57.7, 58.4, 60.7, 113.5, 115.6, 124.7, 131.1, 135.4, 157.1, 174.0; MS (ESI) m/z 360.3 M+H)$^+$. A white solid was obtained as HCl salt of (19). Mp >240° C.; [α]$^{22}_D$=+71.2 (c 1.1, CH$_3$OH) Anal. (C$_{20}$H$_{35}$Cl$_3$N$_4$O$_2$·1.75H$_2$O) C, H, N.

Scheme Q.$^a$

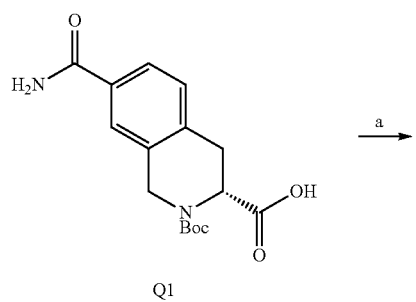

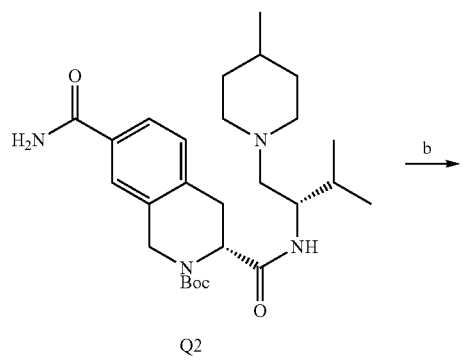

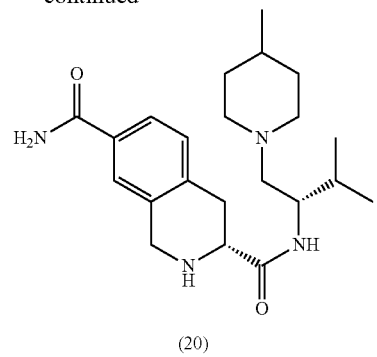

$^a$Reagents and conditions: a) D4, HBTU, CH$_3$CN, rt, overnight; b) HCl in 1,4-dioxane, CH$_3$CN, rt, 3 h.

Synthesis of Q2. The synthesis of Boc-7-carbamoyl-D-Tic(OH) (Q1) was accomplished in three steps as previously reported in the literature.[29] Consequently, Q1 (854 mg, 2.67 mmol) and diamine D4 (590 mg, 3.2 mmol) were coupled using HBTU as described in the General Method 1 to provide Q2 (993.4 mg, 77% yield). $^1$H NMR (CDCl$_3$) δ 0.82-0.94 (m, 9H), 1.52 (s, 9H), 1.67-1.82 (m, 3H), 2.02-2.07 (m, 2H) 2.64-2.71 (m, 1H), 2.80-3.20 (m, 6H), 3.17-3.29 (m, 1H), 3.31-3.52 (m, 2H), 3.94 (br. s., 1H), 4.41-4.46 (d, J=12.4 Hz, 1H), 4.72-4.85 (m, 1H), 6.07 (m, 1H), 6.74-6.86 (m, 1H), 7.24-7.34 (m, 2H), 7.60-7.78 (m, 2H); $^{13}$C NMR (CDCl$_3$) δ 19.1, 21.0, 28.2 (3Cs), 30.7, 31.5, 45.4, 47.1, 51.1, 55.4, 60.4, 63.4, 81.8, 111.1, 118.0, 126.9, 128.0, 134.1, 137.9, 169.3, 171.6, 174.4; MS (ESI) ink 487.5 M+H)$^+$.

(3R)—N$^3$-{(1S)-2-methyl-1-[(4-methylpiperidin-1-yl)methyl]propyl}-1,2,3,4-tetrahydroisoquinoline-3,7-dicarboxamide (20) Dihydrochloride. Compound Q2 (993.4 mg, 2.04 mmol) was treated according to the General Method 2 for removal of the Boc-protection to provide 795 mg (100% yield) of the amine as the final compound (20). Analysis for the free base. $^1$H NMR (300 MHz, CD$_3$OD) δ 0.98-1.01 (m, 9H), 1.35-1.55 (m, 3H), 1.62-1.74 (m, 1H), 1.85-1.93 (m, 2H), 19.5-1.98 (m, 2H), 2.80-2.90 (m, 1H), 2.92-3.10 (m, 2H), 3.12-3.29 (m, 2H), 3.40-53 (m, 2H), 3.76 (br. s., 1H), 4.04-4.21 (m, 2H), 7.22-7.25 (d, J=9.0 Hz, 1H), 7.61 (s, 1H), 7.69 (d, J=9.2 Hz, 1H); $^{13}$C NMR (CD$_3$OD) δ 18.0, 19.3, 21.9, 31.8, 32.0, 47.3, 50.9, 53.2, 55.0, 57.0, 58.1, 60.6, 66.5, 111.1, 118.0, 126.4, 130.1, 135.6, 138.6, 171.6, 175.3, 176.1; MS (ESI) m/z 387.4 (M+H)$^+$. An off white solid was obtained as a dihydrochloride salt of (20). mp=185-87° C.; [α]$^{22.4}_D$=+69.2 (c 1.1, CH$_3$OH) Anal. (C$_{22}$H$_{36}$Cl$_2$N$_4$O$_2$·2.0 H$_2$O) C, H, N.

Scheme R.$^a$

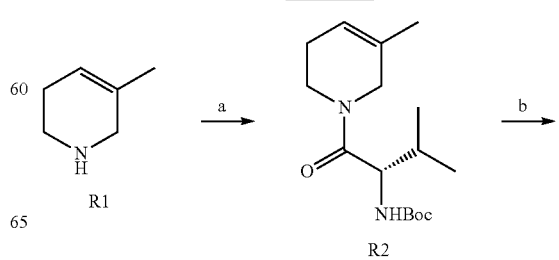

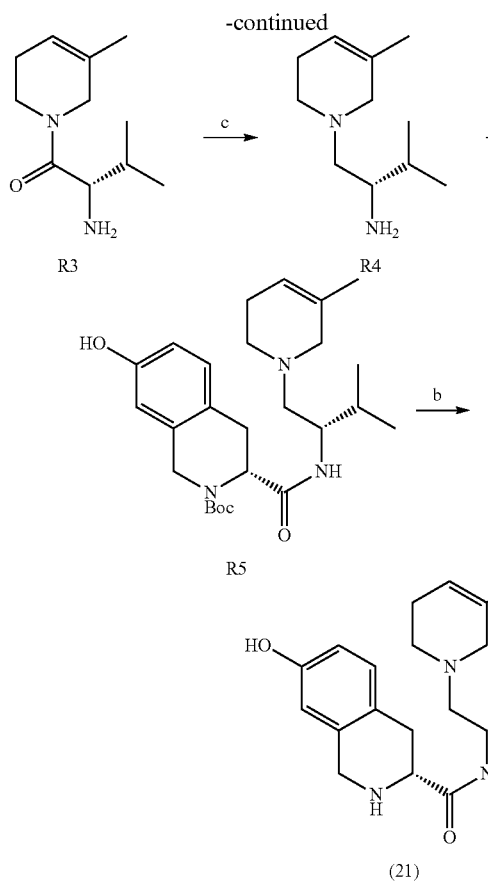

TFA). The product containing fraction was evaporated then applied to silica gel and eluted with 25% DMA80 in $CH_2Cl_2$ to afford 17.7 mg (5% over three steps) of the (21) free base: $^1$H NMR (300 MHz, CHLOROFORM-d) δ 7.10 (d, J=10.17 Hz, 1H), 6.75 (d, J=7.91 Hz, 1H), 6.26-6.38 (m, 2H), 5.49 (br. s., 1H), 4.29 (t, J=11.49 Hz, 1H), 3.61-3.75 (m, 1H), 3.51-3.61 (m, 1H), 3.12-3.30 (m, 2H), 2.65-2.95 (m, 4H), 2.26-2.54 (m, 3H), 1.92-2.18 (m, 2H), 1.66-1.88 (m, 4H), 0.84-1.04 (m, 6H); $^{13}$C NMR (75 MHz, CHLOROFORM-d) δ 173.3, 154.9, 137.4, 131.0, 130.6, 125.1, 119.9, 113.6, 111.9, 59.0, 56.6, 55.1, 49.4, 48.6, 32.1, 29.3, 24.4, 21.0, 19.2, 18.1; MS (ESI) m/z 358.3 M+H)$^+$. The free base was converted to a white powder as the dihydrochloride salt: mp 86-90° C. (fusion), $[α]^{25}_D$+77 (c 0.10, $CH_3OH$). Anal. ($C_{21}H_{33}Cl_2N_3O_2H_2O$) C, H, N.

Scheme S.$^a$

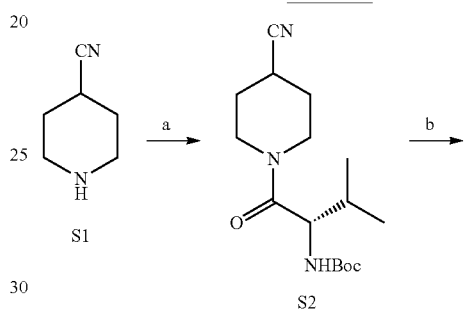

$^a$Reagents and conditions: a) N-Boc-L-Valine, HBTU, $CH_3CN$, rt, overnight; b) HCl aq., $CH_3OH$; c) LAH, THF, rt, 4 h; d) Boc-7-hydroxy-D-Tic(OH), EDC·HCl, HOBt, $NEt_3$, $CH_2Cl_2$, rt, overnight.

Synthesis of R3. The amine R1 was prepared in three steps from 3-picoline. The amine R1 (132 mg, 1.36 mmol) was treated according to General Method 1 to afford crude R2: $^1$H NMR (300 MHz, CHLOROFORM-d) δ 5.47-5.64 (m, 1H), 5.32-5.46 (m, 1H), 5.02 (s, 1H), 4.49 (d, J=9.04 Hz, 1H), 3.82-3.97 (m, 2H), 3.60 (s, 1H), 3.55 (t, J=5.75 Hz, 1H), 2.17 (br. s., 2H), 1.92 (s, 1H), 1.69 (s, 2H), 1.39-1.48 (m, 9H), 0.84-1.00 (m, 6H). The crude R2 was treated with methanol aq. HCl according to General Method 2 to afford 178 mg (67% over two steps) of the desired amine R3: $^1$H NMR (300 MHz, CHLOROFORM-d) δ 5.37-5.75 (m, 3H), 3.71-4.23 (m, 3H), 3.42-3.62 (m, 2H), 1.95-2.31 (m, 3H), 1.72 (s, 3H), 0.89-1.17 (m, 6H).

(3R)-7-Hydroxy-N-{(1S)-2-methyl-1-[(5-methyl-3,6-dihydropyridin-1(2H)-yl)methyl]propyl}-1,2,3,4-tetrahydroisoquinoline-3-carboxamide (21) Dihydrochloride. The amine R3 (178 mg, 0.91 mmol) was treated with LAH according to General Method 3 to afford the crude amine R4. A solution of Boc-7-hydroxy-D-Tic(OH) (290 mg, 1 mmol), EDC·HCl (380 mg, 2 mmol), catalytic HOBt and the crude amine R4 in $CH_2Cl_2$ (10 mL) was treated with $NEt_3$ (0.2 mL, 1.4 mmol). After 12 h, the reaction was concentrated and purified by chromatography on silica gel eluting with a gradient up to 50% DMA80 in $CH_2Cl_2$. The Boc-intermediate R5 containing fractions were concentrated and the residue dissolved in MeOH (5 mL) then treated with HCl (6 M, 5 mL). After 1 h, the reaction was concentrated. The residue was purified by reverse-phase chromatography on C-18 silica gel, eluting with 25% $CH_3CN$ in water (0.1%

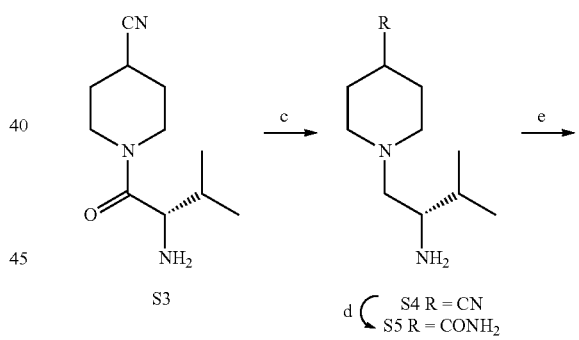

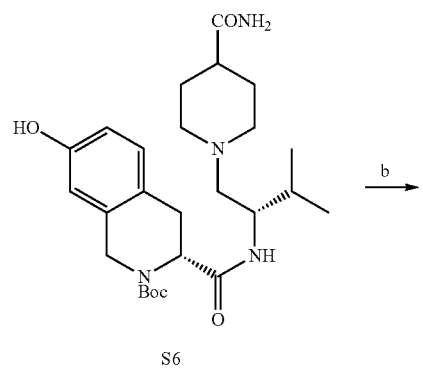

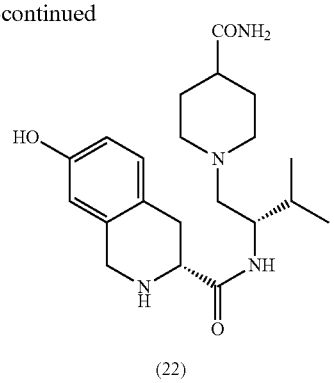

(22)

[a] Reagents and conditions: a) N-Boc-L-Valine, HBTU, CH₃CN, rt, overnight; b) HCl in 1,4-dioxane, CH₃CN, rt, 3 h; c) BH₃•SMe₂, THF, reflux, 3 h; d) i. H₂SO₄, H₂O, 0° C. then rt, 24 h; ii. NaOH e) Boc-1-hydroxy-D-Tic(OH), EDC•HCl, HOBt, NEt₃, CH₂Cl₂, rt, overnight.

Synthesis of S2. A solution of the 4-cyanopiperidine (51) (2.25 g, 20.4 mmol) in acetonitrile (60 mL) was treated with N-Boc-L-valine (5.3 g, 24.5 mmol), HBTU (9.3 g, 24.5 mmol) and TEA (11.4 mL, 4.0 equiv) according to the General Method to provide 6.12 g (97%) of compound S2 upon purification. $^1$H NMR (300 MHz, CHLOROFORM-d) δ 5.32 (d, J=8.85 Hz, 1H), 4.42 (d, J=6.41 Hz, 1H), 3.59-3.93 (m, 2H), 3.30-3.58 (m, 1H), 2.88-3.01 (m, 1H), 1.80-1.98 (m, 3H), 1.43 (br. s., 9H), 1.10-1.36 (m, 3H), 0.73-1.00 (m, 6H). $^{13}$C NMR (CD₃OD) δ 17.2, 19.6, 28.3 (3 C's), 29.1, 31.4, 38.5, 40.1, 43.6, 54.7, 79.6, 120.5, 155.6, 170.7; MS (ESI) intz 310.7 M+H)⁺.

Synthesis of S3. Removal of the Boc-protection from compound S2 was accomplished according to General Method 2 to provide 3.0 g of the amide S3 (72% yield). $^1$H NMR (300 MHz, METHANOL-d4) δ 4.03 (dd, J=5.27, 8.67 Hz, 1H), 3.69-3.93 (m, 1H), 3.46-3.68 (m, 1H), 3.35-3.46 (m, 1H), 3.03-3.25 (m, 1H), 2.76-2.89 (m, 2H), 1.73-2.10 (m, 4H), 0.85-1.15 (m, 6H); $^{13}$C NMR (CD₃OD) δ 17.3, 19.8, 27.2, 30.4, 32.2, 39.1, 41.9, 45.5, 56.5, 122.6, 171.9; MS (ESI) m/z 209.9 M+H)⁺.

Synthesis of S4. Compound S3 (3.0 g, 14.1 mmol) was treated with boranedimethyl sulfide complex (2.7 mL) according to the General Method 3 to provide the 4-cyanopiperidinediamine S4 (2.4 g, 87% yield). $^1$H NMR (300 MHz, METHANOL-d4) δ 3.13 (ddd, J=3.86, 6.45, 10.78 Hz, 1H), 2.71-2.94 (m, 2H), 2.36-2.66 (m, 4H), 2.31 (br. s., 1H), 1.73-2.07 (m, 5H), 0.92-1.16 (m, 6H); $^{13}$C NMR (CD₃OD) δ 17.0, 17.5, 25.3, 28.2, 28.3, 29.0, 50.9, 51.5, 53.8, 57.3, 121.6; MS (ESI) m/z 196.2 M+H)⁺.

Synthesis of S5. Compound S4 (1.7 g, 8.8 mmol) in CH₂Cl₂ (5 ml), cooled to 0° C. was treated with sulfuric acid (20 ml) and water (2 ml) and stirred at room temperature for 24 h. After which the mixture was neutralized with 3M NaOH until the pH of 8-9 was obtained. The organic product was extracted using CH₂Cl₂/MeOH (9:1), (3×100 ml), dried over anhydrous MgSO₄, filtered and concentrated in vacuo to provide 1.2 g (59% yield) of carboxamide S5. $^1$H NMR (300 MHz, METHANOL-d4) δ 5.29-5.45 (m, 1H), 2.91 (d, J=10.74 Hz, 1H), 2.66-2.83 (m, 1H), 2.57 (ddd, J=3.39, 6.22, 9.98 Hz, 1H), 1.93-2.30 (m, 4H), 1.51-1.90 (m, 4H), 1.44 (qd, J=6.73, 13.33 Hz, 1H), 0.69-0.97 (m, 6H); $^{13}$C NMR (75 MHz, METHANOL-d4) δ 179.7, 63.0, 55.3, 53.2, 53.1, 52.3, 42.7, 39.0, 32.1, 29.2, 29.0, 18.7, 17.9; MS (ESI) m/z 214.2 M+H)⁺.

Synthesis of S6. Compound S5 (526 mg, 2.47 mmol) and Boc-7-hydroxy-D-Tic-OH (796 mg, 2.71 mmol) were reacted according to the General Method 4 to provide desired product S6 (882 mg, 73% yield). $^1$H NMR (300 MHz, CHLOROFORM-d) δ 7.57-8.47 (m, 1H), 6.85-7.12 (m, 1H), 6.56-6.79 (m, 2H), 5.78-6.46 (m, 1H), 4.26-5.34 (m, 4H), 3.50-3.95 (m, 1H), 3.39 (d, J=15.82 Hz, 1H), 3.10-3.31 (m, 2H), 2.74-3.07 (m, 2H), 2.64 (d, J=17.14 Hz, 1H), 2.16-2.45 (m, 3H), 1.85 (dd, J=26.56, 44.27 Hz, 1H), 1.38-1.56 (m, 11H), 1.12-1.31 (m, 3H), 0.69-1.05 (m, 4H); $^{13}$C NMR (75 MHz, METHANOL-d4) δ 180.9, 161.2, 157.5, 141.8, 136.2, 129.9, 125.1, 115.4, 114.0, 82.1, 61.5, 57.9, 54.3, 52.9, 49.9, 47.5, 45.2, 43.5, 39.0, 35.9, 32.2, 29.9, 28.8 (3C's), 19.9; MS (ESI) m/z 489.5 M+H)⁺.

(3R)—N-{(1S)-1-[(4-Carbamoylpiperidin-1-yl)methyl]-2-methylprolyl}-7-hydroxy-1,2,3,4-tetrahydroisoquinoline-3-carboxamide (22) Dihydrochloride. Compound S6 (730 mg, 1.5 mmol) was treated according to the General Method 2 to remove the Boc-protection to provide 462 mg mg (80% yield) of the amine as the final compound (22). Analysis for the free base. $^1$H NMR (300 MHz, METHANOL-d4) 6.94 (d, J=8.29 Hz, 1H), 6.62 (d, J=8.10 Hz, 1H), 6.52 (d, J=2.07 Hz, 1H), 3.95 (d, J=6.22 Hz, 2H), 3.62 (q, J=6.97 Hz, 2H), 2.74-3.23 (m, 5H), 2.34-2.56 (m, 2H), 1.56-2.12 (m, 4H), 1.19 (t, J=7.06 Hz, 3H), 1.10 (t, J=7.25 Hz, 3H), 0.80-1.04 (m, 4H); $^{13}$C NMR (75 MHz, METHANOL-d4) δ 175.1, 156.9, 136.5, 131.0, 125.3, 115.3, 113.4, 65.0, 61.3, 58.0, 55.2, 53.8, 52.0, 50.0, 47.8, 47.7, 45.4, 36.7, 32.1, 29.9, 19.9; MS (ESI) m/z 388.5 (M+H)⁺. A white solid was obtained as hydrochloride salt of (22): mp 184-186° C.; $[\alpha]^{23.7}_D$=+62.2 (c 1.1, CH₃OH). Anal. (C₂₁H₃₄Cl₂N₄O₃.1.5H₂O) C, H, N.

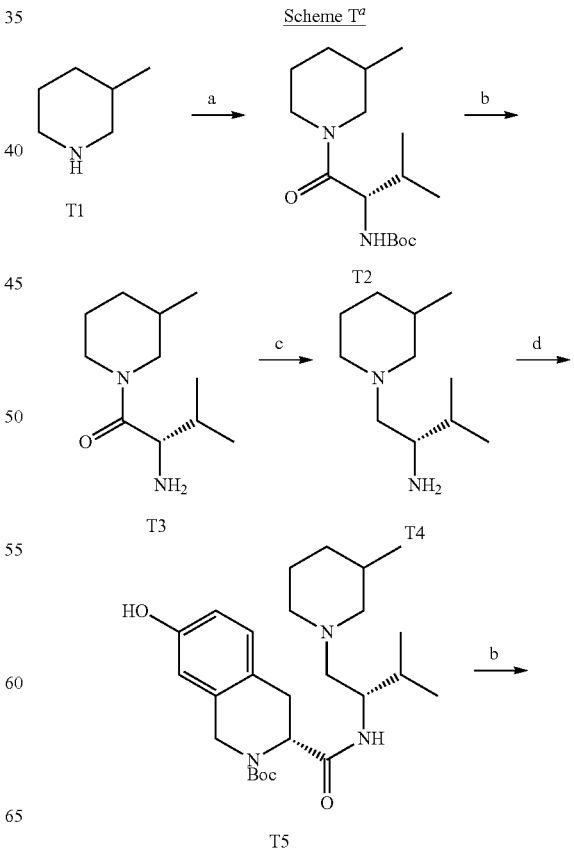

Scheme T[a]

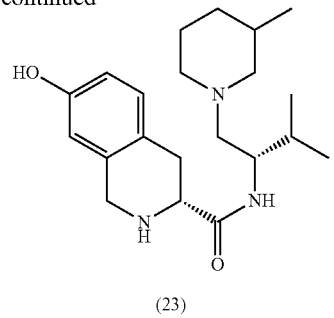

(23)

<sup>a</sup>Reagents and conditions: a) N-Boc-L-Valine, HBTU, CH₃CN, rt, overnight; b) HCl in 1,4-dioxane, CH₃CN, rt, 3 h; c) BH₃•SMe₂, THF, reflux, 3 h; d) Boc-7-hydroxy-D-Tic(OH), EDC•HCl, HOBt, NEt₃, CH₂Cl₂, rt, overnight.

Synthesis of T2. A solution of the 3-methylpiperidine (T1) (1.91 g, 19.2 mmol) in acetonitrile (40 mL) was treated with N-Boc-L-valine (2.61 g, 12.01 mmol), HBTU (5.91 g, 4.55 mmol) and TEA (5.5 mL, 4.0 equiv) according to the General Method 1 to provide 5.2 g (91%) of compound T2. $^1$H NMR (300 MHz, CHLOROFORM-d) δ 5.40 (d, J=8.29 Hz, 1H), 4.33-4.58 (m, 2H), 3.82 (br. s., 1H), 2.63 (br. s., 1H), 2.17-2.42 (m, 1H), 1.80-1.96 (m, 2H), 1.44 (s, 9H), 1.48-1.75 (m, 2H), 1.06-1.32 (m, 2H), 0.83-1.02 (m, 9H); $^{13}$C NMR (75 MHz, CHLOROFORM-d) δ 170.2, 155.9, 79.2, 54.7, 53.4, 49.5, 46.5, 42.7, 33.0, 31.8, 28.3, 25.9, 25.0, 19.7, 17.0; MS (ESI) m/z 299.1 M+H)$^+$.

Synthesis of T3. Removal of the Boc-protection from compound T2 was accomplished according to General Method 2 to provide the amide T3 (2.95 g, 85% yield) as a pale yellow oil. $^1$H NMR (300 MHz, METHANOL-d4) δ 4.17-4.57 (m, 1H), 3.76-4.03 (m, 1H), 3.39-3.74 (m, 2H), 2.94-3.18 (m, 1H), 2.53-2.84 (m, 1H), 2.29-2.50 (m, 1H), 2.07-2.28 (m, 1H), 1.66 (d, J=3.39 Hz, 2H), 1.37-1.64 (m, 1H), 1.05-1.37 (m, 3H), 0.75-1.05 (m, 6H); $^{13}$C NMR (75 MHz, METHANOL-d4) δ 174.3, 66.9, 58.3, 56.6, 43.9, 33.2, 32.6, 31.4, 26.9, 19.3, 17.1; MS (ESI) m/z 199.6 M+H)$^+$.

Synthesis of T4. Compound T3 (2.17 g, 10.9 mmol) was treated with borane dimethyl sulfide (2.1 mL, 2.0 equiv) according to the General Method 3 to provide the diamine T4 (1.1 g, 50% yield) as a foamy compound. $^1$H NMR (300 MHz, METHANOL-d4) δ 3.09-3.20 (m, 1H), 2.93-3.09 (m, 1H), 2.76-2.93 (m, 1H), 2.47-2.66 (m, 2H), 2.20-2.38 (m, 1H), 1.84-2.04 (m, 2H), 1.60-1.84 (m, 5H), 0.86-1.12 (m, 9H); $^{13}$C NMR (75 MHz, METHANOL-d4) δ 64.1, 59.6, 56.4, 55.3, 53.9, 33.7, 32.2, 31.9, 26.0, 19.2, 18.7; MS (ESI) m/z 185.1 M+H)$^+$.

Synthesis of T5. The diamine T4 (839 mg, 4.55 mmol) and Boc-7-hydroxy-D-Tic-OH (1.6 g, 5.46 mmol) were reacted according to the General Method 4 to provide desired product T5 (1.6 g, 59% yield). $^1$H NMR (300 MHz, CHLOROFORM-d) δ 6.82-7.18 (m, 2H), 6.51-6.82 (m, 3H), 5.85-6.40 (m, 1H), 4.68 (br. s., 1H), 4.50-4.64 (m, 1H), 4.29-4.49 (m, 1H), 3.65-3.92 (m, 1H), 3.08-3.34 (m, 2H), 2.81-3.08 (m, 1H), 2.58 (br. s., 2H), 1.95-2.30 (m, 2H), 1.85 (d, J=15.45 Hz, 1H), 1.69 (d, J=9.98 Hz, 1H), 1.50 (s., 9H), 1.34-1.61 (m, 4H), 0.67-0.97 (m, 9H); $^{13}$C NMR (75 MHz, CHLOROFORM-d) δ 171.6, 155.5, 134.1, 129.1, 124.0, 114.7, 113.0, 81.1, 62.6, 60.4, 59.3, 54.6, 53.2, 51.4, 44.9, 32.8, 30.7, 30.1, 28.4, 28.3 (3 C's), 25.3, 19.6, 18.8, 17.5; MS (ESI) intz 460.5 M+H)$^+$.

(3R)-7-Hydroxy-N-{(1S)-2-methyl-1-[(3-methylpiperidin-1-yl)methyl]propyl}-1,2,3,4-tetrahydroisoquinoline-3-carboxamide (23) Dihydrochloride. Compound T5 (1.24 g, 2.69 mmol) was treated according to the General Method 2 to remove the Boc-protection to provide 626 mg (65% yield) of the amine as the final compound (23). Analysis for the free base. $^1$H NMR (300 MHz, METHANOL-d4) δ 6.86-6.95 (m, 1H), 6.61 (dd,J=2.45, 8.10 Hz, 1H), 6.49 (d, J=2.26 Hz, 1H), 3.97-4.09 (m, 1H), 3.83-3.97 (m, 2H), 3.44-3.67 (m, 3H), 2.87-3.09 (m, 2H), 2.64-2.87 (m, 2H), 2.32-2.61 (m, 2H), 1.75-2.00 (m, 2H), 1.45-1.75 (m, 4H), 0.77-1.06 (m, 9H); $^{13}$C NMR (75 MHz, METHANOL-d4) δ 175.3, 156.8, 137.4, 130.9, 125.6, 115.0, 113.3, 66.9, 63.8, 62.7, 61.7, 58.2, 55.8, 54.5, 52.3, 34.0, 32.3, 26.4, 20.0, 18.5, 18.0; MS (ESI) m/z 360.4 (M+H)$^+$. A white solid was obtained as hydrochloride salt of (23): mp 178° C.; $[α]^{22.4}_D$=+75.5 (c 1.1, CH₃OH). Anal. ($C_{21}H_{35}Cl_2N_3O_2 \cdot H_2O$) C, H, N.

Scheme U.$^a$

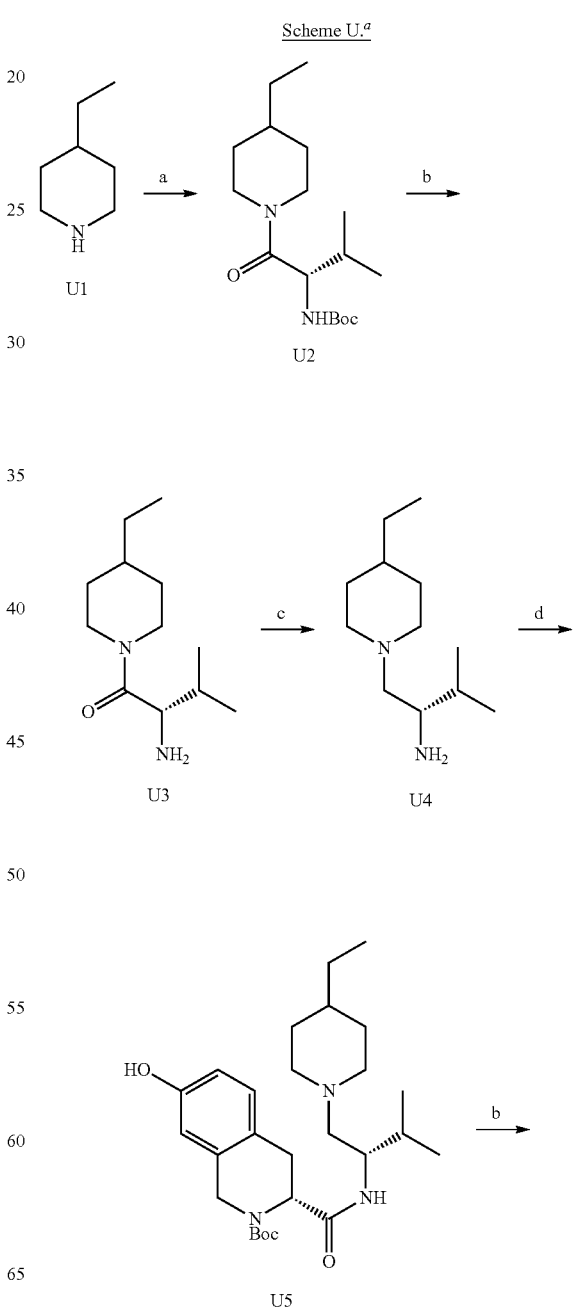

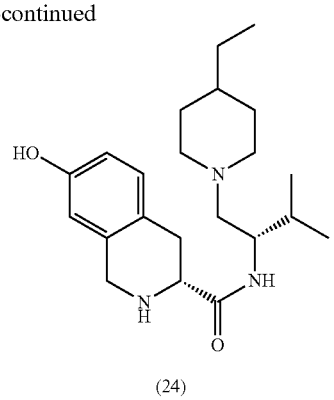

(24)

[a] Reagents and conditions: a) N-Boc-L-Valine, HBTU, CH₃CN, rt, overnight; b) HCl aq., CH₃OH; c) BH₃·SMe₂, THF, reflux, 3 h; d) Boc-7-hydroxy-D-Tic(OH), EDC·HCl, HOBt, NEt₃, CH₂Cl₂, rt, overnight.

Synthesis of U3. A solution of the 4-ethylpiperidine (111) (1.1 g, 9.7 mmol) in acetonitrile (20 mL) was treated with N-Boc-L-valine (2.2 g, 10. mmol), HBTU (3.8 g, 10. mmol) and TEA (4.2 mL, 3 equiv) according to the General Method 1 to provide compound U2 as an oil. Removal of the Boc-protection from compound U2 was accomplished with HCl in aq. Methanol according to General Method 2 to provide the amide U3 (0.25 g, 12% yield over two steps): $^1$H NMR (300 MHz, CHLOROFORM-d) δ 4.64 (d, J=11.68 Hz, 1H), 3.86 (d, J=13.00 Hz, 1H), 3.51 (t, J=5.09 Hz, 1H), 2.88-3.10 (m, 1H), 2.56 (tt, J=3.37, 12.83 Hz, 1H), 1.67-1.92 (m, 3H), 0.78-1.48 (m, 16H).

Synthesis of U4. Compound U3 (250 mg, 1.2 mmol) was treated with borane dimethyl sulfide (1 mL, 10 mmol) according to the General Method 3 to provide the diamine U4 (133 mg, 56% yield): $^1$H NMR (300 MHz, CHLOROFORM-d) δ 2.78-3.04 (m, 3H), 2.33-2.49 (m, 2H), 2.12-2.29 (m, 1H), 1.80-1.97 (m, 2H), 1.67 (d, J=10.93 Hz, 2H), 1.11-1.34 (m, 5H), 1.06 (d, J=6.78 Hz, 3H), 0.97 (d, J=6.78 Hz, 3H), 0.87 (t, J=7.25 Hz, 3H).

(3R)—N-{(1S)-1-[(4-Ethylpiperidin-1-yl)methyl]-2-methylpropyl}-7-hydroxy-1,2,3,4-tetrahydroisoquinoline-3-carboxamide (24) Dihydrochloride. The amine (133 mg, 0.67 mmol) was dissolved in CH₂Cl₂ (5 mL) and added to a solution of 7-hydroxy-Boc-D-Tic(OH) (223 mg, 0.75 mmol), EDC·HCl (306 mg, 1.5 mmol) and catalytic HOBt in CH₂Cl₂ (10 mL). The reaction mixture was stirred overnight, then was concentrated and subjected to chromatography on silica gel using a gradient up to 35% DMA80 in CH₂Cl₂. The product containing fractions were concentrated to afford U5, which was then treated with and concentrated from CH₃OH (5 mL) and HCl (6 M, 5 mL). The concentrated residue was subjected to chromatography on silica gel eluting with 1:2 DMA80 in CH₂Cl₂ to afford 77.5 mg (31%) (24) free base: $^1$H NMR (300 MHz, CHLOROFORM-d) δ 7.16-7.37 (m, 1H), 6.86 (d, J=8.29 Hz, 1H), 6.56 (dd, J=2.35, 8.19 Hz, 1H), 6.44 (d, J=2.07 Hz, 1H), 4.22 (t, J=9.89 Hz, 1H), 3.61 (s, 2H), 3.39 (d, J=10.93 Hz, 1H), 3.25 (dd, J=4.99, 11.59 Hz, 1H), 3.06 (d, J=11.11 Hz, 1H), 2.75-2.94 (m, 2H), 2.30-2.52 (m, 2H), 2.11-2.29 (m, 1H), 1.93-2.10 (m, 1H), 1.62-1.92 (m, 3H), 1.10-1.49 (m, 5H), 0.93 (d, J=6.78 Hz, 6H), 0.77-0.89 (m, 3H); $^{13}$C NMR (75 MHz, CHLOROFORM-d) δ 173.5, 155.0, 137.0, 130.5, 124.9, 113.8, 112.2, 59.7, 56.8, 55.8, 52.3, 49.5, 48.0, 36.9, 31.7, 30.7, 30.5, 29.6, 28.8, 19.0, 18.1, 11.2; MS (ESI) m/z 374.2 M+H)⁺. The free base was converted into a white powder as the dihydrochloride salt: m.p. 176-180° C. (fusion); [α]$^{25}_D$=+75.0 (c 0.20, CH₃OH). Anal. (C₂₂H₃₇Cl₂N₃O₂·H₂O) C, H, N.

Scheme V.[a]

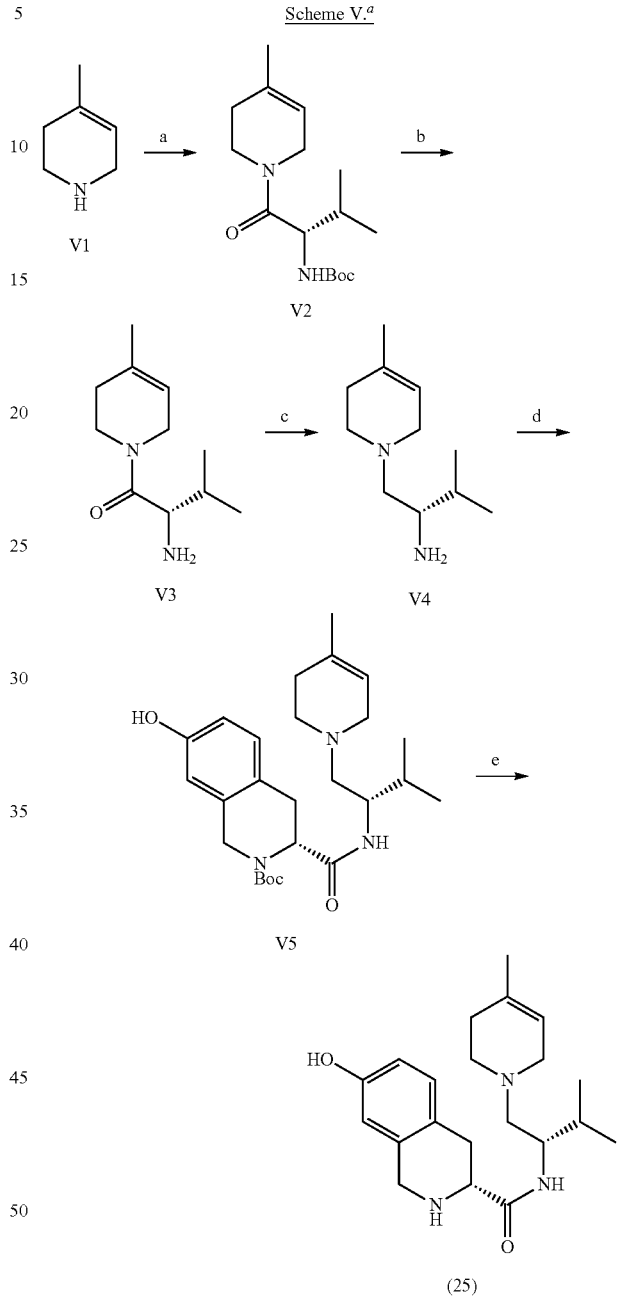

(25)

[a] Reagents and conditions: a) N-Boc-L-Valine, HBTU, CH₃CN, rt, overnight; b) HCl aq., CH₃OH; c) LAH, THF; d) Boc-7-hydroxy-D-Tic(OH), EDC·HCl, HOBt, NEt₃, CH₂Cl₂, rt, overnight; e) HCl aq., CH₃OH.

Synthesis of V4. A solution of V1 (5.0 mmol) in CH₃CN (20 mL) was treated with Boc-L-Valine (1.14 g, 5.25 mmol), HBTU (1.92 g, 5.1 mmol), and finally NEt₃ (2.8 mL, 20 mmol). The solution was stirred 12 h, then partitioned between ether and aq. NaHCO₃. The organic layer was washed (1 M HCl, water, aq. NaHCO₃, brine), then dried Na₂SO₄). The organic layer was concentrated and subjected to chromatography on silica gel eluting with 25% EtOAc in hexanes to afford the Boc intermediate V2, which was dissolved in MeOH (10 mL) and treated with HCl (6 N, 10 mL). After 12 h, the methanol was removed and the aqueous solution was adjusted to pH 10 with NaOH. The product was extracted from the aqueous using EtOAc then $CH_2Cl_2$. The combined organics were dried $Na_2SO_4$) and concentrated to afford crude V3 which was carried forward without further purification. The amine V3 was dissolved in ether (5 mL) and added to a suspension of $LiAlH_4$ (416 mg, 10.9 mmol) at 0° C. The mixture warmed to room temperature overnight, then was diluted with ether, chilled to 0° C., and quenched by addition of 0.4 mL $H_2O$, 0.4 mL 20% NaOH, and 1.2 mL $H_2O$. The filtered, concentrated residue was subjected to chromatography on silica gel to afford 33 mg (3.6% over three steps) of the desired amine V4: $^1$H NMR (300 MHz, CHLOROFORM-d) δ 5.36 (dt, J=1.51, 3.11 Hz, 1H), 2.94-3.10 (m, 1H), 2.60-2.88 (m, 3H), 2.43 (td, J=5.77, 11.26 Hz, 1H), 2.19-2.37 (m, 2H), 2.00-2.11 (m, 2H), 1.64-1.81 (m, 5H), 1.55 (qd, J=6.66, 12.81 Hz, 1H), 0.85-0.97 (m, 6H).

(3R)-7-hydroxy-N-{(1S)-2-methyl-1-[(4-methyl-3,6-di-hydropyridin-1(2H)-yl)nethyl]propyl}-1,2,3,4-tetrahydroisoquinoline-3-carboxamide (25) Dihydrochloride. A solution of Boc-7-hydroxy-D-Tic(OH) (78 mg, 0.25 mmol), EDC·HCl (95 mg, 0.5 mmol), catalytic HOBt and the amine V4 (33 mg, 0.18 mmol) in $CH_2Cl_2$ (10 mL) was treated with $NEt_3$ (0.21 mL, 1.5 mmol). After 12 h, the reaction was concentrated and purified by chromatography on silica gel eluting with a gradient up to 40% DMA80 in $CH_2Cl_2$. The Boc-intermediate containing fractions were dissolved in MeOH (5 mL) and HCl (6 M, 5 mL). After 1 h, the reaction was concentrated. The residue was purified by chromatography on silica gel, eluting with a gradient up to 50% DMA80 in $CH_2Cl_2$ to afford the (25) free base: $^1$H NMR (300 MHz, CHLOROFORM-d) δ 7.06-7.19 (m, 1H), 6.72 (d, J=8.29 Hz, 1H), 6.39 (dd, J=2.54, 8.19 Hz, 1H), 6.33 (d, J=2.26 Hz, 1H), 5.47 (br. s., 1H), 4.19-4.36 (m, 1H), 3.65 (s, 1H), 3.57 (s, 1H), 3.39-3.51 (m, 1H), 3.19 (d, J=6.97 Hz, 1H), 2.70-2.94 (m, 4H), 2.44-2.57 (m, 1H), 2.37 (dd, J=3.20, 12.43 Hz, 2H), 1.85-2.04 (m, 2H), 1.69-1.84 (m, 1H), 1.66 (s, 3H), 0.83-1.02 (m, 6H); $^{13}$C NMR (75 MHz, CHLOROFORM-d) δ 173.3, 154.9, 137.4, 133.4, 130.8, 125.0, 118.0, 113.4, 111.8, 59.1, 56.6, 51.6, 50.8, 50.7, 49.4, 48.7, 32.2, 29.4, 22.6, 19.3, 18.0; MS (ESI) m/z 358.2 (M+H)$^+$. The free base was converted into a 32.5 mg (40%) white powder as the dihydrochloride salt: m.p. 184-188° C. (fusion); $[α]^{25}_D$=+80. (c 0.10, $CH_3OH$). Anal. ($C_{21}H_{33}Cl_2N_3$ $O)_2$·1.25$H_2O$) C, H, N.

Scheme W.$^a$

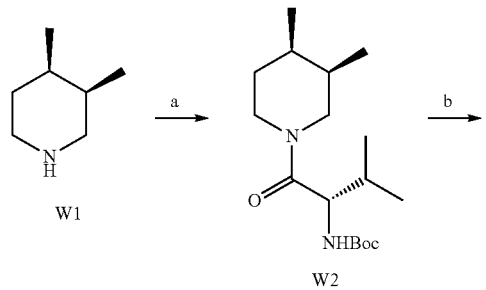

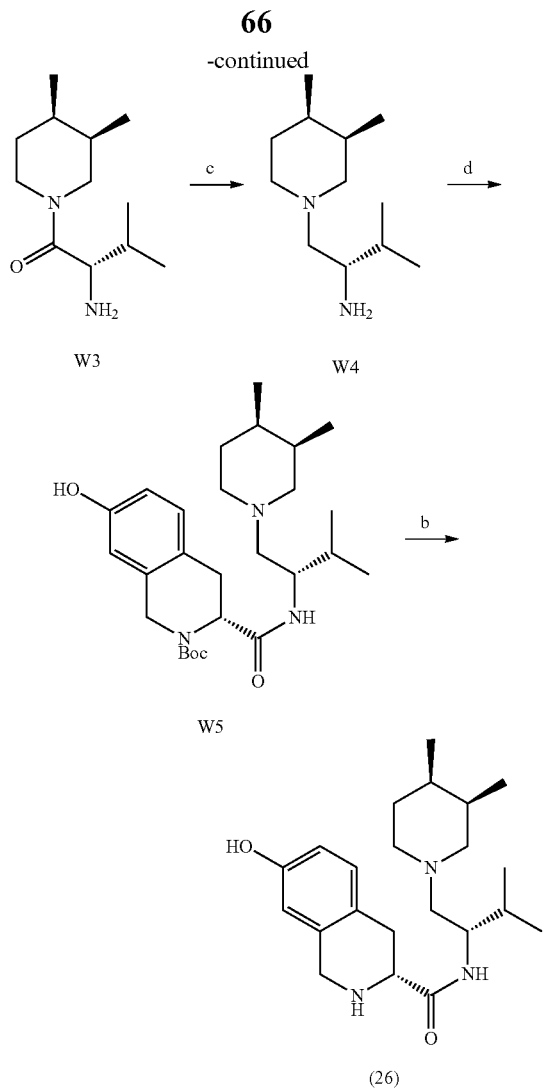

$^a$Reagents and conditions: a) N-Boc-L-Valine, HBTU, $CH_3CN$, rt, overnight; b) HCl in 1,4-dioxane, $CH_3CN$, rt, 3 h; c) $BH_3$·$SMe_2$, THF, reflux, 3 h; d) Boc-7-hydroxy-D-Tic(OH), EDC·HCl, HOBt, $NEt_3$, $CH_2Cl_2$, rt, overnight.

Synthesis of W2. The synthesis of cis-3,4-dimethylpiperidine (W1) was accomplished in three step commencing with the transformation of 3,4-lutidine to 3,4-dimethyl-1,2,5,6-tetrahydropyridine as previously reported in literature.[28] Catalytic hydrogenation of the tetrahydropyridine afforded W1. Coupling of W1 (1.81 g, 12.1 mmol) with Boc-L-valine (2.89 g, 13.3 mmol) according to the General Method 1 afforded W2 (3.5 g, 93% yield) as a mixture of diastereomers. $^1$H NMR (300 MHz, CHLOROFORM-d) δ 5.44 (t, J=8.76 Hz, 1H), 4.36-4.66 (m, 1H), 3.53-4.03 (m, 2H), 2.95-3.52 (m, 2H), 1.76-1.99 (m, 2H), 1.65 (d, J=9.04 Hz, 1H), 1.52 (d, J=5.65 Hz, 1H), 1.43 (br. s., 9H), 1.07-1.34 (m, 2H), 0.77-1.02 (m, 12H); $^{13}$C NMR (75 MHz, CHLOROFORM-d) δ 170.8, 155.8, 79.0, 54.6, 52.9, 51.3, 49.8, 49.0, 47.0, 44.8, 33.0, 31.5, 28.2, 19.5, 17.1; MS (ESI) m/z 313.5 M+H)$^+$.

Synthesis of W3. Deprotection of the amine W2 was done following the General Method 2 to provide the amine W3. $^1$H NMR (300 MHz, CHLOROFORM-d) δ 5.77-6.06 (m, 1H), 3.63-3.89 (m, 1H), 3.45-3.58 (m, 1H), 3.31 (td, J=2.73, 5.09 Hz, 1H), 1.87-2.20 (m, 2H), 1.83 (br. s., 2H), 1.66 (d, J=9.61 Hz, 1H), 1.51 (br. s., 1H), 1.29-1.44 (m, 4H), 1.12-1.26 (m, 1H), 0.80-1.06 (m, 9H); $^{13}$C NMR (75 MHz, CHLOROFORM-d) δ 173.0, 169.5, 59.8, 55.9, 50.8, 46.9, 44.1, 37.6, 31.8, 28.6, 19.9, 16.4; MS (ESI) m/z 213.0 M+H)+.

Synthesis of W4. When compound W3 (1.1 g, 5.15 mmol) was treated with borane-dimethylsufide (1.1 mL, 2.2 equiv) following the General Method 3, the diamine W4 (909 mg, 89% yield) was obtained. $^1$H NMR (300 MHz, METHANOL-d$_4$) δ 3.57-3.67 (m, J=6.97, 6.97, 6.97 Hz, 1H), 2.71-3.19 (m, 2H), 2.11-2.69 (m, 4H), 1.79-2.04 (m, 2H), 1.48-1.78 (m, 2H), 1.25-1.47 (m, 1H), 0.81-1.13 (m, 12H); $^{13}$C NMR (75 MHz, METHANOL-d$_4$) δ 64.3, 61.5, 59.9, 58.3, 55.1, 38.5, 38.5, 34.9, 33.5, 31.4, 19.2, 18.8; MS (ESI) m/z 199.0 M+H)+.

Synthesis of W5. Compound W4 (864 mg, 4.40 mmol) in dichloromethane (30 mL) was coupled with Boc-7-hydroxy-D-Tic-OH (1.36 g, 4.62 mmol) following the protocol described in General Method 4 to provide W5 (1.38 g, 66% yield). $^1$H NMR (300 MHz, CHLOROFORM-d) δ 6.98 (d, J=8.29 Hz, 1H), 6.67 (d, J=8.29 Hz, 1H), 6.59 (br. s., 1H), 5.76-6.35 (m, 1H), 4.64-4.93 (m, 1H), 4.48-4.63 (m, 1H), 4.33-4.48 (m, 1H), 3.80 (br. s., 1H), 3.08-3.32 (m, 2H), 2.81-3.08 (m, 1H), 2.44-2.70 (m, 1H), 1.80-2.39 (m, 6H), 1.69 (d, J=11.30 Hz, 1H), 1.45-1.58 (m, 11H), 1.29-1.42 (m, 1H), 0.71-1.04 (m, 12H); $^{13}$C NMR (75 MHz, CHLOROFORM-d) δ 171.6, 155.6, 134.0, 129.1, 124.1, 114.7, 113.0, 81.4, 62.4, 59.0, 58.2, 56.5, 54.9, 53.6, 51.6, 44.7, 37.3, 34.3, 33.7, 32.0, 30.6, 29.8, 28.4 (3 C's), 19.2, 17.1; MS (ESI) m/z 474.7 M+H)+.

(3R)—N-[(1S)-1-{[(3R,4R)-3,4-Dimethylpiperidin-1-yl]methyl}-2-methylpropyl]-7-hydroxy-1,2,3,4-tetrahydroisoquinoline-3-carboxamide (26) Dihydrochloride. Compound W5 (1.38 g, 2.92 mmol) in acetonitrile (20 mL) was subjected to Boc cleavage following the General Method 2 to provide (26) (1.05 g, 96% yield) as a mixture of diastereomers, $R_a$=H, $R_b$=CH$_3$ and $R_a$=CH$_3$, $R_b$=H. $^1$H NMR (300 MHz, METHANOL-d$_4$) δ 6.93 (d, J=8.29 Hz, 1H), 6.61 (dd, J=2.54, 8.19 Hz, 1H), 6.44-6.54 (m, 1H), 3.85-4.06 (m, 2H), 3.44-3.64 (m, 1H), 2.67-3.01 (m, 3H), 2.09-2.63 (m, 4H), 1.74-1.98 (m, 2H), 1.39-1.72 (m, 3H), 1.05-1.37 (m, 2H), 0.81-1.02 (m, 12H); $^{13}$C NMR (75 MHz, METHANOL-d4) δ 175.3, 156.8, 137.4, 130.9, 125.6, 115.0, 113.2, 63.7, 61.5, 58.2, 56.1, 54.8, 54.1, 53.2, 52.5, 38.7, 35.4, 35.1, 33.6, 32.3, 20.0, 17.9; MS (ESI) m/z 374.3 M+H)+. A beige solid was obtained as dihydrochloride salt of (26): mp 162° C.; [α]$^{23}_D$=+69.4 (c 1.1, CH$_3$OH). Anal. (C$_{22}$H$_{37}$Cl$_2$N$_3$O$_2$·0.75H$_2$O) C, H, N.

Scheme X.$^a$

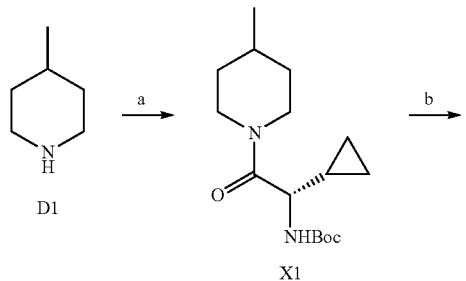

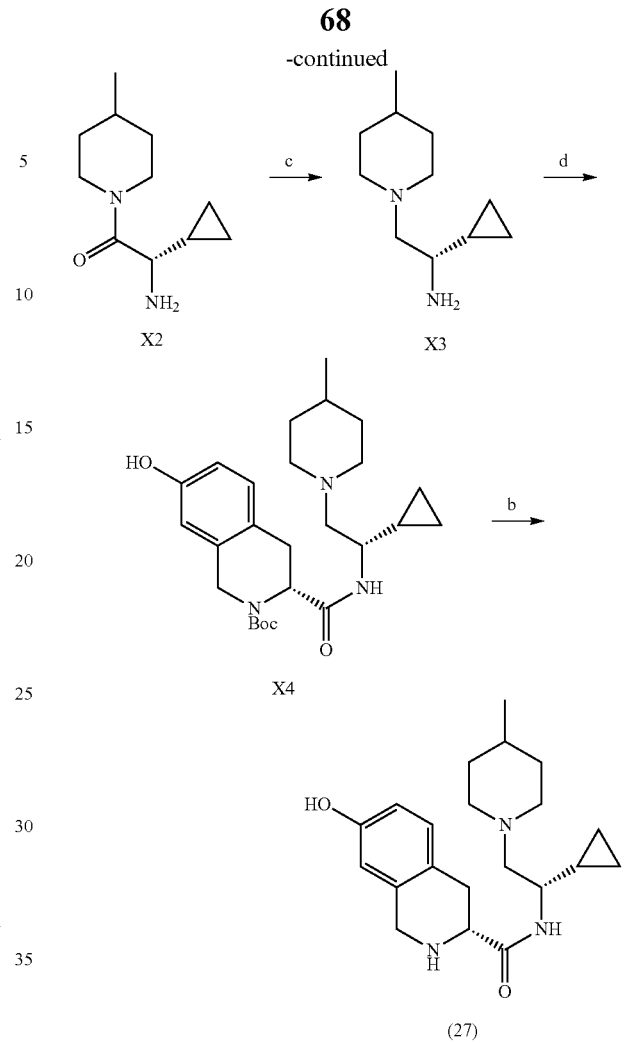

$^a$Reagents and conditions: a) N-Boc-L-cyclopropylglycine, HBTU, CH$_3$CN, rt, overnight; b) HCl in 1,4-dioxane, CH$_3$CN, rt 3h; c) BH$_3$•SMe$_3$, THF, reflux, 3 h; d) Boc-7-hydroxy-D-Tic(OH), EDC•HCl, HOBt, NEt$_3$, CH$_2$Cl$_2$, rt, overnight.

Synthesis of X1. Boc-L-cyclopropylglycine (1.3 g, 6.04 mmol) was coupled 4-methylpiperidine (D1) (780 mg, 7.85 mmol) in the presence of HBTU and TEA as described in General Method 1 to provide compound X1 in quantitative yields. $^1$H NMR (300 MHz, CHLOROFORM-d) δ 5.44-5.57 (m, 1H), 4.41-4.60 (m, 2H), 3.95 (d, J=12.06 Hz, 1H), 3.42-3.52 (m, 1H), 2.97-3.12 (m, 1H), 2.76-2.84 (m, 1H), 2.54-2.68 (m, 1H), 1.56-1.80 (m, 3H), 1.35-1.49 (m, 9H), 1.02-1.17 (m, 2H), 0.96 (t, J=5.37 Hz, 2H), 0.31-0.56 (m, 4H);$^{13}$C NMR (75 MHz, CHLOROFORM-d) δ 167.4, 153.3, 77.1, 48.8, 43.6, 40.4, 36.4, 32.5, 31.6, 28.8, 26.1, 19.4, 12.0, 11.6; MS (ESI) m/z 297.5 M+H)+.

Synthesis of X2. Deprotection of amine in X1 (1.99 g, 6.71 mmol) was done following the General Method 2 to provide X2 (1.13 g, 86%). $^1$H NMR (300 MHz, METHANOL-d4) δ 4.21-4.45 (m, 1H), 3.85 (d, J=13.56 Hz, 1H), 3.42-3.69 (m, J=8.48 Hz, 1H), 3.13-3.28 (m, 1H), 2.89-3.05 (m, 1H), 2.82 (dt, J=3.01, 12.81 Hz, 1H), 2.57 (ddd, J=3.58, 9.37, 12.67 Hz, 1H), 1.73 (d, J=13.19 Hz, 1H), 1.46-1.67 (m, 2H), 0.78-1.12 (m, 5H), 0.20-0.55 (m, 3H); $^{13}$C NMR (75 MHz, METHANOL-d4) δ 172.2, 54.5, 47.4, 45.4, 43.9, 36.1, 35.0, 32.1, 30.2, 22.1, 16.3; MS (ESI) m/z 197.3 M+H)+.

Synthesis of X3. Compound X2 (1.1 g, 5.38 mmol) was treated with borane-dimethylsulfide (1.1 mL, 2.2 equiv)

following the General Method 3, to provide the diamine X3 (677 mg, 69% yield) was obtained. $^1$H NMR (300 MHz, METHANOL-d4) δ 3.33-3.50 (m, 2H), 3.09-3.21 (m, 1H), 2.47-2.80 (m, 1H), 2.16-2.29 (m, 1H), 1.84-2.10 (m, 1H), 1.65 (dt, J=2.17, 11.54 Hz, 1H), 1.34-1.51 (m, 3H), 1.03-1.27 (m, 2H), 0.75 (d, J=6.22 Hz, 2H), 0.51 (tdd, J=4.33, 8.41, 12.50 Hz, 1H), 0.23-0.42 (m, 3H), 0.06-0.22 (m, 1H), −0.07-0.04 (m, 1H); $^{13}$C NMR (75 MHz, METHANOL-d4) δ 64.3, 61.6, 57.1, 55.8, 53.6, 52.8, 34.1, 30.8, 29.0, 21.2, 17.3; MS (ESI) m/z 183.3 M+H)$^+$.

Synthesis of X4. Compound X3 (1.1 g, 3.71 mmol) in dichloromethane (40 mL) was coupled with Boc-7-hydroxy-D-Tic(OH) (1.36 g, 4.62 mmol) following the protocol described in General Method 4 to provide X4 (1.01 g, 60% yield). $^1$H NMR (300 MHz, CHLOROFORM-d) δ 6.98 (d, J=8.29 Hz, 1H), 6.42-6.75 (m, 2H), 6.26 (d, J=7.54 Hz, 1H), 4.74-5.09 (m, 1H), 4.31-4.69 (m, 3H), 3.10-3.44 (m, 2H), 2.80-3.09 (m, 1H), 2.51-2.80 (m, 1H), 2.18-2.47 (m, 2H), 1.90-2.15 (m, 1H), 1.66-1.90 (m, 2H), 1.41-1.64 (m, 9H), 1.00-1.37 (m, 4H), 0.51-0.96 (m, 5H), 0.04-0.50 (m, 4H); $^{13}$C NMR (75 MHz, CHLOROFORM-d) δ 169.2, 153.0, 132.1, 126.3, 121.5, 112.1, 110.6, 78.7, 59.8, 59.3, 57.9, 54.3, 52.4, 51.4, 49.1, 42.6, 42.2, 31.6, 28.4, 27.9, 27.3, 25.8, 19.3, 12.4; MS (ESI) m/z 458.4 M+H)$^+$.

(3R)—N-[(1S)-1-Cyclopropyl-2-(4-methylpiperidine-1-yl)ethyl]-7-hydroxy-1,2,3,4-tetrahydroisoquinoline-3-carboxamide (27) Dihydrochloride. Compound X4 (1.24 g, 2.67 mmol) in acetonitrile (20 mL) was subjected to Boc cleavage following the General Method 2 to provide (27) (626 mg, 65% yield). $^1$H NMR (300 MHz, METHANOL-d$_4$) δ 6.66 (d, J=8.29 Hz, 1H), 6.36 (dd, J=2.07, 8.29 Hz, 1H), 6.24 (d, J=1.70 Hz, 1H), 3.57-3.75 (m, 1H), 3.38 (q, J=7.22 Hz, 2H), 3.24 (q, J=7.03 Hz, 2H), 2.34-2.75 (m, 3H), 2.13-2.32 (m, 1H), 1.76-1.91 (m, 1H), 1.52-1.74 (m, 1H), 1.36 (td, J=2.80, 5.51 Hz, 2H), 0.86-1.15 (m, 7H), 0.59-0.76 (m, 3H), −0.03-0.32 (m, 2H); $^{13}$C NMR (75 MHz, METHANOL-d$_4$) d 175.1, 156.8, 137.4, 130.9, 125.6, 115.1, 113.4, 66.9, 63.8, 62.9, 58.4, 56.0, 54.5, 51.7, 35.2, 31.9, 30.3, 22.5, 18.6, 16.2, 15.7; MS (ESI) m/z 358.3 M+H)$^+$. A white solid was obtained as dihydrochloride salt of (27). mp 162° C.; $[\alpha]^{24}_D$=+62.7 (c 1.1, CH$_3$OH). Anal. (C$_{21}$H$_{33}$Cl$_2$N$_3$O$_2$·1.25H$_2$O) C, H, N.

Scheme Y.$^a$

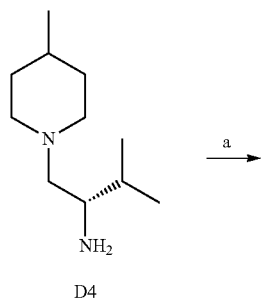

D4

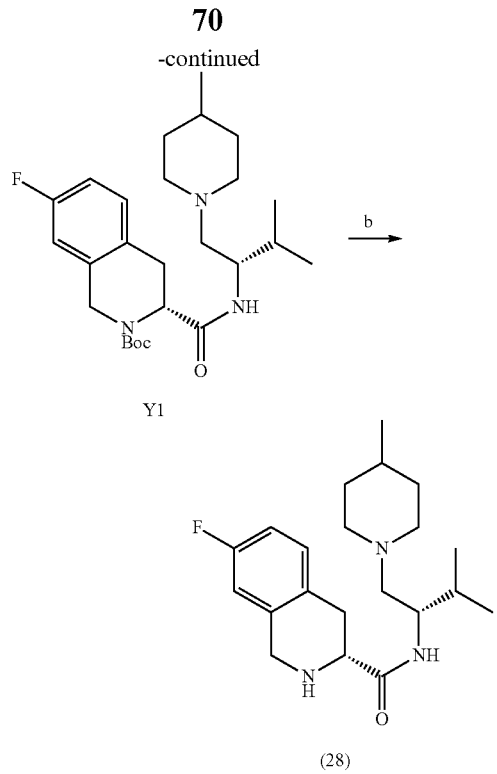

$^a$Reagents and conditions: a) Boc-L-fluoro-D-Tic(OH), EDC·HCl, HOBt, NEt$_3$, CH$_2$Cl$_2$, rt, overnight; b) HCl in 1,4-dioxane, CH$_3$CN, rt, 3 h.

Synthesis of Y1. Boc-7-fluoro-D-Tic(OH) a known compound, was coupled with D4 (742 mg, 4.02 mmol) according to the General Method 4 to furnish Y1 (894.4 mg, 48% yield). $^1$H NMR (300 MHz, CHLOROFORM-d) δ 7.14 (dd, J=5.65, 8.29 Hz, 1H), 6.75-6.98 (m, 2H), 5.86-6.27 (m, 1H), 4.76-5.08 (m, 1H), 4.69 (d, J=16.20 Hz, 1H), 4.51 (d, J=16.39 Hz, 1H), 3.79 (br. s., 1H), 3.35 (dd, J=3.11, 15.54 Hz, 1H), 3.00 (br. s., 1H), 2.61 (br. s., 2H), 2.12 (br. s., 2H), 1.87 (dd, J=6.12, 11.96 Hz, 2H), 1.58-1.74 (m, 1H), 1.52 (br. s., 9H), 1.33-1.45 (m, 2H), 1.00-1.33 (m, 2H), 0.84 (dd, J=6.69, 12.34 Hz, 9H); $^{13}$C NMR (75 MHz, CHLOROFORM-d) δ 170.2, 161.2 (J$_{CF}$=244.7 Hz), 154.8 (broad), 134.6 (broad), 129.5 (J$_{CF}$=24.6 Hz), 128.8, 113.9 (J$_{CF}$=21.8 Hz), 112.5, 80.9, 59.3, 55.4, 54.8, 53.6, 53.2, 51.1, 44.1, 34.3, 34.0, 30.5, 30.1, 28.2 (3C's), 21.6, 18.8, 17.4; MS (ESI) m/z 462.6 M+H)$^+$.

(3R)-7-Fluoro-N-{(1S)-2-methyl-1-[(4-methylpiperidin-1-yl)methyl]propyl}-1,2,3,4-tetrahydroisoquinoline-3-carboxamide (28) Dihydrochloride. Compound Y1 (1.15 g, 2.48 mmol) was subjected to Boc-cleavage according to General Method 2 to provide (28) (588 mg, 66% yield). $^1$H NMR (300 MHz, CHLOROFORM-d) δ 6.97-7.23 (m, 2H), 6.83 (dt, J=2.26, 8.48 Hz, 1H), 6.67-6.76 (m, 1H), 3.89-4.08 (m, 3H), 3.56 (dd, J=5.27, 9.42 Hz, 1H), 3.10 (dd, J=5.18, 16.29 Hz, 1H), 2.62-2.93 (m, 3H), 2.16-2.51 (m, 2H), 1.72-2.08 (m, 4H), 1.53 (t, J=12.90 Hz, 2H), 1.29 (dt, J=3.58, 6.97 Hz, 1H), 1.16 (dt, J=3.20, 11.77 Hz, 1H), 0.97-1.10 (m, 1H), 0.83-0.95 (m, 9H); $^{13}$C NMR (75 MHz, CHLOROFORM-d) δ 172.6, 161.0 (J$_{CF}$=244.7 Hz), 137.6 (J$_{CF}$=6.5 Hz), 130.5 (J$_{CF}$=7.7 Hz), 129.8 (J$_{CF}$=2.4 Hz), 113.4 (J$_{CF}$=21.4 Hz), 112.0 (J$_{CF}$=21.0 Hz), 59.8, 56.3, 55.0, 53.2, 50.8, 47.0, 34.5, 34.2, 30.6, 30.5, 30.2, 21.8, 19.2, 17.7; MS (ESI) m/z 362.4 M+H)$^+$. A white solid was obtained as dihydrochloride salt of (28). mp 172-175° C.; $[\alpha]^{24}_D$=+68.9 (c 1.1, CH$_3$OH). Anal. (C$_{21}$H$_{34}$Cl$_2$FN$_3$O·1.25H$_2$O) C, H, N.

Scheme Z.[a]

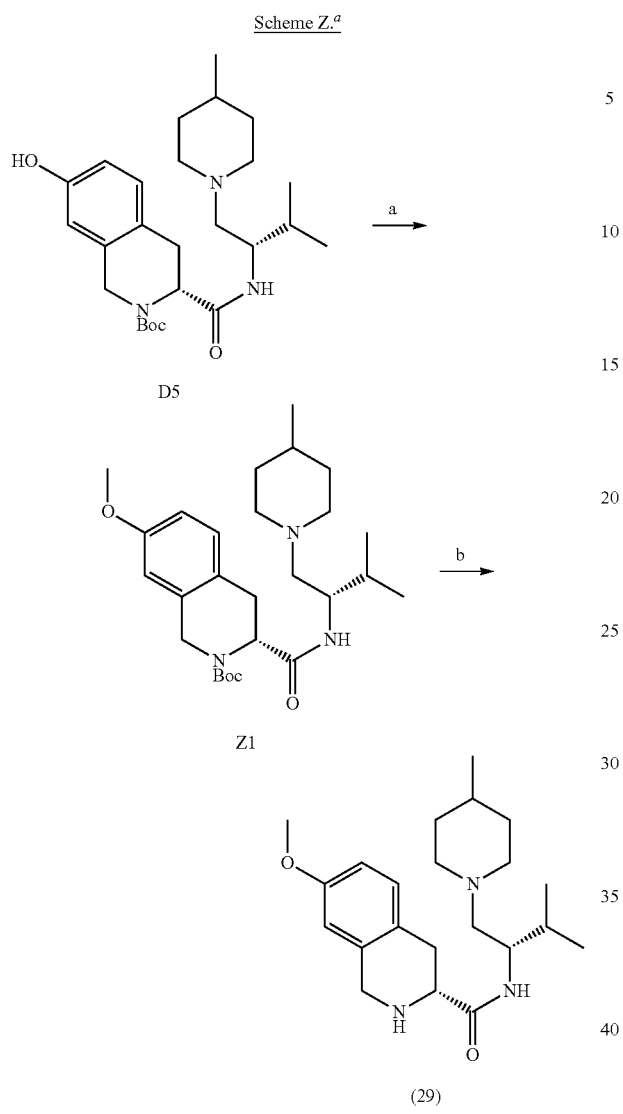

[a]Reagents and conditions: a) TMSCHN$_2$, CH$_3$OH, toluene; b) HCl in 1,4-dioxane, CH$_3$CN, rt, 3 h.

Synthesis of Z1. A solution of D5 (365 mg, 0.793 mmol) and DIPEA (1 mL, 5.00 equiv) in 5 mL acetonitrile/MeOH (4:1) was treated with trimethylsilyl diazomethane (1.7 mL, 2M in Et$_2$O, 3 equiv.) and stirred at room temperature overnight. The excess reagent was quenched with AcOH and solvent was removed in vacuo. The residue was extracted from NaHCO$_3$ with EtOAc (3×50 mL). The combined organic layers were dried (anhydrous Na$_2$SO$_4$), filtered over Celite and concentrated in vacuo. The residue was purified over silica gel, eluted with EtOAc/hexanes to furnish compound Z1 (290 mg, 77% yield). $^1$H NMR (300 MHz, CHLOROFORM-d) δ 6.90-7.21 (m, 1H), 6.58-6.84 (m, 2H), 5.89-6.27 (m, 1H), 4.36-4.76 (m, 3H), 3.79 (s, 1H), 3.51-3.67 (m, 1H), 3.14-3.40 (m, 1H), 2.90-3.14 (m, 1H), 2.60 (br. s., 2H), 2.00-2.28 (m, 2H), 1.63-1.97 (m, 2H), 1.39-1.60 (m, 13H), 0.91-1.34 (m, 4H), 0.76-0.89 (m, 9H); $^{13}$C NMR (75 MHz, CHLOROFORM-d) 171.6, 155.6, 134.0, 129.2, 123.7, 114.5, 113.2, 81.5, 59.3, 56.9, 56.5, 54.3, 53.5, 51.3, 45.1, 44.5, 34.2, 34.0, 30.5, 30.2, 28.3 (3C's), 21.8, 18.9, 17.4; MS (ESI) m/z 474.6 M+H)$^+$.

(3R)-7-Methoxy-N-{(1S)-2-methyl-1-[(4-methylpiperidin-1-yl)methyl]propyl}-1,2,3,4-tetrahydroisoquinoline-3-carboxamide (29) Dihydrochloride. Compound Z1 (290 mg, 0.62 mmol) was subjected to Boc-cleavage according to General Method 2 to provide (29) (155 mg, 63% yield). $^1$H NMR (300 MHz, CHLOROFORM-d) δ 6.89-7.15 (m, 2H), 6.72 (dd, J=2.64, 8.29 Hz, 1H), 6.56 (d, J=2.45 Hz, 1H), 3.89-4.06 (m, 2H), 3.70-3.81 (m, 3H), 3.43-3.58 (m, 1H), 3.11 (dd, J=5.09, 16.20 Hz, 1H), 2.69-2.94 (m, 4H), 2.23-2.51 (m, 2H), 1.95-2.08 (m, 1H), 1.72-1.94 (m, 2H), 1.42-1.62 (m, 2H), 1.20-1.37 (m, 2H), 0.95-1.16 (m, 2H), 0.83-0.93 (m, 9H); $^{13}$C NMR (75 MHz, CHLOROFORM-d) δ 173.0, 157.9, 136.8, 130.1, 126.4, 112.5, 110.5, 59.8, 56.9, 55.2, 55.1, 53.2, 50.7, 47.7, 34.4, 34.2, 30.7, 30.6, 30.3, 21.8, 19.2, 17.7; MS (ESI) m/z 374.6 M+H)$^+$. A beige solid was obtained as dihydrochloride salt of (29). mp 116-120° C.; [α]$^{24.9}_D$=+69.8 (c 1.1, CH$_3$OH). Anal. (C$_{22}$H$_{37}$Cl$_2$N$_3$)$_2$.0.75H$_2$O) C, H, N.

Scheme AA.[a]

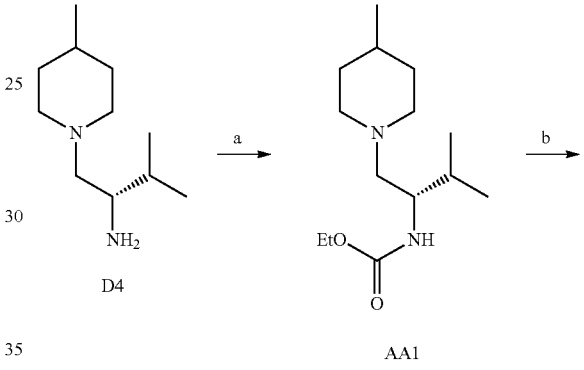

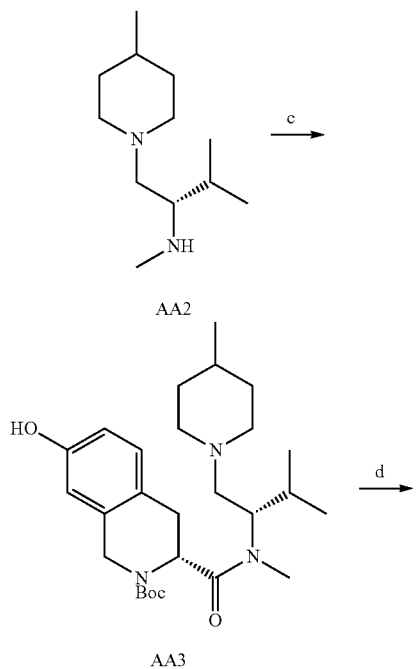

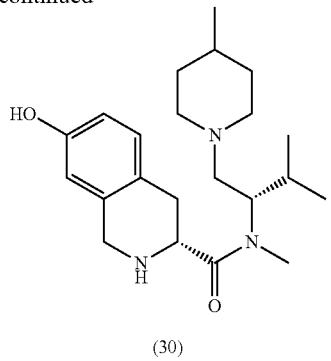

(30)

*Reagents and conditions: a) Ethyl chloroformate, NEt₃, CH₂Cl₂, 0° C. to rt, overnight; b) LAH, THF, reflux, 4 h; c) Boc-7-hydroxy-D-Tic(OH), PyBrop, DIPEA, CH₂Cl₂, 0° C. to overnight; d) HCl in 1,4-dioxane, CH₃CN, rt, 3 h.

Synthesis of AA2. A solution of D4 (796 mg, 4.32 mmol) in CH$_2$Cl$_2$ (20 mL) and triethylamine (0.8 mL, 5.18 mmol) was cooled to 0° C. and treated with ethyl chloroformate (0.5 mL, 5.18 mmol). The mixture was allowed to warm up to room temperature and stirred for 24 h. The solvents were removed in vacuo and the residue was redissolved in CHCl$_3$ (30 mL) and washed with saturated aqueous solution of K$_2$CO$_3$, followed by water. The organic phase was dried (anhydrous Na$_2$SO$_4$), filtered, and concentrated in vacuo to furnish carbamate AA1 that was carried on without further purification. To a solution of AA1 in THF (15 mL) cooled to 0° C. was added in small portions LAH (410 mg, 10.8 mmol). After all the LAH had been added the reaction mixture was heated at reflux for 4 h. After this time, the flask was cooled to 0° C. and the excess hydride was quenched by consecutive addition, under strong stirring, dropwise and cautiously of 0.5 mL of H$_2$O, 0.5 mL of NaOH (10% solution) and 1.5 mL of H$_2$O. The mixture was then filtered and the sludge washed with THF and CHCl$_3$, the combined organic layers were dried, filtered and the solvent was removed in vacuo to provide AA2 (591 mg, 65%). $^1$H NMR (300 MHz, CHLOROFORM-d) δ 2.77-2.98 (m, 1H), 2.71 (d, J=10.93 Hz, 1H), 2.30-2.46 (m, 4H), 1.99-2.28 (m, 3H), 1.65-1.96 (m, 3H), 1.58 (d, J=12.24 Hz, 2H), 1.08-1.40 (m, 3H), 0.78-1.03 (m, 9H); $^{13}$C NMR (75 MHz, CHLOROFORM-d) δ 61.6, 58.8, 56.0, 54.8, 54.1, 52.9, 41.9, 30.9, 28.3, 21.8, 19.0, 16.9; MS (ESI) m/z 199.1 M+H)$^+$.

Synthesis of AA3. Coupling of AA2 with Boc-7-hydroxy-D-Tic(OH): A solution of AA2 (591 mg, 2.98 mmol), Boc-7-hydroxy-D-Tic-OH (961 mg, 3.28 mmol), and PyBrop [bromo-tri-pyrrolidinophosphonium hexafluorophosphate] (1.53 g, 3.28 mmol) in CH$_2$Cl$_2$ (6 mL) at 0° C., was treated under stirring with Hunig's base (DIPEA) (2.1 mL, 4 equiv). The ice-bath was removed after a short while and stirring continued at room temperature overnight. The mixture was then poured into EtOAc (200 mL) and subsequently washed with 5% KHSO$_4$, Saturated aqueous NaHCO$_3$, and brine. The organic layer was dried (anhydrous Na$_2$SO$_4$), filtered over Celite and concentrated in vacuo. The residue was purified on silica gel, eluted with EtOAc/hexanes to furnish AA3 (1.18 g, 85% yield). $^1$H NMR (300 MHz, METHANOL-d$_4$) δ 6.58-6.81 (m, 2H), 4.96-5.22 (m, 1H), 4.35-4.71 (m, J=16.95 Hz, 2H), 3.69 (td, J=6.59, 13.19 Hz, 2H), 3.18 (q, J=7.41 Hz, 4H), 2.92-3.09 (m, 1H), 2.84 (br. s., 1H), 2.59 (s, 1H), 2.02 (s, 1H), 1.38-1.73 (m, 11H), 1.20-1.38 (m, 12H), 0.80-1.09 (m, 3H), 0.74 (t, J=6.31 Hz, 1H); $^{13}$C NMR (75 MHz, METHANOL-d$_4$) δ 171.8, 157.0, 136.9, 130.3, 121.3, 120.3, 115.4, 114.0, 82.5, 61.6, 57.0, 55.8, 54.9, 53.7, 53.4, 43.8, 41.1, 32.9, 32.1, 30.9, 29.6, 28.8 (3Cs), 21.6, 20.4, 18.1; MS (ESI) m/z 474.7 (M+H)$^+$.

(3R)-7-Hydroxy-N-methyl-N-{(1S)-2-methyl-1-[(4-methylpiperidin-1-yl)methyl]propyl}-1,2,3,4-tetrahydroisoquinoline-3-carboxamide (30) Dihydrochloride. Compound AA3 was subjected to Boc-cleavage according to General Method 2 to provide the amine (30). $^1$H NMR (300 MHz, CHLOROFORM-d) δ 6.97-7.15 (m, 2H), 6.72 (dd, J=2.64, 8.48 Hz, 1H), 6.56 (d, J=2.64 Hz, 1H), 3.89-4.06 (m, 3H), 3.73-3.86 (m, 3H), 3.66 (q, J=6.97 Hz, 1H), 3.46-3.57 (m, 1H), 3.11 (dd, J=4.99, 16.29 Hz, 1H), 2.67-2.94 (m, 3H), 2.23-2.47 (m, 2H), 1.94-2.08 (m, 1H), 1.74-1.94 (m, 2H), 1.46-1.62 (m, 2H), 1.23-1.37 (m, 1H), 0.95-1.15 (m, 2H), 0.83-0.95 (m, 9H); $^{13}$C NMR (75 MHz, CHLOROFORM-d) δ 173.8, 155.6, 135.5, 129.9, 123.8, 114.4, 112.4, 58.2, 58.0, 55.8, 53.7, 53.2, 46.8, 33.6, 33.3, 30.6, 30.5, 29.1, 21.7, 20.4, 19.7, 18.3; MS (ESI) m/z 374.3 M+H)$^+$. A white solid was obtained as dihydrochloride salt of (30). mp 212-215° C.; [α]$^{24.7}_D$=+54.5 (c 1.1, CH$_3$OH). Anal. (C$_{22}$H$_{37}$Cl$_2$N$_3$O$_2$·1.25H$_2$O) C, H, N.

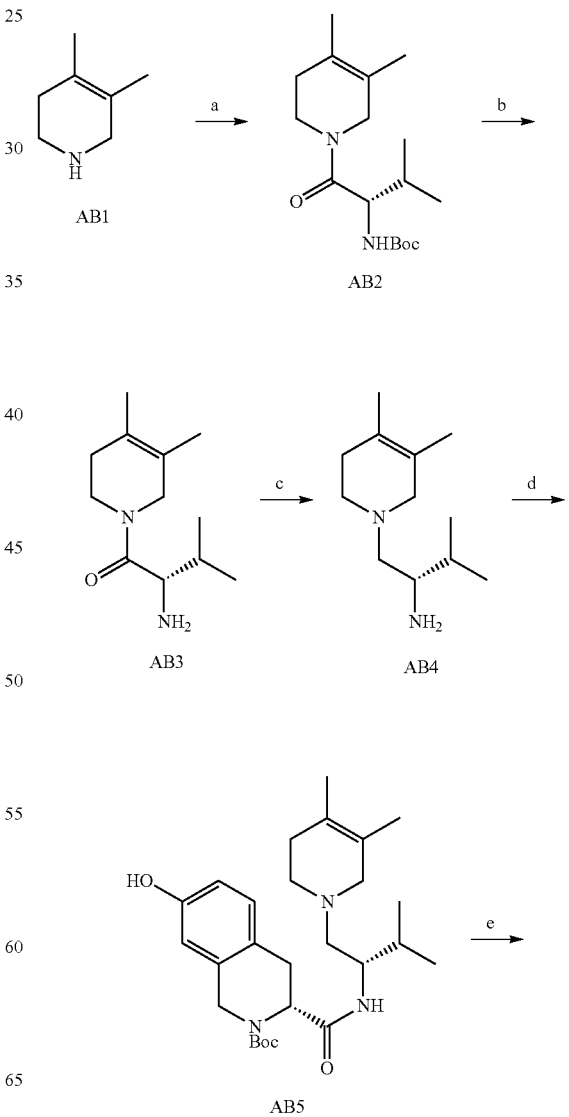

Scheme AB.

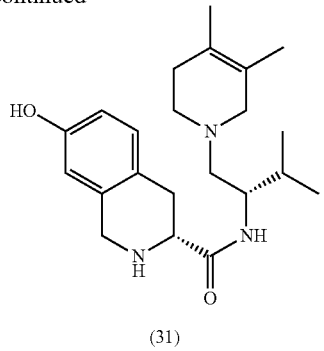

(31)

[a] Reagents and conditions: a) N-Boc-L-Valine, HBTU, CH₃CN, rt, overnight; b) TFA, CH₂Cl₂; c) LAH, THF; d) Boc-7-hydroxy-D-Tic(OH), EDC·HCl, HOBt, NEt₃, CH₂Cl₂, rt, overnight; e) HCl aq., CH₃OH.

Synthesis of AB3. The amine AB1 was prepared similar to V1, except the 1-benzyl-4,5-dimethyl-1,2,3,6-tetrahydropyridine was debenzylated with ACE-Cl in DCE rather than via hydrogenation. The crude AB1 was combined with NEt₃ (2.0 mL, 14 mmol) in CH₃CN (25 mL) and added to a solution of Boc-L-Valine (1.52 g, 7 mmol) and HBTU (2.65 g, 7 mmol) in CH₃CN (50 mL). After 4 h, the solution was concentrated to half then partitioned between EtOAc and aq. NaHCO₃. The organic layer was washed (2 M HCl, aq. NaHCO₃, brine), then dried Na₂SO₄). The organic layer was concentrated then subjected to chromatography on silica gel eluting with a gradient of EtOAc in hexanes. The desired fractions were concentrated to afford AB2, which was then dissolved in DCM (10 mL) and treated with TFA (8 mL). After 2 h, the reaction was concentrated. The residue was subjected to chromatography on silica gel eluting with a gradient up to 33% DMA80 in DCM to afford 0.63 g (24% over 4 steps) of the desired amine AB3: ¹H NMR (300 MHz, CHLOROFORM-d) δ 8.30 (br. s., 2H), 4.18-4.43 (m, 1H), 3.70-3.93 (m, 2H), 3.36-3.61 (m, 2H), 1.97-2.26 (m, 3H), 1.53-1.75 (m, 6H), 0.94-1.20 (m, 6H).

Synthesis of AB4. A solution of amine AB3 (0.63 g, 3.0 mmol) in THF (5 mL) was added to a suspension of LAH (155 mg, 4.0 mmol) in Et₂O (5 mL). The suspension was stirred at room temperature for 4 h, then poured into Et₂O (75 mL) at 0° C. A small quantity of Celite was added, followed by water (0.15 mL). After 10 min, 20% NaOH (0.15 mL) was added. After 10 min, water (0.45 mL) was added. The resulting suspension was filtered and the filtrate concentrated. The residue was subjected to chromatography on silica gel eluting with a gradient up to 33% DMA80 in DCM to afford 55 mg (9%) of the desired amine AB4: ¹H NMR (300 MHz, CHLOROFORM-d) δ 8.30 (br. s., 2H), 4.18-4.43 (m, 1H), 3.70-3.93 (m, 2H), 3.36-3.61 (m, 2H), 1.97-2.26 (m, 3H), 1.53-1.75 (m, 6H), 0.94-1.20 (m, 6H).

(3R)—N-{(1S)-1-[(4,5-dimethyl-3,6-dihydropyridin-1(2H)-yl)methyl]-2-methylpropyl}-7-hydroxy-1,2,3,4-tetrahydroisoquinoline-3-carboxamide (31) Dihydrochloride. A solution of Boc-7-hydroxy-D-Tic(OH) (106 mg, 0.36 mmol), EDC·HCl (112 mg, 0.59 mmol), catalytic HOBt (12 mg) and the amine AB4 (55 mg, 0.28 mmol) in CH₂Cl₂ (6 mL) was treated with NEt₃ (0.3 mL, 2.2 mmol). After 12 h, the reaction was concentrated and purified by chromatography on silica gel eluting with a gradient up to 40% DMA80 in CH₂Cl₂. The Boc-intermediate AB5 containing fractions were concentrated then the residue dissolved in MeOH (5 mL) and HCl (6 M, 5 mL). After 1 h, the reaction was concentrated. The residue was purified by reverse-phase chromatography on C-18 silica gel, eluting with 20% CH₃OH in water (0.1% TFA). The product containing fraction was evaporated then applied to silica gel and eluted with a gradient up to 40% DMA80 in CH₂Cl₂ to afford 36.8 mg (35% over two steps) of the (31) free base: ¹H NMR (300 MHz, CHLOROFORM-d) δ 7.07 (d, J=10.17 Hz, 1H), 6.72 (d, J=8.29 Hz, 1H), 6.32 (d, J=2.26 Hz, 1H), 6.26 (dd, J=2.35, 8.19 Hz, 1H), 4.20-4.37 (m, 1H), 3.62-3.75 (m, 1H), 3.50-3.62 (m, 1H), 3.12-3.30 (m, 2H), 2.65-2.93 (m, 4H), 2.26-2.56 (m, 3H), 1.87-2.01 (m, 2H), 1.71-1.87 (m, 1H), 1.63 (d, J=19.97 Hz, 6H), 0.82-1.05 (m, 6H); ¹³C NMR (75 MHz, CHLOROFORM-d) δ 173.2, 155.1, 137.4, 130.6, 125.1, 125.0, 122.8, 113.3, 111.9, 58.9, 56.6, 56.0, 51.6, 49.5, 48.6, 32.1, 30.5, 29.5, 19.2, 18.1, 18.1, 16.7; MS (ESI) m/z 372.1 M+H)⁺. The free base was converted into a white powder as the dihydrochloride salt: m.p. 135-139° C. (fusion); [α]²⁵_D=+74 (c 0.10, CH₃OH). Anal. (C₂₂H₃₅Cl₂N₃O₂·1.5H₂O) C, H, N.

Scheme AC.[a]

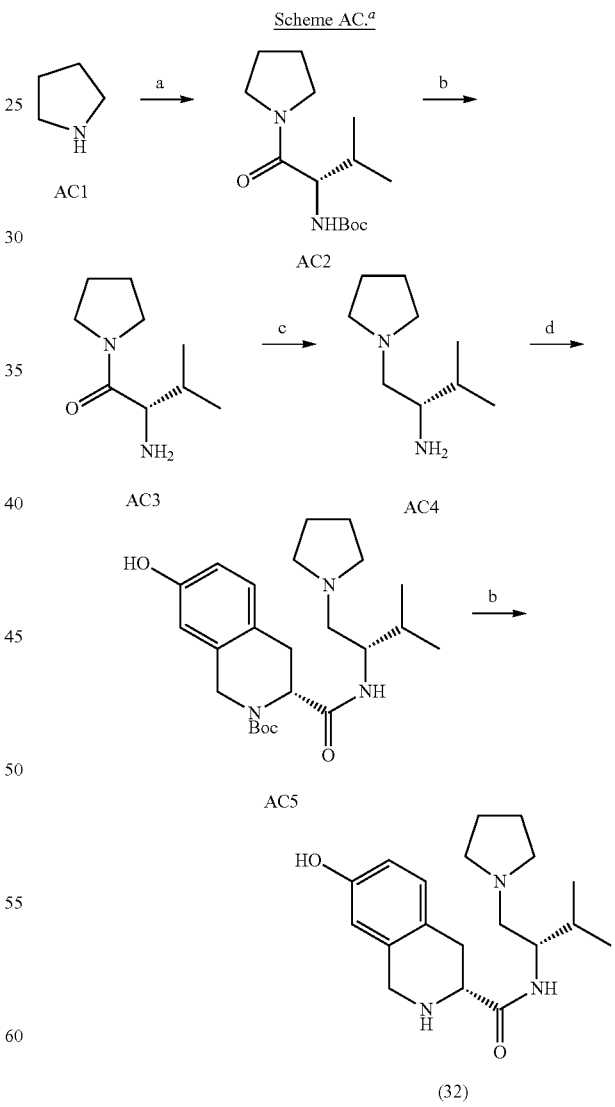

(32)

[a] Reagents and conditions: a) N-Boc-L-Valine, HBTU, CH₃CN, rt, overnight; b) HCl in 1,4-dioxane, CH₃CN, rt, 3 h; c) BH₃·SMe₂, THF, reflux, 3 h; d) Boc-7-hydroxy-D-Tic(OH), EDC·HCl, HOBt, NEt₃, CH₂Cl₂, rt, overnight.

Synthesis of AC3. Pyrrolidine (AC1) (1.28 g, 18.0 mmol) was coupled with Boc-L-valine (4.7 g, 21.6 mmol) according to the General Method 1 to provide AC2 (4.9 g, 100% yield). $^1$H NMR (300 MHz, CHLOROFORM-d) δ 5.31 (d, J=9.23 Hz, 1H), 4.19-4.30 (m, 1H), 3.62-3.74 (m, 1H), 3.36-3.60 (m, 3H), 1.80-2.02 (m, 5H), 1.43 (s, 9H), 0.95 (dd, J=7.25, 9.51 Hz, 6H); $^{13}$C NMR (75 MHz, CHLOROFORM-d) δ 170.8, 155.8, 79.3, 57.0, 46.6, 45.8, 31.4, 28.3 (3Cs), 26.0, 24.2, 19.5, 17.5; MS (ESI) m/z 271.5 (M+H)$^+$. Compound AC2 (5.0 g, 18.5 mmol) in methylene chloride was treated with trifluoroacetic acid (4.2 mL, 3 equiv) for the removal of Boc-protection to provide AC3 (2.7 g, 86% yield). $^1$H NMR (300 MHz, METHANOL-d4) δ 3.23-3.77 (m, 5H), 1.74-2.13 (m, 5H), 0.79-1.17 (m, 6H); $^{13}$C NMR (75 MHz, METHANOL-d$_4$) δ 169.7, 58.4, 47.9, 39.0, 31.4, 27.0, 25.0, 19.3, 17.6; MS (ESI) m/z 171.0 M+H)$^+$.

Synthesis of AC4. Compound AC3 (2.6 g, 15.0 mmol) was treated with borane-dimethylsufide (3.6 mL, 2.0 equiv) following the General Method 3, to provide the diamine AC4 (1.72 g, 73% yield) was obtained. $^1$H NMR (300 MHz, METHANOL-d$_4$) δ 2.89-2.99 (m, 1H), 2.78-2.89 (m, 2H), 2.71-2.78 (m, 1H), 2.55-2.70 (m, 3H), 1.74-1.95 (m, 5H), 1.02 (dd, J=4.33, 6.97 Hz, 6H); $^{13}$C NMR (75 MHz, METHANOL-d$_4$) δ 58.3, 56.3, 55.1, 31.9, 24.5, 18.8, 18.7; MS (ESI) m/z 157.3 M+H)$^+$.

Synthesis of AC5. Compound AC4 (1.03 g, 6.02 mmol) was coupled with Boc-7-hydroxy-D-Tic(OH) (1.77 g, 6.02 mmol) following the protocol described in General Method 4 to provide AC5 (1.43 g, 55% yield). $^1$H NMR (300 MHz, CHLOROFORM-d) δ 7.81 (br. s., 1H), 6.91 (d, J=8.10 Hz, 1H), 6.48-6.70 (m, 2H), 5.94-6.31 (m, 1H), 4.58-4.87 (m, 1H), 4.31-4.57 (m, 2H), 3.56-3.81 (m, 1H), 3.07-3.31 (m, 2H), 2.91 (d, J=10.17 Hz, 1H), 2.08-2.35 (m, 4H), 1.71-1.91 (m, 1H), 1.57 (br. s., 4H), 1.38-1.50 (m, 9H), 1.07-1.34 (m, 1H), 0.77 (dd, J=6.69, 13.28 Hz, 6H); $^{13}$C NMR (75 MHz, CHLOROFORM-d) δ 171.8, 155.5, 134.0, 129.0, 123.8, 114.7, 113.1, 81.3, 60.4, 57.9, 56.5, 54.0, 53.1, 44.9, 44.5, 30.9, 30.2, 28.3, 23.4, 18.8, 17.5; MS (ESI) intz 432.3 M+H)$^+$.

(3R)-7-Hydroxy-N-[(1S)-2-methyl-1-(pyrrolidin-1-ylmethyl)propyl]-1,2,3,4-tetrahydroisoquinoline-3-carboxamide (32) Dihydrochloride. Compound AC5 (1.43 g, 3.32 mmol) was subjected to Boc-cleavage according to General Method 2 to provide the amine (32) (839 mg, 76% yield). $^1$H NMR (300 MHz, CHLOROFORM-d) δ 7.14 (d, J=10.17 Hz, 1H), 6.78 (d, J=8.10 Hz, 1H), 6.22-6.39 (m, 2H), 5.75-6.17 (m, 1H), 4.16 (t, J=10.55 Hz, 1H), 3.59-3.73 (m, 1H), 3.47-3.58 (m, 1H), 3.20 (dd, J=5.27, 11.68 Hz, 1H), 2.95 (t, J=12.15 Hz, 1H), 2.84 (dd, J=5.09, 16.58 Hz, 1H), 2.72 (br. s., 2H), 2.61 (br. s., 2H), 2.27 (dd, J=2.64, 12.43 Hz, 1H), 2.01-2.15 (m, 1H), 1.70-1.92 (m, 5H), 0.75-1.02 (m, 6H); $^{13}$C NMR (75 MHz, CHLOROFORM-d) δ 173.4, 155.1, 137.6, 130.8, 125.0, 113.2, 112.0, 57.2, 56.5, 54.0, 51.8, 48.5, 32.0, 28.9, 23.1, 19.0, 18.0; MS (ESI) m/z 332.5 M+H)$^+$. A white solid was obtained of the dihydrochloride salt of (32). mp 148° C.; [α]$^{24.2}_D$=+67.3 (c 1.1, CH$_3$OH). Anal. (C$_{19}$H$_{31}$Cl$_2$N$_3$O$_2$.H$_2$O) C, H, N. Also obtained was a beige solid of the fumarate salt; mp 152° C.; [α]$^{2.44}_D$=+65.0 (c 1.1, CH$_3$OH). Anal. (C$_{27}$H$_{37}$N$_3$O$_{10}$.1.25H$_2$O) C, H, N.

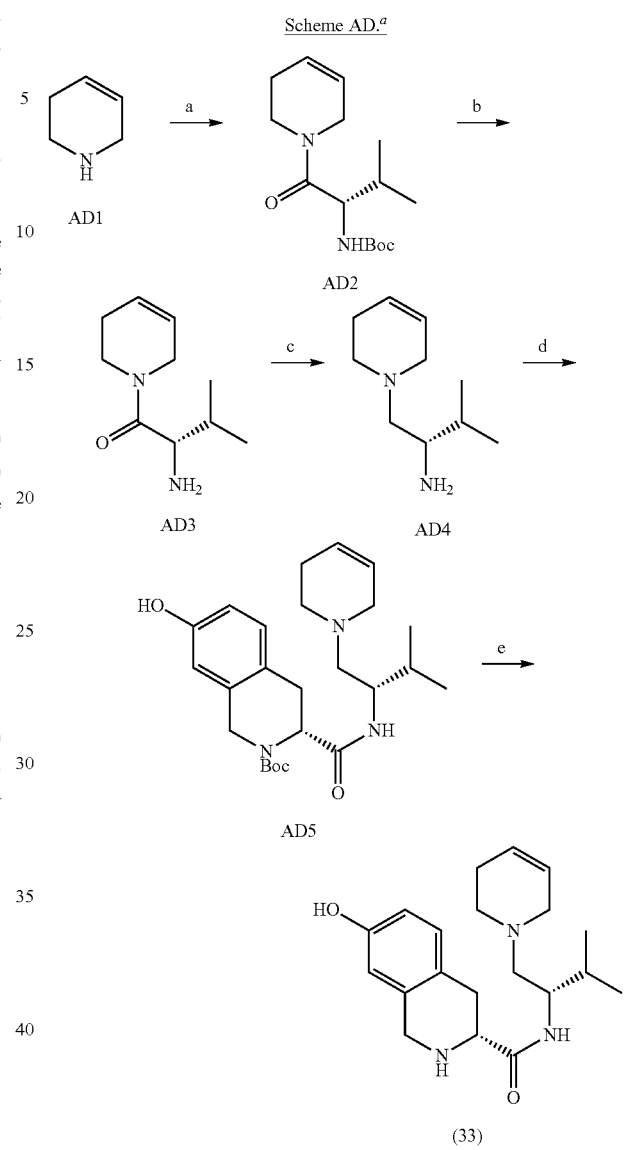

Scheme AD.$^a$ $^a$Reagents and conditions: a) N-Boc-L-Valine, HBTU, CH$_3$CN, rt, overnight; b) TFA, CH$_2$Cl$_2$, rt, 3 h; c) LAH, THF; d) Boc-7-hydroxy-D-Tic(OH), EDC•HCl, HOBt, NEt$_3$, CH$_2$Cl$_2$, rt, overnight; e) HCl aq., CH$_3$OH.

Synthesis of AD3. Amine AD1 (1.0 g, 8.4 mmol) was reacted according to General Method 1 to afford intermediate AD2. A solution of AD2 in DCM (10 mL) was treated with TFA (10 mL) and stirred 12 h, then was concentrated. The residue was subjected to chromatography on silica gel eluting with a gradient up to 33% DMA80 in CH$_2$Cl$_2$ to afford 0.62 g (41% over two steps) of the desired amine AD3: $^1$H NMR (300 MHz, CHLOROFORM-d) δ 5.79-6.01 (m, 1H), 5.57-5.78 (m, 1H), 4.04-4.14 (m, 1H), 3.99 (br. s., 1H), 3.60-3.88 (m, 1H), 3.52-3.59 (m, 1H), 2.09-2.34 (m, 2H), 1.67-2.05 (m, 4H), 0.80-1.08 (m, 6H).

Synthesis of AD4. The amine AD3 (0.62 g, 3.4 mmol) was reduced with LAH according to General Method 3 to afford 156 mg (27%) of the desired diamine AD4: $^1$H NMR (300 MHz, CHLOROFORM-d) δ 5.39-5.87 (m, 2H), 2.98-3.15 (m, 1H), 2.79-2.92 (m, 1H), 2.58-2.78 (m, 2H), 2.43 (td, J=5.60, 11.02 Hz, 1H), 2.19-2.39 (m, 2H), 2.01-2.18 (m, 3H), 1.56 (qd, J=6.65, 13.21 Hz, 1H), 0.76-1.06 (m, 7H).

(3R)-N-[(1S)-1-(3,6-dihydropyridin-1(2H)-ylmethyl)-2-methylpropyl]-7-hydroxy-1,2,3,4-tetrahydroisoquinoline-3-carboxamide (33) Dihydrochloride. A solution of 7-hydroxy-Boc-D-Tic(OH) (285 mg, 0.97 mmol), EDC·HCl (305 mg, 1.6 mmol), catalytic HOBt (53 mg, 0.4 mmol) and the amine AD4 (156 mg, 0.93 mmol) in CH$_2$Cl$_2$ (15 mL) was treated with NEt$_3$ (0.42 mL, 3.0 mmol). After 4 h, the reaction was concentrated and purified by chromatography on silica gel eluting with a gradient up to 35% DMA80 in CH$_2$Cl$_2$. The Boc-intermediate AD5 containing fractions were concentrated and the residue was dissolved in MeOH (5 mL) and HCl (6 M, 5 mL). After 1 h, the reaction was concentrated. The residue was purified by chromatography on silica gel, eluting with a gradient up to 25% DMA80 in CH$_2$Cl$_2$ to afford the (33) free base: $^1$H NMR (300 MHz, CHLOROFORM-d) δ 7.06 (d, J=10.36 Hz, 1H), 6.67 (d, J=8.29 Hz, 1H), 6.34 (dd, J=2.45, 8.10 Hz, 1H), 6.27 (d, J=2.26 Hz, 1H), 5.62-5.79 (m, 2H), 4.13-4.31 (m, 1H), 3.54-3.68 (m, 1H), 3.36-3.54 (m, 2H), 3.12 (dd, J=5.09, 11.87 Hz, 1H), 2.63-2.87 (m, 4H), 2.24-2.50 (m, 3H), 1.84-2.06 (m, 2H), 1.62-1.79 (m, 1H), 0.78-0.95 (m, 6H); $^{13}$C NMR (75 MHz, CHLOROFORM-d) δ 173.4, 154.9, 137.4, 130.7, 125.7, 125.1, 124.1, 113.8, 111.9, 59.5, 56.6, 51.3, 50.8, 49.3, 48.6, 32.2, 29.3, 24.7, 19.3, 18.0; MS (ESI) m/z 344.4 M+H)$^+$. The free base was converted into 75.6 mg (20%) of a white powder as the dihydrochloride salt: m.p. 175° C. (dec.); [α]$^{25}_D$=+75 (c 0.10, CH$_3$OH). Anal. (C$_{20}$H$_{31}$Cl$_2$N$_3$O$_2$·H$_2$O) C, H, N.

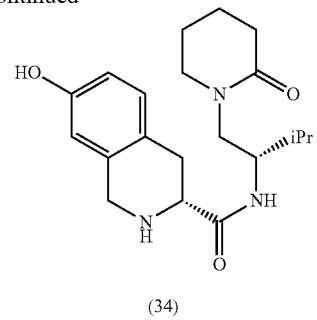

(34)

$^a$Reagents and conditions: a) Benzyl chloroformate, DIPEA, CH$_2$Cl$_2$, 0° C to rt, overnight; b) MsCl, pyridine, CH$_2$Cl$_2$, 0° C. to rt, overnight; c) 2-Hydroxypyridine, K$_2$CO$_3$, TBAB, toluene, H$_2$O, reflux, overnight; d) H$_2$, Pd/C, CH$_3$OH, 50 psi, rt, 24 h; e) Boc-7-hydroxy-D-Tic(OH), EDC·HCl, HOBt, CH$_2$Cl$_2$, rt overnight; f) HCl in 1,4-dioxane, CH$_3$CN, rt, 3 h.

Synthesis of AE5. Preparation of 1-[(2S)-2-amino-3-methylbutyal]piperidin-2-one (AE4): A solution of L-valinol (AE1) (4.81 g, 46.6 mmol) in CH$_2$Cl$_2$ (100 mL) chilled to 0° C. was treated with benzyl chloroformate ((7.3 mL, 51.3 mmol) followed by Hunig's base (16.2 mL, 46.6 mmol). The reaction mixture was allowed to warm up to room temperature and stirred overnight. The reaction mixture was diluted with ethyl acetate (500 mL), and consecutively washed with 10% KH$_2$PO$_4$, saturated NaHCO$_3$ and brine. The organic layer was dried (anhydrous MgSO$_4$) and concentrated in vacuo to provide the protected L-valinol (AE2) (11.14 g, 100%) that was used without further purification. To a solution of AE2 in CH$_2$Cl$_2$ (100 mL) at 0° C. was added pyridine (22.6 mL, 46.6 mmol) and methane sulfonyl chloride. The mixture was allowed to warm up to room temperature and stirred overnight, concentrated, redissolved in EtOAc, and washed with saturated NaHCO$_3$ followed by brine. The organic layer was dried (anhydrous MgSO$_4$) and concentrated in vacuo and the residue was purified on silica gel eluted with EtOAc/hexanes to provide mesylate AE3. A solution of AE3 (4.84, 15.34 mmol) in toluene (112 mL) containing water (620 µL) was treated with tetrabutylammoniun bromide (900 mg, 2.80 mmol), K$_2$CO$_3$ (4.24 g, 30.7 mmol) and 2-hydroxypyridine (1.45 g, 15.3 mmol). The reaction mixture was heated to reflux with stirring, filtered and the filtrate was concentrated in vacuo. The residue was purified on silica gel eluted with EtOAc/CH$_2$Cl$_2$ (gradient) to yield AE4 (1.65 g, 34%). Compound AE4 in MeOH (50 mL) was treated with Pd/C (10% w/w) (500 mg), placed in a Parr shaker, degassed and back-filled with H2 then hydrogenated at 40 psi for 24 h at room temperature to provide AE5 that was used without further purification. $^1$H NMR (300 MHz, METHANOL-d$_4$) δ 3.55 (dd, J=9.42, 13.56 Hz, 1H), 3.20-3.31 (m, 2H), 2.89 (td, J=4.54, 9.18 Hz, 1H), 2.38 (t, J=6.03 Hz, 1H), 2.32 (t, J=6.40 Hz, 1H), 1.72-1.92 (m, 6H), 0.84-1.08 (m, 6H); $^{13}$C NMR (75 MHz, METHANOL-d$_4$) δ 173.3, 55.5, 52.4, 43.0, 33.1, 32.1, 23.1, 21.8, 19.5, 17.7; MS (ESI) m/z 185.2 (M+H)$^+$.

Synthesis of AE6. Compound AE5 (400 mg, 2.2 mmol) was coupled with Boc-7-hydroxy-D-Tic-OH (638 mg, 2.2 mmol) following the protocol described in General Method 4 to provide AE6 (389 mg, 39% yield). $^1$H NMR (300 MHz, CHLOROFORM-d) δ 6.86-7.15 (m, 1H), 6.50-6.77 (m, 2H), 6.34 (br. s., 1H), 4.73 (br. s., 1H), 4.55 (d, J=16.58 Hz, 2H), 4.25-4.48 (m, 1H), 3.73-4.02 (m, 1H), 3.25 (br. s., 1H), 2.87-3.21 (m, 4H), 2.67 (br. s., 1H), 2.11-2.33 (m, 2H), 1.62-1.84 (m, 2H), 1.40-1.62 (m, 12H), 0.86 (br. s., 6H); $^{13}$C NMR (75 MHz, CHLOROFORM-d) δ 172.1, 171.4, 155.9, Scheme AE.$^a$

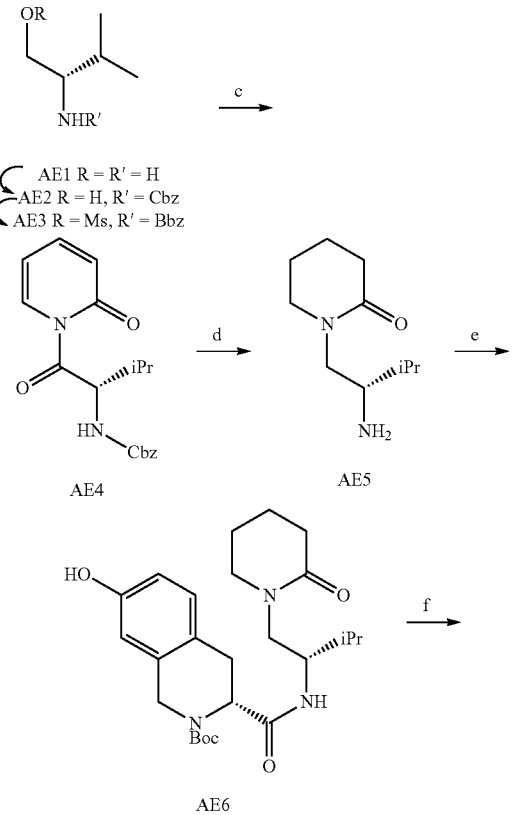

a ⌠ AE1 R = R' = H
  ⌡ AE2 R = H, R' = Cbz
b ⌠ AE3 R = Ms, R' = Bbz

AE4

AE5

AE6

134.3, 128.8, 123.8, 114.4, 113.0, 80.9, 56.6, 54.9, 51.8, 47.6, 45.0, 44.3, 42.1, 31.8, 30.6, 30.3, 28.3, 22.7, 20.8, 19.0, 17.7; MS (ESI) mtz 460.3 M+H)⁺.

(3R)-7-Hydroxy-N-{(1S)-2-methyl-1-[(2-oxopiperidin-1-yl)methyl]propyl}-1,2,3,4-tetrahydroisoquinoline-3-carboxamide (34) Hydrochloride. Compound AE6 (370 mg, 0.81 mmol) was subjected to Boc-cleavage according to General Method 2 to provide the amine (34) (245 mg, 85% yield). ¹H NMR (300 MHz, CHLOROFORM-d) δ 7.09-7.38 (m, 1H), 6.85 (d, J=8.29 Hz, 1H), 6.54-6.71 (m, 1H), 6.40-6.53 (m, 1H), 4.21-4.40 (m, 1H), 3.99-4.19 (m, 1H), 3.48-3.79 (m, 3H), 3.34 (dd, J=4.52, 11.30 Hz, 1H), 2.88-3.19 (m, 2H), 2.65 (dd, J=2.83, 13.37 Hz, 1H), 2.20-2.53 (m, 3H), 1.38-1.89 (m, 5H), 1.13-1.34 (m, 1H), 0.70-1.01 (m, 6H); ¹³C NMR (75 MHz, CHLOROFORM-d) δ 173.6, 171.4, 155.3, 136.8, 130.0, 124.7, 113.9, 112.1, 56.9, 51.4, 48.7, 47.8, 44.8, 41.8, 32.2, 30.8, 22.9, 20.9, 19.4, 18.3; MS (ESI) mtz 360.4 M+H)⁺. A white solid was obtained of the hydrochloride salt of (34). mp 154-157° C. (decomposes); [α]²⁴·²_D=+68.8 (c 1.1, CH₃OH). Anal. (C₂₀H₃₀ClN₃O₃.0.5H₂O) C, H, N.

J=2.35, 8.19 Hz, 1H), 6.56 (d, J=2.26 Hz, 1H), 3.93-4.05 (m, 1H), 3.78 (d, J=15.07 Hz, 1H), 3.56 (d, J=15.07 Hz, 1H), 3.15-3.26 (m, 1H), 2.86-3.05 (m, 2H), 2.62-2.84 (m, 2H), 2.37-2.50 (m, 3H), 2.23-2.36 (m, 2H), 1.73-2.03 (m, 3H), 1.52 (td, J=3.18, 6.64 Hz, 2H), 1.00-1.38 (m, 4H), 0.83-0.96 (m, 9H); ¹³C NMR (75 MHz, CHLOROFORM-d) δ 173.3, 155.2, 135.4, 128.9, 124.2, 114.3, 113.1, 64.6, 59.8, 55.7, 54.8, 53.2, 51.0, 42.3, 34.4, 34.2, 30.6, 28.5, 21.9, 19.3, 17.7; MS (ESI) m/z 374.3 M+H)⁺. A white solid was obtained of the dihydrochloride salt of (35). mp 186-188° C.; [α]²⁴·⁵_D=+61.7 (c 1.1, CH₃OH). Anal. (C₂₂H₃₇Cl₂N₃O₂.H₂O) C, H, N.

Scheme AF.ᵃ

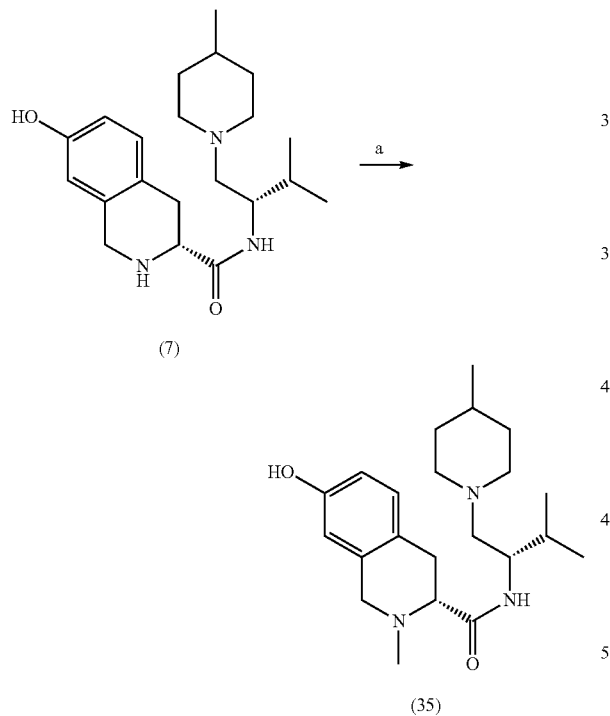

(7)

(35)

ᵃReagents and conditions: a) 37% CH₂O aq., NaBH(OAc)₃, DCM, rt, 24 h.

Synthesis of (35) Dihydrochloride. A solution of (7) (446 mg, 1.24 mmol) in dichloroethane (5 mL) was treated with formalin (0.11 mL, 1.2 equiv) followed by NaBH(OAc)₃ (1.2 g, 5.6 mmol). The reaction mixture was stirred at room temperature for 24 h, then partitioned between CH₂Cl₂ and saturated aqueous NaHCO₃. The organic portion was extracted three times (3×30 mL), combined organic layers were dried over anhydrous Na₂SO₄, filtered and concentrated in vacuo. The residue was purified on silica gel eluted with ethyl acetate/ hexanes to furnish 232 mg (50% yield) of the desired (35). ¹H NMR (300 MHz, CHLOROFORM-d) δ 7.09 (d, J=9.23 Hz, 1H), 6.91 (d, J=8.10 Hz, 1H), 6.66 (dd, Scheme AG.ᵃ

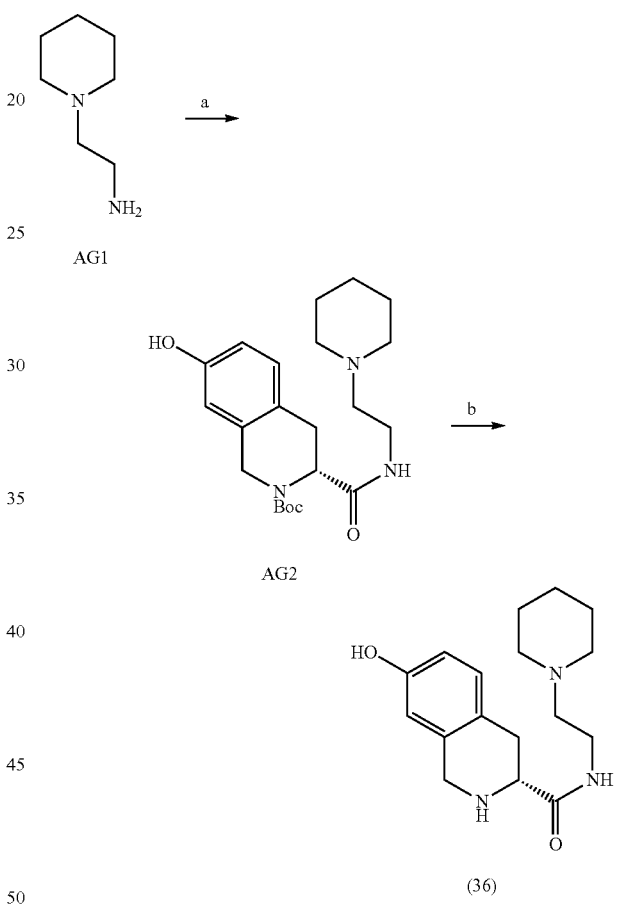

AG1

AG2

(36)

ᵃReagents and conditions: a) Boc-7-hydroxy-D-Tic(OH), DCC, HOBt, THF, rt, overnight; b) HCl aq., CH₃OH.

Synthesis of AG2. The amine AG1 (0.825 g, 6.5 mmol) was added to a solution of dicyclohexylcarbodiimide (DCC) (1.36 g, 6.6 mmol), HOBt (891 mg, 6.6 mmol) and 7-hydroxy-Boc-D-Tic(OH) (1.94 g, 6.6 mmol) in THF (20 mL) at 0° C. The solution was allowed to warm to room temperature overnight, forming a suspension. The solids were filtered, and the filtrate concentrated to a residue which was partitioned between CH₂Cl₂ and NaHCO₃ (aq.). The organic layer was separated and dried Na₂SO₄), then concentrated and the residue subjected to chromatography on silica gel eluting with a gradient up to 50% DMA80 to afford 1.62 g (62%) of the Boc intermediate AG2: ¹H NMR (300 MHz, CHLOROFORM-d) δ 6.99 (d, J=8.10 Hz, 1H), 6.49-6.79

(m, 1H), 6.42 (br. s., 1H), 4.64 (br. s., 1H), 4.32-4.58 (m, 1H), 3.06-3.41 (m, 2H), 2.79-3.06 (m, 1H), 2.05-2.53 (m, 4H), 1.28-1.72 (m, 11H).

(3R)-7-Hydroxy-N-(2-piperidin-1-ylethyl)-1,2,3,4-tetrahydroisoquinoline-3-carboxamide (36) Dihydrochloride. A sample of AG2 (1.00 g, 2.6 mmol) was dissolved in MeOH (10 mL) and HCl (6 N, 10 mL) at room temperature. After 2 h, the solution was concentrated. The residue was subjected to chromatography on silica gel eluting with a gradient up to 50% DMA80 to afford 0.35 g (44%) of the (36) free base: $^1$H NMR (300 MHz, DMSO-$d_6$) δ 9.04 (br. s., 1H), 7.78 (t, J=5.46 Hz, 1H), 6.87 (d, J=8.29 Hz, 1H), 6.53 (dd, J=2.54, 8.19 Hz, 1H), 6.42 (d, J=2.45 Hz, 1H), 3.71-3.90 (m, 2H), 3.33 (dd, J=4.80, 10.08 Hz, 1H), 3.15-3.25 (m, 3H), 2.79 (dd, J=4.71, 15.82 Hz, 1H), 2.59 (dd, J=10.17, 15.82 Hz, 1H), 2.19-2.45 (m, 6H), 1.44-1.58 (m, 4H), 1.39 (d, J=4.90 Hz, 2H); $^{13}$C NMR (75 MHz, DMSO-d6) δ 172.4, 155.2, 136.8, 129.5, 124.3, 113.3, 111.8, 57.5, 56.2, 53.9, 46.8, 35.8, 30.1, 25.5, 24.0. The free base was converted into a pale yellow powder as the dihydrochloride salt: MS (ESI) m/z 304.5 (M+H)$^+$; m.p. 129-133° C. (fusion); $[\alpha]^{25}_D$=+57 (c 1.2, CH$_3$OH). Anal. (C$_{17}$H$_{27}$Cl$_2$N$_3$O$_2$·0.5H$_2$O) C, H, N.

Synthesis of AH2. Cyclohexylacetaldehyde (AH1) (2.1 g, 17 mmol) was treated according to General Method 5 to afford 1.47 g (74%) AH2: $^1$H NMR (300 MHz, CHLOROFORM-d) δ 8.07 (t, J=5.27 Hz, 1H), 2.42 (t, J=6.03 Hz, 2H), 1.61-1.82 (m, 6H), 1.15-1.42 (m, 12H), 1.04 (br. s., 2H); $^{13}$C NMR (75 MHz, CHLOROFORM-d) δ 169.3, 56.3, 43.5, 35.3, 33.0, 33.0, 25.9, 25.8, 22.2.

Synthesis of AH3. The sulfinimine AH2 (1.47 g, 6.4 mmol) was reacted with iPrMgCl according to General Method 6 to afford 0.92 g (53%) of the desired sulfonamide AH3: $^1$H NMR (300 MHz, CHLOROFORM-d) δ 3.20 (br. s., 1H), 3.05 (d, J=8.10 Hz, 1H), 2.00 (dtd, J=3.58, 6.88, 13.75 Hz, 1H), 1.57-1.81 (m, 5H), 1.32-1.45 (m, 1H), 1.09-1.30 (m, 13H), 0.74-1.02 (m, 8H); $^{13}$C NMR (75 MHz, CHLOROFORM-d) δ 59.3, 56.0, 39.3, 34.3, 34.1, 32.8, 32.4, 26.6, 26.4, 26.1, 22.7, 18.2, 17.4.

Synthesis of AH4. The sulfonamide AH3 (0.92g, 3.4 mmol) was treated according to General Method 7 to afford 0.67 g (97%) of AH4 as a fluffy white solid: $^1$H NMR (300 MHz, CHLOROFORM-d) δ 8.33 (br. s., 2H), 3.17 (br. s., 1H), 1.94-2.23 (m, 1H), 1.49-1.91 (m, 9H), 0.72-1.48 (m, 10H); MS (ESI) m/z 170.3 M+H)$^+$.

(3R)-N-[(1R)-1-(cyclohexylmethyl)-2-methylpropyl]-7-hydroxy-1,2,3,4-tetrahydroisoquinoline-3-carboxamide (37) Hydrochloride. A solution of dicyclohexylcarbodiimide (DCC) (105 mg, 0.51 mmol) in THF (0.9 mL) was added to a solution of AH4 (100 mg, 0.49 mmol), NEt$_3$ (0.14 mL, 1.0 mmol), HOBt (69 mg, 0.51 mmol) and 7-hydroxy-Boc-D-Tic(OH) (150 mg, 0.51 mmol) in THF (3 mL) at 0° C. The solution was allowed to warm to room temperature overnight, forming a suspension. The solids were filtered, and the filtrate concentrated to a residue which dissolved in methanol (3 mL) and treated with 6 N HCl (3 mL). After 12 h, the solution was concentrated and the residue was subjected to chromatography on silica gel eluting with a gradient up to 25% DMA80. The cleanest fraction was re-subjected chromatography on silica gel eluting with a gradient up to 100% to EtOAc in hexanes to afford 41.9 mg (25% over two steps) of the (37) free base: $^1$H NMR (300 MHz, CHLOROFORM-d) δ 7.02 (d, J=9.80 Hz, 1H), 6.95 (d, J=8.29 Hz, 1H), 6.69 (dd, J=2.26, 8.10 Hz, 1H), 6.56 (d, J=2.07 Hz, 1H), 3.82-4.02 (m, 3H), 3.58 (dd, J=5.09, 10.17 Hz, 1H), 3.14 (dd, J=5.09, 16.01 Hz, 1H), 2.74 (dd, J=10.17, 16.01 Hz, 1H), 1.46-1.87 (m, 6H), 1.03-1.39 (m, 7H), 0.67-1.00 (m, 9H); $^{13}$C NMR (75 MHz, CHLOROFORM-d) δ 172.9, 154.9, 136.3, 129.9, 125.2, 114.3, 112.3, 56.8, 51.2, 47.3, 39.7, 34.6, 34.2, 32.6, 32.4, 30.6, 26.5, 26.3, 26.1, 19.1, 17.7. The free base was converted into a white powder as the hydrochloride salt: MS (ESI) m/z 345.3 (M+H)$^+$; m.p. 258-262° C. (fusion); $[\alpha]^{25}_D$=+99 (c 0.10, CH$_3$OH). Anal. (C$_{21}$H$_{33}$ClN$_2$O$_2$·0.25H$_2$O) C, H, N.

Scheme AH.$^a$

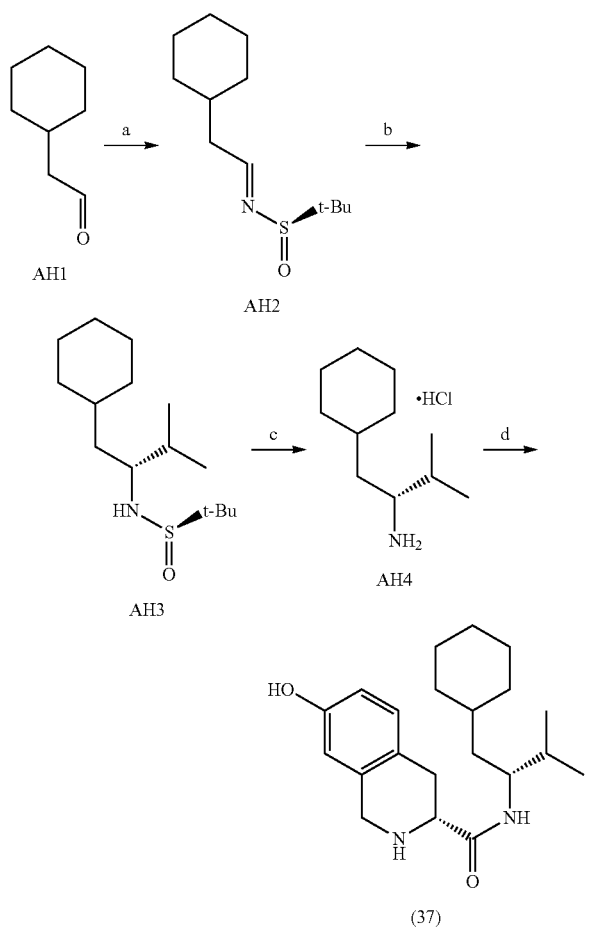

$^a$Reagents and conditions:
a) (R)-tert-Butylsulfinamide, MgSO$_4$, pyridinium tosylate, CH$_2$Cl$_2$, rt, overnight;
b) iPrMgCl, CH$_2$Cl$_2$;
c) HCl in 1,4-dioxane, CH$_3$OH, rt, 3 h;
d) i. Boc-7-hydroxy-D-Tic(OH), DCC, HOBt, NEt$_3$, THF, rt, overnight; ii. 6 N HCl aq., CH$_3$OH.

Scheme AI.$^a$

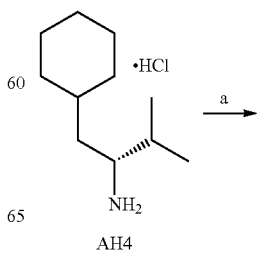

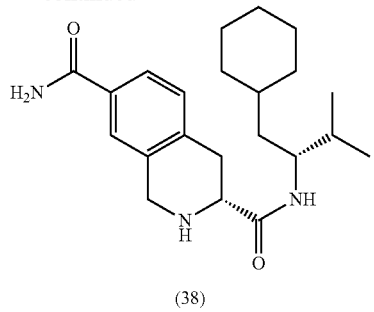

(38)

*Reagents and conditions:
a) i. Boc-7-carbamoyl-D-Tic(OH), DCC, HOBt, NEt₃, THF, rt, overnight; ii. 4 N HCl in 1, 4-dioxane, CH₃OH.

(3R)—N³-[(1R)-1-(Cyclohexylmethyl)-2-methylpropyl]-1,2,3,4-tetrahydroisoquinoline-3,7-dicarboxamide (38) Hydrochloride. A solution of dicyclohexylcarbodiimide (DCC) (105 mg, 0.51 mmol) in THF (0.9 mL) was added to a solution of HOBt (75 mg, 0.55 mmol) and 7-carbamoyl-Boc-D-Tic(OH) (164 mg, 0.51 mmol) in THF (3 mL). After 1 h, the amine AH4 (125 mg, 0.61 mmol) and NEt₃ (0.2 mL, 1.4 mmol) were added to the suspension. The reaction mixture was stirred at room temperature overnight. The solids were filtered, and the filtrate concentrated to a residue. The residue was subjected to chromatography on silica gel eluting with a gradient of EtOAc in hexanes. The product containing fractions were concentrated and the residue dissolved in methanol (3 mL) and treated with 4 N HCl in dioxane (3 mL). After 12 h, the solution was concentrated and the residue was subjected to chromatography on silica gel eluting with a gradient up to 20% DMA80 to afford 140 mg (74% over two steps) of the (38) free base: ¹H NMR (300 MHz, METHANOL-d₄) δ 7.65 (d, J=8.10 Hz, 1H), 7.59 (s, 1H), 7.19 (d, J=7.91 Hz, 1H), 3.95-4.15 (m, 2H), 3.86 (d, J=5.65 Hz, 1H), 3.54-3.70 (m, 1H), 3.33-3.39 (m, 1H), 2.82-3.16 (m, 2H), 1.98-2.08 (m, 2H), 1.85 (d, J=12.06 Hz, 1H), 1.53-1.77 (m, 5H), 1.05-1.40 (m, 7H), 0.69-1.04 (m, 8H); ¹³C NMR (75 MHz, METHANOL-d4) δ 173.6, 170.9, 138.4, 135.7, 131.7, 129.0, 125.6, 125.3, 56.1, 51.5, 46.4, 39.5, 34.5, 34.3, 32.8, 32.5, 32.0, 26.6, 26.4, 26.1, 18.7, 17.3. The free base was converted into a white powder as the hydrochloride salt: MS (ESI) m/z 372.3 (M+H)⁺; m.p. 132-136° C. (fusion); [α]²⁵_D=+96 (c 0.10, CH₃OH). Anal. (C₂₂H₃₄ClN₃O₂·2.25H₂O) C, H, N.

Scheme AJ.ᵃ

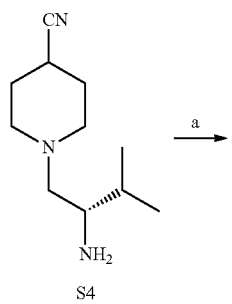

S4 a →

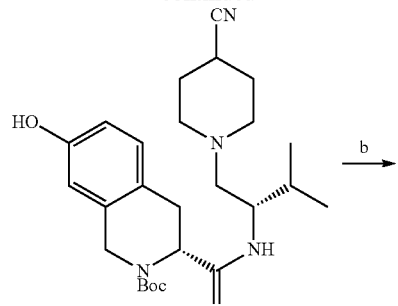

AJ1

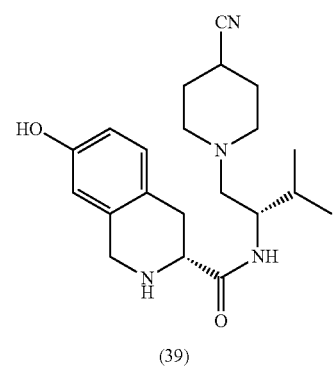

(39)

*Reagents and conditions:
a) Boc-7-hydroxy-D-Tic(OH), EDC·HCl, HOBt, NEt₃, CH₂Cl₂, rt, overnight;
b) HCl in 1-4-dioxane, CH₃CN, rt, 3 h.

Synthesis of AJ1. Amine S4 (470 mg, 2.41 mmol) and Boc-7-hydroxy-D-Tic-OH (705 mg, 2.41 mmol) were reacted according to the General Method 4 to provide the Boc-protected product AJ1 (558 mg, 49% yield). ¹H NMR (300 MHz, CHLOROFORM-d) δ 7.97 (br. s., 1H), 6.93-7.06 (m, 1H), 6.60-6.78 (m, 2H), 4.76 (br. s., 1H), 4.37-4.59 (m, 2H), 3.82 (br. s., 1H), 3.23 (d, J=17.71 Hz, 2H), 2.88-3.03 (m, 1H), 2.05-2.60 (m, 6H), 1.57-1.82 (m, 4H), 1.38-1.56 (m, 9H), 0.66-0.91 (m, 6H); ¹³C NMR (75 MHz, CHLOROFORM-d) δ 171.6, 155.5, 142.9, 134.0, 129.2, 124.2, 121.6, 114.8, 113.2, 81.0, 59.5, 51.1, 50.9, 44.8, 33.8, 30.6, 28.4, 28.4, 28.3, 28.1, 25.6, 24.9, 21.0, 19.2, 17.2; (ESI) mtz 471.4 M+H)⁺.

(3R)—N-{(1S)-1-[(4-Cyanopiperidin-1-yl)methyl]-2-methylprolyl}-7-hydroxy-1,2,3,4-tetrahydroisoquinoline-3-carboxamide (39) Dihydrochloride. A solution of AJ1 (300 mg, 0.64 mmol) in methylene chloride was treated with trifluoroacetic acid (1 ml) and stirred at room temperature overnight to remove the Boc-protection which provided 213 mg (90% yield) of the amine compound (39). Analysis for the free base. ¹H NMR (300 MHz, CHLOROFORM-d) δ 7.24 (d, J=8.85 Hz, 1H), 6.82-6.97 (m, 1H), 6.54-6.70 (m, 1H), 6.38-6.52 (m, 1H), 5.47 (br. s., 2H), 3.94-4.08 (m, 1H), 3.77-3.91 (m, 2H), 3.54 (dd, J=5.09, 9.80 Hz, 1H), 2.88-3.02 (m, 1H), 2.43-2.85 (m, 5H), 2.30-2.42 (m, 1H), 1.72-1.94 (m, 4H), 0.82-1.06 (m, 6H); ¹³C NMR (75 MHz, CHLOROFORM-d) δ 172.9, 155.0, 135.7, 130.1, 124.7, 121.6, 114.3, 112.4, 59.9, 56.5, 51.4, 50.5, 46.9, 31.0, 30.8, 30.0, 28.3, 25.8, 19.3, 17.7; (ESI) m/z 371.3 M+H)⁺. A white solid was obtained as hydrochloride salt of (39): mp 182° C. (decomp); [α]²¹·⁵_D=+82.2 (c 1.1, CH₃OH). Anal. (C₂₁H₃₂Cl₂N₄O₂·0.75H₂O) C, H, N.

Scheme AK.[a]

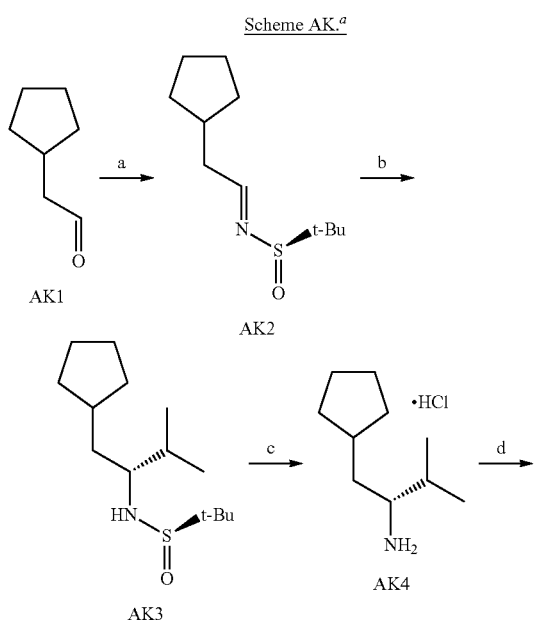

[a]Reagents and conditions:
a) (R)-tert-Butylsulfinamide, MgSO$_4$, pyridinium tosylate, CH$_2$Cl$_2$, rt, overnight;
b) iPrMgCl, CH$_2$Cl$_2$;
c) HCl in 1,4-dioxane, CH$_3$OH, rt, 3 h;
d) i. Boc-7-hydroxy-D-Tic(OH), DCC, HOBt, NEt$_3$, THF, rt, overnight; ii. 6 N HCl aq., CH$_3$OH.

Synthesis of AK2. Cyclopentylacetaldehyde (AK1) (0.97 g, 8.6 mmol) was treated according to General Method 5 to afford 0.46 g (24%) AK2: $^1$H NMR (300 MHz, CHLOROFORM-d) δ 7.99 (t, J=4.99 Hz, 1H), 2.41-2.52 (m, 2H), 2.12 (quind, J=7.69, 15.38 Hz, 1H), 1.65-1.89 (m, 2H), 1.39-1.64 (m, 6H), 0.98-1.23 (m, 9H).

Synthesis of AK3. The sulfinimine AK2 (0.46 g, 2.1 mmol) was reacted with iPrMgCl according to General Method 6 to afford 60 mg (11%) of the desired sulfonamide AK3: $^1$H NMR (300 MHz, CHLOROFORM-d) δ 2.99-3.20 (m, 2H), 1.84-2.10 (m, 2H), 1.69-1.84 (m, 2H), 1.27-1.68 (m, 6H), 1.18-1.26 (m, 9H), 0.98-1.17 (m, 2H), 0.92 (dd, J=6.88, 10.46 Hz, 6H).

Synthesis of AK4. The sulfonamide AK3 (60 mg, 0.23 mmol) was treated according to General Method 7 to afford a quantitative yield of AK4 as a fluffy white solid: $^1$H NMR (300 MHz, METHANOL-d$_4$) δ 3.54-3.78 (m, 1H), 2.98-3.15 (m, 1H), 1.76-2.09 (m, 5H), 1.47-1.75 (m, 7H), 1.05-1.27 (m, 2H), 1.01 (t, J=6.59 Hz, 6H).

(3R)—N-[(1R)-1-(Cyclopentylmethyl)-2-methylpropyl]-7-hydroxy-1,2,3,4-tetrahydroisoquinoline-3-carboxamide (40) Hydrochloride. A solution of dicyclohexylcarbodiimide (DCC) (76 mg, 0.37 mmol) in THF (1 mL) was added to a solution of HOBt (46 mg, 0.33 mmol) and 7-hydroxy-Boc-D-Tic(OH) (94 mg, 0.32 mmol) in THF (2 mL). After 1 h, the amine AK4 (55.8 mg, 0.29 mmol) and NEt$_3$ (0.125 mL, 0.90 mmol) were added to the suspension. The reaction mixture was stirred at room temperature overnight. The solids were filtered, and the filtrate concentrated to a residue. The residue was subjected to chromatography on silica gel eluting with a gradient up to 50% EtOAc in hexanes. The product containing fractions were concentrated and the residue dissolved in CH$_3$CN (5 mL) and treated with 4 N HCl in dioxane (5 mL). After 1 h, the solution was concentrated and the residue was subjected to chromatography on silica gel eluting with a gradient EtOAc in hexanes. The resulting concentrated was converted into 56.6 mg (51% over two steps) of the (40) hydrochloride salt: $^1$H NMR (300 MHz, METHANOL-d$_4$) δ 8.12 (d, J=9.23 Hz, 1H), 7.09 (d, J=8.48 Hz, 1H), 6.75 (dd, J=2.35, 8.38 Hz, 1H), 6.64 (d, J=2.26 Hz, 1H), 4.34 (d, J=4.14 Hz, 2H), 4.15 (dd, J=4.71, 11.87 Hz, 1H), 3.76-3.92 (m, 1H), 3.23-3.37 (m, 2H), 3.10 (d, J=11.87 Hz, 1H), 1.38-1.94 (m, 11H), 1.01-1.20 (m, 2H), 0.92 (d, J=6.59 Hz, 6H); $^{13}$C NMR (75 MHz, METHANOL-d$_4$) δ 169.5, 169.4, 158.1, 131.1, 129.8, 122.1, 116.9, 113.7, 56.9, 55.6, 55.5, 45.5, 39.1, 39.1, 38.4, 34.2, 34.0, 33.4, 30.9, 26.1, 26.0, 19.8, 18.2. The free base was converted into a white powder as the hydrochloride salt: MS (ESI) m/z 331.6 (M+H)$^+$; m.p. 142-146° C. (fusion); [α]$^{25}_D$=+99 (c 0.20, CH$_3$OH). Anal. (C$_{20}$H$_{31}$ClN$_2$O$_2$·0.75H$_2$O) C, H, N.

Scheme AL.[a]

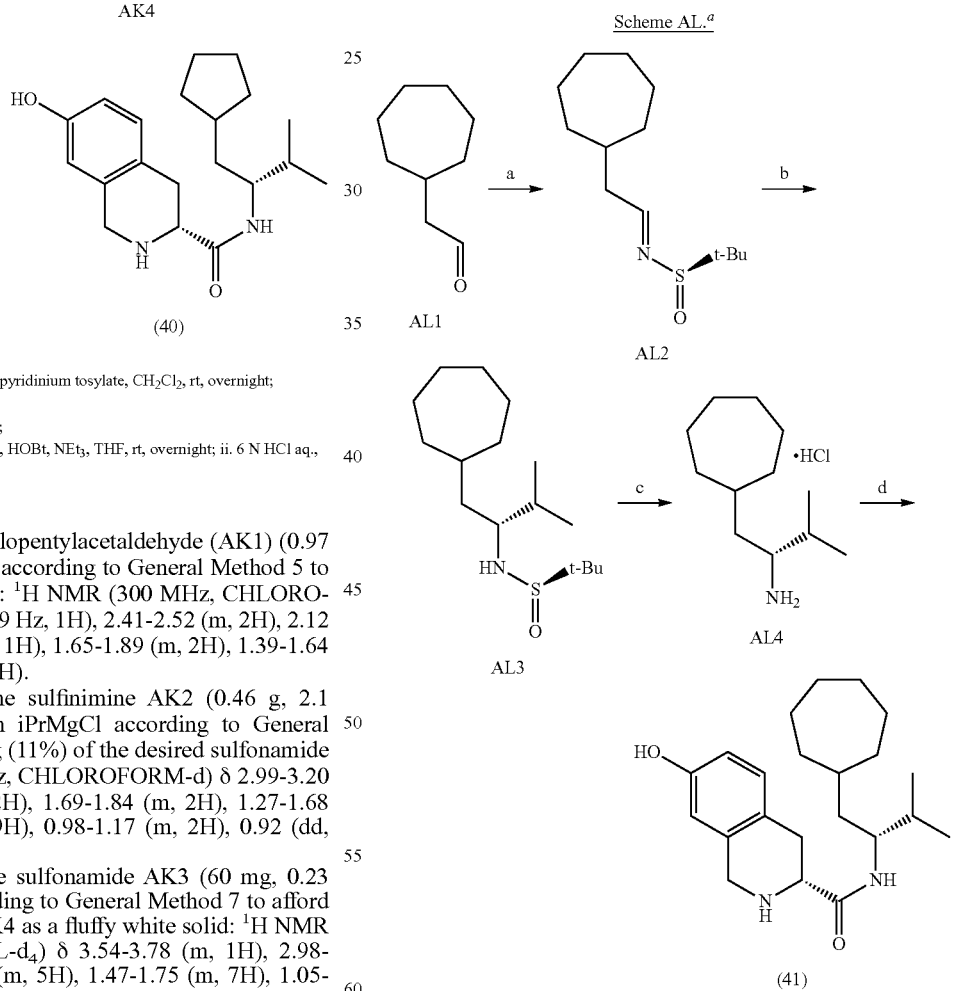

[a]Reagents and conditions:
a) (R)-tert-Butylsulfinamide, MgSO$_4$, pyridinium tosylate, CH$_2$Cl$_2$, rt, overnight;
b) iPrMgCl, CH$_2$Cl$_2$;
c) HCl in 1,4-dioxane, CH$_3$OH, rt, 3 h;
d) i. Boc-7-hydroxy-D-Tic(OH), DCC, HOBt, NEt$_3$, THF, rt, overnight; ii. 4 N HCl in 1,4-dioxane, CH$_3$CN.

Synthesis of AL2. Cycloheptylacetaldehyde (AL1) (4.3 g, 31 mmol) was treated according to General Method 5 to afford 3.58 g (89%) AL2: $^1$H NMR (300 MHz, CDC13) δ 8.06 (t, J=5.18 Hz, 1H), 2.39-2.52 (m, 2H), 1.87-2.07 (m, 1H), 1.82-1.17 (m, 12H), 1.22 (s, 9H).

Synthesis of AL3. The sulfinimine AL2 (1.0 g, 4.1 mmol) was reacted with iPrMgCl according to General Method 6 to afford 0.81 g (69%) of the desired sulfinamide AL3: $^1$H NMR (300 MHz, CDCl$_3$) δ 2.89-3.16 (m, 2H), 1.86-1.96 (m, 1H), 0.92-1.70 (m, 15H), 1.15 (s, 9H), 0.85 (dd, J=6.97, 11.30 Hz, 6H).

Synthesis of AL4. The sulfonamide AL3 (0.81 g, 2.8 mmol) was treated according to General Method 7 to afford 0.57 g (91%) of the amine hydrochloride AL4 as a fluffy white solid: $^1$H NMR (300 MHz, METHANOL-d4) δ 3.09 (dd, J=4.14, 8.48 Hz, 1H), 1.95 (dd, J=4.24, 6.88 Hz, 1H), 1.10-1.84 (m, 16H), 0.90-1.06 (m, 6H).

(3R)—N-[(1R)-1-(Cycloheptylmethyl)-2-methylpropyl]-7-hydroxy-1,2,3,4-tetrahydroisoquinoline-3-carboxamide (41) Hydrochloride. A solution of dicyclohexylcarbodiimide (DCC) (62 mg, 0.30 mmol) in THF (1 mL) was added to a solution of HOBt (38 mg, 0.28 mmol) and 7-hydroxy-Boc-D-Tic(OH) (76 mg, 0.26 mmol) in THF (2 mL). After 1 h, the amine AL4 (135 mg, 0.61 mmol) and NEt$_3$ (0.1 mL, 0.72 mmol) were added to the suspension. The reaction mixture was stirred at room temperature for 3 h. The solids were filtered, and the filtrate concentrated to a residue. The residue was subjected to chromatography on silica gel eluting with a gradient up to 100% EtOAc in hexanes. The product containing fractions were concentrated and the residue dissolved in CH$_3$CN (10 mL) and treated with 4 N HCl in dioxane (4 mL). After 1 h, the solution was concentrated and the residue partitioned between EtOAc and sat. NaHCO$_3$. The organic layer was dried Na$_2$SO$_4$) and concentrated. The residue was subjected to chromatography on silica gel eluting with a gradient EtOAc in hexanes to afford the freebase: $^1$H NMR (300 MHz, CDCl$_3$) δ 6.78-7.04 (m, 2H), 6.61 (dd, J=2.17, 8.19 Hz, 1H), 6.49 (d, J=1.70 Hz, 1H), 3.71-3.96 (m, 3H), 3.50 (dd, J=5.09, 10.17 Hz, 1H), 3.06 (dd, J=5.09, 16.01 Hz, 1H), 2.67 (dd, J=10.17, 16.01 Hz, 1H), 1.57-1.74 (m, 2H), 0.94-1.57 (m, 13H), 0.74-0.87 (m, 6H); $^{13}$C NMR (75 MHz, CDCl$_3$) δ 173.0, 154.9, 136.4, 130.0, 125.3, 114.3, 112.3, 56.8, 51.7, 47.3, 40.3, 35.9, 35.8, 33.4, 32.4, 30.7, 28.6, 28.4, 26.4, 26.1, 19.2, 17.7. The free base was converted into 23.1 mg (23% over two steps) white powder as the hydrochloride salt: MS (ESI) m/z 359.4 (M+H)$^+$; m.p. 138-142° C. (fusion). Anal. (C$_{22}$H$_{35}$ClN$_2$O$_2$·H$_2$O) C, H, N.

Scheme AM.$^a$

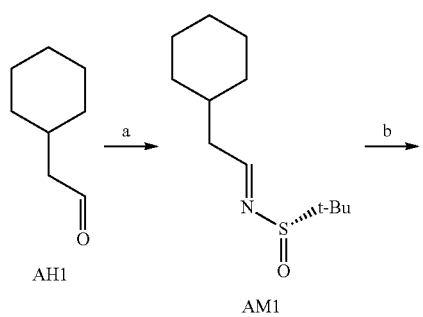

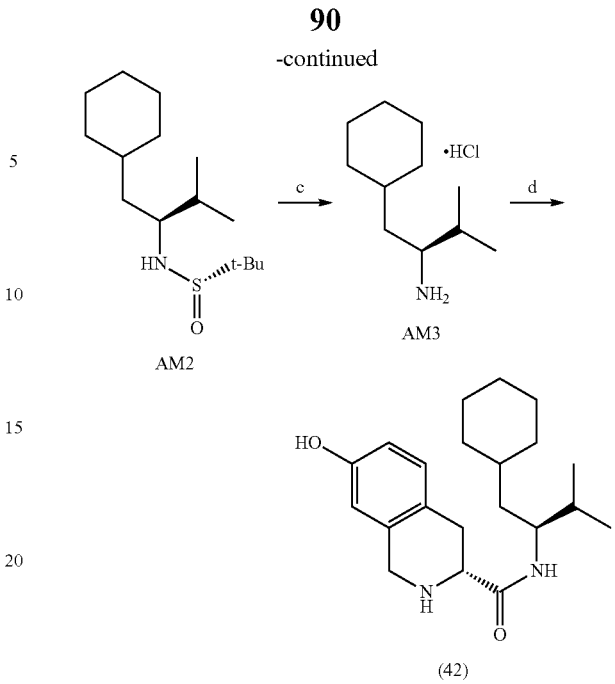

$^a$Reagents and conditions:
a) (S)-tert-Butylsulfinamide, MgSO$_4$, pyridinium tosylate, CH$_2$Cl$_2$, rt, overnight;
b) iPrMgCl, CH$_2$Cl$_2$;
c) HCl in 1,4-dioxane, CH$_3$OH, rt, 3 h;
d) i. Boc-7-hydroxy-D-Tic(OH), DCC, HOBt, NEt$_3$, THF, rt, overnight; ii. 6 N HCl aq., CH$_3$OH.

(3R)—N-[(1S)-1-(Cyclohexylmethyl)-2-methylpropyl]-7-hydroxy-1,2,3,4-tetrahydroisoquinoline-3-carboxamide (42) Hydrochloride. The sequence to prepare amine AM3 from AM2 and AM1 proceeded analogously to the preparation of AH4, substituting (S)-tert-butylsulfinamide. A solution of dicyclohexylcarbodiimide (DCC) (110 mg, 0.53 mmol) in THF (2 mL) was added to a solution of HOBt (70. mg, 0.52 mmol) and 7-hydroxy-Boc-D-Tic(OH) (150 mg, 0.50 mmol) in THF (3 mL). After 1 h, the amine AM3 (90. mg, 0.44 mmol) and NEt$_3$ (0.3 mL, 2.2 mmol) were added to the suspension. The reaction mixture was stirred at room temperature for 12 h. The solids were filtered, and the filtrate concentrated to a residue. The residue was subjected to chromatography on silica gel eluting with a gradient up to 100% EtOAc in hexanes. The product containing fractions were concentrated and the residue dissolved in CH$_3$OH (5 mL) and treated with 6 N HCl aq (5 mL). After 1 h, the solution was concentrated and the residue partitioned between EtOAc and sat. NaHCO$_3$. The organic layer was dried Na$_2$SO$_4$) and concentrated. The residue was subjected to chromatography on silica gel eluting with a gradient EtOAc in hexanes to afford the freebase (42): $^1$H NMR (300 MHz, CDCl$_3$) δ 6.94 (d, J=8.29 Hz, 1H), 6.66 (dd, J=2.45, 8.29 Hz, 1H), 6.52 (d, J=2.26 Hz, 1H), 3.95 (d, J=8.48 Hz, 2H), 3.88 (td, J=4.59, 9.47 Hz, 1H), 3.63 (dd, J=5.09, 10.17 Hz, 1H), 3.06 (dd, J=5.09, 16.01 Hz, 1H), 2.71-2.84 (m, 1H), 1.82 (d, J=13.19 Hz, 1H), 1.54-1.76 (m, 5H), 1.07-1.38 (m, 7H), 0.87-1.04 (m, 1H), 0.83 (d, J=6.97 Hz, 6H); $^{13}$C NMR (75 MHz, CDCl$_3$) δ 172.3, 155.1, 135.3, 129.8, 124.6, 114.3, 112.2, 56.4, 51.2, 46.7, 39.7, 34.6, 34.1, 32.6, 32.3, 30.5, 26.5, 26.3, 26.1, 19.0, 17.4. The free base was converted into 14.5 mg (9% over two steps) white powder as the hydrochloride salt: MS (ESI) m/z 345.2 (M+H)$^+$; m.p. 150-154° C. (fusion); $[\alpha]^{25}{}_D$=+38 (c 0.10, CH$_3$OH). Anal. (C$_{21}$H$_{33}$ClN$_2$O$_2$·1.25H$_2$O) C, H, N.

Scheme AN.[a]

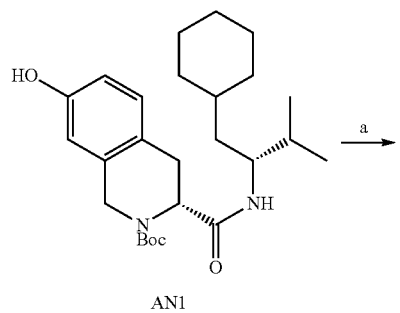

ANI

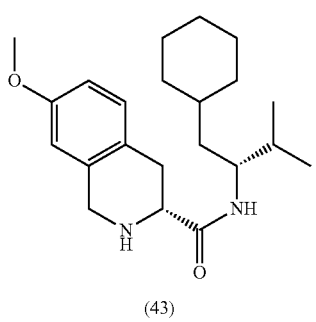

(43)

[a]Reagents and conditions:
a) i. $K_2CO_3$, $CH_3I$, DMF; ii. 6 N HCl aq., $CH_3OH$.

(3R)—N-[(1R)-1-(Cyclohexylmethyl)-2-methylpropyl]-7-methoxy-1,2,3,4-tetrahydroisoquinoline-3-carboxamide (43) Hydrochloride. A solution of Boc-protected (AN1) (127 mg, 0.29 mmol) in acetone (5 mL) was treated with $K_2CO_3$ (140 mg, 1 mmol) and iodomethane (460 mg, 3.2 mmol). After stirring 12 h at ambient temperature, the suspension was filtered. The filtrate was concentrated and the resulting residue dissolved in $CH_3OH$ (5 mL) and treated with 6 M HCl aq. (5 mL). After 2 h, the solution was concentrated and the resulting residue was dissolved in EtOAc and washed with sat. aq. $Na_2CO_3$. The organic layer was concentrated and the residue subjected to chromatography on silica gel eluting with a gradient of EtOAc in hexanes to afford the free base (43): $^1H$ NMR (300 MHz, $CDCl_3$) δ 7.10 (d, J=8.48 Hz, 1H), 6.95 (d, J=9.98 Hz, 1H), 6.76 (dd, J=2.64, 8.29 Hz, 1H), 6.62 (d, J=2.64 Hz, 1H), 3.86-4.05 (m, 3H), 3.79 (s, 3H), 3.53-3.66 (m, 1H), 3.19 (dd, J=5.18, 16.11 Hz, 1H), 2.78 (dd, J=10.17, 16.20 Hz, 1H), 1.51-1.88 (m, 6H), 1.05-1.40 (m, 7H), 0.71-1.00 (m, 8H); $^{13}C$ NMR (75 MHz, $CDCl_3$) δ 172.4, 158.0, 136.6, 130.0, 126.4, 112.6, 110.7, 56.8, 55.3, 50.9, 47.6, 39.8, 34.6, 34.2, 32.6, 32.4, 30.6, 26.5, 26.3, 26.1, 19.1, 17.7. The free base was converted into 29.4 mg (25% over two steps) white powder as the hydrochloride salt: MS (ESI) m/z 359.5 (M+H)$^+$; m.p. 238-242° C. (fusion); $[α]^{25}_D$=+84 (c 0.10, $CH_3OH$). Anal. ($C_{22}H_{35}ClN_2O_2·0.25H_2O$) C, H, N.

Scheme AO.[a]

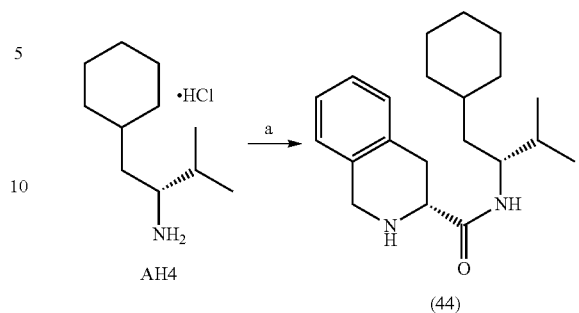

AH4 (44)

[a]Reagents and conditions:
a) i. Boc-D-Tic(OH), DCC, HOBt, $NEt_3$, THF, rt, overnight; ii. $K_2CO_3$, $CH_3I$, DMF; iii. 6 N HCl aq., $CH_3OH$.

(3R)—N-[(1R)-1-(Cyclohexylmethyl)-2-methylpropyl]-1,2,3,4-tetrahydroisoquinoline-3-carboxamide (44) Hydrochloride. Dicyclohexylcarbodiimide (DCC) (47.5 mg, 0.23 mmol) was added to a solution of HOBt (29 mg, 0.22 mmol) and Boc-D-Tic(OH) (55.4 mg, 0.20 mmol) in THF (2 mL). After 1 h, the amine AH4 (49.4 mg, 0.24 mmol) and $NEt_3$ (0.08 mL, 0.6 mmol) were added to the suspension. The reaction mixture was stirred at room temperature for 12 h. The solids were filtered, and the filtrate concentrated to a residue. The residue was subjected to chromatography on silica gel eluting with a gradient of EtOAc in hexanes. The product containing fractions were concentrated and the residue dissolved in $CH_3OH$ (5 mL) and treated with 6 N HCl aq (5 mL). After 1 h, the solution was concentrated and the residue partitioned between $CH_2Cl_2$ and sat. aq. $Na_2CO_3$. The organic layer was dried $Na_2SO_4$) and concentrated. The residue was subjected to chromatography on silica gel eluting with a gradient EtOAc in hexanes to afford the freebase (44): $^1H$ NMR (300 MHz, $CDCl_3$) δ 7.12-7.23 (m, 3H), 7.03-7.12 (m, 1H), 6.97 (d, J=9.80 Hz, 1H), 4.04 (s, 2H), 3.85-3.99 (m, 1H), 3.74-3.82 (m, 1H), 3.56-3.70 (m, 2H), 3.25 (dd, J=5.09, 16.39 Hz, 1H), 2.85 (dd, J=10.17, 16.39 Hz, 1H), 1.51-1.89 (m, 6H), 1.05-1.40 (m, 6H), 0.71-1.01 (m, 7H); $^{13}C$ NMR (75 MHz, $CDCl_3$) δ 172.5, 135.8, 134.4, 129.1, 126.7, 126.2, 125.6, 56.5, 50.9, 47.4, 39.8, 34.6, 34.2, 32.6, 32.4, 31.4, 26.5, 26.4, 26.1, 19.1, 17.7. The free base was converted into 48.5 mg (66% over two steps) white powder as the hydrochloride salt: MS (ESI) m/z 329.3 (M+H)$^+$; m.p. 210-214° C. (fusion); $[α]^{25}_D$=+104 (c 0.10, $CH_3OH$). Anal. ($C_{21}H_{33}ClN_2O$) C, H, N.

Scheme AP.[a]

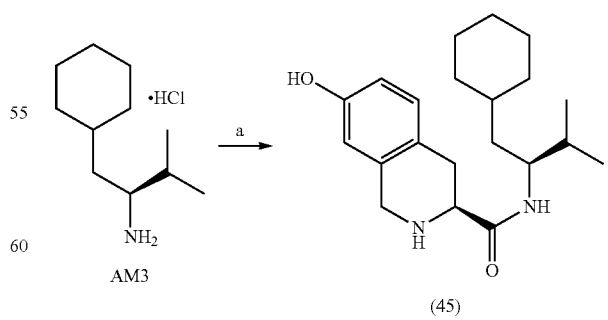

AM3 (45)

[a]Reagents and conditions:
a) i. Boc-7-hydroxy-L-Tic(OH), DCC, HOBt, $NEt_3$, THF, rt, overnight; ii. $K_2CO_3$, $CH_3I$, DMF; ii. 6 N HCl aq., $CH_3OH$.

(3S)—N-[(1S)-1-(Cyclohexylmethyl)-2-methylpropyl]-7-hydroxy-1,2,3,4-tetrahydroisoquinoline-3-carboxamide (45) Hydrochloride. A solution of dicyclohexylcarbodiimide (DCC) (120 mg, 0.58 mmol) in THF (2 mL) was added to a solution of HOBt (72 mg, 0.54 mmol) and 7-hydroxy-Boc-L-Tic(OH) (150 mg, 0.51 mmol) in THF (3 mL). After 1 h, the amine AM3 (116 mg, 0.57 mmol) and NEt$_3$ (0.2 mL, 1.4 mmol) were added to the suspension. The reaction mixture was stirred at room temperature for 12 h. The solids were filtered, and the filtrate concentrated to a residue. The residue was subjected to chromatography on silica gel eluting with a gradient up to 75% EtOAc in hexanes. The product containing fractions were concentrated and the residue dissolved in CH$_3$OH (5 mL) and treated with 6 N HCl aq (5 mL). After 1 h, the solution was concentrated and the taken up in 50% DMA80. The solids were filtered off and the organic layer was concentrated. The residue was subjected to chromatography on silica gel eluting with a 25% DMA80 in CH$_2$Cl$_2$ to afford the freebase (45): $^1$H NMR (300 MHz, CDCl$_3$) δ 6.83-7.02 (m, 2H), 6.61 (dd, J=2.45, 8.10 Hz, 1H), 6.49 (d, J=2.26 Hz, 1H), 3.76-3.97 (m, 3H), 3.52 (dd, J=5.09, 10.17 Hz, 1H), 3.07 (dd, J=5.18, 16.11 Hz, 1H), 2.67 (dd, J=10.17, 16.01 Hz, 1H), 1.40-1.82 (m, 6H), 0.93-1.33 (m, 7H), 0.61-0.92 (m, 9H); $^{13}$C NMR (75 MHz, CDCl$_3$) δ 172.7, 154.7, 136.3, 130.0, 125.4, 114.3, 112.3, 56.7, 51.2, 47.2, 39.7, 34.6, 34.2, 32.6, 32.4, 30.6, 26.5, 26.3, 26.1, 19.1, 17.7. The free base was converted into 68.3 mg (36% over two steps) white powder as the hydrochloride salt: MS (ESI) m/z 345.3 (M+H)$^+$; m.p. 265-269° C. (fusion); [α]$^{25}_D$=101 (c $_{0.10}$ CH$_3$OH). Anal. (C$_{21}$H$_{33}$ClN$_2$O$_2$) C, H, N.

Scheme AQ.$^a$

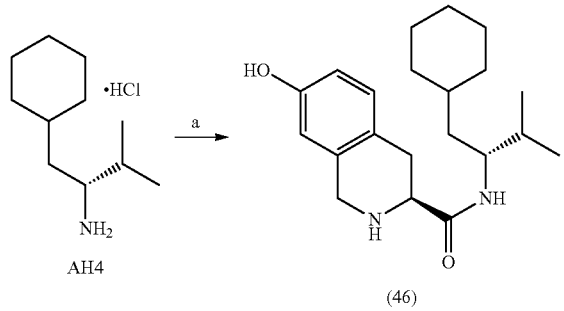

(46)

$^a$Reagents and conditions:
a) i. Boc-7-hydroxy-L-Tic(OH), DCC, HOBt, NEt$_3$, THF, rt, overnight; ii. 6 N HCl aq., CH$_3$OH.

(3S)—N-[(1R)-1-(Cyclohexylmethyl)-2-methylpropyl]-7-hydroxy-1,2,3,4-tetrahydroisoquinoline-3-carboxamide (46) Hydrochloride. A solution of dicyclohexylcarbodiimide (DCC) (120 mg, 0.58 mmol) in THF (2 mL) was added to a solution of HOBt (72 mg, 0.54 mmol) and 7-hydroxy-Boc-L-Tic(OH) (150 mg, 0.51 mmol) in THF (3 mL). After 1 h, the amine AH4 (120 mg, 0.6 mmol) and NEt$_3$ (0.2 mL, 1.4 mmol) were added to the suspension. The reaction mixture was stirred at room temperature for 12 h. The solids were filtered, and the filtrate concentrated to a residue. The residue was subjected to chromatography on silica gel eluting with a gradient up to 75% EtOAc in hexanes. The product containing fractions were concentrated and the residue dissolved in CH$_3$OH (5 mL) and treated with 6 N HCl aq (5 mL). After 1 h, the solution was concentrated and the residue partitioned between EtOAc and 7 M NH$_4$OH aq. The organic layer was dried Na$_2$SO$_4$) and concentrated. The residue was subjected to chromatography on silica gel eluting with a gradient EtOAc in hexanes to afford the freebase (46): $^1$H NMR (300 MHz, CDCl$_3$) δ 7.03 (d, J=9.98 Hz, 1H), 6.97 (d, J=8.29 Hz, 1H), 6.66 (dd, J=2.54, 8.19 Hz, 1H), 6.54 (d, J=2.45 Hz, 1H), 3.85-3.97 (m, 3H), 3.58 (dd, J=5.27, 9.98 Hz, 1H), 3.12 (dd, J=5.18, 16.11 Hz, 1H), 2.76 (dd, J=9.98, 16.01 Hz, 1H), 1.54-1.92 (m, 9H), 1.04-1.38 (m, 6H), 0.72-1.02 (m, 7H); $^{13}$C NMR (75 MHz, CDCl$_3$) δ 172.3, 154.8, 135.7, 129.9, 125.1, 114.2, 112.2, 56.5, 51.2, 46.9, 39.8, 34.6, 34.2, 32.6, 32.3, 30.5, 26.5, 26.4, 26.1, 19.1, 17.5. The free base was converted into 123.3 mg (63% over two steps) white powder as the hydrochloride salt: MS (ESI) m/z 345.2 (M+H)$^+$; m.p. 149-153° C. (fusion); [α]$^{25}_D$=−43 (c 0.10, CH$_3$OH). Anal. (C$_{21}$H$_{33}$ClN$_2$O$_2$·0.5H$_2$O) C, H, N.

Scheme AR.$^a$

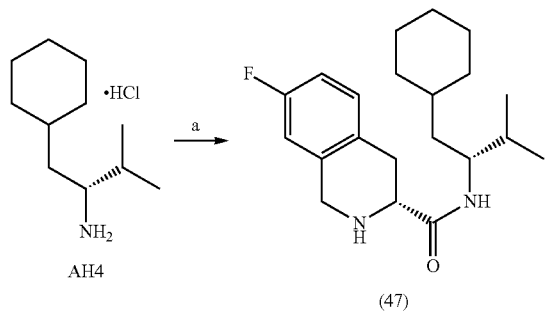

(47)

$^a$Reagents and conditions:
a) i. Boc-7-fluoro-D-Tic(OH), DCC, HOBt, NEt$_3$, THF, rt, overnight; ii. 6 N HCl aq., CH$_3$OH.

(3R)—N-[(1R)-1-(Cyclohexylmethyl)-2-methylpropyl]-7-fluoro-1,2,3,4-tetrahydroisoquinoline-3-carboxamide (47) Hydrochloride. Dicyclohexylcarbodiimide (DCC) (63 mg, 0.31 mmol) was added to a solution of HOBt (44 mg, 0.33 mmol) and 7-fluoro-Boc-D-Tic(OH) (81 mg, 0.27 mmol) in THF (2.5 mL). After 1 h, the amine AH4 (62 mg, 0.30 mmol) and NEt$_3$ (0.2 mL, 1.4 mmol) in THF (0.5 mL) were added to the suspension. The reaction mixture was stirred at room temperature for 12 h. The solids were filtered, and the filtrate concentrated to a residue. The residue was subjected to chromatography on silica gel eluting with a gradient up to 50% EtOAc in hexanes. The product containing fractions were concentrated and the residue dissolved in CH$_3$OH (5 mL) and treated with 6 N HCl aq (5 mL). After 12 h, the solution was concentrated and the residue partitioned between EtOAc and sat. aq. Na$_2$CO$_3$. The organic layer was dried Na$_2$SO$_4$) and concentrated. The residue was subjected to chromatography on silica gel eluting with a gradient up to 75% EtOAc in hexanes to afford the freebase (47): $^1$H NMR (300 MHz, CDCl$_3$) δ 7.13 (dd, J=5.65, 8.29 Hz, 1H), 6.83-7.00 (m, 2H), 6.78 (dd, J=2.45, 9.04 Hz, 1H), 4.01 (d, J=5.09 Hz, 2H), 3.93 (dt, J=4.90, 9.80 Hz, 1H), 3.59 (dd, J=5.27, 9.80 Hz, 1H), 3.20 (dd, J=5.18, 16.29 Hz, 1H), 2.81 (dd, J=9.80, 16.20 Hz, 1H), 1.95 (br. s., 1H), 1.51-1.87 (m, 6H), 1.02-1.40 (m, 6H), 0.70-1.01 (m, 8H); $^{13}$C NMR (75 MHz, CDCl$_3$) δ 172.2, 161.2 (d, J=243 Hz), 137.4 (d, J=7.3 Hz), 130.5 (d, J=7.3 Hz), 129.9 (d, J=3.6 Hz), 113.7 (d, J=21 Hz), 112.1 (d, J=21 Hz), 56.4, 50.9, 47.3, 39.8, 34.6, 34.2, 32.6, 32.4, 30.6, 26.5, 26.3, 26.1, 19.1, 17.7. The free base was converted into 58.1 mg (56% over two steps) white powder as the hydrochloride salt: MS (ESI) m/z 347.5

(M+H)+; m.p. 232-236° C. (fusion); [α]$_D^{25}$=+107 (c 0.10, CH$_3$OH). Anal. (C$_{21}$H$_{32}$ClFN$_2$O.0.25H$_2$O) C, H, N.

Scheme AS.$^a$

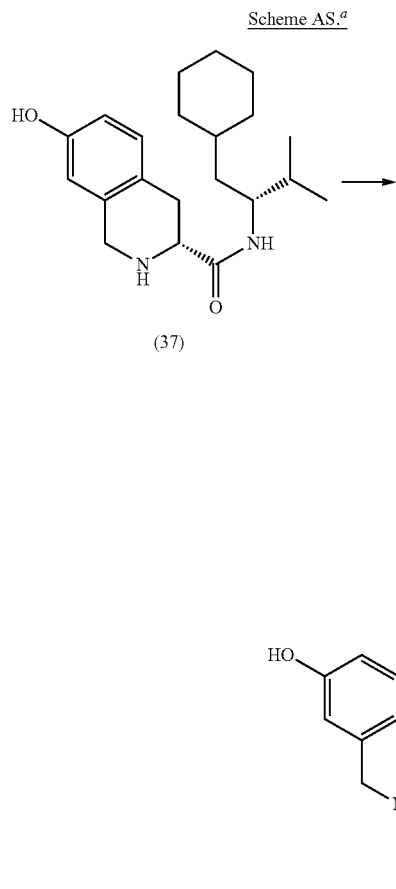

(37)

(48)

$^a$Reagents and conditions:
a) CH$_2$O aq., NaBH(OAc)$_3$, DCE.

(3R)—N-[(1R)-1-(Cyclohexylmethyl)-2-methylpropyl]-7-hydroxy-2-methyl-1,2,3,4-tetrahydroisoquinoline-3-carboxamide (48) Hydrochloride. A sample of (37) hydrochloride (60 mg, 0.16 mmol) in dichloroethane (1.6 mL) was treated with 37% formaldehyde (0.1 mL, 1.3 mmol) and NaBH(OAc)$_3$ (170 mg, 0.8 mmol). The sealed vial was left to stir for 72 h. The reaction was then diluted with CH$_2$Cl$_2$ and dried with Na$_2$SO$_4$. The solids were filtered and washed with EtOAc. The filtrates were combined and concentrated. The residue was subjected to chromatography on silica gel eluting with a gradient of EtOAc in hexanes to afford 54.4 mg (95%) of the free base (48): $^1$H NMR (300 MHz, CDCl$_3$) δ 8.10 (br. s., 1H), 7.20-7.33 (m, 1H), 6.94 (d, J=8.10 Hz, 1H), 6.72 (dd, J=2.26, 8.10 Hz, 1H), 6.60 (d, J=2.07 Hz, 1H), 3.82-3.95 (m, 1H), 3.60-3.82 (m, 2H), 3.39 (t, J=6.78 Hz, 1H), 2.90-3.11 (m, 2H), 2.50 (s, 3H), 1.53-1.83 (m, 4H), 1.46 (d, J=12.24 Hz, 1H), 1.03-1.34 (m, 6H), 0.61-0.99 (m, 9H); $^{13}$C NMR (75 MHz, CDCl$_3$) δ 172.4, 155.3, 135.0, 128.9, 124.1, 114.6, 113.0, 64.2, 55.3, 51.2, 42.2, 39.4, 34.2, 34.2, 32.5, 32.3, 28.9, 26.5, 26.2, 26.0, 19.1, 17.7. The free base was converted into a white powder as the hydrochloride salt: MS (ESI) m/z 359.5 (M+H)$^+$; m.p. 248-250° C. (fusion); [α]$^{25}_D$=+105 (c 0.10, CH$_3$OH). Anal. (C$_{22}$H$_{35}$ClN$_2$O$_2$) C, H, N.

Scheme AT.$^a$

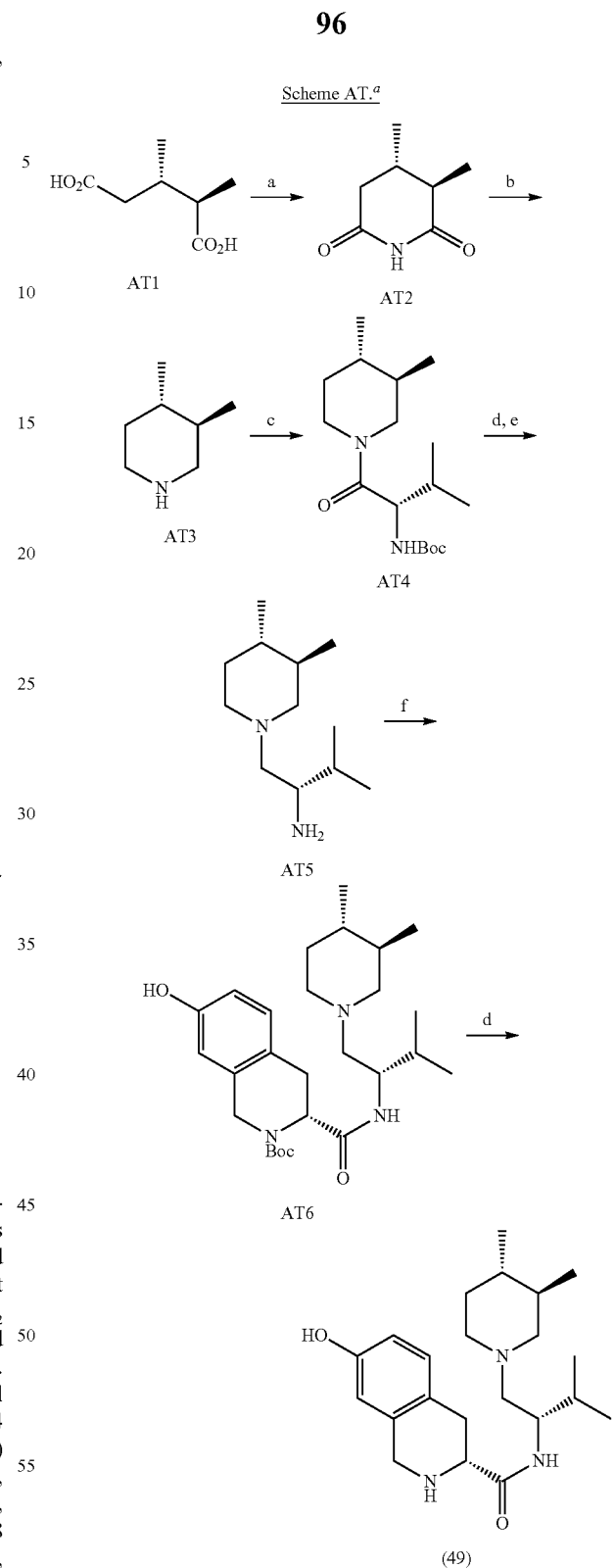

$^a$Reagents and conditions:
(a) Urea of formamide, 180° C., 5 h;
(b) (i) BF$_3$•OEt$_2$, NaBH$_4$, THF, 2 h, at rt then at reflux, 2 h (ii) piperizine, H$_2$O, reflux, overnight;
(d) HCl in 1, 4-dioxane, ACN, rt, 3 h;
(e) BH$_3$•SMe$_2$, THF, reflux 3 h;
(f) Boc-7- hydroxy-D- Tic-OH, EDC•HCl, HOBt, NEt$_3$, DCM, rt, overnight.

Trans-3,4-Dimethylpiperidine-2,6-dione (AT2). AT1 (9 g, 0.056 mol) and urea (6.73 g, 0.112 mol) were placed in flask and heated at 180° C. for 3 h. After cooling the mixture was diluted with a saturated aqueous solution of NaHCO₃ (100 mL) and extracted with EtOAc (3×100 mL). The combined organic layers were dried (anhydrous MgSO₄), filtered and concentrated in vacuo to provide 4.28 g (54%) as a mixture of the trans and cis isomers of 2,6-dimethylpiperidone in the ratio of 2:1 as observed by HNMR. Recrystallization of the mixture using ethyl acetate and hexanes resulted in clean trans isomer, AT2, crushing out. White solid Mp 103-107° C. ¹H NMR (300 MHz, CHLOROFORM-d) δ 7.90 (br. s., 1H), 2.65 (dd, J=4.24, 17.43 Hz, 8H), 2.19-2.31 (m, 1H), 2.07-2.18 (m, 1H), 1.88 (ddt, J=4.33, 6.59, 10.55 Hz, 1H), 1.58 (s, 1H), 1.24 (d, J=6.97 Hz, 3H), 1.06 (d, J=6.59 Hz, 3H), 0.94 (d, J=6.97 Hz, 2H); ¹³C NMR (75 MHz, CHLOROFORM-d) δ 175.5, 172.2, 43.2, 39.5, 31.8, 19.4, 13.2.

Trans-3,4-Dimethylpiperidine (AT3). To a solution AT2 (1.28 g, 9.1 mmol) in THF (20 mL) at −5° C. was added NaBH₄ (757 mg, 20.0 mmol) portionwise followed by boron trifluoride diethyl etherate (3.5 mL, 17.9 mmol). The mixture was removed from the cooling bath and stirred at room temperature for 2 h and was then heated at reflux for an additional 2 h, after which it was cooled back down to 0° C. and treated dropwise with a solution of piperazine (1.5 g) in water (15 mL). The mixture was heated at reflux overnight. After cooling it was diluted with water (30 mL) and extracted with methylene dichloride (3×50 mL). The combined organic layers were dried Na₂SO₄), filtered and concentrated in vacuo. To provide 985 mg (96% yield) of the crude amine (AT3) that was carried on to the next step without further purification.

Synthesis of AT4. Compound AT3 (762 mg, 6.73 mmol) was coupled with Boc-L-valine (1.91 g, 8.75 mmol) according to the General Method 1 to provide AT4 (1.6 g, 76% yield) as a mixture of diastereomers. ¹H NMR (300 MHz, CHLOROFORM-d) δ 5.03 (br. s., 1H), 3.99-4.21 (m, 2H), 2.47 (d, J=11.68 Hz, 1H), 2.02-2.20 (m, 2H), 1.68 (br. s., 2H), 1.32-1.53 (m, 11H), 1.10-1.32 (m, 3H), 0.77-0.98 (m, 10H); ¹³C NMR (75 MHz, CHLOROFORM-d) δ 170.8, 155.8, 79.0, 54.6, 52.9, 51.3, 49.8, 49.0, 47.0, 44.8, 33.0, 31.5, 28.2, 19.5, 17.1; MS (ESI) m/z 313.5 (M+H)⁺.

Synthesis of AT5. Deprotection of AT4 was done following the General Method 2 to provide the amine AT5. ¹H NMR (300 MHz, CHLOROFORM-d) δ 5.77-6.06 (m, 1H), 3.63-3.89 (m, 1H), 3.45-3.58 (m, 1H), 3.31 (td, J=2.73, 5.09 Hz, 1H), 1.87-2.20 (m, 2H), 1.83 (br. s., 2H), 1.66 (d, J=9.61 Hz, 1H), 1.51 (br. s., 1H), 1.29-1.44 (m, 4H), 1.12-1.26 (m, 1H), 0.80-1.06 (m, 9H); ¹³C NMR (75 MHz, CHLOROFORM-d) δ 173.0, 169.5, 59.8, 55.9, 50.8, 46.9, 44.1, 37.6, 31.8, 28.6, 19.9, 16.4; MS (ESI) m/z 213.0 M+H)⁺. Treatment of the intermediate (564 mg, 2.66 mmol) with borane-dimethylsulfide (0.50 mL, 2.2 equiv) following the General Method 3, the diamine AT5 (184 mg, 35% yield) was obtained. ¹H NMR (300 MHz, CHLOROFORM-d) δ 3.46-3.64 (m, 1H), 3.18-3.31 (m, 1H), 2.46-2.84 (m, 5H), 1.92-2.29 (m, 2H), 1.30-1.68 (m, 3H), 1.03-1.28 (m, 1H), 0.70-0.90 (m, 11H); ¹³C NMR (75 MHz, CHLOROFORM-d) δ 64.2, 62.9, 58.4, 56.4, 53.0, 37.8, 34.8, 31.9, 30.8, 19.2, 18.3, 17.1.

Synthesis of AT6. Compound AT5 (184 mg, 0.927 mmol) in dichloromethane (30 mL) was coupled with Boc-7-hydroxy-D-Tic-OH (327 mg, 1.11 mmol) following the protocol described in General Method 4 to provide AT6 (276 mg, 63% yield ¹H NMR (300 MHz, CHLOROFORM-d) δ 6.99 (d, J=8.48 Hz, 1H), 6.53-6.81 (m, 2H), 4.69 (br. s., 1H), 4.49-4.63 (m, 1H), 4.28-4.49 (m, 1H), 3.75-3.91 (m, OH), 3.50-3.61 (m, 1H), 3.20 (dd, J=3.01, 14.88 Hz, 1H), 2.98 (d, J=14.32 Hz, 1H), 2.07-2.30 (m, 1H), 1.50 (br. s., 9H), 1.40 (d, J=7.16 Hz, 1H), 1.02-1.29 (m, 6H), 0.75-0.97 (m, 7H), 0.64 (br. s., 2H); ¹³C NMR (75 MHz, CHLOROFORM-d) δ 171.5, 155.6, 134.6, 129.2, 128.9, 124.2, 114.6, 113.0, 81.4, 65.8, 58.3, 56.9, 54.9, 53.5, 50.9, 45.0, 37.5, 37.3, 34.3, 34.4, 30.1, 28.7, 28.4, 19.2, 17.0; MS (ESI) m/z 474.7 M+H)⁺.

(3R)—N-[(1S)-1-{[(3S,4R)-3,4-Dimethylpiperidin-1-yl]methyl}-2-methylpropyl]-7-hydroxy-1,2,3,4-tetrahydroisoquinoline-3-carboxamide (49) Dihydrochloride. Compound AT6 (276 mg, 0.584 mmol) in methanol (20 mL) was subjected to Boc cleavage following the General Method 2 to provide (49) (218 mg, 91% yield) as a mixture of diastereomers. ¹H NMR (300 MHz, METHANOL-d₄) δ 6.93 (d, J=8.29 Hz, 1H), 6.61 (dd, J=2.54, 8.19 Hz, 1H), 6.44-6.54 (m, 1H), 3.85-4.06 (m, 2H), 3.44-3.64 (m, 1H), 2.67-3.01 (m, 3H), 2.09-2.63 (m, 4H), 1.74-1.98 (m, 2H), 1.39-1.72 (m, 3H), 1.05-1.37 (m, 2H), 0.81-1.02 (m, 12H); ¹³C NMR (75 MHz, METHANOL-d4) δ 175.3, 156.8, 137.4, 130.9, 125.6, 115.0, 113.2, 63.7, 61.5, 58.2, 56.1, 54.8, 54.1, 53.2, 52.5, 38.7, 35.4, 35.1, 33.6, 32.3, 20.0, 17.9; MS (ESI) m/z 374.3 M+H)⁺. A beige solid was obtained as the dihydrochloride salt of (49) .2HCl: mp 178° C.; [α]²³_D=+82.1 (c 0.2, CH₃OH). Anal. (C₂₂H₃₇Cl₂N₃O₂·1.5H₂O) C, H, N.

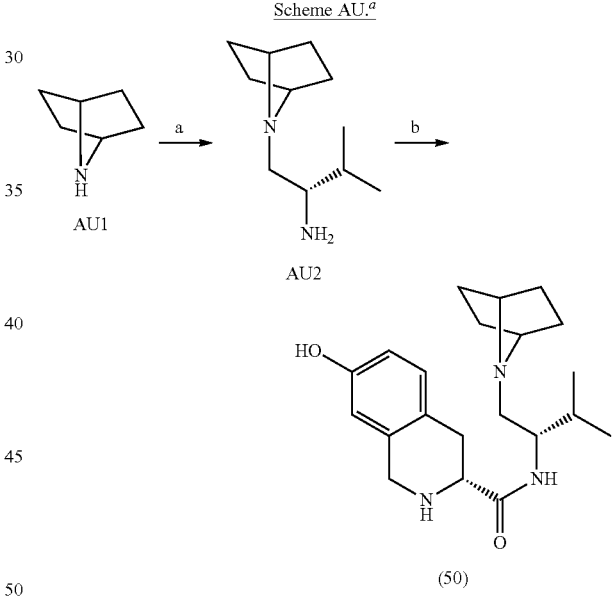

Scheme AU.ª

ªReagents and conditions:
(a) (i) Boc-L-Valine, HBTU, CH₃CN, NEt₃ (ii) TFA, CHCl₃ (iii) BH₃•SMe₂, THF;
(b) 7-hydroxy-Boc-D-Tic(OH), DCC, HOBt, THF, Net₃ (ii) HCl aq., MeoH.

Synthesis of AU2. A solution of the amine (AU1) hydrochloride (1.08 g, 8.1 mmol), Boc-L-Valine (2.28 g, 10.5 mmol), and HBTU (3.98 g, 10.5 mmol) in CH3CN (40 mL) in an ice bath was treated with NEt₃ (8.8 mL, 63 mmol). The solution was warmed to room temperature overnight then concentrated. The residue was suspended in aq. NaHCO₃ (30 mL) and extracted with EtOAc (3×50 mL). The combined organic layers were dried Na₂SO₄) and concentrated. The residue was subjected to chromatography on a short plug of silica gel eluting with 50% EtOAc in hexanes. The product containing fractions were concentrated to a residue, which was then dissolved in CHCl₃ (10 mL) and treated with TFA (10 mL). After 4 h, the solution was concentrated and the resulting residue was dissolved in EtOAc and washed with aq. NaHCO$_3$. The organic layer was dried Na$_2$SO$_4$) and concentrated to afford 1.28 g (80% over two steps) of the intermediate amide. The crude amide was dissolved in THF (75 mL) and treated with BH$_3$.SMe$_2$ (2.5 mL, 25 mmol). The resulting solution was heated at reflux overnight, then cooled in an ice bath to be quenched by addition of CH$_3$OH. The resulting solution was concentrated twice from CH$_3$OH then dissolved in CH$_2$Cl$_2$ and washed with dilute aq. NaOH. The aqueous layer was back extracted with EtOAc. The combined organics were washed with aq. NaHCO$_3$ then brine, then dried Na$_2$SO$_4$). The concentrated residue was subjected to chromatography on silica gel eluting with a gradient up to 50% CMA80 to afford 0.63 g (53% from the amide) of the desired diamine AU2: $^1$H NMR (300 MHz, CDCl$_3$) δ 3.30 (br. s., 2H), 2.63 (ddd, J=3.30, 5.60, 10.13 Hz, 1H), 2.41 (dd, J=3.30, 12.34 Hz, 1H), 2.17 (dd, J=10.36, 12.24 Hz, 1H), 1.95-2.09 (m, 2H), 1.67-1.83 (m, 4H), 1.50-1.67 (m, 1H), 1.23-1.37 (m, 4H), 0.87-0.97 (m, 6H); MS (ESI) m/z 183.3 (M+H)$^+$.

(3R)—N-[(1S)-1-(7-Azabicyclo[2.2.1]hept-7-ylmethyl)-2-methylpropyl]-7-hydroxy-1,2,3,4-tetrahydroisoquinoline-3-carboxamide (50). A solution of dicyclohexylcarbodiimide (DCC) (120 mg, 0.58 mmol) in THF (2 mL) was added to a solution of HOBt (72 mg, 0.54 mmol) and 7-hydroxy-Boc-D-Tic(OH) (150 mg, 0.51 mmol) in THF (3 mL). After 1 h, the amine AU2 (140 mg, 0.77 mmol) and NEt$_3$ (0.2 mL, 1.4 mmol) were added to the suspension. The reaction mixture was stirred at room temperature for 12 h. The solids were filtered, and the filtrate concentrated to a residue. The residue was subjected to chromatography on silica gel eluting with a gradient up to 50% DMA80. The product containing fractions were concentrated and the residue dissolved in CH$_3$OH (5 mL) and treated with 6 N HCl aq (5 mL). After 12 h, the solution was concentrated and the residue partitioned between CH$_2$Cl$_2$ and 7 M NH$_4$OH aq. The organic layer was dried Na$_2$SO$_4$) and concentrated. The residue was subjected to chromatography on silica gel eluting with a gradient up to 75% DMA80 to afford 36.4 mg (10%) of the freebase (50): $^1$H NMR (300 MHz, CDCl$_3$) δ 7.11 (d, J=9.61 Hz, 1H), 6.78 (d, J=8.10 Hz, 1H), 6.44 (dd, J=2.35, 8.19 Hz, 1H), 6.32 (d, J=2.26 Hz, 1H), 3.86-4.00 (m, 1H), 3.36-3.68 (m, 4H), 3.08 (dd, J=5.09, 11.68 Hz, 1H), 2.81 (dd, J=4.90, 16.39 Hz, 1H), 2.51-2.71 (m, 1H), 2.40 (dd, J=2.54, 12.90 Hz, 1H), 2.13-2.30 (m, 1H), 1.63-1.91 (m, 5H), 1.23-1.44 (m, 4H), 0.72-0.94 (m, 6H); $^{13}$C NMR (75 MHz, CDCl$_3$) δ 173.4, 155.2, 137.4, 130.6, 125.0, 113.8, 112.1, 59.8, 56.7, 52.2, 48.4, 48.0, 31.7, 29.7, 28.2, 18.8, 18.3. The free base was converted into a pale yellow powder as the dihydrochloride salt: MS (ESI) m/z 358.4 (M+H)+; m.p. 194-198° C. (fusion); [α]$_D^{25}$=+72 (c 0.10, CH$_3$OH). Anal. (C$_2$H$_{33}$Cl$_2$N$_3$O$_2$·1.5H$_2$O) C, H, N.

Scheme AV.$^a$

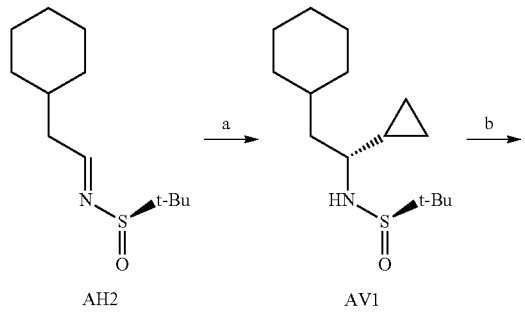

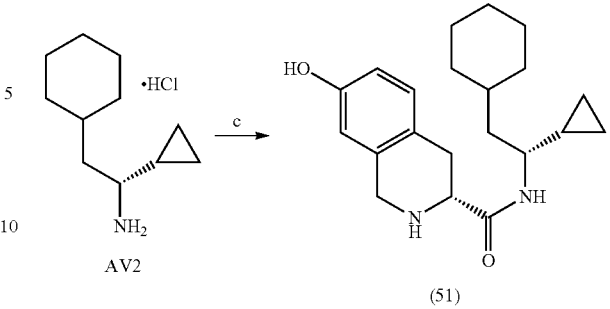

$^a$Reagents and conditions:
a) Cyclopropylmagnesium bromide, CH$_2$Cl$_2$;
b) 4 N HCl, dioxane, CH$_3$OH;
c) (i) 7-hydroxy-Boc-D-Tic(OH), DCC, HOBt, THF, NEt$_3$ (ii) 6 N HCl, CH$_3$OH.

Synthesis of AV1. A solution of sulfinimine AH2 (1.0 g, 4.36 mmol) in CH$_2$Cl$_2$ (20 mL) at −78° C. was treated with cyclopropylmagnesium bromide (8.0 mL, 1.0 M in 2-methyltetrahydrofuran). The solution was allowed to warm to room temperature overnight, then was quenched by the addition of NH$_4$Cl (sat.). The organic layer was washed with aq. NaHCO$_3$ and dried Na$_2$SO$_4$). The concentrated residue was subjected to chromatography on silica gel eluting with a gradient up to 50% EtOAc in hexanes to afford 0.66 g (56%) of the desired sulfinamide AV1 as a white solid: $^1$H NMR (300 MHz, CDCl$_3$) δ 2.95-3.24 (m, 1H), 2.45-2.64 (m, 1H), 1.38-1.81 (m, 9H), 1.08-1.34 (m, 11H), 0.75-1.05 (m, 3H), 0.54-0.67 (m, 2H), 0.39-0.49 (m, 1H), 0.22-0.34 (m, 1H).

Synthesis of AV2. The sulfinamide AV1 was dissolved in methanol (20 mL) and treated with hydrogen chloride (5 mL, 4 N in dioxane) at room temperature. The resulting solution was evaporated under a stream of nitrogen overnight to afford 0.49 g (99%) of the amine hydrochloride AV2: $^1$H NMR (300 MHz, CD$_3$OD) δ 2.43-2.60 (m, 1H), 1.47-1.80 (m, 8H), 1.16-1.38 (m, 5H), 0.80-1.06 (m, 4H), 0.55-0.80 (m, 2H), 0.30-0.51 (m, 2H).

(3R)—N-[(1R)-2-Cyclohexyl-1-cyclopropylethyl]-7-hydroxy-1,2,3,4-tetrahydroisoquinoline-3-carboxamide (51) Hydrochloride. A solution of dicyclohexylcarbodiimide (DCC) (120 mg, 0.58 mmol) in THF (2 mL) was added to a solution of HOBt (72 mg, 0.54 mmol) and 7-hydroxy-Boc-D-Tic(OH) (150 mg, 0.51 mmol) in THF (3 mL). After 1 h, the amine AV2 (120 mg, 0.59 mmol) and NEt$_3$ (0.2 mL, 1.4 mmol) were added to the suspension. The reaction mixture was stirred at room temperature for 12 h. The solids were filtered, and the filtrate concentrated to a residue. The residue was subjected to chromatography on silica gel eluting with a gradient up to 50% EtOAc in hexanes. The product containing fractions were concentrated and the residue dissolved in CH$_3$OH (5 mL) and treated with 6 N HCl aq (5 mL). After 12 h, the solution was concentrated and the residue partitioned between EtOAc and aq. NaHCO$_3$. The organic layer was dried Na$_2$SO$_4$) and concentrated. The residue was subjected to chromatography on silica gel eluting with a gradient up to 100% EtOAc in hexanes to afford 51.8 mg (30%) of the freebase (51) : $^1$H NMR (300 MHz, CD$_3$OD) δ 6.91 (d, J=8.29 Hz, 1H), 6.60 (dd, J=2.45, 8.29 Hz, 1H), 6.49 (d, J=2.26 Hz, 1H), 3.83-4.00 (m, 2H), 3.37-3.55 (m, 2H), 2.67-2.99 (m, 2H), 1.79 (d, J=12.43 Hz, 1H), 1.55-1.73 (m, 4H), 1.40-1.50 (m, 2H), 1.05-1.39 (m, 6H), 0.72-1.04 (m, 4H), 0.25-0.57 (m, 3H), 0.11-0.25 (m, 1H); $^{13}$C NMR (75 MHz, CD$_3$OD) δ 174.8, 156.8, 137.1, 130.9, 125.6, 115.0, 113.2, 58.0, 51.8, 47.8, 44.2, 35.4, 35.2, 33.9, 32.4, 27.7, 27.4, 27.3, 17.9, 4.2, 2.9. The free base was converted into a off-white powder as the hydrochloride salt (51) HCl: MS (ESI) m/z 343.4 (M+H)$^+$; m.p. >250° C.; $[\alpha]_D^{25}$=+88 (c 0.10, CH$_3$OH). Anal. (C$_{21}$H$_{31}$ClN$_2$O$_2$) C, H, N.

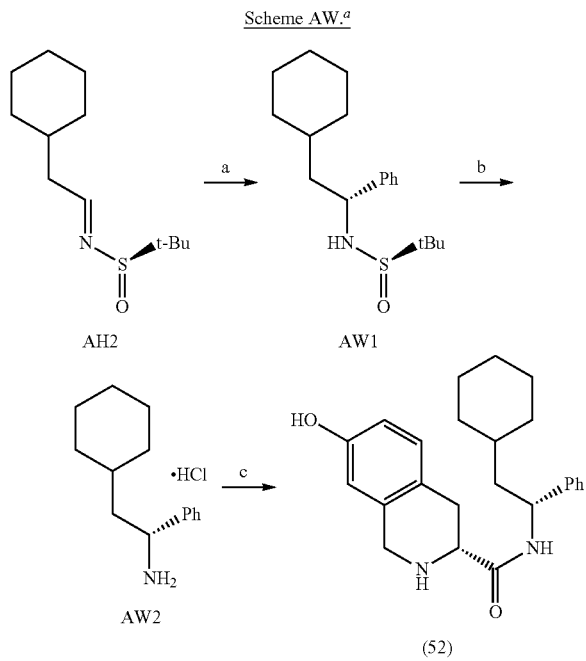

Scheme AW.$^a$ $^a$Reagents and condtions: a) PhMgBr, CH$_2$Cl$_2$; b) 4N HCl, dioxane, CH$_3$OH; c) (i) 7-hydroxy-Boc-D-Tic(OH), DCC, HOBt, THF, NEt$_3$ (ii) 6N HCl, CH$_3$OH.

Synthesis of AW1. A solution of sulfinimine AH2 (1.0 g, 4.36 mmol) in CH$_2$Cl$_2$ (20 mL) at −78° C. was treated with phenylmagnesium bromide (8.0 mL, 1.0 M in THF). The solution was allowed to warm to room temperature overnight, then was quenched by the addition of NH$_4$Cl (sat.). The organic layer was washed with aq. NaHCO$_3$ and dried Na$_2$SO$_4$). The concentrated residue was subjected to chromatography on silica gel eluting with a gradient up to 50% EtOAc in hexanes to afford 1.17 g (87%) of the desired sulfonamide AW1 as a colorless oil: $^1$H NMR (300 MHz, CDCl$_3$) δ 7.25-7.40 (m, 5H), 4.37-4.53 (m, 1H), 1.51-1.97 (m, 11H), 1.23 (s, 9H), 0.79-1.07 (m, 3H).

Synthesis of AW2. The sulfinamide AW1 was dissolved in methanol (20 mL) and treated with hydrogen chloride (5 mL, 4 N in dioxane) at room temperature. The resulting solution was evaporated under a stream of nitrogen overnight to afford 0.84 g (92%) of the amine hydrochloride AW2 as a white solid: $^1$H NMR (300 MHz, CD$_3$OD) δ 7.34-7.55 (m, 5H), 4.27-4.42 (m, 1H), 3.52-3.79 (m, 1H), 1.77-1.97 (m, 2H), 1.55-1.76 (m, 4H), 0.87-1.24 (m, 9H).

(3R)—N-[(1R)-2-Cyclohexyl-1-phenylethyl]-7-hydroxy-1,2,3,4-tetrahydroisoquinoline-3-carboxamide (52) Hydrochloride. A solution of dicyclohexylcarbodiimide (DCC) (120 mg, 0.58 mmol) in THF (2 mL) was added to a solution of HOBt (72 mg, 0.54 mmol) and 7-hydroxy-Boc-D-Tic (OH) (150 mg, 0.51 mmol) in THF (3 mL). After 1 h, the amine AW2 (144 mg, 0.60 mmol) and NEt$_3$ (0.2 mL, 1.4 mmol) were added to the suspension. The reaction mixture was stirred at room temperature for 12 h. The solids were separated by filtration and the filtrate concentrated to a residue. The residue was subjected to chromatography on silica gel eluting with a gradient up to 50% EtOAc in hexanes. The product containing fractions were concentrated and the residue dissolved in CH$_3$OH (5 mL) and treated with 4 N HCl in dioxane (5 mL). After 12 h, the solution was concentrated and the residue partitioned between EtOAc and aq. NaHCO$_3$. The organic layer was dried Na$_2$SO$_4$) and concentrated. The residue was subjected to chromatography on silica gel eluting with a gradient up to 100% EtOAc in hexanes to afford the freebase (52): $^1$H NMR (300 MHz, CD$_3$OD) δ 7.14-7.38 (m, 5H), 6.88 (d, J=8.10 Hz, 1H), 6.57 (dd, J=2.54, 8.19 Hz, 1H), 6.48 (d, J=2.26 Hz, 1H), 5.00 (dd, J=6.03, 9.42 Hz, 1H), 3.91 (s, 2H), 3.53 (dd, J=4.71, 10.17 Hz, 1H), 2.74-2.90 (m, 1H), 2.58-2.74 (m, 1H), 1.47-1.87 (m, 8H), 1.07-1.36 (m, 5H), 0.80-1.06 (m, 3H); $^{13}$C NMR (75 MHz, METHANOL-d$_4$) δ 174.7, 156.8, 144.8, 137.1, 130.8, 129.6, 128.1, 127.5, 125.5, 114.9, 113.1, 58.0, 52.0, 47.8, 45.5, 35.6, 34.7, 33.9, 32.1, 27.6, 27.3, 27.2. The free base was converted in to 25.3 mg (12%) of an off-white powder as the hydrochloride salt (52) HCl: MS (ESI) m/z 379.5 (M+H)$^+$; m.p. 139-143° C. (fusion); $[\alpha]_D^{25}$=+67 (c 0.10, CH$_3$OH). Anal. (C$_{24}$H$_{31}$ClN$_2$O$_2$·0.75H$_2$O) C, H, N.

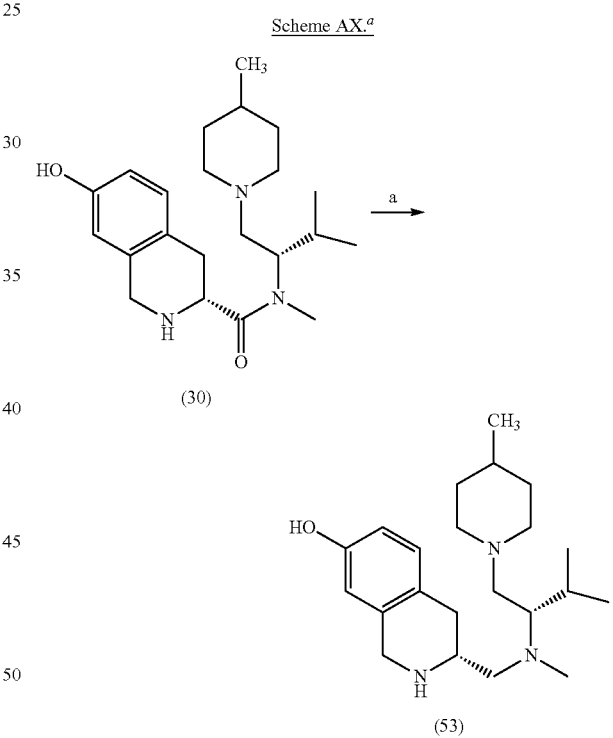

Scheme AX.$^a$ $^a$Reagents and conditions: a) BH$_3$·SMe$_2$, THF, reflux, overnight.

(3R)-3-[(Methyl{(1S)-2-methyl-1-[(4-methylpiperidin-1-yl)methyl]propyl}amino)methyl]-1,2,3,4-tetrahydroisoquinolin-7-ol (53) Trihydrochloride. A solution of 30 (112 mg, 0.299 mmol) in anhydrous THF was treated with borane dimethyl sulfide (0.2 mL) and heated at reflux overnight and rest of the protocol carried out as per the General Method 3 to provide 87.5 mg (81%) of the desired product (53). $^1$H NMR (300 MHz, METHANOL-d$_4$) δ 6.93 (d, J=8.29 Hz, 1H), 6.61 (dd, J=2.45, 8.29 Hz, 1H), 6.52 (d, J=2.26 Hz, 1H), 3.98 (s, 1H), 3.17 (d, J=11.49 Hz, 1H), 2.88-3.07 (m, 3H), 2.55-2.74 (m, 3H), 2.31-2.54 (m, 7H), 2.12-2.28 (m, J=2.26 Hz, 1H), 1.66-1.88 (m, 3H), 1.44-1.59 (m, 1H), 1.17-1.43 (m, 3H), 0.86-1.06 (m, 9H); $^{13}$C NMR (75 MHz, METHANOL-d$_4$) δ 156.7, 136.7, 131.1, 125.9, 115.1, 113.5, 68.3, 63.4, 59.6, 56.1, 54.6, 54.5, 49.2, 36.2, 34.7, 34.3, 32.6, 31.4, 30.7, 22.1, 22.0, 20.9; MS (ESI) mtz 360.4 M+H)$^+$. The free base was converted to a hydrochloride salt to furnish (53) .3HCl as a light orange solid. mp 158° C. (sublimes); $[α]^{21.6}_D$=+14.1 (c 0.11, CH$_3$OH). Anal. (C$_{22}$H$_{40}$Cl$_3$N$_3$O.0.5H$_2$O) C, H, N.

Scheme AY.$^a$

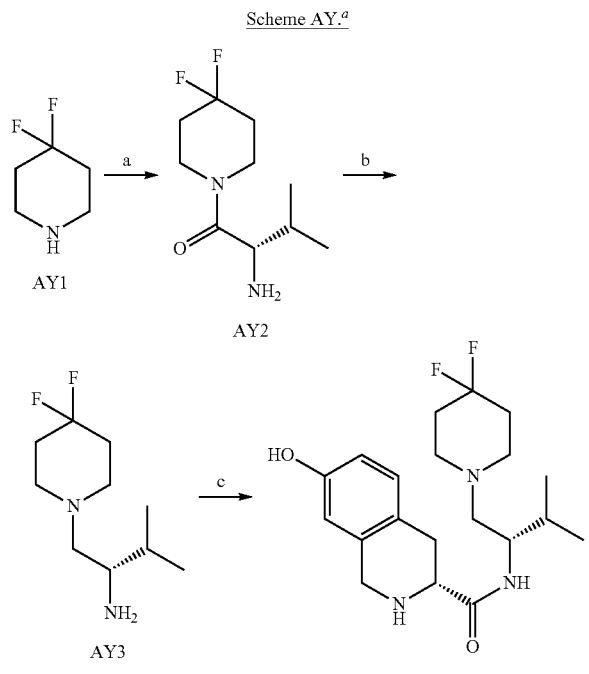

(54)

$^a$Reagents and Conditions: a) i. Boc-L-valine, HBTU, Et$_3$N, ACN, rt, overnight; ii. HCl in 1,4-dioxane, MeOH; b) BH$_3$•SMe$_2$, THF, reflux 3 h; c) i. Boc-7-hydroxy-D-Tic-OH, EDC•HCl, HOBt, NEt$_3$, DCM, rt overnight; ii. HCl, CH$_3$OH.

Synthesis of Compound AY2. Compound AY1 (1.0 g, 6.42 mmol) was coupled with Boc-L-valine (1.67 g, 7.70 mmol) according to the General Method 1 to provide 2.0 g, (99% yield) of the Boc-protected intermediate. $^1$H NMR (300 MHz, CHLOROFORM-d) δ 5.38 (d, J=9.23 Hz, 1H), 4.34 (dd, J=6.50, 9.14 Hz, 1H), 3.84 (d, J=13.38 Hz, 1H), 3.63 (d, J=13.75 Hz, 1H), 3.45 (dt, J=6.88, 13.42 Hz, 2H), 1.75-2.02 (m, 4H), 1.31 (s, 9H), 0.81 (dd, J=6.78, 14.51 Hz, 6H); $^{13}$C NMR (75 MHz, CHLOROFORM-d) δ 170.7, 155.7, 121.3, 79.3, 54.7, 42.4, 38.8, 34.6, 33.7, 31.2, 28.2 (3 C's), 19.4, 17.2; MS (ESI) m/z 343.3 (M +Na)$^+$. Removal of the Boc protection was done following the General Method 2 to provide the amine AY2. $^1$H NMR (300 MHz, CHLOROFORM-d) δ 3.72 (br. s., 1H), 3.33-3.60 (m, 4H), 1.74-2.01 (m, 4H), 1.60-1.74 (m, 1H), 0.71-0.89 (m, 6H); $^{13}$C NMR (75 MHz, CHLOROFORM-d) δ 173.5, 121.4, 56.1, 42.0, 38.8, 34.5, 33.7, 32.0, 19.9, 16.4; MS (ESI) m/z 221.4 M+H)$^+$.

Synthesis of Compound AY3. Treatment of compound AY2 (1.36 g, 6.16 mmol) with borane-dimethylsufide (1.8 mL, 3.0 equiv) following the General Method 3, provided the diamine AY3 (992 mg, 78% yield). $^1$H NMR (300 MHz, METHANOL-d$_4$) δ 2.61-2.77 (m, 3H), 2.36-2.54 (m, 3H), 2.18-2.35 (m, 1H), 1.87-2.12 (m, 4H), 1.60 (qd, J=6.68, 13.30 Hz, 1H), 0.96 (dd, J=3.96, 6.78 Hz, 6H); $^{13}$C NMR (75 MHz, METHANOL-d$_4$) δ 123.2, 62.4, 54.6, 51.6, 35.4, 35.1, 34.8, 32.9, 19.5, 18.8; MS (ESI) m/z 207.3 M+H)$^+$.

(3R)—N-{[(1S)-1-[4,4-Difluoropiperidin-1-yl]methyl]-2-methylpropyl}-7-hydroxy-1,2,3,4-tetrahydroisoquinoline-3-carboxamide (54) Dihydrochloride. Compound AY3 (992 mg, 4.807 mmol) in dichloromethane (40 mL) was coupled with Boc-7-hydroxy-D-Tic-OH (1.41 g, 1.0 equiv) following the protocol described in General Method 4 to provide 1.73 g, (75% yield) of the Boc-protected (54). $^1$H NMR (300 MHz, CHLOROFORM-d) δ 6.95 (d, J=8.10 Hz, 1H), 6.53-6.71 (m, 2H), 4.72 (br. s., 1H), 4.33-4.56 (m, 2H), 3.78 (br. s., 1H), 3.11-3.28 (m, 1H), 2.95 (dd, J=6.03, 15.26 Hz, 1H), 2.25 (br. s., 5H), 1.61-1.84 (m, 5H), 1.47 (s, 9H), 1.22 (t, J=7.16 Hz, 1H), 0.80 (dd, J=6.69, 17.99 Hz, 6H); $^{13}$C NMR (75 MHz, CHLOROFORM-d) δ 171.8, 155.6, 133.9, 129.1, 124.0, 121.8, 114.7, 112.9, 81.6, 60.4, 58.6, 56.6, 54.9, 51.6, 50.1, 44.9, 33.7, 30.7, 30.2, 28.3, 21.0, 19.2, 17.3; MS (ESI) m/z 482.4 M+H)$^+$. A solution of the Boc-protected compound (1.733 g, 4.77 mmol) in methanol (20 mL) was subjected to Boc cleavage following the General Method 2 to provide the amine (54) (1.25 g, 69% yield). $^1$H NMR (300 MHz, CHLOROFORM-d) δ 7.15 (d, J=9.61 Hz, 1H), 6.90 (d, J=8.29 Hz, 1H), 6.54-6.72 (m, 1H), 6.46-6.53 (m, 1H), 3.95-4.16 (m, 1H), 3.72-3.88 (m, 2H), 3.47 (dd, J=5.18, 10.27 Hz, 1H), 3.02 (dd, J=4.99, 16.29 Hz, 1H), 2.60-2.75 (m, 3H), 2.39-2.53 (m, 3H), 1.78-1.99 (m, 5H), 0.70-0.97 (m, 6H); $^{13}$C NMR (75 MHz, CHLOROFORM-d) δ 173.7, 155.1, 136.6, 130.1, 124.8, 121.8, 114.1, 112.3, 58.9, 56.7, 51.0, 50.2, 47.3, 33.7, 30.6, 30.3, 19.3, 17.7; MS (ESI) m/z 382.8 (M+H)$^+$. A white solid was obtained as dihydrochloride salt, (54) 2HCl: mp 195-197° C.; $[α]^{19}_D$=+67.9 (c 0.5, CH$_3$OH). Anal. (C$_{20}$H$_{31}$Cl$_2$F$_2$N$_3$O$_2$H$_2$O) C, H, N.

Scheme AZ.$^a$

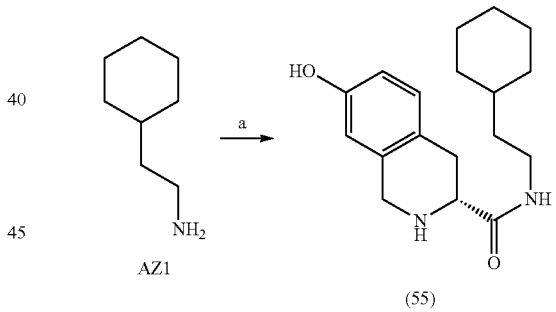

(55)

$^a$Reagents and conditions: a) (i) 7-hydroxy-Boc-D-Tic(OH), DCC, HOBt, THF, NEt$_3$; (ii) 4N HCl, dioxane, CH$_3$OH.

(3R)—N-(2-Cyclohexylethyl)-7-hydroxy-1,2,3,4-tetrahydroisoquinoline-3-carboxamide (55) Hydrochloride. A solution of dicyclohexylcarbodiimide (DCC) (120 mg, 0.58 mmol) in THF (2 mL) was added to a solution of HOBt (72 mg, 0.54 mmol) and 7-hydroxy-Boc-D-Tic(OH) (150 mg, 0.51 mmol) in THF (3 mL). After 1 h, the 2-cyclohexylethylamine (AZ1) hydrochloride (96 mg, 0.6 mmol) and NEt$_3$ (0.25 mL, 1.7 mmol) were added to the suspension. The reaction mixture was stirred at room temperature for 12 h. The solids were removed by filtration, and the filtrate concentrated to a residue. The residue was subjected to chromatography on silica gel eluting with a gradient up to 50% EtOAc in hexanes. The product containing fractions were concentrated and the residue dissolved in CH$_3$OH (5 mL) and treated with 4 N HCl in dioxane (5 mL). After 12 h, the solution was concentrated and the residue partitioned between EtOAc and aq. NaHCO₃. The organic layer was dried Na₂SO₄) and concentrated. The residue was subjected to chromatography on silica gel eluting with a gradient up to 100% EtOAc in hexanes to afford the freebase (55): $^1$H NMR (300 MHz, CD₃OD) δ 8.38 (br. s., 1H), 7.08 (d, J=8.48 Hz, 1H), 6.75 (dd, J=2.45, 8.48 Hz, 1H), 6.63 (s, 1H), 4.33 (s, 2H), 4.11 (dd, J=4.80, 11.77 Hz, 1H), 3.53-3.78 (m, 1H), 3.22 (d, J=4.71 Hz, 1H), 2.92-3.13 (m, 1H), 1.60-1.82 (m, 6H), 1.07-1.53 (m, 7H), 0.80-1.06 (m, 2H); $^{13}$C NMR (75 MHz, CD₃OD) δ 169.5, 169.4, 158.1, 131.1, 129.7, 122.1, 116.9, 113.7, 56.9, 45.6, 38.5, 38.4, 37.8, 36.5, 34.3, 34.2, 30.4, 27.6, 27.3. The free base was converted into 50 mg (28%) of an off-white powder as the hydrochloride salt (55) HCl: MS (ESI) m/z 303.1 (M+H)⁺; m.p. 78-82° C. (fusion); $[\alpha]_D^{25}$=+99 (c 0.32, CH₃OH). Anal. (C₁₈H₂₇ClN₂O₂·0.75H₂O) C, H, N.

Scheme BA.$^a$

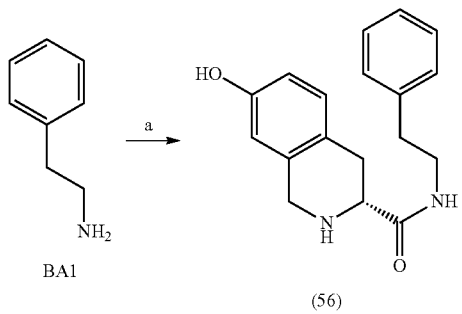

(56)

$^a$Reagents and conditions: a) (i) 7-hydroxy-Boc-D-Tic(OH), DCC, HOBt, THF; (ii) 4N HCl, dioxane, CH₃OH.

(3R)-7-Hydroxy-N-(2-phenylethyl)-1,2,3,4-tetrahydroisoquinoline-3-carboxamide (56) Hydrochloride. A solution of dicyclohexylcarbodiimide (DCC) (120 mg, 0.58 mmol) in THF (2 mL) was added to a solution of HOBt (72 mg, 0.54 mmol) and 7-hydroxy-Boc-D-Tic(OH) (150 mg, 0.51 mmol) in THF (3 mL). After 1 h, phenethylamine BA1 (0.3 mL) was added to the suspension. The reaction mixture was stirred at room temperature for 12 h. The solids were separated by filtration and the filtrate concentrated to a residue. The residue was subjected to chromatography on silica gel eluting with a gradient up to 50% EtOAc in hexanes. The product containing fractions were concentrated and the residue dissolved in CH₃OH (5 mL) and treated with 4 N HCl in dioxane (5 mL). After 12 h, the solution was concentrated and the residue partitioned between EtOAc and aq. NaHCO₃. The organic layer was dried Na₂SO₄) and concentrated. The residue was subjected to chromatography on silica gel eluting with a gradient up to 100% EtOAc in hexanes to afford the freebase (56): $^1$H NMR (300 MHz, CD₃OD) δ 7.13-7.34 (m, 5H), 6.90 (d, J=8.29 Hz, 1H), 6.58 (dd, J=2.45, 8.29 Hz, 1H), 6.47 (d, J=2.26 Hz, 1H), 3.88 (s, 2H), 3.36-3.52 (m, 3H), 2.75-2.88 (m, 3H), 2.60-2.74 (m, 1H); $^{13}$C NMR (75 MHz, CD₃OD) δ 175.6, 156.8, 140.4, 137.3, 130.8, 129.9, 129.5, 127.4, 125.6, 114.9, 113.1, 58.1, 41.8, 36.5, 32.0. The free base was converted into 113.6 mg (66%) of a pale yellow powder as the hydrochloride salt (56) HCl: MS (ESI) m/z 297.3 (M+H)⁺; m.p. 89-93° C. (fusion); $[\alpha]_D^{25}$=+84 (c 0.10, CH₃OH). Anal. (C₁₈H₂₁ClN₂O₂·0.5H₂O) C, H, N.

Scheme BB.$^a$

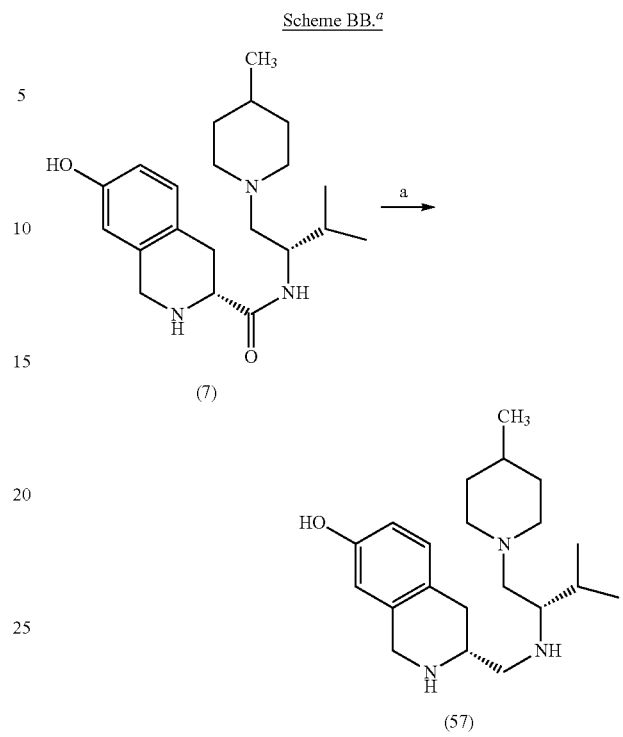

$^a$Reagents and conditions: a) BH₃•SMe₂, THF, reflux, overnight.

(3R)-3-[({(1S)-2-Methyl-1-[(4-methylpiperidin-1-yl)methyl]propyl}amino)methyl]-1,2,3,4-tetrahydroisoquinolin-7-ol (57) Trihydrochloride. A solution of 7 (113 mg, 0.314 mmol) in anhydrous THF was treated with borane dimethyl sulfide (0.3 mL) and heated at reflux overnight and rest of the protocol carried out as per the General Method 3 to provide 81.2 mg (75%) of the reduced desired product. $^1$H NMR (300 MHz, METHANOL-d₄) δ 6.83 (d, J=8.29 Hz, 1H), 6.53 (dd, J=2.45, 8.29 Hz, 1H), 6.43 (d, J=2.26 Hz, 1H), 3.91 (s, 1H), 3.42-3.54 (m, 1H), 3.24 (s, 1H), 2.82-3.10 (m, 4H), 2.38-2.73 (m, 6H), 2.32 (t, J=10.93 Hz, 1H), 1.66 (d, J=13.00 Hz, 2H), 1.32-1.56 (m, 2H), 1.06-1.30 (m, 2H), 0.76-0.99 (m, 9H); $^{13}$C NMR (75 MHz, METHANOL-d₄) δ 156.8, 135.6, 131.1, 125.2, 115.5, 113.5, 60.4, 59.3, 55.7, 55.5, 53.2, 51.8, 48.0, 33.6, 33.4, 31.9, 30.8, 30.2, 21.8, 19.6, 17.5; MS (ESI) m/z 346.4 M+H)⁺. The free base was converted to a hydrochloride salt to furnish (57) 3HCl as a white solid. mp 172° C. (sublimes); $[\alpha]^{187}_D$=+27.3 (c 0.2, CH₃OH). Anal. (C₂₁H₃₈Cl₃N₃O.0.75H₂O) C, H, N.

Scheme BC.$^a$

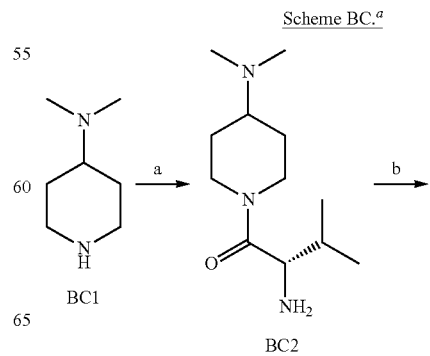

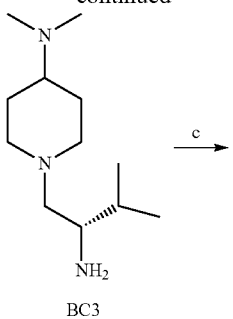

BC3

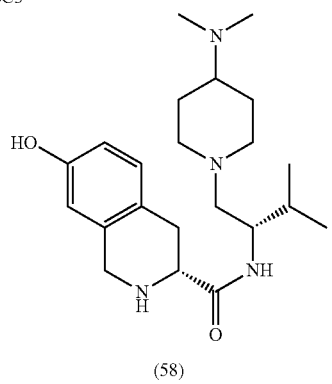

(58)

<sup>a</sup>Reagents and Conditions: a) i. Boc-L-valine, HBTU, Et₃N, ACN, rt, overnight; ii. HCl in 1,4-dioxane, MeOH; b) BH₃•SMe₂, THF, reflux 3 h; c) i. Boc-7-hydroxy-D-Tic-OH, EDC•HCl, HOBt, NEt₃, DCM, rt overnight; ii. HCl, CH₃OH.

Synthesis of Compound BC2. Compound BC1 (2.1 g, 16.4 mmol) was coupled with Boc-L-valine (4.63 g, 21.3 mmol) according to the General Method 1 to provide 2.0 g, of the Boc-protected intermediate. $^1$H NMR (300 MHz, METHANOL-$d_4$) δ 3.14-3.31 (m, 2H), 2.79-2.96 (m, 1H), 2.65 (dq, J=1.70, 7.10 Hz, 1H), 2.09 (br. s., 1H), 1.78 (q, J=7.28 Hz, 4H), 1.35-1.51 (m, 4H), 1.24 (br. s., 1H), 0.65-0.85 (m, 1H), 0.47-0.63 (m, 2H), 0.04-0.38 (m, 1H), 0.00 (s, 5H), −0.24-0.06 (m, 6H), −0.57-0.41 (m, 3H); $^{13}$C NMR (75 MHz, METHANOL-$d_4$) δ 171.6, 156.7, 79.5, 63.3, 60.4, 55.6, 44.1, 40.5, 39.6, 30.7, 27.6, 27.0, 26.0, 18.6, 17.1, 13.4, 8.1; MS (ESI) m/z 328.4 (M+Na)$^+$. Removal of the Boc-protection from the amine was conducted following the General Method 2 to provide the amine BC2. $^1$H NMR (300 MHz, METHANOL-$d_4$) δ 4.67 (d, J=12.24 Hz, 1H), 3.80-4.24 (m, 2H), 3.58 (d, J=10.74 Hz, 2H), 2.92-3.27 (m, 2H), 2.74 (t, J=12.62 Hz, 1H), 2.62 (d, J=7.72 Hz, 5H), 1.95-2.28 (m, 2H), 1.31-1.79 (m, 2H), 0.87-1.24 (m, 6H); $^{13}$C NMR (75 MHz, METHANOL-$d_4$) δ 171.5, 63.7, 56.3, 53.4, 45.7, 42.2, 41.0, 32.3, 28.8, 27.9, 19.6, 17.4; MS (ESI) m/z 228.5 M+H)$^+$.

Synthesis of Compound BC3. Compound BC2 (1.94 g, 6.16 mmol) was treated with borane-dimethylsulfide (3.2 mL, 4.0 equiv) following the General Method 3, to furnish diamine BC3 (994mg, 55% yield). $^1$H NMR (300 MHz, METHANOL-$d_4$) δ 3.31-3.39 (m, 3H), 3.01-3.13 (m, 1H), 2.85-2.96 (m, 1H), 2.72-2.84 (m, 1H), 2.26-2.42 (m, 7H), 2.12-2.25 (m, 2H), 1.81-1.96 (m, 2H), 1.41-1.73 (m, 2H), 0.97 (dd, J=5.56, 6.69 Hz, 6H); $^{13}$C NMR (75 MHz, METHANOL-$d_4$) δ 63.7, 62.3, 56.0, 54.7, 52.9, 49.9, 41.9, 32.5, 29.5, 29.2, 19.3, 18.9; MS (ESI) m/z 214.2 (M+H)$^+$.

(3R)—N-[(1S)-1-{[4-(Dimethylamino)piperidin-1-yl]methyl}-2-methylpropyl]-7-hydroxy-1,2,3,4-tetrahydroisoquinoline-3-carboxamide (58) Trihydrochloride. Compound BC3 (994 mg, 4.66 mmol) in dichloromethane (40 mL) was coupled with Boc-7-hydroxy-D-Tic-OH (1.4 g, 1.0 equiv) following the protocol described in General Method 4 to provide 1.94 g, (85%) of the Boc-protected (58). $^1$H NMR (300 MHz, CHLOROFORM-d) δ 6.95 (d, J=8.10 Hz, 1H), 6.53-6.71 (m, 2H), 4.72 (br. s., 1H), 4.33-4.56 (m, 2H), 3.78 (br. s., 1H), 3.11-3.28 (m, 1H), 2.95 (dd, J=6.03, 15.26 Hz, 1H), 2.25 (br. s., 5H), 1.61-1.84 (m, 5H), 1.47 (s, 9H), 1.22 (t, J=7.16 Hz, 1H), 0.80 (dd, J=6.69, 17.99 Hz, 6H); $^{13}$C NMR (75 MHz, CHLOROFORM-d) δ 171.8, 155.6, 133.9, 129.1, 124.0, 121.8, 114.7, 112.9, 81.6, 60.4, 58.6, 56.6, 54.9, 51.6, 50.1, 44.9, 33.7, 30.7, 30.2, 28.3, 21.0, 19.2, 17.3; MS (ESI) m/z 489.7 M+H)$^+$. Removal of the Boc protection following the General Method 2 furnished compound (58) (1.38 g, 72% yield). $^1$H NMR (300 MHz, METHANOL-$d_4$) δ 6.76 (d, J=8.29 Hz, 1H), 6.44 (d, J=8.10 Hz, 1H), 6.34 (s, 1H), 3.73-3.87 (m, 3H), 3.42 (dd, J=4.80, 9.89 Hz, 1H), 2.83-3.05 (m, 3H), 2.58-2.83 (m, 3H), 2.20-2.40 (m, 2H), 2.00-2.15 (m, 2H), 1.82-1.98 (m, 2H), 1.60-1.81 (m, 4H), 1.44-1.59 (m, 1H), 1.22-1.42 (m, 2H), 1.08 (t, J=7.16 Hz, 1H), 0.93 (t, J=7.16 Hz, 1H), 0.77 (t, J=6.12 Hz, 6H); $^{13}$C NMR (75 MHz, METHANOL-$d_4$) δ 175.3, 156.9, 137.3, 130.9, 125.6, 115.1, 113.4, 63.8, 61.0, 58.2, 54.7, 53.5, 52.6, 47.9, 45.3, 41.8, 39.1, 35.9, 32.3, 28.9, 20.1, 18.2; MS (ESI) m/z 389.5 M+H)$^+$. A beige solid was obtained as trihydrochloride salt (58) .3HCl: mp 184° C.; $[α]^{20.1}_D$=+91.6 (c 0.14, CH₃OH). Anal. ($C_{22}H_{39}Cl_3N_4O_2 \cdot 1.75H_2O$) C, H, N.

Scheme BD.$^a$

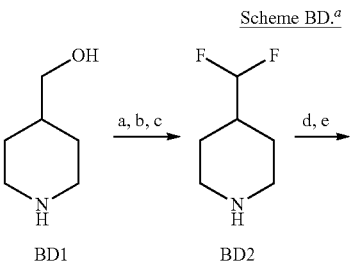

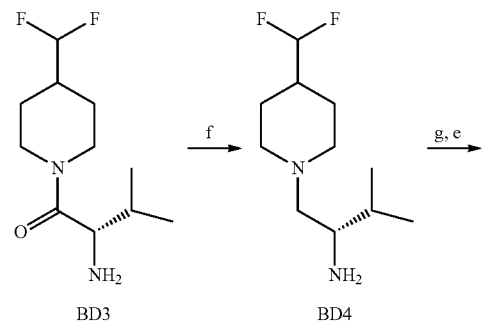

-continued

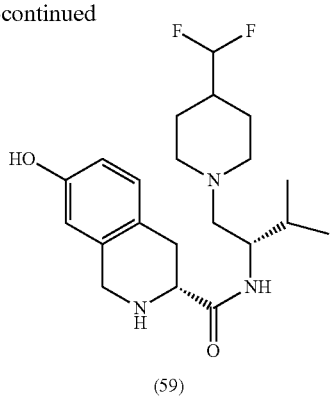

(59)

[a]Reagents and conditions: a) (Boc)$_2$O, Et$_3$N, CH$_2$Cl$_2$, rt, overnight; b) (i) Dess-Martin, CH$_2$Cl$_2$, rt, 2 h (ii) 10% aq. Na$_2$S$_2$O$_3$/sat. NaHCO$_3$, rt, 45 min (iii) DAST (3 equiv), CH$_2$Cl$_2$, 0° C. then rt overnight; c) TFA, CH$_2$Cl$_2$, rt, overnight. d) N-Boc-L-Valine, HBTU, ACN, rt overnight; e) HCl in 1,4-dioxane, ACN, rt, overnight; f) BH$_3$·SMe$_2$, THF, reflux 3 h; g) Boc-7-hydroxy-D-Tic-OH, EDC·HCl, HOBt, NEt$_3$, DCM, rt overnight.

Synthesis of Compound BD3. The 4-(diflouromethyl)piperidine (BD2) obtained as trifluoroacetate salt was prepared in the lab in three steps from 4-(hydroxymethyl)piperidine (BD1) (2.6 g 22.6 mmol) following a procedure adapted from the literature.[32] Compound BD2 (2.1 g, 16.4 mmol) was coupled with Boc-L-valine (2.63 g, 11.3 mmol) according to the General Method 1 to provide the Boc-protected product. Removal of the Boc-protection was done immediately following the General Method 2 to provide the amine BD3 (2.36 g, 89% yield over two steps). $^1$H NMR (300 MHz, CHLOROFORM-d) δ 4.44 (dd, J=5.65, 9.04 Hz, 1H), 2.56 (d, J=3.20 Hz, 1H), 1.87 (ddd, J=6.22, 12.81, 19.21 Hz, 2H), 1.28-1.50 (m, 8H), 0.75-1.03 (m, 6H); $^{13}$C NMR (75 MHz, CHLOROFORM-d) δ 170.5, 155.9, 79.4, 54.7, 45.1, 41.3, 31.4, 28.3, 25.1, 19.5, 17.0; MS (ESI) m/z 235.3 M+H)$^+$.

Synthesis of Compound BD4. Compound BD3 (2.36 g, 10.1 mmol) in anhydrous THF was treated with borane-dimethylsulfide (2.9 mL, 4.0 equiv) and heated at reflux overnight and following the General Method 3, to give the diamine BD4 (1.07 g, 48% yield) was obtained. $^1$H NMR (300 MHz, CHLOROFORM-d) δ 5.29-5.74 (m, 1H), 2.96 (d, J=11.30 Hz, 1H), 2.79 (d, J=11.30 Hz, 1H), 2.63 (ddd, J=3.58, 5.84, 9.98 Hz, 1H), 2.17-2.26 (m, 1H), 2.04-2.15 (m, 1H), 1.95-2.04 (m, 2H), 1.60-1.80 (m, 4H), 1.29-1.55 (m, 2H), 0.79-0.91 (m, 6H); $^{13}$C NMR (75 MHz, CHLOROFORM-d) δ 128.1, 118.7, 63.0, 54.7, 53.1, 51.5, 40.0, 32.0, 25.0, 19.2, 18.0; MS (ESI) m/z 221.4 M+H)$^+$.

(3R)—N-[(1S)-1-{[4-(Difluoromethyl)piperidin-1-yl]methyl}-2-methylpropyl]-7-hydroxy-1,2,3,4-tetrahydroisoquinoline-3-carboxamide (59) Dihydrochloride. Compound BD4 (994 mg, 4.66 mmol) in dichloromethane (40 mL) was coupled with Boc-7-hydroxy-D-Tic-OH (1.0 g, 3.41 equiv) following the protocol described in General Method 4 to provide 1.22 g, (73% yield) of the Boc-protected (59). $^1$H NMR (300 MHz, CHLOROFORM-d) δ 6.98 (d, J=8.29 Hz, 1H), 6.67 (dd, J=2.07, 8.10 Hz, 1H), 6.54 (br. s., 1H), 5.52 (d, J=4.71 Hz, 1H), 4.76 (br. s., 1H), 4.37-4.60 (m, 2H), 3.74-3.87 (m, 1H), 3.24 (dd, J=3.01, 15.45 Hz, 1H), 2.96 (dd, J=5.84, 15.26 Hz, 1H), 2.67 (br. s., 2H), 1.98-2.27 (m, 2H), 1.82 (dd, J=6.12, 11.40 Hz, 2H), 1.55-1.73 (m, 3H), 1.50 (s, 9H), 1.18-1.43 (m, 2H), 0.95-1.16 (m, 1H), 0.83 (dd, J=6.69, 16.67 Hz, 6H); $^{13}$C NMR (75 MHz, CHLOROFORM-d) δ 171.5, 155.6, 133.8, 129.2, 124.1, 118.8, 114.7, 113.0, 81.6, 59.4, 56.3, 53.2, 52.0, 51.1, 44.8, 39.7, 30.3, 28.4, 24.7, 19.1, 17.4; MS (ESI) m/z 496.6 M+H)$^+$. Boc-deprotection was accomplished following the General Method 2 to provide the amine compound (59) (873 mg, 90% yield). $^1$H NMR (300 MHz, CHLOROFORM-d) δ 7.12 (d, J=9.61 Hz, 1H), 6.85 (d, J=8.29 Hz, 1H), 6.57 (d, J=7.35 Hz, 1H), 6.42 (s, 1H), 5.23-5.73 (m, 1H), 4.04 (td, J=4.52, 9.04 Hz, 1H), 3.74 (s, 2H), 3.06 (d, J=10.55 Hz, 1H), 2.81-3.01 (m, 2H), 2.38-2.65 (m, 2H), 2.24-2.37 (m, 1H), 2.02 (t, J=11.11 Hz, 1H), 1.54-1.90 (m, 4H), 1.17-1.53 (m, 2H), 0.62-0.99 (m, 6H); $^{13}$C NMR (75 MHz, CHLOROFORM-d) δ 173.6, 155.1, 136.6, 130.1, 124.7, 118.6, 114.1, 112.3, 59.8, 56.7, 53.8, 51.6, 50.5, 50.0, 47.4, 39.6, 30.9, 30.2, 24.5, 19.2, 17.7; MS (ESI) m/z 396.4 M+H)$^+$. A beige solid was obtained as trihydrochloride salt, (59) 2HCl. mp 186-188° C.; [α]$^{196}_D$=+154 (c 1.1, CH$_3$OH). Anal. (C$_{21}$H$_{33}$Cl$_2$F$_2$N$_3$O$_2$·H$_2$O) C, H, N.

Scheme BE.[a]

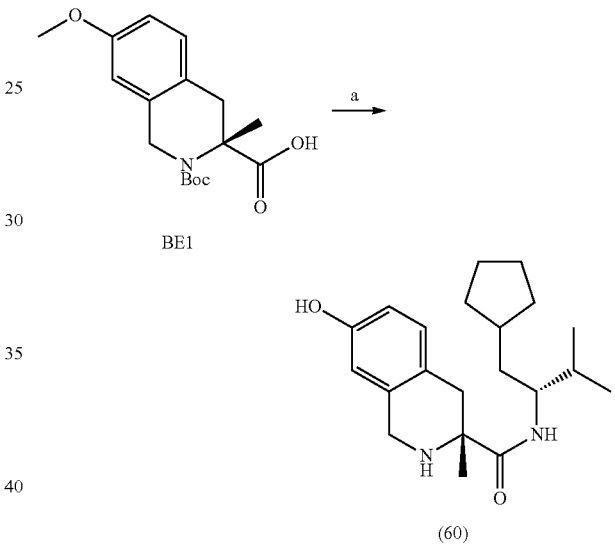

[a]Reagents and conditions: a) (i) DCC, HOBt, THF, AK4, NEt$_3$ (ii) BBr$_3$, CH$_2$Cl$_2$.

(3R)—N-[(1R)-1-(Cyclopentylmethyl)-2-methylpropyl]-7-hydroxy-3-methyl-1,2,3,4-tetrahydroisoquinoline-3-carboxamide (60) Hydrochloride. A solution of dicyclohexylcarbodiimide (DCC) (132 mg, 0.64 mmol) in THF (2.5 mL) was added to a solution of HOBt (83 mg, 0.62 mmol) and 7-methoxy-3-methyl-Boc-D-Tic(OH) (BE1)[33] (172 mg, 0.54 mmol) in THF (3 mL). After 1 h, the amine hydrochloride AK4 (127 mg, 0.66 mmol) and NEt$_3$ (0.30 mL, 2.0 mmol) were added to the suspension. The reaction mixture was stirred at room temperature for 12 h. The solids were separated by filtration and the filtrate concentrated to a residue. The residue was subjected to chromatography on silica gel eluting with a gradient up to 40% EtOAc in hexanes. The product containing fractions were concentrated and the residue dissolved in CH$_2$Cl$_2$ (5 mL), cooled to −78° C. and treated with BBr$_3$ (4 mL, 1.0 M in CH$_2$Cl$_2$) and left to warm to room temperature. After 12 h, the solution was cooled then quenched with CH$_3$OH and concentrated. The residue was partitioned between CH$_2$Cl$_2$ and aq. NaHCO$_3$. The organic layer was dried Na$_2$SO$_4$) and concentrated. The residue was subjected to chromatography on silica gel eluting with a gradient up to 100% EtOAc in hexanes to afford the freebase (60): ¹H NMR (300 MHz, CDCl₃) δ 7.38 (d, J=9.98 Hz, 1H), 6.95 (d, J=8.10 Hz, 1H), 6.69 (dd, J=2.35, 8.19 Hz, 1H), 6.61 (d, J=2.07 Hz, 1H), 3.97 (s, 1H), 3.78-3.88 (m, 1H), 3.63-3.78 (m, 1H), 3.08 (d, J=15.64 Hz, 1H), 2.74 (d, J=15.45 Hz, 1H), 1.57-1.79 (m, 3H), 1.27-1.56 (m, 10H), 0.89-1.10 (m, 2H), 0.84 (dd, J=5.37, 6.69 Hz, 6H); ¹³C NMR (75 MHz, CDCl₃) δ 176.1, 155.2, 136.4, 129.7, 125.3, 114.1, 112.2, 58.5, 53.1, 45.2, 38.5, 37.0, 36.4, 33.3, 32.4, 26.6, 25.1, 25.0, 19.2, 17.5. The free base was converted into 43.1 mg (20% over two steps) of a white powder as the hydrochloride salt (60) HCl: MS (ESI) m/z 345.4 (M+H)⁺; m.p. 157-161° C. (fusion); $[\alpha]_D^{25}$=+33 (c 0.10, CH₃OH). Anal. ($C_{21}H_{33}ClN_2O_2 \cdot 0.75H_2O$) C, H, N.

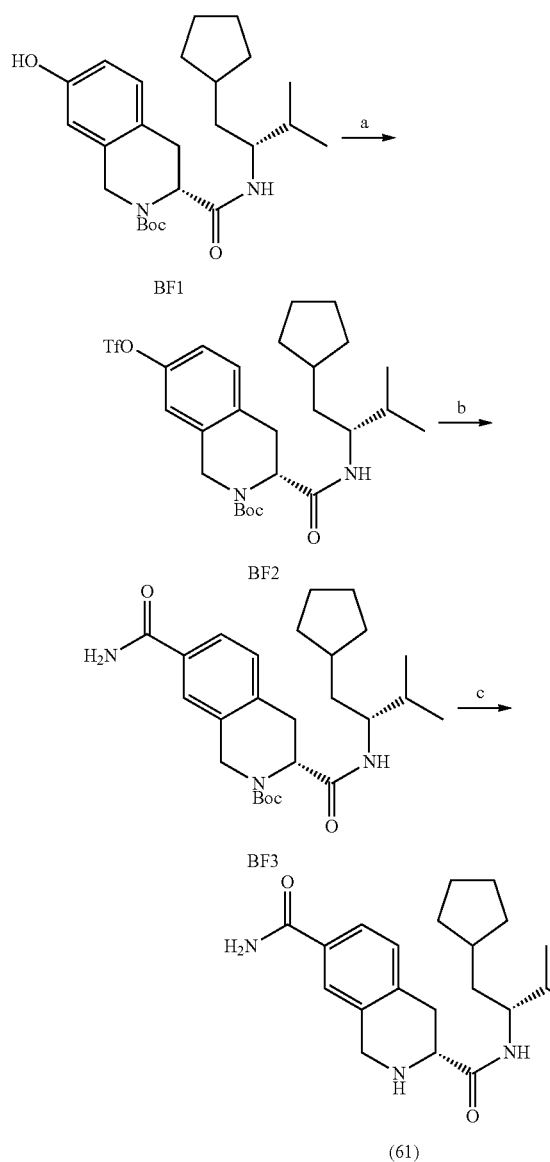

BF1

BF2

BF3

(61)

ᵃReagents and conditions: a) PhNTf₂, NEt₃, CH₂Cl₂; b) Hermann's palladacycle, XPhos, NH₂OH·HCl, Mo(CO)₆, Cs₂CO₃, DMAP, dioxane; c) 4N HCl in dioxane, CH₃CN.

Synthesis of BF2. A sample of Boc-protected 40 (BF1) (215 mg, 0.50 mmol) was dissolved in CH₂Cl₂ (10 mL) and treated with PhNTf₂ (200 mg, 0.55 mmol) and NEt3 (1.0 mmol, 140 μL). After 12 h, the reaction was concentrated to a residue which was subjected to chromatography on silica gel eluting with a gradient of EtOAc in hexanes to afford 210 mg (75%) of the desired aryl triflate BF2: ¹H NMR (300 MHz, CDCl₃) δ 7.24-7.37 (m, 1H), 7.00-7.20 (m, 2H), 5.30-6.05 (m, 1H), 4.69-5.04 (m, 1H), 4.57 (br. s., 2H), 3.66 (br. s., 1H), 3.44 (dd, J=2.26, 15.45 Hz, 1H), 2.85-3.15 (m, 1H), 0.69-1.77 (m, 27H); ¹⁹F NMR (282 MHz, CDCl₃) δ -72.93.

Synthesis of BF3. The aryl triflate was converted to the corresponding benzamide according to literature procedure.[34] A 0.1 M solution of triflate BF2 (0.19 mmol) in dioxane was added to a microwave vial containing Cs₂CO₃ (326 mg), DMAP (55 mg), NH₂OHHCl (30 mg), Mo(CO)₆ (67 mg), XPhos ligand (7.2 mg) and cataCXium® C (Hermann's palladacycle) (4.7 mg). After heating according to the literature method, the reaction was filtered through Celite using EtOAc. The organic layer was washed with dilute citric acid then dried Na₂SO₄). The concentrated residue was subjected to chromatography on silica gel eluting with a gradient up to 100% EtOAc in hexanes to afford 38.1 mg (44%) of the desired benzamide BF3: ¹H NMR (300 MHz, CDCl₃) δ 7.42-7.73 (m, 2H), 7.08-7.34 (m, 2H), 5.26-6.27 (m, 2H), 4.75 (br. s., 1H), 4.47 (br. s., 2H), 3.56 (br. s., 1H), 3.40 (d, J=14.13 Hz, 1H), 2.97 (dd, J=6.03, 15.45 Hz, 1H), 0.37-1.64 (m, 27H).

(3R)—N³-[(1R)-1-(Cyclopentylmethyl)-2-methylpropyl]-1,2,3,4-tetrahydroisoquinoline-3,7-dicarboxamide (61) Hydrochloride. The Boc-protected compound BF3 (55.4 mg, 0.12 mmol) was dissolved in CH₃CN (5 mL) and treated with HCl (4 N in dioxane, 4 mL). After 1 h, the reaction was concentrated and the residue subjected to chromatography on silica gel eluting with a gradient up to 50% DMA80 in CH₂Cl₂ to afford 37.7 mg (88%) of the desired free base (61): ¹H NMR (300 MHz, CD₃OD) δ 7.53-7.73 (m, 2H), 7.22 (d, J=7.91 Hz, 1H), 3.94-4.18 (m, 2H), 3.76 (dd, J=4.43, 9.70 Hz, 1H), 3.66 (dd, J=5.09, 9.61 Hz, 1H), 2.82-3.14 (m, 2H), 1.85-1.96 (m, 3H), 1.29-1.84 (m, 10H), 0.97-1.17 (m, 2H), 0.91 (dd, J=3.01, 6.78 Hz, 6H); ¹³C NMR (75 MHz, CD₃OD) δ 174.6, 172.1, 139.4, 136.6, 133.0, 130.1, 126.8, 126.4, 57.2, 54.8, 47.4, 39.2, 38.3, 34.3, 34.0, 33.4, 33.1, 26.1, 26.0, 19.8, 18.3. The free base was converted in to a pale yellow powder as the hydrochloride salt, 61·HCl: MS (ESI) m/z 358.2 (M+H)+; m.p. 153-157° C. (fusion); $[\alpha]_D^{25}$=+98 (c 0.10, CH3OH). Anal. ($C_{21}H_{32}ClN_3O_2H_2O$) C, H, N.

Scheme BG.ᵃ

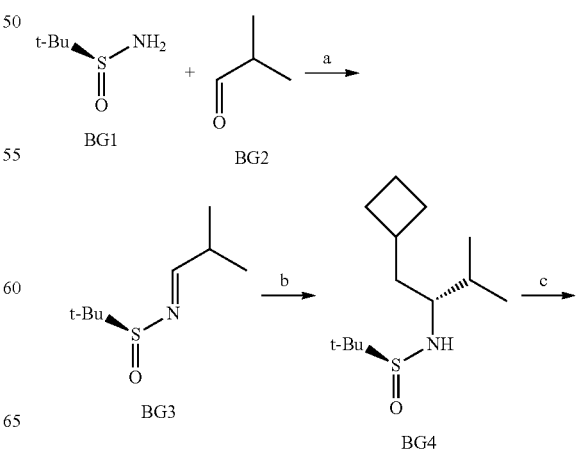

BG1

BG2

BG3

BG4

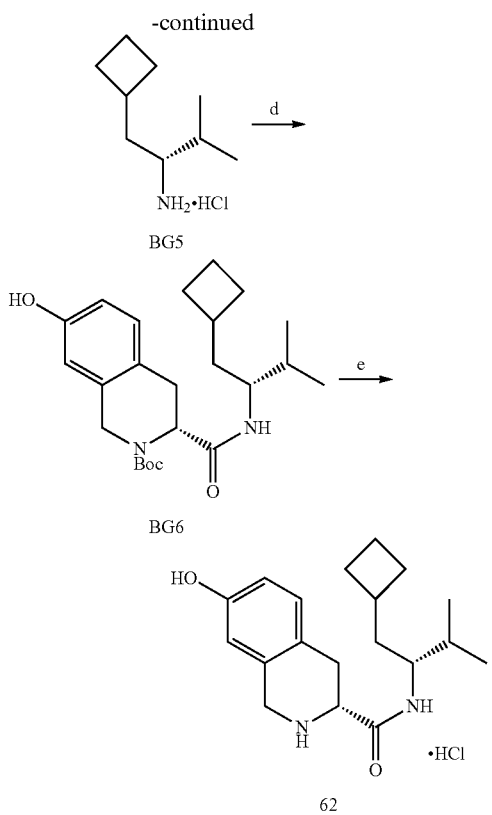

<sup>a</sup>Reagents and conditions: a) MgSO<sub>4</sub>, CH<sub>2</sub>Cl<sub>2</sub>; b) cyclopropylmethyl Grignard, CH<sub>2</sub>Cl<sub>2</sub>; c) 4N HCl in dioxane, CH<sub>3</sub>OH; d) T<sub>3</sub>P in EtOAc, THF; e) HCl in CH<sub>3</sub>OH.

Synthesis of BG3. A solution of (S)-tert-butylsulfinamide (BG1) (3.62 g, 0.030 mol), pyridinium tosylate (245 mg, 1 mmol) and isobutyraldehyde (BG2) (10 mL) in CH$_2$Cl$_2$ (50 mL) was treated with MgSO$_4$ (10 g). The resulting suspension was stirred for 34 h, then separated by filtration and the resulting filtrate concentrated. The resulting residue was purified by chromatography on silica gel eluting with a gradient up to 35% EtOAc in hexanes to afford 3.46 g (66%) of the desired sulfinimine BG3: $^1$H NMR (300 MHz, CDCl$_3$) δ 7.98 (d, J=4.33 Hz, 1H), 2.55-2.84 (m, 1H), 1.18 (s, 9H), 1.17 (d, J=1.32 Hz, 3H), 1.15 (d, J=1.32 Hz, 3H).

Synthesis of BG4. A solution of the cyproxyl methyl Grignard reagent was prepared by treating Mg metal (0.5 g, 10 mmol) in THF (15 mL), maintained at a gentle reflux, with cyclopropylmethyl bromide (2.5 mL, 10 mmol). After 30 minutes heating at reflux, the resulting solution was transferred to a solution of sulfinimine BG3 (1.31 g, 0.075 mol) in CH$_2$Cl$_2$ (40 mL) maintained below 50° C. The resulting solution was allowed to warm to room temperature overnight. A saturated solution of NH$_4$Cl aq. was added to quench the reaction and CH$_2$Cl$_2$ was used to extract the aqueous layer. The combined organic layers were dried Na$_2$SO$_4$) and concentrated. The resulting residue was subjected to chromatography on silica gel eluting with a gradient up to 25% EtOAc in hexanes to afford 1.92 g of the desired sulfinamide BG4 containing traces of solvent: $^1$H NMR (300 MHz, CDCl$_3$) δ 2.85-3.02 (m, 1H), 2.63-2.82 (m, 1H), 2.31-2.50 (m, 1H), 2.02 (br. s., 2H), 1.45-1.91 (m, 7H), 1.15 (s, 9H), 0.79 (d, J=3.20 Hz, 6H). The sulfinamide was dissolved in CH$_3$OH (20 mL) and treated with HCl (4 N in dioxane, 5 mL). The reaction was concentrated to afford 1.45 g BG5 (109% yield over two steps) of a white solid which was deemed sufficiently clean by NMR to carry forward: $^1$H NMR (300 MHz, CD$_3$OD) δ 2.86-3.01 (m, 1H), 2.33-2.54 (m, 1H), 2.13 (tdd, J=3.63, 7.23, 10.76 Hz, 2H), 1.80-2.04 (m, 3H), 1.55-1.80 (m, 4H), 1.09-1.23 (m, 2H), 0.90-1.05 (m, 6H); $^{13}$C NMR (75 MHz, CD$_3$OD) δ 37.5, 33.3, 31.3, 29.2, 29.0, 19.2, 18.2, 17.8.

Synthesis of (3R)—N-[(1R)-1-(Cyclobutylmethyl)-2-methylpropyl]-7-hydroxy-1,2,3,4-tetrahydroisoquinoline-3-carboxamide (62). A solution of the amine hydrochloride BG5 (250 mg, 1.4 mmol) and 7-hydroxy-Boc-D-Tic(OH) (154 mg, 0.5 mmol) in THF (5 mL) was treated with T3P (50 wt. % in EtOAc, 0.9 mL) and DIEA (0.5 mL) in an ice bath. The reaction mixture was warmed to room temperature overnight then was partitioned between aq. NaHCO$_3$ and EtOAc. The aqueous layer was extracted with EtOAc and the combine organic layers were washed with water, then dried Na$_2$SO$_4$) and concentrated. The resulting residue was subjected to chromatography on silica gel eluting with a gradient up to 50% EtOAc in hexanes to afford 120.2 mg (58%) of the desired Boc-protected product BG6, which was used without further characterization. Acetyl chloride (0.5 mL) was added to CH$_3$OH (2.5 mL) at 50° C. The resulting solution warmed to 0° C. A solution of the Boc-protected compound BG6 (120.2 mg, 0.29 mmol) in CH$_3$OH (2.5 mL) was then added to the HCl solution at 50° C. External cooling was removed then the reaction was transferred to the rotary evaporator for concentration. The residue was dissolved in fresh CH$_3$OH, concentrated then concentrated again from EtOAc to afford 100 mg (quantitative yield) of the hydrochloride salt, 62·HCl, as a white solid: MS (ESI) m/z 317.3 (M+H)$^+$; m.p. begins at 115° C. (fusion); $[α]_D^{25}$=+102 (c 0.10, CH$_3$OH). Anal. (C$_{19}$H$_{29}$ClN$_2$O$_2$·0.5 H$_2$O) C, H, N. A sample of the hydrochloride salt was converted to the free base 62: $^1$H NMR (300 MHz, CD$_3$OD) δ 6.94 (d, J=8.29 Hz, 1H), 6.55-6.68 (m, 1H), 6.50 (s, 1H), 3.95 (s, 1H), 3.65 (td, J=4.69, 9.65 Hz, 1H), 3.56 (dd, J=4.80, 10.27 Hz, 1H), 2.70-2.99 (m, 2H), 2.14-2.38 (m, 1H), 1.94-2.11 (m, 2H), 1.39-1.93 (m, 8H), 0.89 (dd, J=3.49, 6.69 Hz, 6H); $^{13}$C NMR (126 MHz, CD$_3$OD) δ 175.0, 157.1, 136.9, 130.9, 125.5, 115.2, 113.3, 58.1, 54.0, 47.8, 40.2, 34.8, 33.8, 32.7, 29.7, 29.6, 19.9, 19.5, 18.4.

Scheme BH.<sup>a</sup>

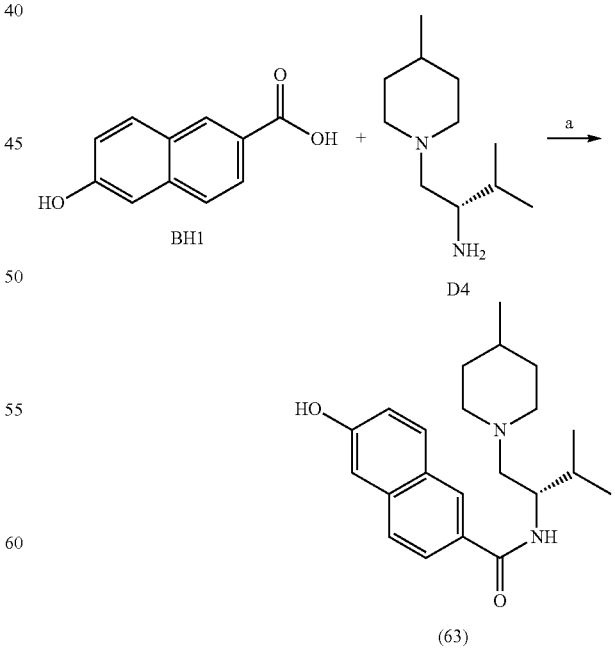

<sup>a</sup>Reagents and conditions: a) EEDQ, DMF, 100° C. 3 h.

6-Hydroxy-N-{(1S)-2-methyl-1-[(4-methylpiperidine-1-yl)methyl]propyl}naphthalene-2-carboxamide (63) Hydrochloride. A solution of 6-hydroxynapthalene-2-carboxylic acid (233 mg, 1.24 mmol) (BH1), (2S)-3-methyl-1-(4-methylpiperidine-1-yl)butan-2-amine (D4), (220 mg, 1.24 mg) and N-ethoxycarbonyl-2-ethoxy-1,2-dihydroquinoline (EEDQ) (367.1 mg, 1.48 mmol) in DMF was heated at 100° C. for 3 h then transferred to a rotavap and heated for an additional 1 hour under reduced pressure until all the solvent was evacuated. The residue was purified on silica gel eluted with ethyl acetate /hexanes to provide 96 mg (22% yield) of (63) as a clear oil. $^1$H NMR (300 MHz, CHLOROFORM-d) δ 7.58 (s, 1H), 7.47 (dd, J=1.60, 8.57 Hz, 1H), 7.15-7.25 (m, 1H), 7.10 (d, J=8.67 Hz, 1H), 6.74 (dd, J=2.26, 8.85 Hz, 1H), 6.46-6.58 (m, 1H), 4.29-4.42 (m, 1H), 3.26 (d, J=11.49 Hz, 1H), 2.89 (d, J=11.49 Hz, 1H), 2.77 (t, J=12.24 Hz, 1H), 2.36 (dd, J=3.86, 12.72 Hz, 1H), 2.13 (t, J=10.93 Hz, 1H), 1.85-2.03 (m, 2H), 1.69 (d, J=12.62 Hz, 1H), 1.44-1.61 (m, 1H), 1.10-1.40 (m, 3H), 0.74-1.00 (m, 9H); $^{13}$C NMR (75 MHz, CHLOROFORM-d) δ 168.2, 155.9, 135.9, 130.5, 128.5, 126.5, 126.4, 123.6, 118.8, 109.0, 58.7, 55.6, 51.9, 50.7, 33.6, 33.4, 31.9, 30.4, 29.7, 21.6, 19.0, 18.3; MS (ESI) m/z 355.4 M+H)$^+$. A beige solid was obtained as a hydrochloride salt of 63·HCl: mp 128-132° C.; $[α]^{21.2}_D$=+33 (c 0.11, CH$_3$OH). Anal. (C$_{22}$H$_{31}$ClN$_2$O$_2$·0.75H$_2$O) C, H, N.

(3R)—N-[(1R)-2-Cyclopentyl-1-cyclopropylethyl]-7-hydroxy-1,2,3,4-tetrahydroisoquinoline-3-carboxamide (64) Hydrochloride. To a rapidly stirring solution of dicyclohexylcarbodiimide (DCC) (0.66 g, 3.2 mmol) and HOBt (0.36 g, 2.6 mmol) in THF (7.5 mL) was added 7-hydroxy-Boc-D-Tic(OH) (752 g, 2.5 mmol). After 1 h, the amine BI2 hydrochloride (519 mg, 2.7 mmol) was free based then dissolved in THF (2.5 mL) and added to the suspension. The reaction mixture was stirred at room temperature for 12 h. The solids were separated by filtration and the filtrate concentrated to a residue. The residue was subjected to chromatography on silica gel eluting with a gradient up to 5% isopropanol in CH$_2$Cl$_2$ to afford 1.03 g (96%) Boc-protected 64 as a white foam. A cold volume of methanol (5 mL) was treated with acetyl chloride (1 mL) at −78° C. then allowed to warm to room temperature. The solution was chilled before the addition of the Boc compound (253 mg, 0.59 mmol) in methanol (5 mL). After 12 h under a stream of nitrogen, the solids were re-dissolved in a minimum of methanol and diluted with EtOAc. A small addition of hexanes initiated crystallization. The solids were collected and dried to afford 197 mg (92%) of the desired 64·HCl as a white crystalline solid: $^1$H NMR (300 MHz, CD$_3$OD) δ 8.32 (d, J=9.04 Hz, 1H), 7.10 (d, J=8.29 Hz, 1H), 6.76 (dd, J=1.98, 8.38 Hz, 1H), 6.65 (s, 1H), 4.24-4.44 (m, 2H), 4.03-4.19 (m, 1H), 3.19-3.55 (m, 2H), 2.99-3.14 (m, 1H), 1.02-2.06 (m, 13H), 0.82-1.01 (m, 1H), 0.56 (dt, J=4.99, 8.62 Hz, 1H), 0.45 (dt, J=3.86, 8.52 Hz, 1H), 0.14-0.37 (m, 2H) Anal. (C$_{20}$H$_{29}$ClN$_2$O$_2$·0.5H$_2$O) C, H, N.

Scheme BI.$^a$

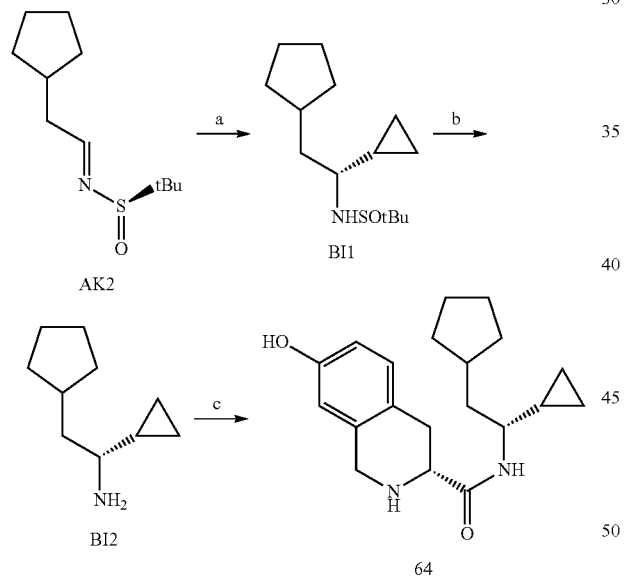

$^a$Reagents and conditions: a) Cyclopropylmagnesium bromide, CH$_2$Cl$_2$; b) HCl, CH$_3$OH; c) (i) DCC HOBt, 7-hydroxy-Boc-D-Tic(OH) (ii) MeOH, HCl.

Synthesis of BI2. A solution of sulfinimine AK2 (0.96 g, 4.5 mmol) in CH$_2$Cl$_2$ (20 mL) at −78° C. was treated with cyclopropylmagnesium bromide (8.0 mL, 1.0 M in 2-methyltetrahydrofuran). The solution was allowed to warm to room temperature overnight, then was quenched by the addition of sat. aq. NH$_4$Cl. The organic layer was washed with aq. NaHCO$_3$ and dried Na$_2$SO$_4$). The concentrated residue was subjected to chromatography on silica gel eluting with a gradient up to 50% EtOAc in hexanes to afford the sulfinamide BI1 which was dissolved in methanol (10 mL) and treated with hydrogen chloride (5 mL, 4 N in dioxane) at room temperature. The resulting solution was evaporated under a stream of nitrogen overnight to afford 0.52 g (61% over two steps) of the amine BI2 hydrochloride.

Scheme BJ.$^a$

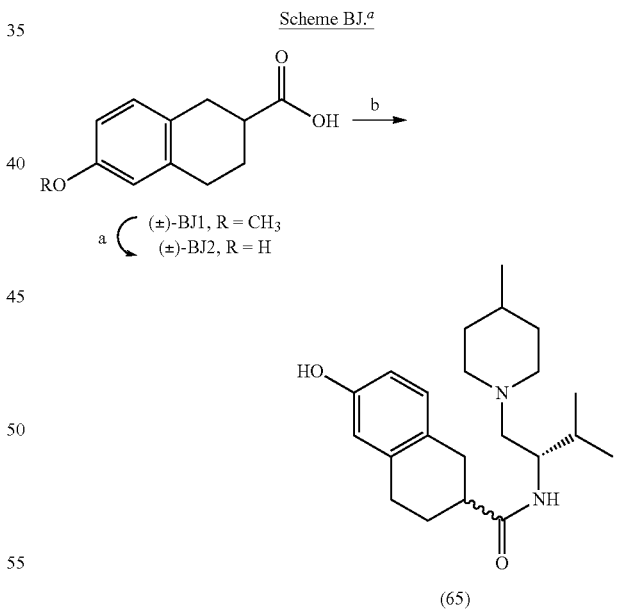

$^a$Reagents and conditions: a) HBr (48% aq.), AcOH, 105° C., 5 h; b) D4, BOP, NEt$_3$, THF, rt, overnight.

6-Hydroxy-N-{(1S)-2-methyl-1-[(4-methylpiperidine-1-yl)methyl]propyl}-1,2,3,4-tetrahydronaphthalene-2-carboxamide (65) Hydrochoride. A solution of 6-methoxy-1,2,3,4-tetrahydronaphthalene-2-carboxylic acid (BJ1) (378 mg, 1.833 mmol) in aqueous HBr (48%) (10 mL) and acetic acid (10 mL) was heated at reflux for 5 h then cooled. Solvent was removed in vacuo to provide compound BJ2 which was carried on to the next step without further purification. A solution of BJ2, (2S)-3-methyl-1-(4-methylpiperidine-1-yl)butan-2-amine, (220 mg, 1.24 mg), BOP (973 mg, 2.2 mmol, 1.2 equiv), and TEA (0.880 mL, 5.5 mmol, 3 equiv) in THF (20 mL) was stirred at room temperature overnight. A saturation aqueous solution of NaHCO$_3$ (50 mL) was then added to the mixture, followed by extraction using EtOAc (3×50 mL). The combined organic layers were dried (anhydrous Na$_2$SO$_4$), filtered over Celite and concentrated in vacuo. The residue was purified on silica gel eluted with 10% MeOH/CH$_2$Cl$_2$ to provide a clear oil 563 mg, 86% yield over two steps, of 65 as a mixture of diastereomers. $^1$H NMR (300 MHz, CHLOROFORM-d) δ 6.82 (t, J=8.48 Hz, 1H), 6.48-6.70 (m, 2H), 6.02-6.22 (m, 1H), 4.02 (dt, J=4.99, 9.28 Hz, 1H), 2.94-3.07 (m, 1H), 2.70-2.93 (m, 2H), 2.44-2.70 (m, 6H), 2.08-2.44 (m, 3H), 1.83-1.95 (m, 2H), 1.59-1.79 (m, 3H), 1.12-1.48 (m, 3H), 0.77-1.01 (m, 9H); $^{13}$C NMR (75 MHz, CHLOROFORM-d) δ 176.1, 154.9, 136.9, 129.8, 126.0, 115.3, 113.5, 58.6, 55.2, 52.6, 50.5, 42.2, 36.8, 33.7, 32.1, 30.7, 30.4, 28.6, 26.0, 23.3, 18.7, 17.9; MS (ESI) m/z 359.5 M+H)$^+$. A beige solid was obtained as a hydrochloride salt 65·HCl: mp 118° C.; [α]$^{18.1}_D$=+40.3 (c 0.3, CH$_3$OH). Anal. (C$_{22}$H$_{35}$ClN$_{22}$·1.25H$_2$O) C, H, N.

Scheme BK.$^a$

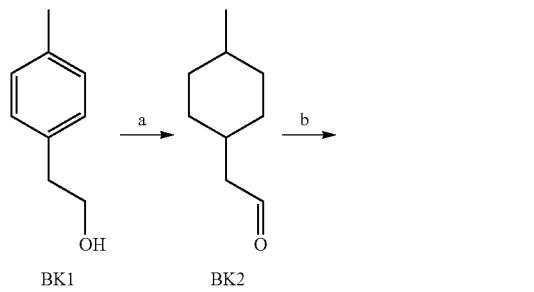

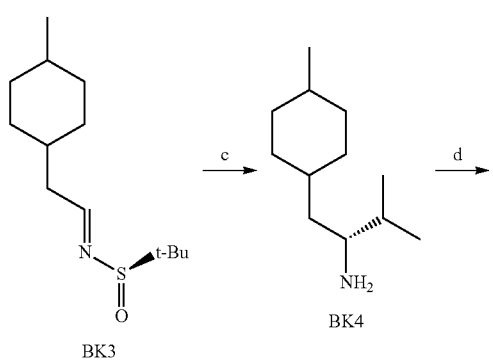

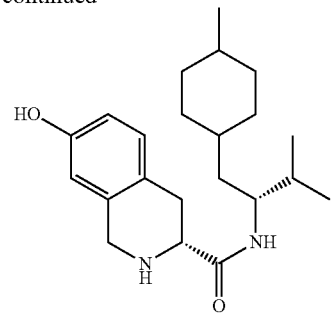

66

$^a$Reagents and condtions: a) Na, NH$_3$, THF, tBuOH (ii) Pd(OH)$_2$, H$_2$, EtOH (iii) Swern oxidation; b) (R)-tert-butylsulfinamide, CH$_2$Cl$_2$, MgSO$_4$; c) (i) iPrMgCl, CH$_2$Cl$_2$ (ii) HCl, CH$_3$OH; d) (i) 7-hydroxy-Boc-D-Tic(OH), DCC, HOBt, THF (ii) HCl, CH$_3$OH.

Synthesis of BK2. Sodium metal (2.2 g) was added portionwise to a solution of the tolylethanol (BK1) (prepared from borane dimethylsulfide reduction of phenylacetic acid) in THF (75 mL), tBuOH (10 mL) and liquid ammonia (200 mL) at −78° C. The solution was warmed to reflux and the persistent blue color faded. The concentrated residue was subjected to chromatography on silica gel eluting with a gradient up to 50% EtOAc in hexanes to afford 3.71 g of the desired product. Two spots were isolated, which appeared to be closely related isomers by $^1$H-NMR. This semi-crude combined product mixture from the Birch reduction was treated with Pd(OH)$_2$ on carbon in ethanol under hydrogen (45 psi). The filtered concentrated reaction was concentrated and the residue subjected to chromatography on silica gel eluting with a gradient up to 20% EtOAc in hexanes to afford 537 mg (3.8 mmol) of the desired 2-(4-methylcyclohexyl)ethanol: $^1$H NMR (300 MHz, CDCl$_3$) δ 3.51 (br. s., 2H), 0.96-1.67 (m, 10H), 0.72 (dd, J=4.14, 11.49 Hz, 5H). Swern oxidation of the alcohol (537 mg, 3.8 mmol) in CH$_2$Cl$_2$ (1.5 ml) was effected by slowly addition to a solution reagent prepared from oxalyl chloride (0.53 g) in CH$_2$Cl$_2$ (3 mL) treated with DMSO (0.71 g) in CH$_2$Cl$_2$ (1.5 mL). Finally, NEt$_3$ (2.6 mL) was added. The crude aldehyde BK2 was isolated by work up and carried forward without further purification.

Synthesis of BK3. Condensation of BK2 with (R)-tert-butylsulfinamide was effected in CH$_2$Cl$_2$ at room temperature with excess MgSO$_4$. The mixture was filtered, concentrated and the resulting residue purified by column chromatography on silica gel to afford 806 mg (87% of BK3 over two steps) of the desired sulfinimine.

Synthesis of BK4. A solution of sulfinimine BK3 (806 mg, 3.3 mmol) in CH$_2$Cl$_2$ (10 mL) at −78° C. was treated with isopropylmagnesium chloride (5.0 mL, 2.0 M in THF). The solution was allowed to warm to room temperature overnight, then was quenched by the addition of sat. aq. NH$_4$Cl. The organic layer was washed with aq. NaHCO$_3$ and dried Na$_2$SO$_4$). The concentrated residue was subjected to chromatography on silica gel eluting with a gradient up to 50% EtOAc in hexanes, to afford a product showing the characteristic $^1$H-NMR (300 MHz, CDCl$_3$) δ 8.04 (t, J=3 Hz, 1H). The sulfinamide was dissolved in methanol (10 mL) and treated with hydrogen chloride (5 mL, 4 N in dioxane) at room temperature. The resulting solution was evaporated under a stream of nitrogen overnight to afford the amine BK4 hydrochloride, which was free based with CH$_2$Cl$_2$ and saturated aqueous NaHCO$_3$ to afford 419 mg (70%) of the desired amine BK4: $^1$H NMR (300 MHz, CD$_3$OD) δ 3.02-3.23 (m, 1H), 1.89-2.06 (m, 1H), 1.21-1.88 (m, 10H), 0.81-1.09 (m, 12H).

(3R)-7-Hydroxy-N-{(1R)-2-methyl-1-[(4-methylcyclohexyl)methyl]propyl}-1,2,3,4-tetrahydroisoquinoline-3-carboxamide (66) Hydrochloride. To a rapidly stirring solution of dicyclohexylcarbodiimide (DCC) (0.66 g, 3.2 mmol) and HOBt (0.33 g, 2.5 mmol) in THF (7.5 mL) was added 7-hydroxy-Boc-D-Tic(OH) (600 mg, 2.0 mmol). After 1 h, the amine BK4 (419 mg, 2.3 mmol) in THF (2.5 mL) was added to the suspension. The reaction mixture was stirred at room temperature for 12 h. The solids were separated by filtration and the filtrate concentrated to a residue. The residue was subjected to chromatography on silica gel. The resulting Boc compound was treated with a solution of HCl in methanol prepared from acetyl chloride. The solvent was concentrated to afford 236 mg (60%) of the 66·HCl, m.p. 173-177° C. (fusion); $^1$H NMR (300 MHz, CD$_3$OD) δ 8.12 (d, J=9.04 Hz, 1H), 7.09 (d, J=8.29 Hz, 1H), 6.75 (d, J=7.54 Hz, 1H), 6.65 (s, 1H), 4.24-4.45 (m, 2H), 4.17 (dd, J=4.62, 11.77 Hz, 1H), 3.81-4.00 (m, 1H), 3.48 (q, J=7.10 Hz, 1H), 2.98-3.17 (m, 1H), 1.91 (d, J=7.54 Hz, 1H), 1.61-1.82 (m, 4H), 1.08-1.59 (m, 7H), 0.75-1.07 (m, 12H); $^{13}$C NMR (75 MHz, CD$_3$OD) δ 168.0, 156.6, 129.7, 128.3, 120.6, 115.4, 112.2, 55.4, 55.4, 52.1, 52.0, 44.0, 39.0, 38.9, 35.0, 34.8, 33.9, 33.9, 32.6, 32.5, 32.1, 29.4, 21.6, 18.3, 16.7; MS (ESI) m/z 459.4 [M+H]$^+$; [α]$_D$=+94.2 (c 1.00, CH$_3$OH). Anal. (C$_{22}$H$_{35}$ClN$_2$O$_2$ ½H$_2$O) C, H, N.

7. REFERENCES (1) Dhawan, B. N.; Cesselin, F.; Raghubir, R.; Reisine, T.; Bradley, P. B.; Portoghese, P. S.; Hamon, M. International Union of Pharmacology. XII. Classification of opioid receptors. *Pharmacol. Rev.* 1996, 48, 567-592.

(2) Aldrich, J. V.; Vigil-Cruz, S. C. Narcotic Analgesics. In *Burger's Medicinal Chemistry and Drug Discovery*, 6th ed.; Abraham, D. J., Ed. John Wiley & Sons: New York, N.Y., 2003; Vol. 6, Chapter 7, pp 329-481.

(3) Husbands, S. M. Kappa-opioid receptor ligands. *Expert Opin. Ther. Patents* 2004, 14, 1725-1741.

(4) Prisinzano, T. E.; Tidgewell, K.; Harding, W. W. Kappa opioids as potential treatments for stimulant dependence. *AAPS J.* 2005, 7, E592-E599.

(5) Metcalf, M. D.; Coop, A. Kappa opioid antagonists: past successes and future prospects. *AAPS J.* 2005, 7, E704-E722.

(6) Carroll, F. I.; Thomas, J. B.; Dykstra, L. A.; Granger, A. L.; Allen, R. M.; Howard, J. L.; Pollard, G. T.; Aceto, M. D.; Harris, L. S. DUPLICATE OF 718: DO NOT USE Pharmacological properties of JDTic: A novel k-opioid receptor antagonist. *Eur. J. Pharmacol.* 2004, 501, 111-119.

(7) Thomas, J. B.; Atkinson, R. N.; Vinson, N. A.; Catanzaro, J. L.; Perretta, C. L.; Fix, S. E.; Mascarella, S. W.; Rothman, R. B.; Xu, H.; Dersch, C. M.; Cantrell, B. E.; Zimmerman, D. M.; Carroll, F. I. Identification of (3R)-7-hydroxy-N-((1S)-1-[[(3R,4R)-4-(3-hydroxyphenyl)-3,4-dimethyl-1-piperidinyl]methyl]-2-methylpropyl)-1,2,3,4-tetrahydro-3-isoquinolinecarboxamide as a novel potent and selective opioid kappa receptor antagonist. *J. Med. Chem.* 2003, 46, 3127-3137.

(8) Thomas, J. B.; Atkinson, R. N.; Rothman, R. B.; Fix, S. E.; Mascarella, S. W.; Vinson, N. A.; Xu, H.; Dersch, C. M.; Lu, Y.; Cantrell, B. E.; Zimmerman, D. M.; Carroll, F. I. Identification of the first trans-(3R,4R)-dimethyl-4-(3-hydroxyphenyl)piperidine derivative to possess highly potent and selective opioid kappa receptor antagonist activity. *J. Med. Chem.* 2001, 44, 2687-90.

(9) Kreek, M. J.; LaForge, K. S.; Butelman, E. Pharmacotherapy of addictions. *Nat. Rev. Drug Discov.* 2002, 1, 710-726.

(10) Thomas, J. B.; Fall, M. J.; Cooper, J. B.; Rothman, R. B.; Mascarella, S. W.; Xu, H.; Partilla, J. S.; Dersch, C. M.; McCullough, K. B.; Cantrell, B. E.; Zimmerman, D. M.; Carroll, F. I. Identification of an opioid ☐ receptor subtype-selective N-substituent for (+)-(3R,4R)-dimethyl-4-(3-hydroxyphenyl)piperidine. *J. Med. Chem.* 1998, 41, 5188-5197.

(11) Beardsley, P. M.; Howard, J. L.; Shelton, K. L.; Carroll, F. I. Differential effects of the novel kappa opioid receptor antagonist, JDTic, on reinstatement of cocaine-seeking induced by footshock stressors vs cocaine primes and its antidepressant-like effects in rats. *Psychopharmacology (Berl.)* 2005, 183, 118-126.

(12) Knoll, A. T.; Meloni, E. G.; Thomas, J. B.; Carroll, F. I.; Carlezon, W. A., Jr. Anxiolytic-like effects of ☐-opioid receptor antagonists in models of unlearned and learned fear in rats. *J. Pharmacol. Exp. Ther.* 2007, 323, 838-845.

(13) Buda, J. J.; Carroll, F. I.; Kosten, T. R.; Swearingen, D.; Walters, B. B. A Double-Blind, Placebo-Controlled Trial to Evaluate the Safety, Tolerability, and Pharmacokinetics of Single, Escalating Oral Doses of JDTic. *Neuropsychopharmacology* 2015, 40, 2059-65.

(14) Brugel, T. A.; Smith, R. W.; Balestra, M.; Becker, C.; Daniels, T.; Hoerter, T. N.; Koether, G. M.; Throner, S. R.; Panko, L. M.; Folmer, J. J.; Cacciola, J.; Hunter, A. M.; Liu, R.; Edwards, P. D.; Brown, D. G.; Gordon, J.; Ledonne, N. C.; Pietras, M.; Schroeder, P.; Sygowski, L. A.; Hirata, L. T.; Zacco, A.; Peters, M. F. Discovery of 8-azabicyclo[3.2.1]octan-3-yloxy-benzamides as selective antagonists of the kappa opioid receptor. Part 1. *Bioorg. Med. Chem. Lett.* 2010, 20, 5847-52.

(15) Peters, M. F.; Zacco, A.; Gordon, J.; Maciag, C. M.; Litwin, L. C.; Thompson, C.; Schroeder, P.; Sygowski, L. A.; Piser, T. M.; Brugel, T. A. Identification of short-acting kappa-opioid receptor antagonists with anxiolytic-like activity. *Eur. J. Pharmacol.* 2011, 661, 27-34.

(16) Verhoest, P. R.; Sawant Basak, A.; Parikh, V.; Hayward, M.; Kauffman, G. W.; Paradis, V.; McHardy, S. F.; McLean, S.; Grimwood, S.; Schmidt, A. W.; Vanase-Frawley, M.; Freeman, J.; Van Deusen, J.; Cox, L.; Wong, D.; Liras, S. Design and Discovery of a Selective Small Molecule kappa Opioid Antagonist (2-Methyl-N-((2'-(pyrrolidin-1-ylsulfonyl)biphenyl-4-yl)methyl)propan-1-amine, PF-4455242). *J. Med. Chem.* 2011, 54, 5868-5877.

(17) Rorick-Kehn, L. M.; Witkin, J. M.; Statnick, M. A.; Eberle, E. L.; McKinzie, J. H.; Kahl, S. D.; Forster, B. M.; Wong, C. J.; Li, X.; Crile, R. S.; Shaw, D. B.; Sahr, A. E.; Adams, B. L.; Quimby, S. J.; Diaz, N.; Jimenez, A.; Pedregal, C.; Mitch, C. H.; Knopp, K. L.; Anderson, W. H.; Cramer, J. W.; McKinzie, D. L. LY2456302 is a novel, potent, orally-bioavailable small molecule kappa-selective antagonist with activity in animal models predictive of efficacy in mood and addictive disorders. *Neuropharmacology* 2014, 77, 131-144.

(18) Carroll, F. I.; Carlezon, J., William A. Development of Kappa Opioid Receptor Antagonists. *J. Med. Chem.* 2013, 56, 2178-2195.

(19) Mague, S. D.; Pliakas, A. M.; Todtenkopf, M. S.; Tomasiewicz, H. C.; Zhang, Y.; Stevens, W. C., Jr.; Jones, R. M.; Portoghese, P. S.; Carlezon, W. A., Jr. Antidepressant-like effects of kappa-opioid receptor antagonists in the forced swim test in rats. *J. Pharmacol. Exp. Ther.* 2003, 305, 323-330.

(20) McLaughlin, J. P.; Marton-Popovici, M.; Chavkin, C. Kappa opioid receptor antagonism and prodynorphin gene disruption block stress-induced behavioral responses. *J. Neurosci.* 2003, 23, 5674-5683.

(21) Redila, V. A.; Chavkin, C. Stress-induced reinstatement of cocaine seeking is mediated by the kappa opioid system. *Psychopharmacology (Berl.)* 2008, 200, 59-70.

(22) Carey, A. N.; Borozny, K.; Aldrich, J. V.; McLaughlin, J. P. Reinstatement of cocaine place-conditioning prevented by the peptide kappa-opioid receptor antagonist arodyn. *Eur. J. Pharmacol.* 2007, 569, 84-89.

(23) Walker, B. M.; Koob, G. F. Pharmacological evidence for a motivational role of □-opioid systems in ethanol dependence. *Neuropsychopharmacology* 2007, 33, 643-652.

(24) Bodnar, R. J.; Glass, M. J.; Ragnauth, A.; Cooper, M. L. General, mu and kappa opioid antagonists in the nucleus accumbens alter food intake under deprivation, glucoprivic and palatable conditions. *Brain Res.* 1995, 700, 205-212.

(25) Bortolato, M.; Aru, G. N.; Frau, R.; Orru, M.; Fa, M.; Manunta, M.; Puddu, M.; Mereu, G.; Gessa, G. L. Kappa opioid receptor activation disrupts prepulse inhibition of the acoustic startle in rats. *Biol. Psychiatry* 2005, 57, 1550-1558.

(26) Benesh, D. R.; Blanco-Pillado, M.-J. Preparation of 4-(5-Aminomethyl)indole-1-ylmethyl)benzamide Derivatives as Opioid Receptor Antagonists for the Treatment of Obesity, PCT Int. Appl. WO 2005 90,303. 2005.

(27) McHardy, S.; Liras, S.; Guediche, S.; Coe, J. W. 4-Phenyl-piperidine Compounds and Their Use as Modulators of Opioid Receptors, US Patent Application Publication No. 204/0204453 A1. 2004.

(28) Quagliato, D. A.; Andrae, P. M.; Matelan, E. M. Efficient procedure for the reduction of alpha-amino acids to enantiomerically pure alpha-methylamines. *J Org Chem* 2000, 65, 5037-42.

(29) Kormos, C. M.; Gichinga, M. G.; Maitra, R.; Runyon, S. P.; Thomas, J. B.; Brieaddy, L. E.; Mascarella, S. W.; Navarro, H. A.; Carroll, F. I. Design, synthesis, and biological evaluation of (3R)-1,2,3,4-tetrahydro-7-hydroxy-N-[(1S)-1-[[3R,4R)-4-(3-hydroxyphenyl)-3,4-dimethyl-1-piperidinyl]methyl]-2-methylpropyl]-3-isoquinolinecarboxamide (JDTic) analogues: in vitro pharmacology and ADME profile. *J. Med. Chem.* 2014, 57, 7367-81.

(30) Ozegowski, R.; Kunath, A.; Schick, H. Enzymes in organic synthesis .26. Synthesis of enantiomerically enriched 2,3- and 3,4-dimethylpentan-5-olides by lipase-catalyzed regio- and enantioselective alcoholysis of cis- and trans-2,3-dimethylpentanedioic anhydrides. *Liebigs Annalen* 1996, 1443-1448.

(31) Carroll, F. I.; Chaudhari, S.; Thomas, J. B.; Mascarella, S. W.; Gigstad, K. M.; Deschamps, J.; Navarro, H. A. N-Substituted cis-4a-(3-hydroxyphenyl)-8a-methyloctahydroisoquinolines are opioid receptor pure antagonists. *J. Med. Chem.* 2005, 48, 8182-8193.

(32) Markby, D.; Rice, K. C. Benzoxazepines as inhibitors of pi3K/mtor and methods of their use as antituor angents and manufacture. WO2012068096 A3 (PCTUS2011/060771), 2012.

(33) Cueva, J. P.; Cai, T. B.; Mascarella, S. W.; Thomas, J. B.; Navarro, H. A.; Carroll, F. I. Synthesis and In Vitro Opioid Receptor Functional Antagonism of Methyl-Substituted Analogues of (3R)-7-Hydroxy-N-[(1S)-1-{[(3R,4R)-4-(3-hydroxyphenyl)-3,4-dimethyl-1-piperidinyl]methyl}-2-methylpropyl]-1,2,3,4-tetrahydro-3-isoquinolinecarboxamide (JDTic). *J. Med. Chem.* 2009, 52, 7463-7472.

(34) Odell, L. R.; Savmarker, J.; Larhed, M. Microwave-promoted aminocarbonylation of aryl triflates using Mo(CO)(6) as a solid CO source. *Tetrahedron Letters* 2008, 49, 6115-6118.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.It is to be understood that, while the disclosure has been described in conjunction with the detailed description, thereof, the foregoing description is intended to illustrate and not limit the scope. Other aspects, advantages, and modifications are within the scope of the claims set forth below. All publications, patents, and patent applications cited in this specification are herein incorporated by reference as if each individual publication or patent application were specifically and individually indicated to be incorporated by reference.

What is claimed is:
1. A compound of formula I:

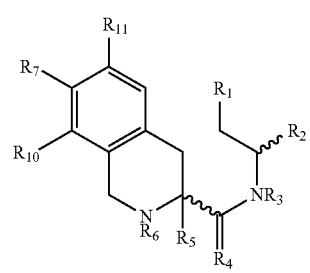

I or a pharmaceutically acceptable salt or stereoisomer thereof, wherein:

$R_1$ is H, $C_{1-6}$ alkyl, $NHR_9$, $N(C_{1-8}$ alkyl)$R_9$, $N(C_{2-8}$ alkenyl)$R_9$, $N(C_{3-8}$ cycloalkyl)$R_9$, $OR_8$, $C_{3-8}$ cycloalkyl, $C_{5-8}$ cycloalkenyl, heterocycloalkyl, heterocycloalkenyl, phenyl, or heteroaryl, wherein the heterocycloalkyl or heterocycloalkenyl is optionally substituted with one or more independently selected alkyl substituents;

$R_2$ is H, $C_{1-4}$ alkyl, $CH_2(CH_2)_n OH$, $C_{3-6}$ cycloalkyl, or aryl;

$R_3$ is H or $C_{1-4}$ alkyl;

$R_4$ is O or S;

$R_5$ is H or $C_{1-4}$ alkyl;

$R_6$ is H or $C_{1-4}$ alkyl;

$R_7$ is halogen, CN, $NO_2$, $N_3$, $CF_3$, $CH_2(CH_2)_n Y$, $C(O)NR_8R_9$, $C(O)OR_8$, $C(S)NR_8R_9$, $NH_2$, $NHC(O)R_8$, $NHC(O)OR_8$, $OR_8$, or $S(O)_2CF_3$;

Y is H, $CF_3$, $C(O)OR_8$, or $NR_8R_9$;

each $R_8$ is independently H, $C_{1-8}$ alkyl, $C_{2-8}$ alkenyl, or $C_{3-8}$ cycloalkyl;

each $R_9$ is independently H, $C_{1-8}$ alkyl, $C_{2-8}$ alkenyl, or $C_{3-8}$ cycloalkyl; or $R_8$ and $R_9$, together with the nitrogen atom to which they are attached, form a $C_3$-$C_8$ heterocycloalkyl;

$R_{10}$ is H, $C_{1-8}$ alkyl, $C_{3-8}$ alkynyl, $OC_{1-8}$ alkyl, or $C_{3-8}$ cycloalkyl;

$R_{11}$ is H, $C_{1-8}$ alkyl, $C_{3-8}$ alkynyl, $OC_{1-8}$ alkyl, or $C_{3-8}$ cycloalkyl; and each n is independently 0, 1, 2, 3, 4, 5, 6, 7, or 8.

2. The compound of claim 1, or a stereoisomer thereof, wherein the stereoisomer of the compound is of formula II:

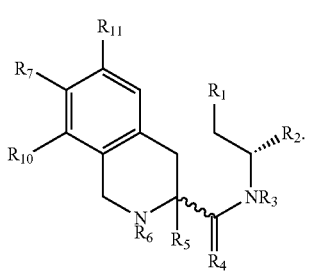

or a pharmaceutically acceptable salt thereof.

3. The compound of claim 1, or a stereoisomer thereof, wherein the stereoisomer of the compound is of formula III:

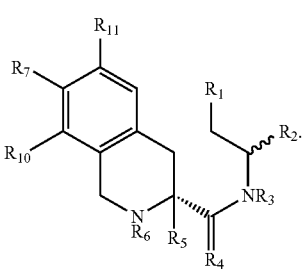

or a pharmaceutically acceptable salt thereof.

4. The compound of claim 3, or a pharmaceutically acceptable salt thereof, wherein $R_1$ is $C_{3-8}$ cycloalkyl.

5. The compound of claim 1, or a pharmaceutically acceptable salt or stereoisomer thereof, wherein $R_1$ is $NHR_9$, $N(C_{1-8}$ alkyl)$R_9$, $N(C_{2-8}$ alkenyl)$R_9$, $N(C_{3-8}$ cycloalkyl)$R_9$, OH, heterocycloalkyl, heterocycloalkenyl, or heteroaryl.

6. The compound of claim 5, or a pharmaceutically acceptable salt or stereoisomer thereof, wherein $R_1$ is heterocycloalkyl, heterocycloalkenyl, or heteroaryl, wherein the heterocycloalkyl, heterocycloalkenyl, or heteroaryl contains at least one nitrogen heteroatom.

7. The compound of claim 6, or a pharmaceutically acceptable salt or stereoisomer thereof, wherein $R_1$ is heterocycloalkyl, wherein the heterocycloalkyl contains at least one nitrogen heteroatom.

8. The compound of claim 7, or a pharmaceutically acceptable salt or stereoisomer thereof, wherein $R_1$ is a 6-membered heterocycloalkyl, wherein the 6-membered heterocycloalkyl contains at least one nitrogen heteroatom.

9. The compound of claim 1, or a pharmaceutically acceptable salt or stereoisomer thereof, wherein $R_1$ is $C_{2-6}$ alkyl, $C_{3-8}$ cycloalkyl, $C_{5-8}$ cycloalkenyl, or phenyl.

10. The compound of claim 1, or a pharmaceutically acceptable salt or stereoisomer thereof, wherein $R_2$ is H, $C_{3-4}$ alkyl, $CH_2OH$, $C_{3-4}$ cycloalkyl, or phenyl.

11. The compound of claim 1, or a pharmaceutically acceptable salt or stereoisomer thereof, wherein $R_3$ is H or $CH_3$.

12. The compound of claim 1, or a pharmaceutically acceptable salt or stereoisomer thereof, wherein $R_4$ is O.

13. The compound of claim 1, or a pharmaceutically acceptable salt or stereoisomer thereof, wherein:

$R_5$ is H; or $R_6$ is H.

14. The compound of claim 1, or a pharmaceutically acceptable salt or stereoisomer thereof, wherein:

$R_5$ is H; and $R_6$ is H.

15. The compound of claim 1, or a pharmaceutically acceptable salt or stereoisomer thereof, wherein:

$R_3$ is H;

$R_5$ is H; and $R_6$ is H.

16. The compound of claim 1, or a pharmaceutically acceptable salt or stereoisomer thereof, wherein $R_7$ is halogen, $C(O)NH_2$, or OH.

17. The compound of claim 1, or a pharmaceutically acceptable salt or stereoisomer thereof, wherein:

$R_{10}$ is H; or $R_{11}$ is H.

18. The compound of claim 1, or a pharmaceutically acceptable salt or stereoisomer thereof, wherein:

$R_{10}$ is H; and $R_{11}$ is H.

19. The compound of claim 1, or a stereoisomer thereof, wherein the compound, or stereoisomer thereof, is selected from the group consisting of:

(19) 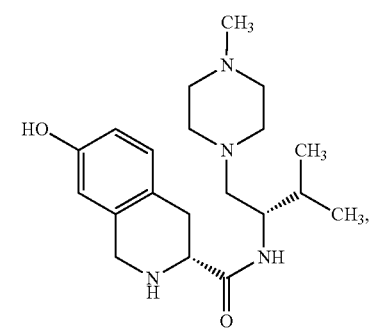
(20) 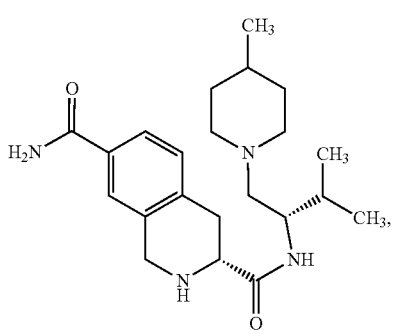
(21) 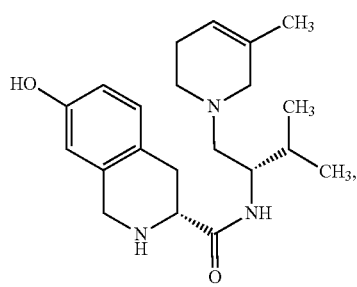
(23) 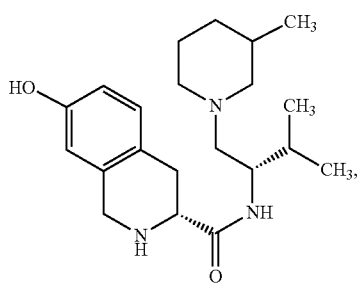
(24) 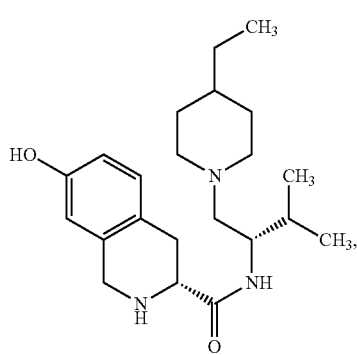
-continued
(25) 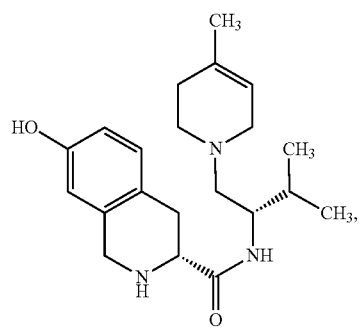
(26) 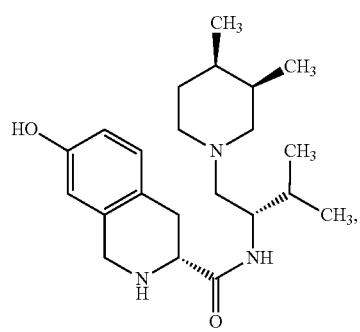
(27) 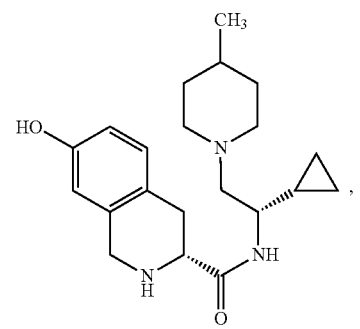
(28) 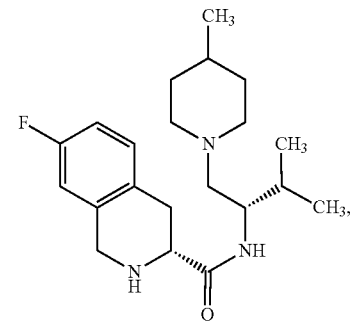
(29) 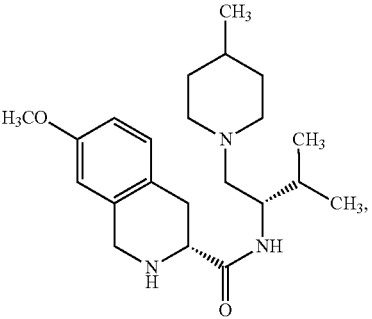

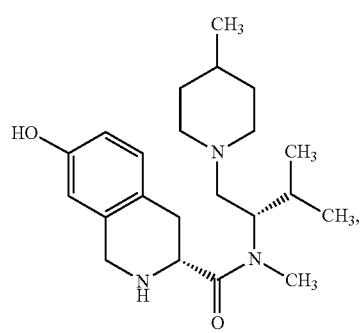
(30)
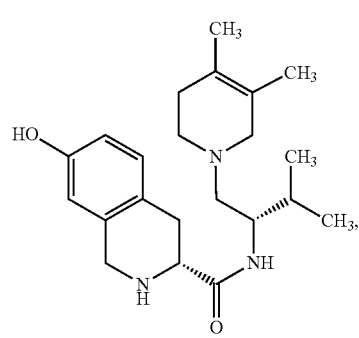
(31)
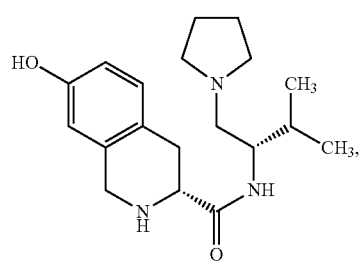
(32)
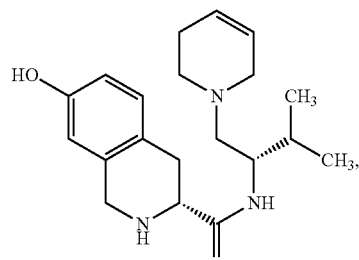
(33)
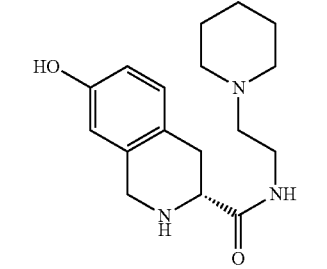
(36)
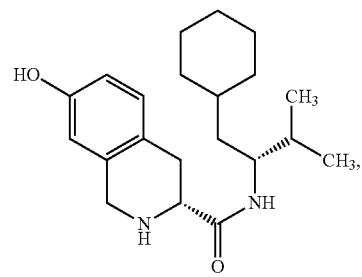
(37)
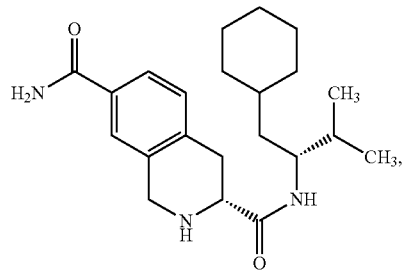
(38)
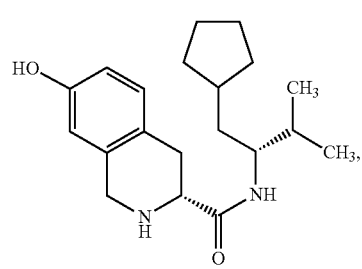
(40)
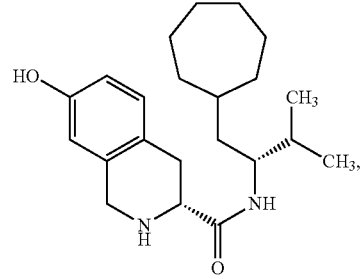
(41)
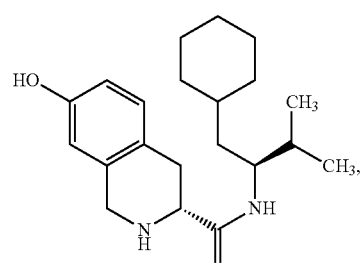
(42)

(43) 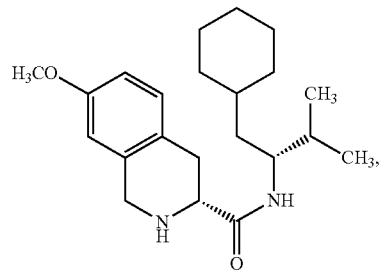
(44) 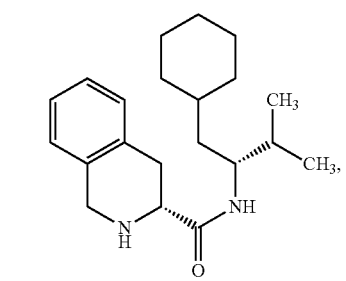
(45) 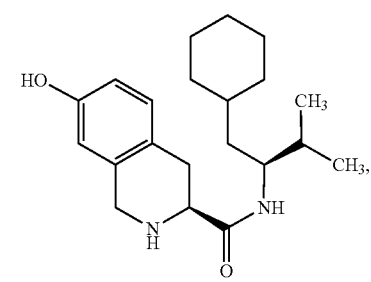
(46) 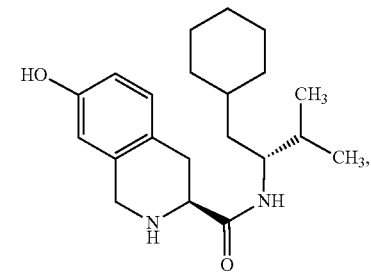
(47) 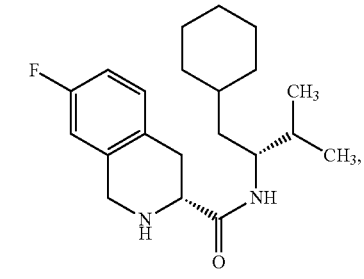
(48) 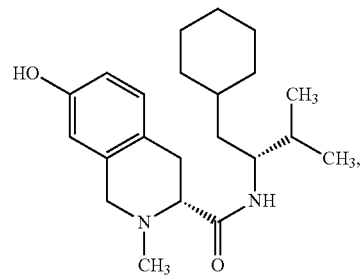
(49) 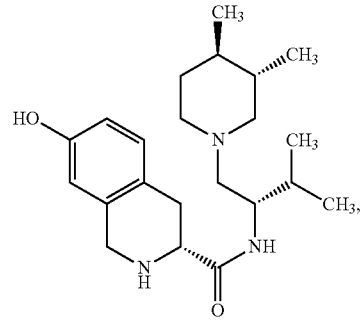
(50) 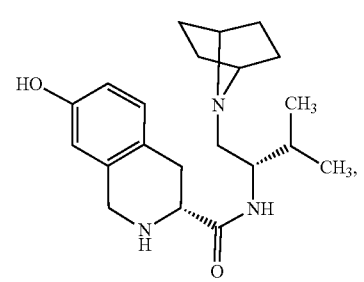
(51) 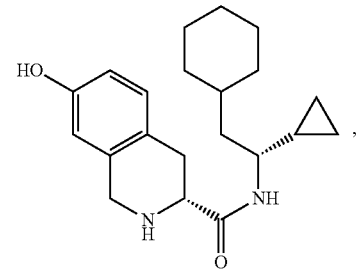
(52) 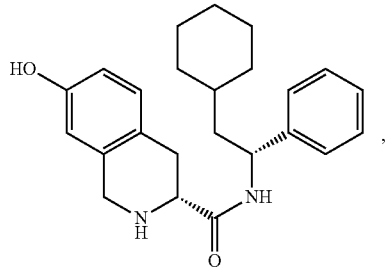

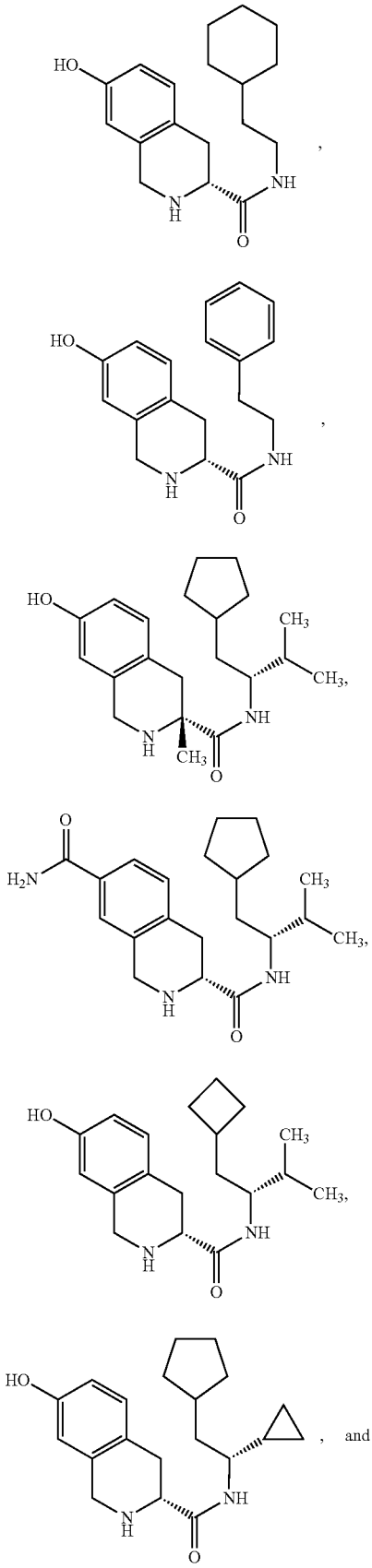

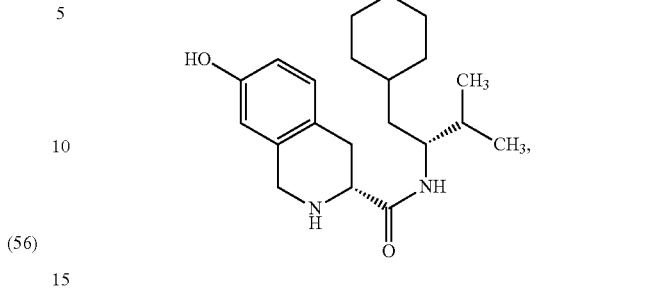

or a pharmaceutically acceptable salt thereof.

20. A pharmaceutical composition comprising at least one pharmaceutically acceptable excipient and a therapeutically effective amount of the compound of claim 1, or a pharmaceutically acceptable salt or stereoisomer thereof.

21. A method for treating anxiety, depression, an eating disorder, or schizophrenia in a subject, wherein the method comprises administering to the subject in need thereof a therapeutically effective amount of a compound of formula I:

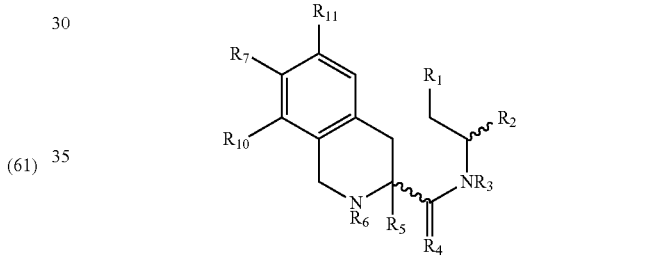

or a pharmaceutically acceptable salt or stereoisomer thereof, wherein:

$R_1$ is H, $C_{1-6}$ alkyl, $NHR_9$, $N(C_{1-8}$ alkyl)$R_9$, $N(C_{2-8}$ alkenyl)$R_9$, $N(C_{3-8}$ cycloalkyl)$R_9$, $OR_8$, $C_{3-8}$ cycloalkyl, $C_{5-8}$ cycloalkenyl, heterocycloalkyl, heterocycloalkenyl, phenyl, or heteroaryl, wherein the heterocycloalkyl or heterocycloalkenyl is optionally substituted with one or more independently selected alkyl substituents;

$R_2$ is H, $C_{1-4}$ alkyl, $CH_2(CH_2)_nOH$, $C_{3-6}$ cycloalkyl, or aryl;

$R_3$ is H or $C_{1-4}$ alkyl;

$R_4$ is O or S;

$R_5$ is H or $C_{1-4}$ alkyl;

$R_6$ is H or $C_{1-4}$ alkyl;

$R_7$ is halogen, CN, $NO_2$, $N_3$, $CF_3$, $CH_2(CH_2)_nY$, $C(O)NR_8R_9$, $C(O)OR_8$, $C(S)NR_8R_9$, $NH_2$, $NHC(O)R_8$, $NHC(O)OR_8$, $OR_8$, or $S(O)_2CF_3$;

Y is H, $CF_3$, $C(O)OR_8$, or $NR_8R_9$;

each $R_8$ is independently H, $C_{1-8}$ alkyl, $C_{2-8}$ alkenyl, or $C_{3-8}$ cycloalkyl;

each $R_9$ is independently H, $C_{1-8}$ alkyl, $C_{2-8}$ alkenyl, or $C_{3-8}$ cycloalkyl; or $R_8$ and $R_9$, together with the nitrogen atom to which they are attached, form a $C_3$-$C_8$ heterocycloalkyl;

$R_{10}$ is H, $C_{1-8}$ alkyl, $C_{3-8}$ alkynyl, $OC_{1-8}$ alkyl, or $C_{3-8}$ cycloalkyl;

$R_{11}$ is H, $C_{1-8}$ alkyl, $C_{3-8}$ alkynyl, $OC_{1-8}$ alkyl, or $C_{3-8}$ cycloalkyl; and each n is independently 0, 1, 2, 3, 4, 5, 6, 7, or 8.

22. A method for treating substance abuse addiction in a subject, wherein the method comprises administering to the subject in need thereof a therapeutically effective amount of a compound of formula I:

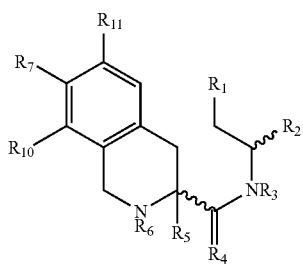

I or a pharmaceutically acceptable salt or stereoisomer thereof, wherein:

$R_1$ is H, $C_{1-6}$ alkyl, $NHR_9$, $N(C_{1-8}$ alkyl$)R_9$, $N(C_{2-8}$ alkenyl$)R_9$, $N(C_{3-8}$ cycloalkyl$)R_9$, $OR_8$, $C_{3-8}$ cycloalkyl, $C_{5-8}$ cycloalkenyl, heterocycloalkyl, heterocycloalkenyl, phenyl, or heteroaryl, wherein the heterocycloalkyl or heterocycloalkenyl is optionally substituted with one or more independently selected alkyl substituents;

$R_2$ is H, $C_{1-4}$ alkyl, $CH_2(CH_2)_nOH$, $C_{3-6}$ cycloalkyl, or aryl;

$R_3$ is H or $C_{1-4}$ alkyl;

$R_4$ is O or S;

$R_5$ is H or $C_{1-4}$ alkyl;

$R_6$ is H or $C_{1-4}$ alkyl;

$R_7$ is halogen, CN, $NO_2$, $N_3$, $CF_3$, $CH_2(CH_2)_nY$, $C(O)NR_8R_9$, $C(O)OR_8$, $C(S)NR_8R_9$, $NH_2$, $NHC(O)R_8$, $NHC(O)OR_8$, $OR_8$, or $S(O)_2CF_3$;

Y is H, $CF_3$, $C(O)OR_8$, or $NR_8R_9$;

each $R_8$ is independently H, $C_{1-8}$ alkyl, $C_{2-8}$ alkenyl, or $C_{3-8}$ cycloalkyl;

each $R_9$ is independently H, $C_{1-8}$ alkyl, $C_{2-8}$ alkenyl, or $C_{3-8}$ cycloalkyl; or $R_8$ and $R_9$, together with the nitrogen atom to which they are attached, form a $C_3$-$C_8$ heterocycloalkyl;

$R_{10}$ is H, $C_{1-8}$ alkyl, $C_{3-8}$ alkynyl, $OC_{1-8}$ alkyl, or $C_{3-8}$ cycloalkyl;

$R_{11}$ is H, $C_{1-8}$ alkyl, $C_{3-8}$ alkynyl, $OC_{1-8}$ alkyl, or $C_{3-8}$ cycloalkyl; and each n is independently 0, 1, 2, 3, 4, 5, 6, 7, or 8.

23. The method of claim 22, wherein the substance abuse addiction is selected from the group consisting of alcohol addiction, cocaine addiction, methamphetamine addiction, nicotine addiction, and opioid addiction.

24. A compound of formula I:

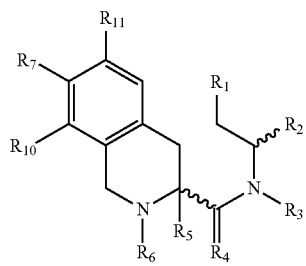

I or a pharmaceutically acceptable salt or stereoisomer thereof, wherein:

$R_1$ is H, $C_{1-6}$ alkyl, $NHR_9$, $N(C_{1-8}$ alkyl$)R_9$, $N(C_{2-8}$ alkenyl$)R_9$, $N(C_{3-8}$ cycloalkyl$)R_9$, $OR_8$, $C_{3-8}$ cycloalkyl, $C_{5-8}$ cycloalkenyl, heterocycloalkyl, heterocycloalkenyl, phenyl, or heteroaryl, wherein the heterocycloalkyl or heterocycloalkenyl is optionally substituted with one or more independently selected alkyl substituents;

$R_2$ is H, $C_{1-4}$ alkyl, $CH_2(CH_2)_nOH$, $C_{3-6}$ cycloalkyl, or aryl;

$R_3$ is H or $C_{1-4}$ alkyl;

$R_4$ is O or S;

$R_5$ is H or $C_{1-4}$ alkyl;

$R_6$ is H or $C_{1-4}$ alkyl;

$R_7$ is halogen, CN, $NO_2$, $N_3$, $CF_3$, $CH_2(CH_2)_nY$, $C(O)NR_8R_9$, $C(O)OR_8$, $C(S)NR_8R_9$, $NH_2$, $NHC(O)R_8$, $NHC(O)OR_8$, $OR_8$, or $S(O)_2CF_3$;

Y is H, $CF_3$, $C(O)OR_8$, or $NR_8R_9$;

each $R_8$ is independently H, $C_{1-8}$ alkyl, $C_{2-8}$ alkenyl, or $C_{3-8}$ cycloalkyl;

each $R_9$ is independently H, $C_{1-8}$ alkyl, $C_{2-8}$ alkenyl, or $C_{3-8}$ cycloalkyl;

$R_{10}$ is H, $C_{1-8}$ alkyl, $C_{3-8}$ alkynyl, $OC_{1-8}$ alkyl, or $C_{3-8}$ cycloalkyl;

$R_{11}$ is H, $C_{1-8}$ alkyl, $C_{3-8}$ alkynyl, $OC_{1-8}$ alkyl, or $C_{3-8}$ cycloalkyl; and each n is independently 0, 1, 2, 3, 4, 5, 6, 7, or 8.

25. A compound, or a stereoisomer thereof, wherein the stereoisomer of the compound is selected from the group consisting of:

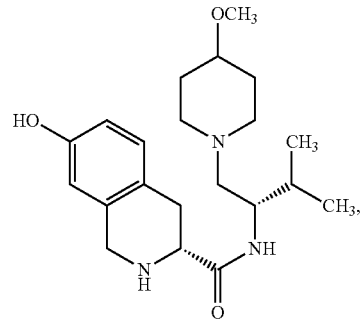

(13)

(14) 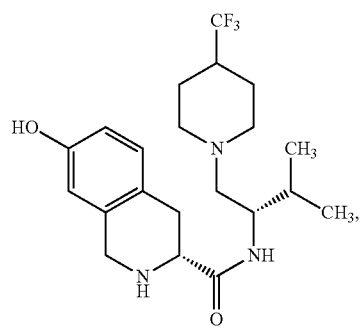
(22) 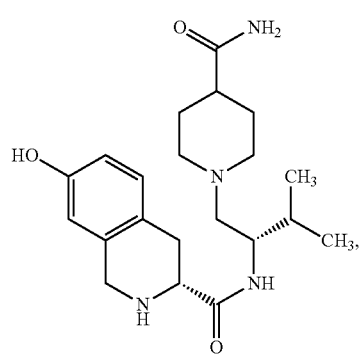
(34) 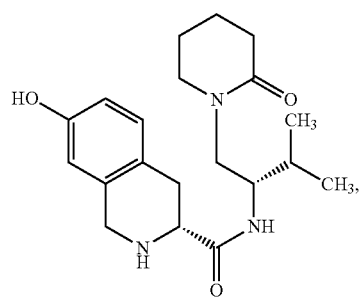
(35) 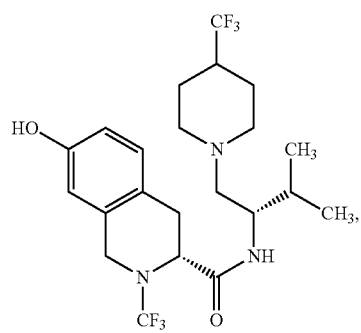
(39) 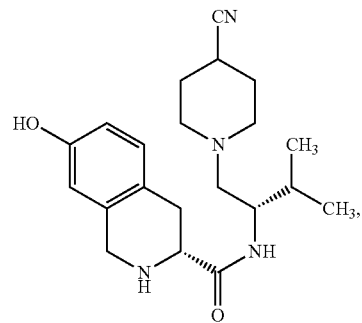
(54) 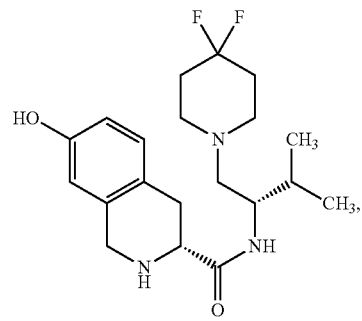
(58) 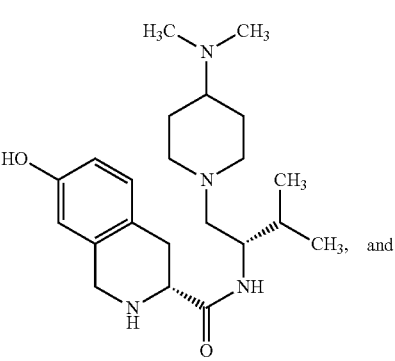
and
(59) 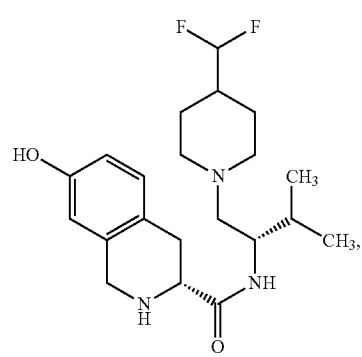
or a pharmaceutically acceptable salt thereof.
* * * * *